US012691095B2

(12) United States Patent
Kanouni et al.

(10) Patent No.: US 12,691,095 B2
(45) **Date of Patent: *Jul. 28, 2026**

(54) MODULATORS OF TNF-ALPHA ACTIVITY

(71) Applicant: Forward Therapeutics, Inc., Palm Beach Gardens, FL (US)

(72) Inventors: Toufike Kanouni, Palm Beach Gardens, FL (US); Yoshiyuki Fukase, San Diego, CA (US)

(73) Assignee: FORWARD THERAPEUTICS, INC., Palm Beach Gardens, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/370,127

(22) Filed: Oct. 27, 2025

(65) Prior Publication Data

US 2026/0048035 A1 Feb. 19, 2026

Related U.S. Application Data

(63) Continuation of application No. 19/287,701, filed on Jul. 31, 2025, now Pat. No. 12,521,368, which is a continuation of application No. PCT/US2025/022514, filed on Apr. 1, 2025.

(60) Provisional application No. 63/738,425, filed on Dec. 23, 2024, provisional application No. 63/673,995, filed on Jul. 22, 2024, provisional application No. 63/573,786, filed on Apr. 3, 2024.

(51) Int. Cl.
*A61K 31/395* (2006.01)
*C07D 405/04* (2006.01)

(52) U.S. Cl.
CPC .......... *A61K 31/395* (2013.01); *C07D 405/04* (2013.01)

(58) Field of Classification Search
CPC ............................ C07D 405/04; A61K 31/395
See application file for complete search history.

(56) References Cited

U.S. PATENT DOCUMENTS

| | | | |
|---|---|---|---|
| 5,846,514 A | 12/1998 | Foster et al. | |
| 6,334,997 B1 | 1/2002 | Foster et al. | |
| 10,202,405 B2 | 2/2019 | De Haro Garcia et al. | |
| 10,457,677 B2 | 10/2019 | Fuchss et al. | |
| 12,521,368 B2 * | 1/2026 | Kanouni | A61K 31/395 |
| 2021/0155637 A1 | 5/2021 | De Haro Garcia et al. | |
| 2024/0247014 A1 | 7/2024 | Kanouni et al. | |

FOREIGN PATENT DOCUMENTS

| | | | |
|---|---|---|---|
| CN | 120965696 | A | 11/2025 |
| WO | WO-2016050975 | A1 | 4/2016 |
| WO | WO-2016155884 | A1 | 10/2016 |
| WO | WO-2017167993 | A1 | 10/2017 |
| WO | WO-2017167994 | A1 | 10/2017 |
| WO | WO-2017167995 | A1 | 10/2017 |
| WO | WO-2018167176 | A1 | 9/2018 |
| WO | WO-2018197503 | A1 | 11/2018 |
| WO | WO-2020084008 | A1 | 4/2020 |
| WO | WO-2024112796 | A1 | 5/2024 |
| WO | WO-2024129763 | A1 | 6/2024 |
| WO | WO-2024148191 | A1 | 7/2024 |
| WO | WO-2024223740 | A1 | 10/2024 |
| WO | WO-2024251282 | A1 | 12/2024 |
| WO | WO-2025001449 | A1 | 1/2025 |
| WO | WO-2025008402 | A1 | 1/2025 |
| WO | WO-2025024723 | A1 | 1/2025 |
| WO | WO-2025038927 | A1 | 2/2025 |
| WO | WO-2025068505 | A1 | 4/2025 |
| WO | WO-2025137267 | A1 | 6/2025 |
| WO | WO-2025201449 | A1 | 10/2025 |
| WO | WO-2025212627 | A1 | 10/2025 |
| WO | WO-2025240514 | A1 | 11/2025 |
| WO | WO-2025244936 | A1 | 11/2025 |

OTHER PUBLICATIONS 53699-724.601 SSS results completed on Mar. 27, 2025.
Berge, Stephen M. et al. Pharmaceutical Salts. Journal of Pharmaceutical Sciences 66(1):1-19 (1977).
Braga, Fowler et al. et al. Overview of TNF Inhibitors for Treating Inflammatory Bowel Disease. US Pharm. 46(5):34-37 (2021).
Chemical search results dated Aug. 5, 2025 (4 pgs).
Chemical Structure Search dated Jun. 9, 2025 (pp. 1-3).
Chemical Structure Search dated Jun. 9, 2025 (pp. 1-42).
Co-pending U.S. Appl. No. 19/287,701, inventors Kanouni; Toufike et al., filed Jul. 31, 2025.
Dean, Dennis C. Recent Advances in the Synthesis and Applications of Radiolabeled Compounds for Drug Discovery and Development. Current Pharmaceutical Design 6(10):1-2 (2000). [Preface only].
Dietrich, Justin D. et al. Development of orally efficacious allosteric inhibitors of TNFα via fragment-based drug design. Journal of Medicinal Chemistry 64(1):417-429 (2020).
Domling, Alexander et al. TNF-α: The shape of small molecules to come?. Drug discovery today 27(1):3-7 (2022).
Evans, Anthony E. Synthesis of Radiolabeled Compounds. Journal of Radioanalytical and Nuclear Chemistry 64(1-2):9-32 (1981).
Finkbeiner, Peter et al., Phosphine Oxides from a Medicinal Chemist's Perspective: Physicochemical and in Vitro Parameters Relevant for Drug Discovery. Journal of Medicinal Chemistry 63(13):7081-7107 (2020).
Fresegna, Diego et al. Re-examining the role of TNF in MS pathogenesis and therapy. Cells 9(10):2290, 1-26 (2020).
He, Molly M. et al. Small-molecule inhibition of TNF-α. Science 310(5750):1022-1025 (2005).

(Continued)

*Primary Examiner* — Timothy R Rozof
(74) *Attorney, Agent, or Firm* — WILSON SONSINI GOODRICH & ROSATI

(57) ABSTRACT

Provided herein are inhibitors of TNF-alpha, pharmaceutical compositions comprising the inhibitory compounds, and methods for using the TNF-alpha inhibitory compounds for the treatment of diseases or disorders.

26 Claims, No Drawings

(56) References Cited

OTHER PUBLICATIONS

Kabalka, George W. et al. The Synthesis of Radiolabeled Compounds via Organometallic Intermediates. Tetrahedron 45(21):6601-6621 (1989).
Martin et al. Synthesis and Evaluation of a Phosphonate Analogue of the Soluble Guanylate Cyclase Activator YC-1. Bioorg Med Chem Lett 17(17):4938-4941 (2007).
O'Connell, James et al. Small molecules that inhibit TNF signalling by stabilising an asymmetric form of the trimer. Nature communications 10(1):5795, 1-12 (2019).
Orti-Casan, Natalia et al. Targeting TNFR2 as a novel therapeutic strategy for Alzheimer's disease. Frontiers in neuroscience 13:49, 1-8 (2019).
PCT/US2023/080758 International Search Report and Written Opinion dated Mar. 6, 2024.
PCT/US2025/022514 International Search Report and Written Opinion dated Jun. 12, 2025.
Shulman, Abraham et al. Neuroinflammation and tinnitus. The Behavioral Neuroscience of Tinnitus pp. 161-174 (2021).
U.S. Appl. No. 18/516,560, filed Nov. 21, 2023 File History.
U.S. Appl. No. 18/516,560 Office Action dated Jul. 8, 2024.
U.S. Appl. No. 18/516,560 Office Action dated Mar. 12, 2024.
Wang, Weihua et al. Neuroinflammation mediates noise-induced synaptic imbalance and tinnitus in rodent models. PLoS biology 17(6):e3000307, 1-25 (2019).
Xiao, Hai-Yun et al. Biologic-like in vivo efficacy with small molecule inhibitors of TNFα identified using scaffold hopping and structure-based drug design approaches. Journal of Medicinal Chemistry 63(23):15050-15071 (2020).
Domling, Alexander et al. Balinatunfib: A Clinical Oral Small Molecule TNFα Inhibitor. ChemMedChem 20(14):e202500258 (2025).
Nassr, Nassr et al. First-in-Human Single and Multiple Ascending Dose Studies of Balinatunfib, a Small Molecule Inhibitor of TNFR1 Signaling in Healthy Participants. Clin Pharmacol Ther 118(1):164-176 (2025).
Vugler, Alexander et al. An orally available small molecule that targets soluble TNF to deliver anti-TNF biologic-like efficacy in rheumatoid arthritis. Front Pharmacol 13:1037983 (2022).

* cited by examiner

MODULATORS OF TNF-ALPHA ACTIVITY

CROSS-REFERENCE TO RELATED APPLICATIONS

This application is a continuation of U.S. application Ser. No. 19/287,701, filed Jul. 31, 2025, which claims priority to International Application No. PCT/US2025/022514, filed Apr. 1, 2025, and claims the benefit of U.S. Provisional Application No. 63/573,786, filed Apr. 3, 2024, U.S. Provisional Application No. 63/673,995, filed Jul. 22, 2024, and U.S. Provisional Application No. 63/738,425, filed Dec. 23, 2024, all of which are incorporated herein by reference in their entirety.

BACKGROUND

Tumor necrosis factor alpha (TNFα) is an inflammatory cytokine that is responsible for a wide range of signaling events within cells. Aberrant TNFα signaling gives rise to inflammatory conditions and is thought to be an important component of inflammatory disease, such as rheumatoid arthritis.

BRIEF SUMMARY OF THE INVENTION

Provided herein are inhibitors of TNFα, pharmaceutical compositions comprising said inhibitory compounds, and methods for using said inhibitory compounds for the treatment of inflammatory or autoimmune disease or disorder.

One embodiment provides a compound of Formula (I), or pharmaceutically acceptable salt, solvate, deuteroisotope, or N-oxide thereof:

(I)

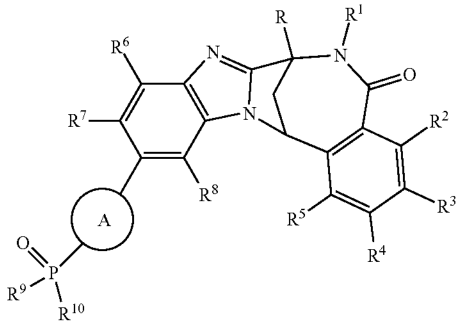

wherein,

Ring A is selected from

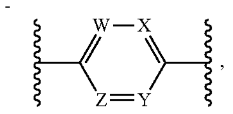

wherein the * denotes point of attachment to phosphorous, or an optionally substituted heteroarylene selected from pyrazolene, imidazoline, oxazolene, or thiazolene;

W is N or C—$R^{11}$;

X is N or C—$R^{12}$;

Y is N or C—$R^{13}$,

Z is N or C—$R^{14}$;

R is selected from H, D, or optionally substituted C1-C6 alkyl;

$R^1$ is selected from H, optionally substituted C1-C6 alkyl, optionally substituted C3-C6 cycloalkyl, or optionally substituted C4-C7 cycloalkylalkyl;

$R^2$ is selected from H, D, Cl, F, optionally substituted C1-C6 alkyl, or optionally substituted C3-C6 cycloalkyl;

$R^3$, $R^4$, and $R^5$ are selected from H, D, Cl, or F; with the provision that at least one of $R^2$, $R^3$, $R^4$, or $R^5$ is not H or D;

$R^6$ is selected from H, D, halogen, or optionally substituted C1-C6 alkyl;

$R^7$ is selected from H, D, or halogen;

$R^8$ is selected from H, D, or halogen;

$R^9$ and $R^{10}$ are independently optionally substituted C1-C6 alkyl; or $R^9$ and $R^{10}$ join to form optionally substituted phosphorus-containing 3- to 8-membered ring; and $R^{11}$, $R^{12}$, $R^{13}$, and $R^{14}$ are independently selected from H, D, halogen, —CN, —$NH_2$, optionally substituted C1-C3 alkyl, optionally substituted C1-C3 alkoxy, or —NH (optionally substituted C1-C3 alkyl).

One embodiment provides a compound of Formula (I), or pharmaceutically acceptable salt, solvate, deuteroisotope, or N-oxide thereof, having the structure of Formula (Ia):

(Ia)

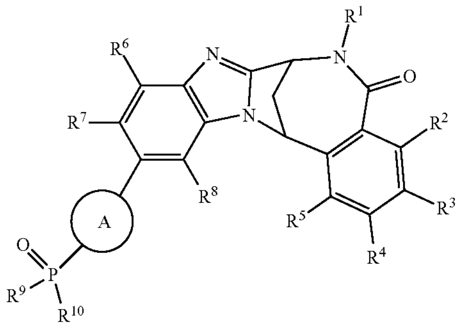

wherein,

Ring A is selected from

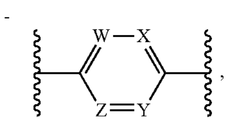

wherein the * denotes point of attachment to phosphorous, or an optionally substituted heteroarylene selected from pyrazolene, imidazoline, oxazolene, or thiazolene;

W is N or C—$R^{11}$;

X is N or C—$R^{12}$;

Y is N or C—$R^{13}$;

Z is N or C—$R^{14}$;

$R^1$ is selected from H, optionally substituted C1-C6 alkyl, optionally substituted C3-C6 cycloalkyl, or optionally substituted C4-C7 cycloalkylalkyl;

$R^2$ is selected from H, D, Cl, F, optionally substituted C1-C6 alkyl, or optionally substituted C3-C6 cycloalkyl;

$R^3$, $R^4$, and $R^5$ are selected from H, D, Cl, or F; with the provision that at least one of $R^2$, $R^3$, $R^4$, or $R^5$ is not H or D;

$R^6$ is selected from H, D, halogen, or optionally substituted C1-C6 alkyl;

$R^7$ is selected from H, D, or halogen;

$R^8$ is selected from H, D, or halogen;

$R^9$ and $R^{10}$ are independently optionally substituted C1-C6 alkyl; or $R^9$ and $R^{10}$ join to form optionally substituted phosphorus-containing 3- to 8-membered ring; and $R^{11}$, $R^{12}$, $R^{13}$, and $R^{14}$ are independently selected from H, D, halogen, —CN, —$NH_2$, optionally substituted C1-C3 alkyl, optionally substituted C1-C3 alkoxy, or —NH (optionally substituted C1-C3 alkyl).

One embodiment provides a pharmaceutical composition comprising a compound of Formula (I), or pharmaceutically acceptable salt, solvate, deuteroisotope, or N-oxide thereof, and at least one pharmaceutically acceptable excipient.

One embodiment provides a method of treating a disease or disorder in a patient in need thereof comprising administering to the patient a compound of Formula (I), or pharmaceutically acceptable salt, solvate, deuteroisotope, or N-oxide thereof. Another embodiment provides the method wherein the disease or disorder is rheumatoid arthritis.

INCORPORATION BY REFERENCE

All publications, patents, and patent applications mentioned in this specification are herein incorporated by reference for the specific purposes identified herein.

DETAILED DESCRIPTION OF THE INVENTION

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

Definitions

As used in the specification and appended claims, unless specified to the contrary, the following terms have the meaning indicated below.

"Amino" refers to the —$NH_2$ radical.

"Cyano" refers to the —CN radical.

"Nitro" refers to the —$NO_2$ radical.

"Oxa" refers to the —O— radical.

"Oxo" refers to the =O radical.

"Thioxo" refers to the =S radical.

"Imino" refers to the =N—H radical.

"Oximo" refers to the =N—OH radical.

"Hydrazino" refers to the =N—$NH_2$ radical.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_8$alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —$C(O)R^a$, —$C(O)OR^a$, —$C(O)N(R^a)_2$, —$N(R^a)C(O)OR^a$, —OC(O)—$N(R^a)_2$, —$N(R^a)C(O)R^a$, —$N(R^a)S(O)_tR^a$ (where t is 1 or 2), —$S(O)_tOR^a$ (where t is 1 or 2), —$S(O)_tR^a$ (where t is 1 or 2) and —$S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl). In certain embodiments, an optionally substituted alkyl is a haloalkyl. In other embodiments, an optionally substituted alkyl is a fluoroalkyl. In other embodiments, an optionally substituted alkyl is a —$CF_3$ group.

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl comprises two to six carbon atoms. In other embodiments, an alkynyl comprises two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkylene" or "alkylene chain" refers to a straight or branched divalent hydrocarbon chain linking the rest of the molecule to a radical group, consisting solely of carbon and hydrogen, containing no unsaturation, and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group are through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkenylene" or "alkenylene chain" refers to a straight or branched divalent hydrocarbon chain linking the rest of the molecule to a radical group, consisting solely of carbon and hydrogen, containing at least one carbon-carbon double bond, and having from two to twelve carbon atoms. The alkenylene chain is attached to the rest of the molecule through a single bond and to the radical group through a single bond. In certain embodiments, an alkenylene comprises two to eight carbon atoms (e.g., $C_2$-$C_8$ alkenylene). In other embodiments, an alkenylene comprises two to five carbon atoms (e.g., $C_2$-$C_5$ alkenylene). In other embodiments, an alkenylene comprises two to four carbon atoms (e.g., $C_2$-$C_4$ alkenylene). In other embodiments, an alkenylene comprises two to three carbon atoms (e.g., $C_2$-$C_3$ alkenylene). In other embodiments, an alkenylene comprises two carbon atoms (e.g., $C_2$ alkenylene). In other embodiments, an alkenylene comprises five to eight carbon atoms (e.g., $C_5$-$C_8$ alkenylene). In other embodiments, an alkenylene comprises three to five carbon atoms (e.g., $C_3$-$C_5$ alkenylene). Unless stated otherwise specifically in the specification, an alkenylene chain is optionally substituted by one or more of the following substituents: halo, cyano, nitro, oxo, thioxo, imino, oximo, trimethylsilanyl, —OR$^a$, —$SR^a$, —OC(O)—$R^a$, —$N(R^a)_2$, —C(O)$R^a$, —C(O)O$R^a$, —C(O)$N(R^a)_2$, —$N(R^a)$C(O)O$R^a$, —OC(O)—$N(R^a)_2$, —$N(R^a)$C(O)$R^a$, —$N(R^a)S(O)_tR^a$ (where t is 1 or 2), —$S(O)_tOR^a$ (where t is 1 or 2), —$S(O)_tR^a$ (where t is 1 or 2) and —$S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynylene" or "alkynylene chain" refers to a straight or branched divalent hydrocarbon chain linking the rest of the molecule to a radical group, consisting solely of carbon and hydrogen, containing at least one carbon-carbon triple bond, and having from two to twelve carbon atoms. The alkynylene chain is attached to the rest of the molecule through a single bond and to the radical group through a single bond. In certain embodiments, an alkynylene comprises two to eight carbon atoms (e.g., $C_2$-$C_8$ alkynylene). In other embodiments, an alkynylene comprises two to five carbon atoms (e.g., $C_2$-$C_5$ alkynylene). In other embodiments, an alkynylene comprises two to four carbon atoms (e.g., $C_2$-$C_4$ alkynylene). In other embodiments, an alkynylene comprises two to three carbon atoms (e.g., $C_2$-$C_3$ alkynylene). In other embodiments, an alkynylene comprises two carbon atoms (e.g., $C_2$ alkynylene). In other embodiments, an alkynylene comprises five to eight carbon atoms (e.g., $C_5$-$C_8$ alkynylene). In other embodiments, an alkynylene comprises three to five carbon atoms (e.g., $C_3$-$C_5$ alkynylene). Unless stated otherwise specifically in the specification, an alkynylene chain is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)O$R^a$, —C(O)$N(R^a)_2$, —$N(R^a)$C(O)O$R^a$, —OC(O)—$N(R^a)_2$, —$N(R^a)$C(O)$R^a$, —$N(R^a)S(O)_tR^a$ (where t is 1 or 2), —$S(O)_tOR^a$ (where t is 1 or 2), —$S(O)_tR^a$ (where t is 1 or 2) and —$S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from optionally substituted alkyl, optionally substituted alkenyl, optionally substituted alkynyl, halo, cyano, nitro, —$R^b$—$OR^a$, —$R^b$—OC(O)—$R^a$, —$R^b$—OC(O)—O$R^a$, —$R^b$—OC(O)—$N(R^a)_2$, —$R^b$—$N(R^a)_2$, —$R^b$—C(O)$R^a$, —$R^b$—C(O)O$R^a$, —$R^b$—C(O)$N(R^a)_2$, —$R^b$—O—$R^c$—C(O)$N(R^a)_2$, —$R^b$—$N(R^a)$C(O)O$R^a$, —$R^b$—$N(R^a)$C(O)$R^a$, —$R^b$—$N(R^a)S(O)_tR^a$ (where t is 1 or 2), —$R^b$—$S(O)_tR^a$ (where t is 1 or 2), —$R^b$—$S(O)_tOR^a$ (where t is 1 or 2) and —$R^b$—$S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the $R^a$, $R^b$, or $R^c$ substituents is unsubstituted unless otherwise indicated.

"Aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula —O—$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl is saturated (i.e., containing single C—C bonds only) or unsaturated (i.e., containing one or more double bonds or triple bonds). A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from optionally substituted alkyl, optionally substituted alkenyl, optionally substituted alkynyl, halo, oxo, thioxo, cyano, nitro, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—C(O)$R^a$, —$R^b$—C(O)O$R^a$, —$R^b$—C(O)$N(R^a)_2$, —$R^b$—O—$R^c$—C(O)$N(R^a)_2$, —$R^b$—$N(R^a)$C(O)O$R^a$, —$R^b$—$N(R^a)$C(O)$R^a$, —$R^b$—$N(R^a)S(O)_tR^a$ (where t is 1 or 2), —$R^b$—$S(O)_tR^a$ (where t is 1 or 2), —$R^b$—$S(O)_tOR^a$ (where t is 1 or 2) and —$R^b$—$S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the $R^a$, $R^b$, or $R^c$ substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical is optionally substituted as defined above.

"Carbocyclylalkynyl" refers to a radical of the formula —$R^c$-carbocyclyl where $R^c$ is an alkynylene chain as defined above. The alkynylene chain and the carbocyclyl radical is optionally substituted as defined above.

"Carbocyclylalkoxy" refers to a radical bonded through an oxygen atom of the formula —O—$R^c$-carbocyclyl where $R^c$ is an alkylene chain as defined above. The alkylene chain and the carbocyclyl radical is optionally substituted as defined above.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic, or tetracyclic ring system, which optionally includes fused or bridged ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from optionally substituted alkyl, optionally substituted alkenyl, optionally substituted alkynyl, halo, fluoroalkyl, oxo, thioxo, cyano, nitro, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—C(O)$R^a$, —$R^b$—C(O)O$R^a$, —$R^b$—C(O)$N(R^a)_2$, —$R^b$—O—$R^c$—C(O)$N(R^a)_2$, —$R^b$—$N(R^a)$C(O)O$R^a$, —$R^b$—$N(R^a)$C(O)$R^a$, —$R^b$—$N(R^a)S(O)_tR^a$ (where t is 1 or 2), —$R^b$—$S(O)_tR^a$ (where t is 1 or 2), —$R^b$—$S(O)_tOR^a$ (where t is 1 or 2) and —$R^b$—$S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the $R^a$, $R^b$, or $R^c$ substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals.

Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen, and sulfur. As used herein, the heteroaryl radical is a monocyclic, bicyclic, tricyclic, or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a, 7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from optionally substituted alkyl, optionally substituted cycloalkylalkyl, optionally substituted heterocyclylalkyl, optionally substituted alkenyl, optionally substituted alkynyl, halo, optionally substituted fluoroalkyl, optionally substituted haloalkenyl, optionally substituted haloalkynyl, oxo, thioxo, cyano, nitro, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—C(O)$R^a$, —$R^b$—C(O)$OR^a$, —$R^b$—C(O)$N(R^a)_2$, —$R^b$—O—$R^c$—C(O)$N(R^a)_2$, —$R^b$—N($R^a$)C(O)$OR^a$, —$R^b$—N($R^a$)C(O)$R^a$, —$R^b$—N($R^a$)$S(O)_tR^a$ (where t is 1 or 2), —$R^b$—$S(O)_tR^a$ (where t is 1 or 2), —$R^b$—$S(O)_tOR^a$ (where t is 1 or 2) and —$R^b$—$S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the $R^a$, $R^b$, or $R^c$ substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein, in some embodiments, contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

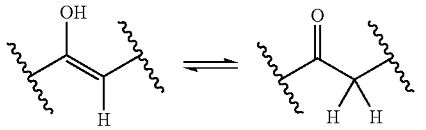

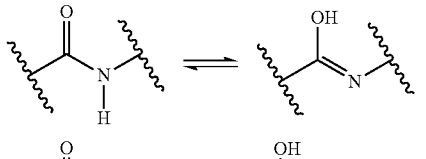

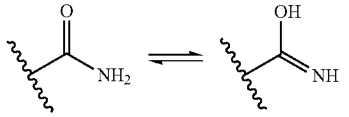

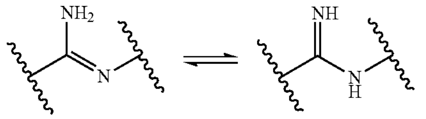

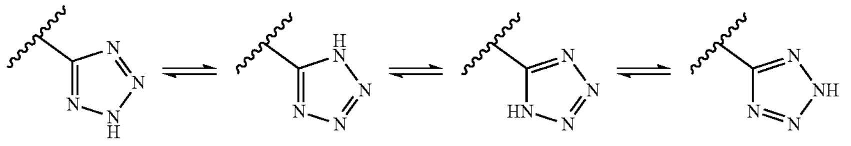

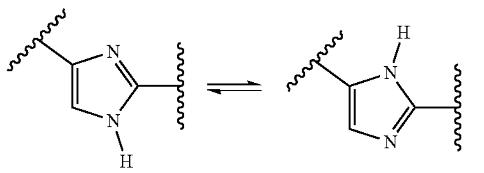

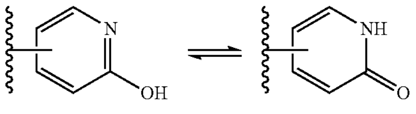

The compounds disclosed herein, in some embodiments, are used in different enriched isotopic forms, e.g., enriched in the content of 2H, 3H, 11C, 13C and/or 14C. In one particular embodiment, the compound is deuterated in at least one position. Such deuterated forms are referred to as deuteroisotopes herein and can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, structures depicted herein are intended to include compounds which differ only in the presence of one or more isotopically enriched atoms. For example, compounds having the present structures except for the replacement of a hydrogen by a deuterium or tritium, or the replacement of a carbon by 13C- or 14C-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^{2}$H), tritium ($^{3}$H), iodine-125 ($^{125}$I) or carbon-14 ($^{14}$C). Isotopic substitution with $^{2}$H, $^{11}$C, $^{13}$C, $^{14}$C, $^{15}$C, $^{12}$N, $^{13}$N, $^{15}$N, $^{16}$N, $^{16}$O, $^{17}$O, $^{14}$F, $^{15}$F, $^{16}$F, $^{17}$F, $^{18}$F, $^{33}$S, $^{34}$S, $^{35}$S, $^{36}$S, $^{35}$Cl, $^{37}$Cl, $^{79}$Br, $^{81}$Br, $^{125}$I are all contemplated. In some embodiments, isotopic substitution with $^{18}$F is contemplated. All isotopic variations of the compounds of the present invention, whether radioactive or not, are encompassed within the scope of the present invention.

In certain embodiments, the compounds disclosed herein have some or all of the $^{1}$H atoms replaced with $^{2}$H atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [Curr., Pharm. Des., 2000; 6 (10)] 2000, 110 pp; George W.; Varma, Rajender S. The Synthesis of Radiolabeled Compounds via Organometallic Intermediates, Tetrahedron, 1989, 45 (21), 6601-21; and Evans, E. Anthony. Synthesis of radiolabeled compounds, J. Radioanal. Chem., 1981, 64 (1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

Deuterium-transfer reagents suitable for use in nucleophilic substitution reactions, such as iodomethane-$d_3$ ($CD_3I$), are readily available and may be employed to transfer a deuterium-substituted carbon atom under nucleophilic substitution reaction conditions to the reaction substrate. The use of $CD_3I$ is illustrated, by way of example only, in the reaction schemes below.

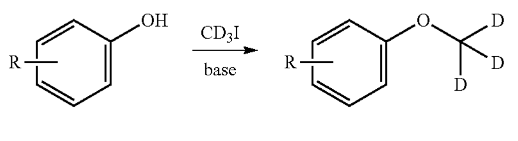

-continued

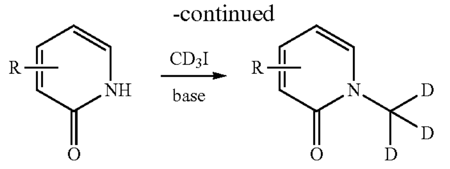

Deuterium-transfer reagents, such as lithium aluminum deuteride ($LiAlD_4$), are employed to transfer deuterium under reducing conditions to the reaction substrate. The use of $LiAlD_4$ is illustrated, by way of example only, in the reaction schemes below.

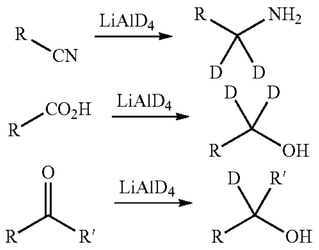

Deuterium gas and palladium catalyst are employed to reduce unsaturated carbon-carbon linkages and to perform a reductive substitution of aryl carbon-halogen bonds as illustrated, by way of example only, in the reaction schemes below.

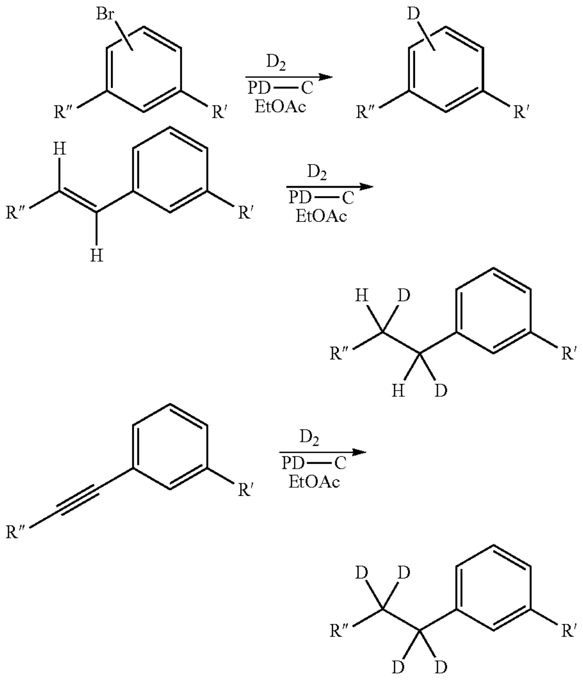

In one embodiment, the compounds disclosed herein contain one deuterium atom. In another embodiment, the compounds disclosed herein contain two deuterium atoms. In another embodiment, the compounds disclosed herein contain three deuterium atoms. In another embodiment, the compounds disclosed herein contain four deuterium atoms. In another embodiment, the compounds disclosed herein contain five deuterium atoms. In another embodiment, the compounds disclosed herein contain six deuterium atoms. In another embodiment, the compounds disclosed herein contain more than six deuterium atoms. In another embodiment, the compound disclosed herein is fully substituted with deuterium atoms and contains no non-exchangeable $^1H$ hydrogen atoms. In one embodiment, the level of deuterium incorporation is determined by synthetic methods in which a deuterated synthetic building block is used as a starting material.

"Pharmaceutically acceptable salt" includes both acid and base addition salts. A pharmaceutically acceptable salt of any one of the TNFα inhibitory compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

"Pharmaceutically acceptable solvate" refers to a composition of matter that is the solvent addition form. In some embodiments, solvates contain either stoichiometric or non-stoichiometric amounts of a solvent, and are formed during the process of making with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. The compounds provided herein exist in either unsolvated or solvated forms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

As used herein, "treatment" or "treating," or "palliating" or "ameliorating" are used interchangeably. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are, in some embodiments, administered to a patient at risk of developing a particular disease, or to a patient reporting one or more of the physiological symptoms of a disease, even though a diagnosis of this disease has not been made.

Tumor Necrosis Factor Alpha (TNFα) Protein and Function

Tumor necrosis factor alpha (TNFα) proteins are members of the TNF superfamily, comprising various transmembrane proteins with a homologous TNF domain forming trimers. The TNF superfamily comprises 19 family members, including, but not limited to tumor necrosis factor alpha (also known as tumor necrosis factor, or TNF), lymphotoxin alpha (TNFβ), lymphotoxin beta (TNFγ), OX40 ligand, CD40 ligand, Fas ligand, CD27 ligand, CD30 ligand, CD137 ligand, CD137 ligand, and TNF-related apoptosis-inducing ligand. TNFα proteins are cytokines and adipokines (cytokines secreted by adipose tissue).

TNFα is a transmembrane protein, with soluble TNFα (sTNFα) released via protein cleavage. The sTNFα can propagate signaling by binding to two receptors, TNFR1 and TNER2. TNFα is a regulator of immune responses for cell signaling and can mediate cell survival and cell death inducing signaling. There are two receptors for TNF signaling, TNFR1 and TNER2. sTNFα-TNFR1 signaling promotes immune cell activation and drives acute and chronic inflammation. Membrane TNFα-TNFR2 signaling promotes inflammation resolution, immune cell regulatory functions and cell survival.

The extracellular region of both TNFR1 and TNER2 have four homologous cysteine-rich domains, but they have structurally different intracellular regions. TNFR1 has a protein binding region called a death domain which allows homo- and hetero-typic interactions with other death domain-containing proteins. In contrast, TNFR2 has a TNF Receptor Associated Factor (TRAF) that interacts with TRAF family of signaling adaptors. The distinct profiles and differences of the two TNF receptors influence the cellular activity and physiological roles. TNFR1 can activate NF-κB and MAPK signaling, and cell death, and is important to regulate inflammatory diseases. TNFR2 is highly regulated and restricted to specific cell types such as endothelial cells and T cells. TNFR1 primarily promotes tissue degeneration and inflammation, while TNFR2 typically mediates local homeostatic effects such as tissue regeneration and cell survival (D. Fresegna et al., Cells, 2020, 9, 2290).

Binding of TNFα to TNFR1 can activate NF-κB for mediating transcription of various proteins involved in cell survival and proliferation, anti-apoptotic factors, and inflammatory response. Further, the MAPK pathway can also be activated by binding of TNFα to TNFR1, which is involved in cell differentiation and proliferation. When TNFα binds to TNFR1, it triggers receptor trimerization, leading to the assembly of a TNFR1-associated signaling complex. This complex recruits the receptor interacting protein 1 (RIP1) and TNF receptor associated death domain (TRADD) to the TNFR1 through the receptive death domains. TRADD then recruits adaptor proteins TRAF2 and TRAF5, which can engage the E3 ligases cellular inhibitors of apoptosis (c-IAP1, c-IAP2). c-IAP1/2 are important for TNFR1 complex signaling, which can eventually lead to the recruitment of the signaling kinase complexes of kinase IKKα and IKKβ, which are inhibitors of kappa B kinase 1 and 2, and transforming growth factor beta-activated kinase 1 (TAK1) leading to activation of NF-κB and MAPK signaling. Activation of these signaling pathways can result in gene activation and expression of pro-inflammatory cytokines and pro-survival proteins.

TNF signaling is regulated by post-translational ubiquitination, which is essential for my biological processes. Post-translational modifications of TNFR1-associated signaling complexes can result in a change from inflammatory gene signaling to cell death. This switch is dependent upon the ubiquitination status of RIP1, which is formed as part of the TNFR1-associated signaling complex from TNFα binding.

TNF has long been known to be a key regulator of the inflammatory response, and recently has been known to be involved in brain functioning (D. Fresegna et al., Cells, 2020, 9, 2290). As a regulator of the inflammatory response, TNF can regulate many aspects of T cell biology including, but not limited to proliferation, survival, priming, and apoptotic fate. TNF is also known to play a role in conclusion of lymphocyte response, by the ability to promote cell death in both CD4 and CD8P T cells, through TNFR1. Specific inflammatory conditions can also result in TNFR2 promoting or supporting T cell apoptosis.

In normal adult brains, TNF is expressed at low levels, and it is believed that the expression could be influenced by presence or absence of cytokines that can cross the blood brain barrier. TNFRs in the brain are expressed by glia and neurons cells, and have regulatory functions, including, but not limited to homeostatic synaptic plasticity, astrocyte-mediated synaptic transmission, and neurogenesis. These functions are useful for regulating learning and memory functions amongst other roles.

TNF is recognized to be physiological gliotransmitter for the communication between neurons and glial cells, which in turn affects synaptic regulation. Glial TNF is important for maintenance of normal surface expression of AMPA receptors, and for homeostatic synaptic scaling, which allows for adjustment of the strength of all synapses on a neuron.

Prior Art Small Molecules Inhibitors

Diseases treated with biologic TNFα inhibitors include, but are not limited to rheumatoid arthritis, inflammatory bowel disease, psoriatic arthritis, psoriasis, and ankylosing spondylitis. Patients with neuroinflammatory conditions and degenerative disease, including, but not limited to Alzheimer's disease, Parkinson's disease, multiple sclerosis, treatment resistant depression, and tinnitus, may benefit from treatment with oral CNS sTNFα inhibitors by disrupting the sTNFα signaling and sparing the mTNFα signaling. Previous reports have also indicated targeting TNFR2 for treating Alzheimer's Disease (N. Orti-Casañ et al., Front Neurosci. 2019; 13:49).

Small molecules have been developed for treatment of rheumatoid arthritis as some patients have responded poorly to monotherapy of approved anti-TNFα drugs (J. D. Dietrich et al., J. Med. Chem. 2021, 64, 417-429). Anti-TNFα drugs have also been expanded for use in other chronic autoimmune diseases, including, but not limited to, Crohn's disease, psoriasis, psoriatic arthritis, ulcerative colitis, inflammatory bowel disease, ankylosing spondylitis, and juvenile rheumatoid arthritis. Small molecules have been developed as an alternative to anti-TNFα biologics since the long-term clinical response rate is generally around 60-70% for rheumatoid arthritis.

Previous research has also indicated that TNFα inhibitors can be therapeutic for treatment of multiple sclerosis (D. Fresegna et al., Cells, 2020, 9, 2290). There has been evidence of the involvement of TNF in various pathological issues of multiple sclerosis, including immune dysregulation, demylination, synaptopathy, and neuroinflammation. TNFα inhibitors have the potential for treatment of multiple sclerosis, other potential chronic neurodegenerative diseases of the central nervous system.

More than 50 million Americans struggle with tinnitus, which is the hearing of a sound with no external source. It has been shown that TNFα is necessary for noise-induced neuroinflammation and synaptic imbalance (W. Wang et al., PLOS Biol. 2019 Jun. 18; 17 (6): e3000307; A. Shulman et al., Curr Top Behav Neurosci. 2021; 51:161-174). It is believed that certain inhibitors of TNFα have activities for treating tinnitus.

Recent reports also indicate that TNFα inhibitors can be used alone or in combination for treatment with inflammatory bowel disease (S. F. Fowler Braga and K. J. Clark, US Pharm. 2021; 46 (5): 34-37). TNFα is a mediator of the abnormal immune response of inflammatory bowel disease, which leads to disruption of the intestinal mucosa and epithelial wall barrier. The anti-TNF agents can block TNF-mediated activation of the proinflammatory pathways to result in decreased immune-mediated inflammation.

Small molecule sTNF α inhibitors are active in pharmacology models of sTNFα/TNFR1 signaling in addition to demonstrating efficacy in a model of collagen antibody induced arthritis. There is currently limited data in the public domain for small molecule sTNF α inhibitors. Some TNFα inhibitors include, but are not limited to XPro1595, Etanercept, Infliximab, Adalimumab, Certolizumab pegol, Golimumamb, and other inhibitors described in "TNF-α: The Shape of Small Molecules to Come?" (A. Domling and X. Li, Drug Discov Today 2022 January; 27 (1): 3-7) and "Small Molecules that Inhibit TNF Signalling by Stabilising an Asymmetric Form of the Trimer (J. O'Connell et al., Nature Communications 10, 5795 (2019)). Additional small molecule inhibitors of TNFα include, but are not limited to the inhibitors described in "Biologic-like In Vivo Efficacy with Small Molecule Inhibitors of TNFα Identified Using Scaffold Hopping and Structure-Based Drug Design Approaches" (H-Y Xiao et al., J. Med. Chem. 2020, 15050-15071), "Development of Orally Efficacious Allosteric Inhibitors of TNFα via Fragment-Based Drug Design" (J. D. Dietrich et al., J. Med. Chem. 2021, 64, 417-429), and "Small-Molecule Inhibition of TNF-α" (M. M. He et al., Science, 310 (2015), 1022-1025).

Small molecule sTNFα inhibitors have potential as a valuable therapy for patients currently treated with biologic TNFα inhibitors which affect mTNFα with the ability to fine tune oral dosing requirements and avoid anti-drug antibody responses, thereby improving short and long responses (A. Dömling and X. Li, Drug Discov Today 2022 January; 27 (1): 3-7).

Novel Compounds Inhibiting TNFα

In one aspect, provided herein are TNFα inhibitory compounds.

One embodiment provides a compound of Formula (I), or pharmaceutically acceptable salt, solvate, deuteroisotope, or N-oxide thereof:

(I)

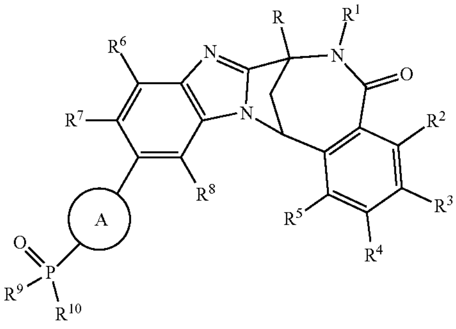

wherein,

Ring A is selected from

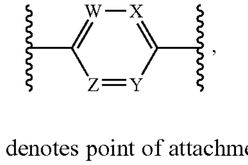

wherein the * denotes point of attachment to phosphorous, or an optionally substituted heteroarylene selected from pyrazolene, imidazoline, oxazolene, or thiazolene;

W is N or C—$R^{11}$;

X is N or C—$R^{12}$;

Y is N or C—$R^{13}$;

Z is N or C—$R^{14}$;

R is selected from H, D, or optionally substituted C1-C6 alkyl;

$R^1$ is selected from H, optionally substituted C1-C6 alkyl, optionally substituted C3-C6 cycloalkyl, or optionally substituted C4-C7 cycloalkylalkyl;

$R^2$ is selected from H, D, Cl, F, optionally substituted C1-C6 alkyl, or optionally substituted C3-C6 cycloalkyl;

$R^3$, $R^4$, and $R^5$ are selected from H, D, Cl, or F; with the provision that at least one of $R^2$, $R^3$, $R^4$, or $R^5$ is not H or D;

$R^6$ is selected from H, D, halogen, or optionally substituted C1-C6 alkyl;

$R^7$ is selected from H, D, or halogen;

$R^8$ is selected from H, D, or halogen;

$R^9$ and $R^{10}$ are independently optionally substituted C1-C6 alkyl; or $R^9$ and $R^{10}$ join to form optionally substituted phosphorus-containing 3- to 8-membered ring; and $R^{11}$, $R^{12}$, $R^{13}$, and $R^{14}$ are independently selected from H, D, halogen, —CN, —$NH_2$, optionally substituted C1-C3 alkyl, optionally substituted C1-C3 alkoxy, or —NH (optionally substituted C1-C3 alkyl).

Another embodiment provides the compound of Formula (I), or pharmaceutically acceptable salt, solvate, deuteroisotope, or N-oxide thereof, wherein R is H or D.

Another embodiment provides the compound of Formula (I), or pharmaceutically acceptable salt, solvate, deuteroisotope, or N-oxide thereof, wherein R is optionally substituted C1-C6 alkyl.

Another embodiment provides the compound of Formula (I), or pharmaceutically acceptable salt, solvate, deuteroisotope, or N-oxide thereof, wherein R is optionally substituted C1 alkyl.

Another embodiment provides the compound of Formula (I), or pharmaceutically acceptable salt, solvate, deuteroisotope, or N-oxide thereof, wherein R is $CH_3$.

One embodiment provides a compound of Formula (I), or pharmaceutically acceptable salt, solvate, deuteroisotope, or N-oxide thereof, having the structure of Formula (Ia)

(Ia)

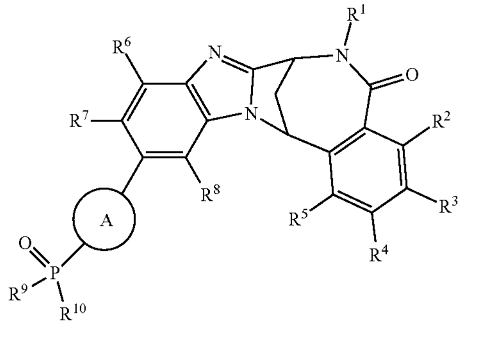

wherein,

Ring A is selected from

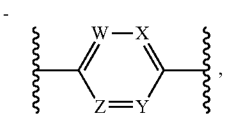

wherein the * denotes point of attachment to phosphorous, or an optionally substituted heteroarylene selected from pyrazolene, imidazoline, oxazolene, or thiazolene;

W is N or C—$R^{11}$;

X is N or C—$R^{12}$;

Y is N or C—$R^{13}$,

Z is N or C—$R^{14}$, $R^1$ is selected from H, optionally substituted C1-C6 alkyl, optionally substituted C3-C6 cycloalkyl, or optionally substituted C4-C7 cycloalkylalkyl;

$R^2$ is selected from H, D, Cl, F, optionally substituted C1-C6 alkyl, or optionally substituted C3-C6 cycloalkyl;

$R^3$, $R^4$, and $R^5$ are selected from H, D, Cl, or F; with the provision that at least one of $R^2$, $R^3$, $R^4$, or $R^5$ is not H or D;

$R^6$ is selected from H, D, halogen, or optionally substituted C1-C6 alkyl;

$R^7$ is selected from H, D, or halogen;

$R^8$ is selected from H, D, or halogen;

$R^9$ and $R^{10}$ are independently optionally substituted C1-C6 alkyl; or $R^9$ and $R^{10}$ join to form optionally substituted phosphorus-containing 3- to 8-membered ring; and $R^{11}$, $R^{12}$, $R^{13}$, and $R^{14}$ are independently selected from H, D, halogen, —CN, —$NH_2$, optionally substituted C1-C3 alkyl, optionally substituted C1-C3 alkoxy, or —NH (optionally substituted C1-C3 alkyl).

Another embodiment provides the compound of Formula (I) or (Ia), or pharmaceutically acceptable salt, solvate, deuteroisotope, or N-oxide thereof, wherein ring A is selected from

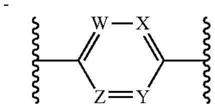, wherein the * denotes point of attachment to L. Another embodiment provides the compound, or pharmaceutically acceptable salt, solvate, deuteroisotope, or N-oxide thereof, wherein W is N. Another embodiment provides the compound, or pharmaceutically acceptable salt, solvate, deuteroisotope, or N-oxide thereof, wherein W is C—$R^{11}$. Another embodiment provides the compound, or pharmaceutically acceptable salt, solvate, deuteroisotope, or N-oxide thereof, wherein X is N. Another embodiment provides the compound, or pharmaceutically acceptable salt, solvate, deuteroisotope, or N-oxide thereof, wherein X is C—$R^{12}$. Another embodiment provides the compound, or pharmaceutically acceptable salt, solvate, deuteroisotope, or N-oxide thereof, wherein Y is N. Another embodiment provides the compound, or pharmaceutically acceptable salt, solvate, deuteroisotope, or N-oxide thereof, wherein Y is C—$R^{13}$. Another embodiment provides the compound, or pharmaceutically acceptable salt, solvate, deuteroisotope, or N-oxide thereof, wherein Z is N. Another embodiment provides the compound, or pharmaceutically acceptable salt, solvate, deuteroisotope, or N-oxide thereof, wherein Z is C—$R^{14}$.

Another embodiment provides the compound of Formula (I) or (Ia), or pharmaceutically acceptable salt, solvate, deuteroisotope, or N-oxide thereof, wherein each $R^{11}$, $R^{12}$, $R^{13}$, and $R^{14}$ is independently selected from H, D, or halogen.

Another embodiment provides the compound of Formula (I) or (Ia), or pharmaceutically acceptable salt, solvate, deuteroisotope, or N-oxide thereof, wherein $R^1$ is H. Another embodiment provides the compound of Formula (I)

or (Ia), or pharmaceutically acceptable salt, solvate, deuteroisotope, or N-oxide thereof, wherein $R^1$ is optionally substituted C1-C6 alkyl. Another embodiment provides the compound, or pharmaceutically acceptable salt, solvate, deuteroisotope, or N-oxide thereof, wherein $R^1$ is optionally substituted C1 alkyl.

Another embodiment provides the compound of Formula (I) or (Ia), or pharmaceutically acceptable salt, solvate, deuteroisotope, or N-oxide thereof, wherein $R^9$ and $R^{10}$ are each independently methyl, ethyl, n-propyl, iso-propyl, n-butyl, or iso-butyl. Another embodiment provides the compound of Formula (I) or (Ia), wherein $R^9$ and $R^{10}$ are each methyl. Another embodiment provides the compound, or pharmaceutically acceptable salt, solvate, deuteroisotope, or N-oxide thereof, wherein $R^9$ and $R^{10}$ are each ethyl.

Another embodiment provides the compound of Formula (I) or (Ia), or pharmaceutically acceptable salt, solvate, deuteroisotope, or N-oxide thereof, wherein $R^9$ and $R^{10}$ join to form an optionally substituted phosphorus-containing 3- to 8-membered heterocyclyl. Another embodiment provides the compound, or pharmaceutically acceptable salt, solvate, deuteroisotope, or N-oxide thereof, wherein $R^9$ and $R^{10}$ join to form an optionally substituted phosphorus-containing 4- to 6-membered heterocyclyl. Another embodiment provides the compound, or pharmaceutically acceptable salt, solvate, deuteroisotope, or N-oxide thereof, wherein $R^9$ and $R^{10}$ join to form an optionally substituted phosphorus-containing 4-membered heterocyclyl. Another embodiment provides the compound, or pharmaceutically acceptable salt, solvate, deuteroisotope, or N-oxide thereof, wherein $R^9$ and $R^{10}$ join to form an optionally substituted phosphorus-containing 5-membered heterocyclyl. Another embodiment provides the compound, or pharmaceutically acceptable salt, solvate, deuteroisotope, or N-oxide thereof, wherein $R^9$ and $R^{10}$ join to form an optionally substituted phosphorus-containing 6-membered heterocyclyl. Another embodiment provides the compound, or pharmaceutically acceptable salt, solvate, deuteroisotope, or N-oxide thereof, wherein $R^9$ and $R^{10}$ taken together with the phosphorus atom to which they are attached join to form a ring selected from:

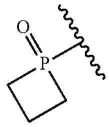, 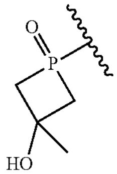, 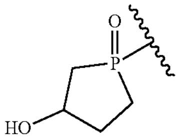,

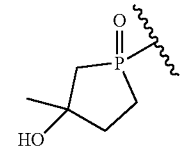, or 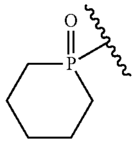,

Another embodiment provides the compound, or pharmaceutically acceptable salt, solvate, deuteroisotope, or N-oxide thereof, wherein $R^9$ and $R^{10}$ taken together with the phosphorus atom to which they are attached to join to form a ring selected from:

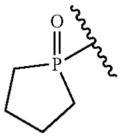, 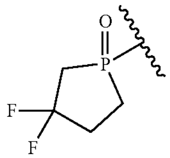, 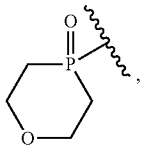,

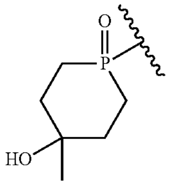, or 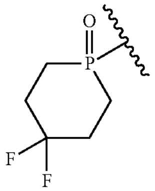.

Another embodiment provides the compound of Formula (I) or (Ia), or pharmaceutically acceptable salt, solvate, deuteroisotope, or N-oxide thereof, wherein $R^6$ is H or D. Another embodiment provides the compound of Formula (I) or (Ia), or pharmaceutically acceptable salt, solvate, deuteroisotope, or N-oxide thereof, wherein $R^6$ is halogen.

Another embodiment provides the compound of Formula (I) or (Ia), or pharmaceutically acceptable salt, solvate, deuteroisotope, or N-oxide thereof, wherein $R^7$ is H or D. Another embodiment provides the compound of Formula (I) or (Ia), or pharmaceutically acceptable salt, solvate, deuteroisotope, or N-oxide thereof, wherein $R^7$ is halogen.

Another embodiment provides the compound of Formula (I) or (Ia), or pharmaceutically acceptable salt, solvate, deuteroisotope, or N-oxide thereof, wherein ring A is an optionally substituted heteroarylene.

Another embodiment provides the compound of Formula (I) or (Ia), or pharmaceutically acceptable salt, solvate, deuteroisotope, or N-oxide thereof, wherein $R^8$ is H or D. Another embodiment provides the compound of Formula (I) or (Ia), or pharmaceutically acceptable salt, solvate, deuteroisotope, or N-oxide thereof, wherein $R^8$ is F. Another embodiment provides the compound of Formula (I) or (Ia), or pharmaceutically acceptable salt, solvate, deuteroisotope, or N-oxide thereof, wherein $R^8$ is Cl.

Another embodiment provides the compound of Formula (I) or (Ia), or pharmaceutically acceptable salt, solvate, deuteroisotope, or N-oxide thereof, wherein $R^5$ is Cl. Another embodiment provides the compound of Formula (I) or (Ia), or pharmaceutically acceptable salt, solvate, deuteroisotope, or N-oxide thereof, wherein $R^5$ is F. Another embodiment provides the compound of Formula (I) or (Ia), or pharmaceutically acceptable salt, solvate, deuteroisotope, or N-oxide thereof, wherein $R^5$ is Br.

Another embodiment provides the compound of Formula (I) or (Ia), or pharmaceutically acceptable salt, solvate, deuteroisotope, or N-oxide thereof, wherein $R^2$, $R^3$, and $R^4$ are H or D. Another embodiment provides the compound of Formula (I) or (Ia), or pharmaceutically acceptable salt, solvate, deuteroisotope, or N-oxide thereof, wherein $R^2$ is methyl, and $R^5$ is Cl or F. Another embodiment provides the compound of Formula (I) or (Ia), or pharmaceutically acceptable salt, solvate, deuteroisotope, or N-oxide thereof, wherein $R^4$ is Cl or F. Another embodiment provides the compound of Formula (I) or (Ia), or pharmaceutically acceptable salt, solvate, deuteroisotope, or N-oxide thereof, wherein $R^4$ is Cl or F, and $R^5$ is Cl or F. Another embodiment provides the compound of Formula (I) or (Ia), or pharmaceutically acceptable salt, solvate, deuteroisotope, or N-oxide thereof, wherein $R^2$ and $R^3$ are H or D.

One embodiment provides a TNFα inhibitory compound, or a pharmaceutically acceptable salt, solvate, deuteroisotope, or N-oxide thereof, having a structure presented in Table 1.

TABLE 1

| Synthetic Chemistry Example | Compound Structure | Compound Name |
|---|---|---|
| 1 | 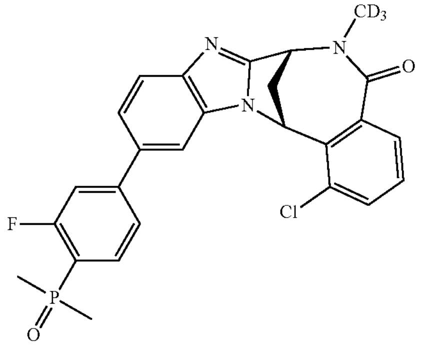 [SMILES: [2H]C([2H])([2H])N1C(=O)c2cccc(Cl)c2[C@H]2C[C@@H]1c1nc3ccc(-c4ccc(P(C)(C)=O)c(F)c4)cc3n12] | (7R,14R)-1-chloro-11-(4-(dimethylphosphoryl)-3-fluorophenyl)-6-(methyl-d3)-6,7-dihydro-7,14-methanobenzo[f]benzo[4,5]imidazo[1,2-a][1,4]diazocin-5(14H)-one |

TABLE 1-continued

| Synthetic Chemistry Example | Compound Structure | Compound Name |
|---|---|---|
| 2 | 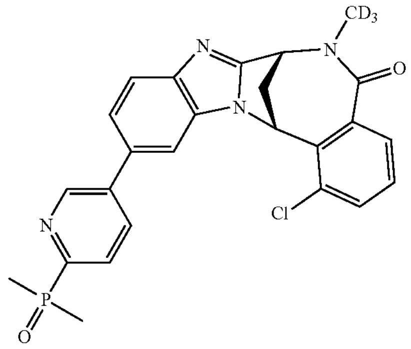 [SMILES: [2H]C([2H])([2H])N1C(=O)c2cccc(Cl)c2[C@H]2C[C@@H]1c1nc3ccc(-c4ccc(P(C)(C)=O)nc4)cc3n12] | (7R,14R)-1-chloro-11-(6-(dimethylphosphoryl)pyridin-3-yl)-6-(methyl-d3)-6,7-dihydro-7,14-methanobenzo[f]benzo[4,5]imidazo[1,2-a][1,4]diazocin-5(14H)-one |
| 3 | 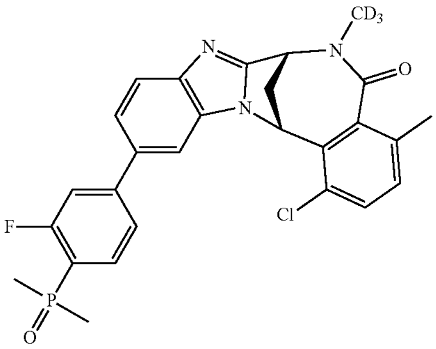 [SMILES: [2H]C([2H])([2H])N1C(=O)c2c(C)ccc(Cl)c2[C@H]2C[C@@H]1c1nc3ccc(-c4ccc(P(C)(C)=O)c(F)c4)cc3n12] | (7R,14R)-1-chloro-11-(4-(dimethylphosphoryl)-3-fluorophenyl)-4-methyl-6-(methyl-d3)-6,7-dihydro-7,14-methanobenzo[f]benzo[4,5]imidazo[1,2-a][1,4]diazocin-5(14H)-one |
| 4 | 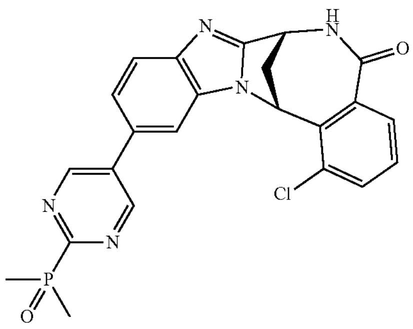 [SMILES: CP(C)(=O)c1ncc(-c2ccc3nc4n(c3c2)[C@@H]2C[C@H]4NC(=O)c3cccc(Cl)c32)cn1] | (7R,14R)-1-chloro-11-(2-(dimethylphosphoryl)pyrimidin-5-yl)-6,7-dihydro-7,14-methanobenzo[f]benzo[4,5]imidazo[1,2-a][1,4]diazocin-5(14H)-one |
| 5 | 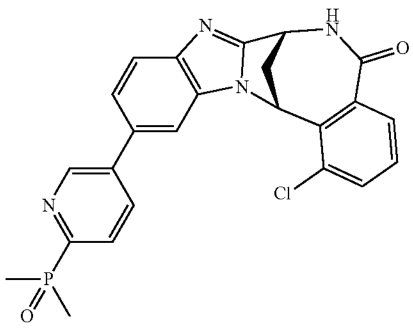 [SMILES: CP(C)(=O)c1ccc(-c2ccc3nc4n(c3c2)[C@@H]2C[C@H]4NC(=O)c3cccc(Cl)c32)cn1] | (7R,14R)-1-chloro-11-(6-(dimethylphosphoryl)pyridin-3-yl)-6,7-dihydro-7,14-methanobenzo[f]benzo[4,5]imidazo[1,2-a][1,4]diazocin-5(14H)-one |

TABLE 1-continued

| Synthetic Chemistry Example | Compound Structure | Compound Name |
|---|---|---|
| 6 | 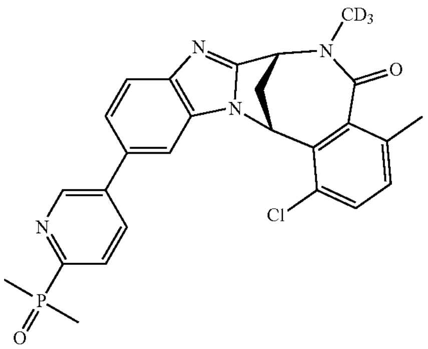 | (7R,14R)-1-chloro-11-(6-(dimethylphosphoryl)pyridin-3-yl)-4-methyl-6-(methyl-d3)-6,7-dihydro-7,14-methanobenzo[f]benzo[4,5]imidazo[1,2-a][1,4]diazocin-5(14H)-one |
| 7 | 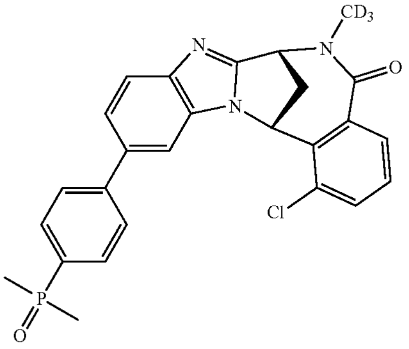 [SMILES: [2H]C([2H])([2H])N1C(=O)c2cccc(Cl)c2[C@H]2C[C@@H]1c1nc3ccc(-c4ccc(P(C)(C)=O)cc4)cc3n12] | (7R,14R)-1-chloro-11-(4-(dimethylphosphoryl)phenyl)-6-(methyl-d3)-6,7-dihydro-7,14-methanobenzo[f]benzo[4,5]imidazo[1,2-a][1,4]diazocin-5(14H)-one |
| 8 | 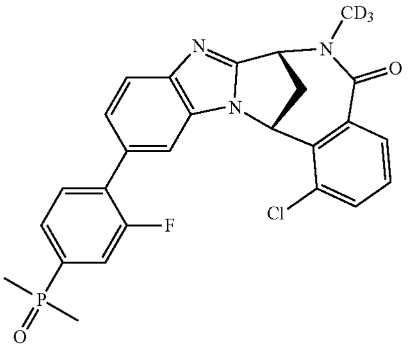 [SMILES: [2H]C([2H])([2H])N1C(=O)c2cccc(Cl)c2[C@H]2C[C@@H]1c1nc3ccc(-c4ccc(P(C)(C)=O)cc4F)cc3n12] | (7R,14R)-1-chloro-11-(4-(dimethylphosphoryl)-2-fluorophenyl)-6-(methyl-d3)-6,7-dihydro-7,14-methanobenzo[f]benzo[4,5]imidazo[1,2-a][1,4]diazocin-5(14H)-one |
| 9 | 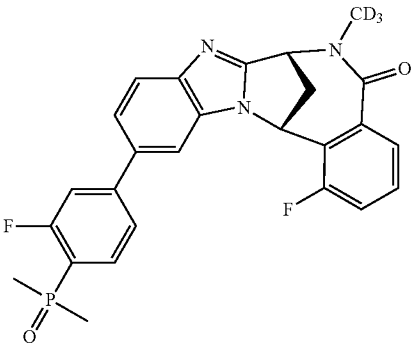 [SMILES: [2H]C([2H])([2H])N1C(=O)c2cccc(F)c2[C@H]2C[C@@H]1c1nc3ccc(-c4ccc(P(C)(C)=O)c(F)c4)cc3n12] | (7R,14R)-11-(4-(dimethylphosphoryl)-3-fluorophenyl)-1-fluoro-6-(methyl-d3)-6,7-dihydro-7,14-methanobenzo[f]benzo[4,5]imidazo[1,2-a][1,4]diazocin-5(14H)-one |

TABLE 1-continued

| Synthetic Chemistry Example | Compound Structure | Compound Name |
| --- | --- | --- |
| 10 | 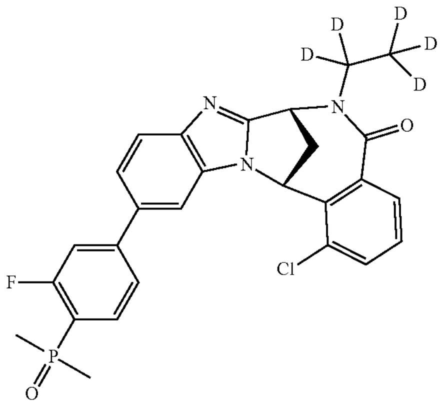 [SMILES: [2H]C([2H])([2H])C([2H])([2H])N1C(=O)c2cccc(Cl)c2[C@H]2C[C@@H]1c1nc3ccc(-c4ccc(P(C)(C)=O)c(F)c4)cc3n12] | (7R,14R)-1-chloro-11-(4-(dimethylphosphoryl)-3-fluorophenyl)-6-(ethyl-d5)-6,7-dihydro-7,14-methanobenzo[f]benzo[4,5]imidazo[1,2-a][1,4]diazocin-5(14H)-one |
| 11 | 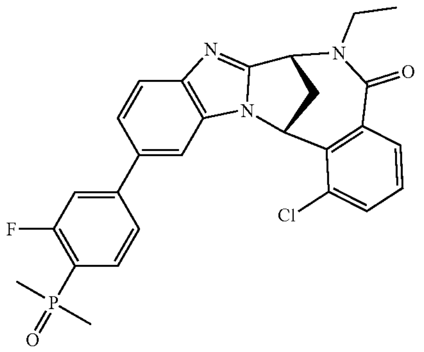 [SMILES: CCN1C(=O)c2cccc(Cl)c2[C@H]2C[C@@H]1c1nc3ccc(-c4ccc(P(C)(C)=O)c(F)c4)cc3n12] | (7R,14R)-1-chloro-11-(4-(dimethylphosphoryl)-3-fluorophenyl)-6-ethyl-6,7-dihydro-7,14-methanobenzo[f]benzo[4,5]imidazo[1,2-a][1,4]diazocin-5(14H)-one |
| 12 | 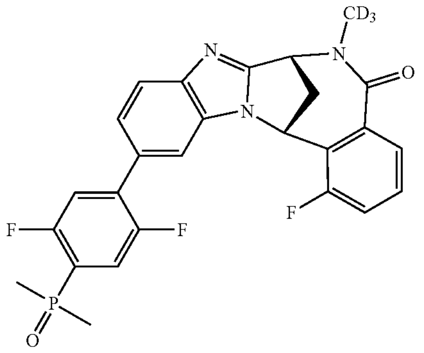 [SMILES: [2H]C([2H])([2H])N1C(=O)c2cccc(F)c2[C@H]2C[C@@H]1c1nc3ccc(-c4cc(F)c(P(C)(C)=O)cc4F)cc3n12] | (7R,14R)-11-(4-(dimethylphosphoryl)-2,5-difluorophenyl)-1-fluoro-6-(methyl-d3)-6,7-dihydro-7,14-methanobenzo[f]benzo[4,5]imidazo[1,2-a][1,4]diazocin-5(14H)-one |
| 13 | 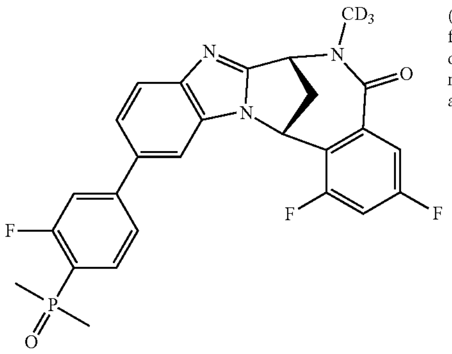 | (7R,14R)-11-(4-(dimethylphosphoryl)-3-fluorophenyl)-1,3-difluoro-6-(methyl-d3)-6,7-dihydro-7,14-methanobenzo[f]benzo[4,5]imidazo[1,2-a][1,4]diazocin-5(14H)-one |

TABLE 1-continued

| Synthetic Chemistry Example | Compound Structure | Compound Name |
|---|---|---|
| 14 | 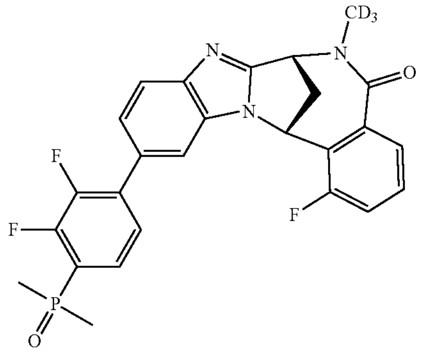 [SMILES: [2H]C([2H])([2H])N1C(=O)c2cccc(F)c2[C@H]2C[C@@H]1c1nc3ccc(-c4ccc(P(C)(C)=O)c(F)c4F)cc3n12] | (7R,14R)-11-(4-(dimethylphosphoryl)-2,3-difluorophenyl)-1-fluoro-6-(methyl-d3)-6,7-dihydro-7,14-methanobenzo[f]benzo[4,5]imidazo[1,2-a][1,4]diazocin-5(14H)-one |
| 15 | 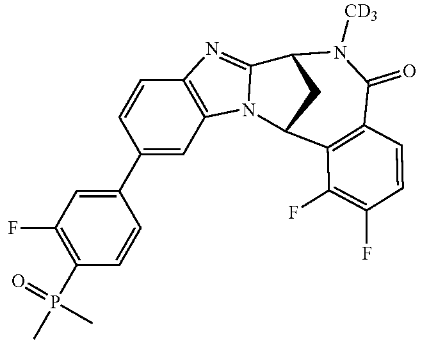 [SMILES: [2H]C([2H])([2H])N1C(=O)c2ccc(F)c(F)c2[C@H]2C[C@@H]1c1nc3ccc(-c4ccc(P(C)(C)=O)c(F)c4)cc3n12] | (7R,14R)-11-(4-(dimethylphosphoryl)-3-fluorophenyl)-1,2-difluoro-6-(methyl-d3)-6,7-dihydro-7,14-methanobenzo[f]benzo[4,5]imidazo[1,2-a][1,4]diazocin-5(14H)-one |
| 16 | 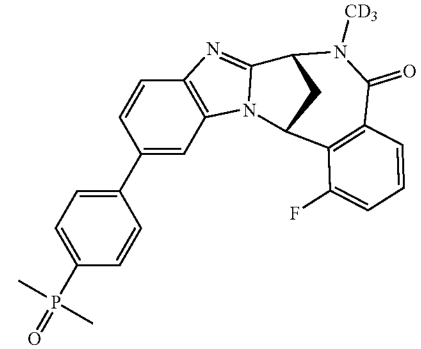 [SMILES: [2H]C([2H])([2H])N1C(=O)c2cccc(F)c2[C@H]2C[C@@H]1c1nc3ccc(-c4ccc(P(C)(C)=O)cc4)cc3n12] | (7R,14R)-11-(4-(dimethylphosphoryl)phenyl)-1-fluoro-6-(methyl-d3)-6,7-dihydro-7,14-methanobenzo[f]benzo[4,5]imidazo[1,2-a][1,4]diazocin-5(14H)-one |
| 17 | 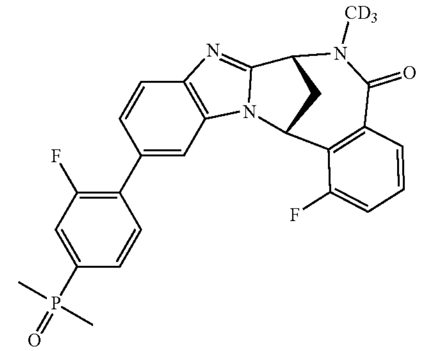 [SMILES: [2H]C([2H])([2H])N1C(=O)c2cccc(F)c2[C@H]2C[C@@H]1c1nc3ccc(-c4ccc(P(C)(C)=O)cc4F)cc3n12] | (7R,14R)-11-(4-(dimethylphosphoryl)-2-fluorophenyl)-1-fluoro-6-(methyl-d3)-6,7-dihydro-7,14-methanobenzo[f]benzo[4,5]imidazo[1,2-a][1,4]diazocin-5(14H)-one |

TABLE 1-continued

| Synthetic Chemistry Example | Compound Structure | Compound Name |
|---|---|---|
| 18 | 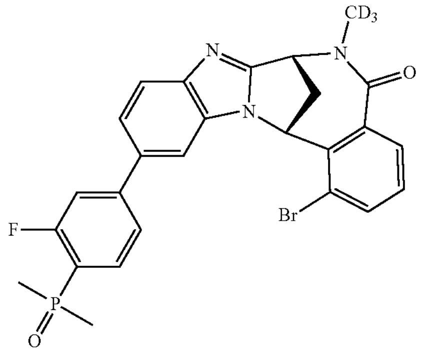 [SMILES: [2H]C([2H])([2H])N1C(=O)c2cccc(Br)c2[C@H]2C[C@@H]1c1nc3ccc(-c4ccc(P(C)(C)=O)c(F)c4)cc3n12] | (7R,14R)-1-bromo-11-(4-(dimethylphosphoryl)-3-fluorophenyl)-6-(methyl-d3)-6,7-dihydro-7,14-methanobenzo[f]benzo[4,5]imidazo[1,2-a][1,4]diazocin-5(14H)-one |
| 19 | 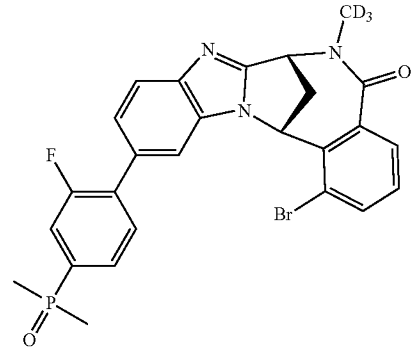 [SMILES: [2H]C([2H])([2H])N1C(=O)c2cccc(Br)c2[C@H]2C[C@@H]1c1nc3ccc(-c4ccc(P(C)(C)=O)cc4F)cc3n12] | (7R,14R)-1-bromo-11-(4-(dimethylphosphoryl)-2-fluorophenyl)-6-(methyl-d3)-6,7-dihydro-7,14-methanobenzo[f]benzo[4,5]imidazo[1,2-a][1,4]diazocin-5(14H)-one |
| 20 | 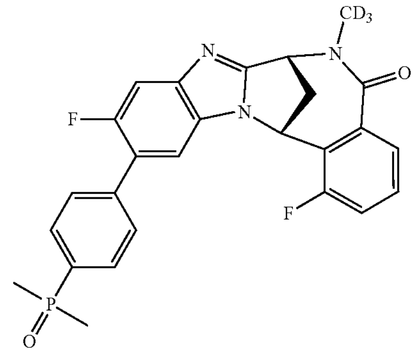 [SMILES: [2H]C([2H])([2H])N1C(=O)c2cccc(F)c2[C@H]2C[C@@H]1c1nc3cc(F)c(-c4ccc(P(C)(C)=O)cc4)cc3n12] | (7R,14R)-11-(4-(dimethylphosphoryl)phenyl)-1,10-difluoro-6-(methyl-d3)-6,7-dihydro-7,14-methanobenzo[f]benzo[4,5]imidazo[1,2-a][1,4]diazocin-5(14H)-one |
| 21 | 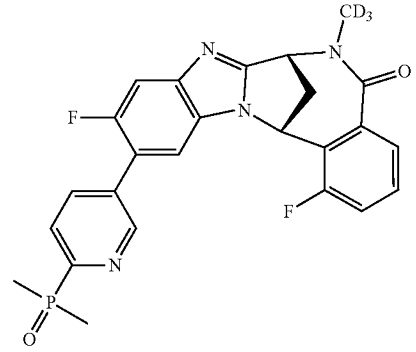 [SMILES: [2H]C([2H])([2H])N1C(=O)c2cccc(F)c2[C@H]2C[C@@H]1c1nc3cc(F)c(-c4ccc(P(C)(C)=O)nc4)cc3n12] | (7R,14R)-11-(6-(dimethylphosphoryl)pyridin-3-yl)-1,10-difluoro-6-(methyl-d3)-6,7-dihydro-7,14-methanobenzo[f]benzo[4,5]imidazo[1,2-a][1,4]diazocin-5(14H)-one |

TABLE 1-continued

| Synthetic Chemistry Example | Compound Structure | Compound Name |
|---|---|---|
| 22 | 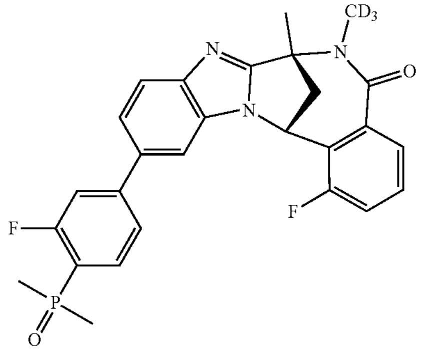 [SMILES: [2H]C([2H])([2H])N1C(=O)c2cccc(F)c2[C@H]2C[C@]1(C)c1nc3ccc(-c4ccc(P(C)(C)=O)c(F)c4)cc3n12] | (7R,14R)-11-(4-(dimethylphosphoryl)-3-fluorophenyl)-1-fluoro-7-methyl-6-(methyl-d3)-6,7-dihydro-7,14-methanobenzo[f]benzo[4,5]imidazo[1,2-a][1,4]diazocin-5(14H)-one |
| 23 | 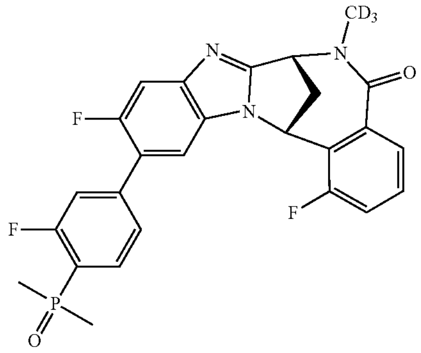 [SMILES: [2H]C([2H])([2H])N1C(=O)c2cccc(F)c2[C@H]2C[C@@H]1c1nc3cc(F)c(-c4ccc(P(C)(C)=O)c(F)c4)cc3n12] | (7R,14R)-11-(4-(dimethylphosphoryl)-3-fluorophenyl)-1,10-difluoro-6-(methyl-d3)-6,7-dihydro-7,14-methanobenzo[f]benzo[4,5]imidazo[1,2-a][1,4]diazocin-5(14H)-one |
| 24 | 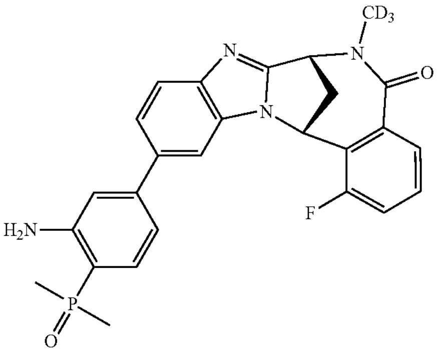 [SMILES: [2H]C([2H])([2H])N1C(=O)c2cccc(F)c2[C@H]2C[C@@H]1c1nc3ccc(-c4ccc(P(C)(C)=O)c(N)c4)cc3n12] | (7R,14R)-11-(3-amino-4-(dimethylphosphoryl)phenyl)-1-fluoro-6-(methyl-d3)-6,7-dihydro-7,14-methanobenzo[f]benzo[4,5]imidazo[1,2-a][1,4]diazocin-5(14H)-one |
| 25 | 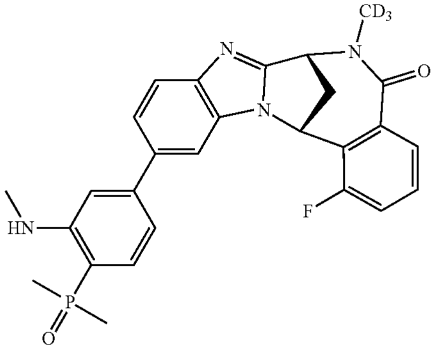 [SMILES: [2H]C([2H])([2H])N1C(=O)c2cccc(F)c2[C@H]2C[C@@H]1c1nc3ccc(-c4ccc(P(C)(C)=O)c(NC)c4)cc3n12] | (7R,14R)-11-(4-(dimethylphosphoryl)-3-(methylamino)phenyl)-1-fluoro-6-(methyl-d3)-6,7-dihydro-7,14-methanobenzo[f]benzo[4,5]imidazo[1,2-a][1,4]diazocin-5(14H)-one |

Another embodiment provides a TNFα inhibitory compound, or a pharmaceutically acceptable salt, solvate, deuteroisotope, or N-oxide thereof, having a structure presented in Table 2.

TABLE 2

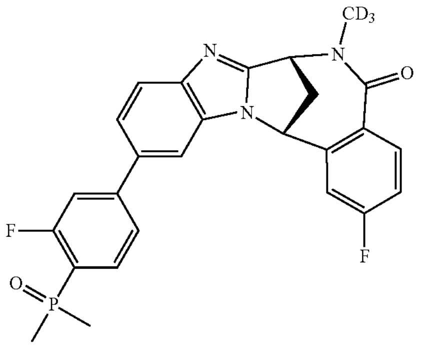 [SMILES: [2H]C([2H])([2H])N1C(=O)c2ccc(F)cc2[C@H]2C[C@@H]1c1nc3ccc(-c4ccc(P(C)(C)=O)c(F)c4)cc3n12]

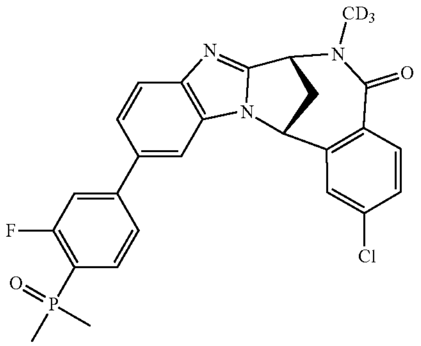 [SMILES: [2H]C([2H])([2H])N1C(=O)c2ccc(Cl)cc2[C@H]2C[C@@H]1c1nc3ccc(-c4ccc(P(C)(C)=O)c(F)c4)cc3n12]

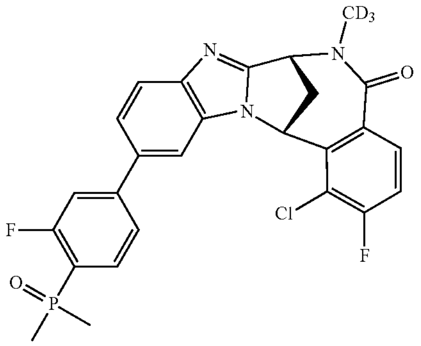

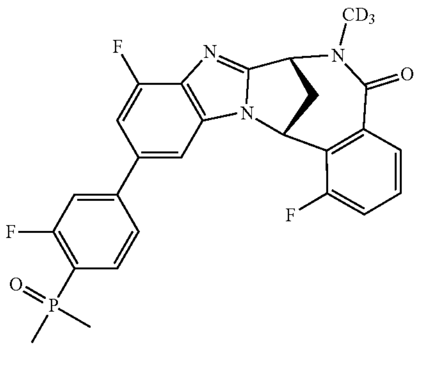 [SMILES: [2H]C([2H])([2H])N1C(=O)c2cccc(F)c2[C@H]2C[C@@H]1c1nc3c(F)cc(-c4ccc(P(C)(C)=O)c(F)c4)cc3n12]

TABLE 2-continued

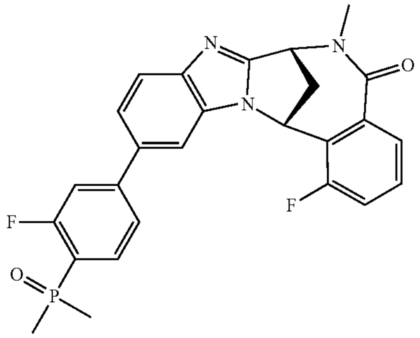 [SMILES: CN1C(=O)c2cccc(F)c2[C@H]2C[C@@H]1c1nc3ccc(-c4ccc(P(C)(C)=O)c(F)c4)cc3n12]

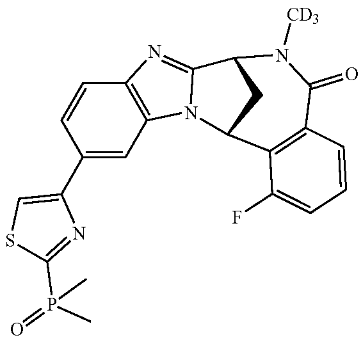 [SMILES: [2H]C([2H])([2H])N1C(=O)c2cccc(F)c2[C@H]2C[C@@H]1c1nc3ccc(-c4csc(P(C)(C)=O)n4)cc3n12]

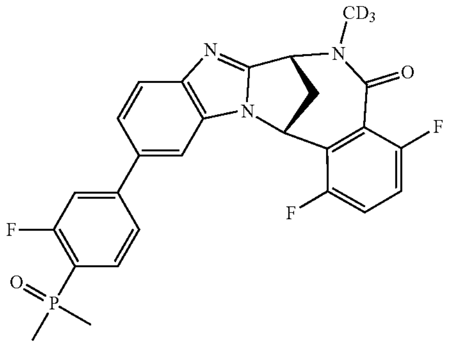 [SMILES: [2H]C([2H])([2H])N1C(=O)c2c(F)ccc(F)c2[C@H]2C[C@@H]1c1nc3ccc(-c4ccc(P(C)(C)=O)c(F)c4)cc3n12]

Preparation of Compounds

The compounds used in the synthetic chemistry reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, PA), Aldrich Chemical (Milwaukee, WI, including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, PA), Crescent Chemical Co. (Hauppauge, NY), Eastman Organic Chemicals, Eastman Kodak Company (Rochester, NY), Fisher Scientific Co. (Pittsburgh, PA), Fisons Chemicals (Leicestershire, UK), Frontier Scientific (Logan, UT), ICN Biomedicals, Inc. (Costa Mesa, CA), Key Organics (Cornwall, U.K.), Lancaster Synthesis (Windham, NH), Maybridge Chemical Co. Ltd. (Cornwall, U.K.), Parish Chemical Co. (Orem, UT), Pfaltz & Bauer, Inc. (Waterbury, CN), Polyorganix (Houston, TX), Pierce Chemical Co. (Rockford, IL), Riedel de Haen AG (Hanover, Germany), Spectrum Quality Product, Inc. (New Brunswick, NJ), TCI America (Portland, OR), Trans World Chemicals, Inc. (Rockville, MD), and Wako Chemicals USA, Inc. (Richmond, VA).

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are optionally identified through the indices of known chemicals prepared by the Chemical Abstract Service of the American Chemical Society, which are available in most public and university libraries, as well as through on-line databases (contact the American Chemical Society, Washington, D.C. for more details). Chemicals that are known but not commercially available in catalogs are optionally prepared by custom chemical synthesis houses, where many of the standard chemical supply houses (e.g., those listed above) provide custom synthesis services. A reference useful for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

Novel Synthesis Methods

Provided herein are novel methods of chemical synthesis of the pentacyclic benzimidazoles described herein. The prior art describes the synthesis 2,3-dihydro-1H-benzo[d]pyrrolo[1,2-a]imidazoles, see U.S. Pat. No. 10,202,405. The synthesis routes described herein utilize a protected phenol group, see compound 1-1, which has complementary reactivity to the aryl bromide group. The aryl bromide group is subjected to a palladium-catalyzed carbonylation and in situ ring formation to afford the pentacyclic benzimidazole. Removal of the phenolic protecting group and conversion to the triflate affords the functionality for the subsequent palladium-mediated Suzuki reaction. This improved synthetic route provides for a more convergent route to the desired final product and the reduced reactivity of the protected phenol allows for a wider variety of condition in the palladium-catalyzed carbonylation.

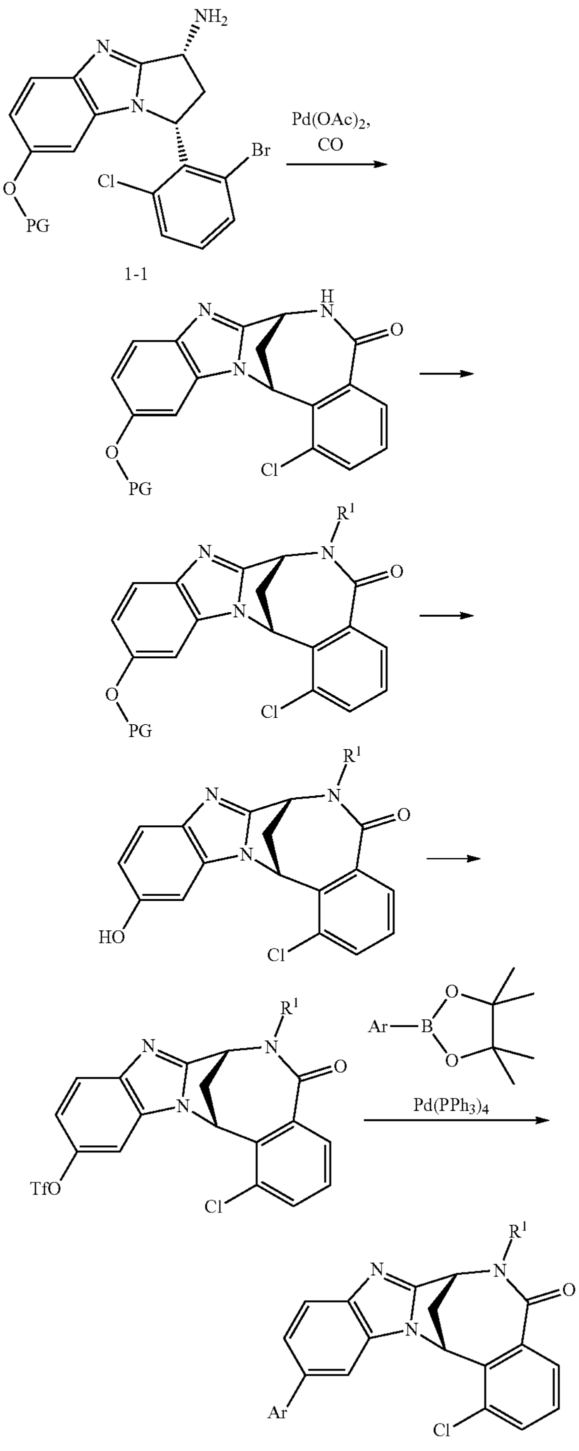

Provided herein in one embodiment is a compound of Formula (A):

(A)

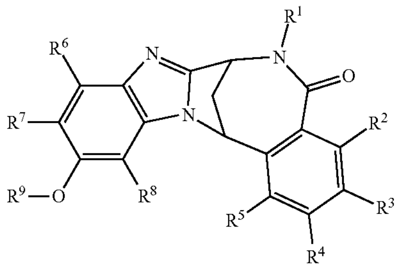

wherein, $R^1$ is selected from H, optionally substituted C1-C6 alkyl, optionally substituted C3-C6 cycloalkyl, or optionally substituted C4-C7 cycloalkylalkyl;

$R^2$ is selected from H, D, Cl, F, optionally substituted C1-C6 alkyl, or optionally substituted C3-C6 cycloalkyl;

$R^3$ and $R^4$, are selected from H, D, Cl, or F;

$R^5$ is selected from H, —OH, —O (optionally substituted C1-C6 alkyl), —O (optionally substituted C3-C6 cycloalkyl), optionally substituted C2-C6 alkynyl, or halogen;

$R^6$ is selected from H, D, halogen, or optionally substituted C1-C6 alkyl;

$R^7$ is selected from H, D, or halogen;

$R^8$ is selected from H, D, or halogen; and $R^9$ is selected from the group consisting of H, $—SO_2CF_3$, optionally substituted C1-C6 alkyl, optionally substituted aralkyl, optionally substituted C1-C6 alkenyl, —CO (optionally substituted C1-C6 alkyl), —CO (optionally substituted C6 aryl), $—CO_2$ (optionally substituted C1-C6 alkyl), $—CO_2$ (optionally substituted aralkyl), $—CO_2$ (optionally substituted C1-C6 alkenyl), $—CH_2CH_2Si(Ph)_2(t\text{-}C_4H_9)$, $—Si(C1\text{-}C6\ alkyl)_3$, $—CH_2O$ (optionally substituted C1-C6 alkyl), or 4- to 7-membered oxygen-containing heterocyclyl.

Another embodiment provides the compound of Formula (A), wherein $R^9$ is methyl, $—CH_2SCH_3$ or $—CH_2OCH_3$.

Another embodiment provides the compound of Formula (A), wherein $R^9$ is $—CH_2OCH_2CCl_3$, $—CH_2OCH_2CH_2OCH_3$, $—CH_2OCH_2CH_2OCH_3$, or $—CH_2OCH_2CH_2Si(CH_3)_3$.

Another embodiment provides the compound of Formula (A), wherein $R^9$ is $—C(Ph)_3$, 4-methoxybenzyl, or $—CH_2Ph$.

Another embodiment provides the compound of Formula (A), wherein $R^9$ is $—CH_2CH{=}CH_2$.

Another embodiment provides the compound of Formula (A), wherein $R^9$ is $—COCH_3$, $—COCH_2Cl$, $—COCHCl_2$, $—COCCl_3$, $—COCF_3$, or $—COC(CH)_3$.

Another embodiment provides the compound of Formula (A), wherein $R^9$ is —COPh, —CO (4-methoxyphenyl), or —CO (4-bromophenyl).

Another embodiment provides the compound of Formula (A), wherein $R^9$ is $—CO_2CH_3$, $—CO_2CH_2CCl_3$, $—CO_2CH_2CH_2Si(CH_3)_3$, or $—CO_2C(CH_3)_3$.

Another embodiment provides the compound of Formula (A), wherein $R^9$ is $—CO_2CH_2Ph$, $—CO_2$ (4-methoxybenzyl), or $—CO_2$ (9-fluorenylmethyl).

Another embodiment provides the compound of Formula (A), wherein $R^9$ is $—CO_2CH_2CH{=}CH_2$.

Another embodiment provides the compound of Formula (A), wherein $R^9$ is $—CH_2CH_2Si(Ph)_2(t\text{-}C_4H_9)$.

Another embodiment provides the compound of Formula (A), wherein $R^9$ is $—Si(CH_3)_3$, $—Si(CH_2CH_3)_3$, $—Si(i\text{-}Pr)(CH_3)_2$, $—Si(iPr)(CH_2CH_3)_2$, $—Si(t\text{-}C_4H_9)(CH_3)_2$, $—Si(t\text{-}C_4H_9)(Ph)_2$, or $—Si(i\text{-}Pr)_3$.

Another embodiment provides the compound of Formula (A), wherein $R^9$ is

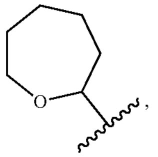,
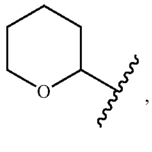,
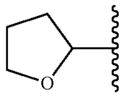
or
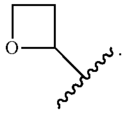.

Another embodiment provides the compound of Formula (A), wherein $R^9$ is

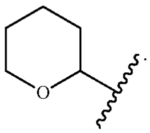 [SMILES: *C1CCCCO1].

Another embodiment provides the compound of Formula (A), wherein $R^1$ is H. Another embodiment provides the compound of Formula (A), wherein $R^1$ is $CH_3$ or $CD_3$.

Another embodiment provides the compound of Formula (A), wherein $R^2$ is H.

Another embodiment provides the compound of Formula (A), wherein $R^3$ is H.

Another embodiment provides the compound of Formula (A), wherein $R^4$ is H.

Another embodiment provides the compound of Formula (A), wherein $R^5$ is Cl.

Another embodiment provides the compound of Formula (A), wherein $R^5$ is $—OCHF_2$.

Another embodiment provides the compound of Formula (A), wherein $R^5$ is —C≡CH or $—C{\equiv}CCH_3$.

Another embodiment provides the compound of Formula (A), wherein $R^6$ is H, D, or F.

Another embodiment provides the compound of Formula (A), wherein $R^7$ is H, D, or F.

Another embodiment provides the compound of Formula (A), wherein $R^1$ is $CH_3$ or $CD_3$; $R^2$, $R^3$, and $R^4$ are H; $R^5$ is $—OCHF_2$; $R^6$ is H; and $R^7$ is F. Another embodiment provides the compound, wherein $R^9$ is $CH_3$. Another embodiment provides the compound, wherein $R^9$ is H. Another embodiment provides the compound, wherein $R^9$ is $—SO_2CF_3$.

Another embodiment provides the compound of Formula (A), wherein $R^1$ is $CH_3$ or $CD_3$; $R^2$, $R^3$, and $R^4$ are H; $R^5$ is —Cl; $R^6$ is H; and $R^7$ is F. Another embodiment provides the compound, wherein $R^9$ is $CH_3$. Another embodiment provides the compound, wherein $R^9$ is H. Another embodiment provides the compound, wherein $R^9$ is $—SO_2CF_3$.

Pharmaceutical Compositions

In certain embodiments, the TNFα inhibitory compound described herein is administered as a pure chemical. In other embodiments, the TNFα inhibitory compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 2181 Ed. Mack Pub. Co., Easton, PA (2005)).

Provided herein is a pharmaceutical composition comprising at least one TNFα inhibitory compound as described herein, or pharmaceutically acceptable salt, solvate, deuteroisotope, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject or the patient) of the composition.

One embodiment provides a pharmaceutical composition comprising a pharmaceutically acceptable excipient and the compound of Formula (I) or (Ia), or pharmaceutically acceptable salt, solvate, deuteroisotope, or N-oxide thereof.

One embodiment provides a method of preparing a pharmaceutical composition comprising mixing the compound of Formula (I) or (Ia), or a pharmaceutically acceptable salt, solvate, deuteroisotope, or N-oxide thereof, and a pharmaceutically acceptable carrier.

In certain embodiments, the TNFα inhibitory compound as described by Formula (I), or a pharmaceutically acceptable salt, solvate, deuteroisotope, or N-oxide thereof, is substantially pure, in that it contains less than about 5%, or less than about 2%, or less than about 1%, or less than about 0.5%, or less than about 0.1%, of other organic small molecules, such as unreacted intermediates or synthesis by-products that are created, for example, in one or more of the steps of a synthesis method.

One embodiment provides a pharmaceutical composition comprising a pharmaceutically acceptable excipient and a compound of Table 1 or Table 2, or a pharmaceutically acceptable salt, solvate, deuteroisotope, or N-oxide thereof.

One embodiment provides a method of preparing a pharmaceutical composition comprising mixing a compound of Table 1 or Table 2, or a pharmaceutically acceptable salt, solvate, deuteroisotope, or N-oxide thereof, and a pharmaceutically acceptable carrier.

In certain embodiments, the TNFα inhibitory compound as described by Table 1 or Table 2, or a pharmaceutically acceptable salt, solvate, deuteroisotope, or N-oxide thereof, is substantially pure, in that it contains less than about 5%, or less than about 2%, or less than about 1%, or less than about 0.5%, or less than about 0.1%, of other organic small molecules, such as unreacted intermediates or synthesis by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. In some embodiments, suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. (See, e.g., *Remington: The Science and Practice of Pharmacy* (Gennaro, $21^{st}$ Ed. Mack Pub. Co., Easton, PA (2005)).

In some embodiments, the TNFα inhibitory compound as described by Formula (I), (Ia), or Table 1 or Table 2, or pharmaceutically acceptable salt, solvate, deuteroisotope, or N-oxide thereof, is formulated for administration by injection. In some instances, the injection formulation is an aqueous formulation. In some instances, the injection formulation is a non-aqueous formulation. In some instances, the injection formulation is an oil-based formulation, such as sesame oil, or the like.

The dose of the composition comprising at least one TNFα inhibitory compound as described herein differs depending upon the subject or patient's (e.g., human) condition. In some embodiments, such factors include general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. The optimal dose depends upon the body mass, weight, or blood volume of the patient.

Oral doses typically range from about 1.0 mg to about 1000 mg, one to four times, or more, per day.

Methods of Treatment

One embodiment provides the compound of Formula (I) or (Ia), or a pharmaceutically acceptable salt, solvate, deuteroisotope, or N-oxide thereof, for use in a method of treatment of the human or animal body.

One embodiment provides the compound of Formula (I) or (Ia), or a pharmaceutically acceptable salt, solvate, deuteroisotope, or N-oxide thereof, for use in a method of treatment of inflammatory or autoimmune disease or disorder. Another embodiment provides the compound of Formula (I) or (Ia), or a pharmaceutically acceptable salt, solvate, deuteroisotope, or N-oxide thereof, for use in a method of treatment of inflammatory disease or disorder. Yet another embodiment provides the compound of Formula (I) or (Ia), or a pharmaceutically acceptable salt, solvate, deuteroisotope, or N-oxide thereof, for use in a method of treatment of autoimmune disease or disorder.

One embodiment provides a pharmaceutical composition comprising the compound of Formula (I) or (Ia), or a pharmaceutically acceptable salt, solvate, deuteroisotope, or N-oxide thereof, and a pharmaceutically acceptable excipient for use in a method of treatment of inflammatory or autoimmune disease or disorder.

One embodiment provides a use of the compound of Formula (I) or (Ia), or a pharmaceutically acceptable salt, solvate, deuteroisotope, or N-oxide thereof, in the manufacture of a medicament for the treatment of inflammatory or autoimmune disease or disorder.

In some embodiments is provided a method of treating an inflammatory or autoimmune disease or disorder, in a patient in need thereof, comprising administering to the patient the compound of Formula (I) or (Ia), or a pharmaceutically acceptable salt, solvate, deuteroisotope, or N-oxide thereof. In some embodiments is provided a method of treating inflammatory or autoimmune disease or disorder, in a patient in need thereof, comprising administering to the patient a pharmaceutical composition comprising the compound of Formula (I) or (Ia), or a pharmaceutically acceptable salt, solvate, deuteroisotope, or N-oxide thereof, and a pharmaceutically acceptable excipient. One embodiment provides a method of treating an inflammatory disease or disorder. Another embodiment provides a method of treating an autoimmune disease or disorder.

One embodiment provides a compound of Table 1 or Table 2, or a pharmaceutically acceptable salt, solvate, deuteroisotope, or N-oxide thereof, for use in a method of treatment of the human or animal body.

One embodiment provides a compound of Table 1 or Table 2, or a pharmaceutically acceptable salt, solvate, deuteroisotope, or N-oxide thereof, for use in a method of treatment of inflammatory or autoimmune disease or disorder.

One embodiment provides a pharmaceutical composition comprising a compound of Table 1 or Table 2, or a pharmaceutically acceptable salt, solvate, deuteroisotope, or N-oxide thereof, and a pharmaceutically acceptable excipient for use in a method of treatment of inflammatory or autoimmune disease or disorder.

One embodiment provides a use of a compound of Table 1 or Table 2, or a pharmaceutically acceptable salt, solvate, deuteroisotope, or N-oxide thereof, in the manufacture of a medicament for the treatment of inflammatory or autoimmune disease or disorder.

In some embodiments is provided a method of treating an inflammatory or autoimmune disease or disorder in a patient in need thereof, comprising administering to the patient a compound of Table 1 or Table 2, or a pharmaceutically acceptable salt, solvate, deuteroisotope, or N-oxide thereof. In some embodiments is provided a method of treating an inflammatory or autoimmune disease or disorder, in a patient in need thereof, comprising administering to the patient a pharmaceutical composition comprising a compound of Table 1 or Table 2, or a pharmaceutically acceptable salt, solvate, deuteroisotope, or N-oxide thereof, and a pharmaceutically acceptable excipient.

In some embodiments the inflammatory and autoimmune disease or disorder is selected from, but are not limited to: rheumatoid arthritis, psoriatic arthritis, systemic onset juvenile idiopathic arthritis, multiple sclerosis, lupus nephritis, systemic lupus erythematosus, psoriasis, Crohn's disease, colitis, asthma, graft versus host disease, allograft rejection, chronic obstructive pulmonary disease, multiple sclerosis, Alzheimer's disease, Graves' disease, cutaneous lupus, ankylosing spondylitis, cryopyrin-associated periodic syndromes (CAPS), gout, and gouty arthritis, ulcerative TNF receptor associated periodic syndrome (TRAPS), Wegener's granulomatosis, sarcoidosis, familial Mediterranean fever (FMF), neuropathic pain, and adult onset stills.

Provided herein is the method wherein the pharmaceutical composition is administered orally. Provided herein is the method wherein the pharmaceutical composition is administered by injection.

One embodiment provides a method of inhibiting TNFα activity comprising contacting the TNFα protein with the compound of Formula (I) or (Ia), or Table 1 or Table 2. Another embodiment provides the method of inhibiting TNFα activity, wherein the TNFα protein is contacted in an in vivo setting. Another embodiment provides the method of inhibiting TNFα activity, wherein the TNFα protein is contacted in an in vitro setting.

Other embodiments and uses will be apparent to one skilled in the art considering the present disclosures. The following examples are provided merely as illustrative of various embodiments and shall not be construed to limit the invention in any way.

EXAMPLES

I. Chemical Synthesis

In some embodiments, the TNFα inhibitory compounds disclosed herein are synthesized according to the following examples. As used below, and throughout the description of the invention, the following abbreviations, unless otherwise indicated, shall be understood to have the following meanings:

ACN acetonitrile
° C. degrees Celsius
$\delta_H$ chemical shift in parts per million downfield from tetramethylsilane
DCM dichloromethane ($CH_2Cl_2$)
DIAD diisopropyl azodicarboxylate
DIEA diisopropylethylamine
DMF dimethylformamide
DMSO dimethylsulfoxide
EA ethyl acetate
EtOAc ethyl acetate
ESI electrospray ionization
Et ethyl
g gram(s)
h hour(s)
HPLC high performance liquid chromatography
Hz hertz
J coupling constant (in NMR spectrometry)
LCMS liquid chromatography mass spectrometry
μ micro
m multiplet (spectral); meter(s); milli
M molar
$M^+$ parent molecular ion
Me methyl
MsCl methanesulfonyl chloride
MHz megahertz
min minute(s)
mol mole(s); molecular (as in mol wt)
mL milliliter
MS mass spectrometry
nm nanometer(s)
NMR nuclear magnetic resonance
pH potential of hydrogen; a measure of the acidity or basicity of an aqueous solution
PE petroleum ether
RT room temperature
S singlet (spectral)
t triplet (spectral)
SFC Supercritical fluid chromatography
T temperature TFA trifluoroacetic acid
THF tetrahydrofuran
TPP Triphenylphosphine
Example 1: (7R,14R)-1-chloro-11-(4-(dimethylphosphoryl)-3-fluorophenyl)-6-(methyl-d3)-6,7-dihydro-7,14-methanobenzo[f]benzo[4,5]imidazo[1,2-a][1,4]diazocin-5(14H)-one
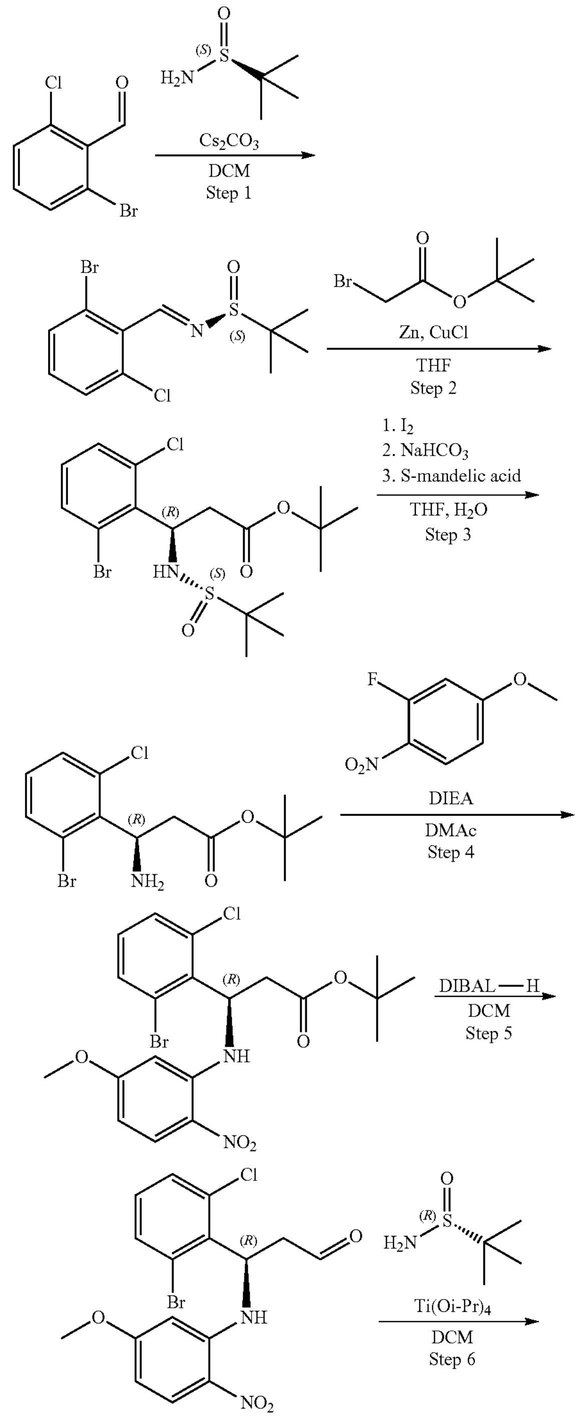
-continued
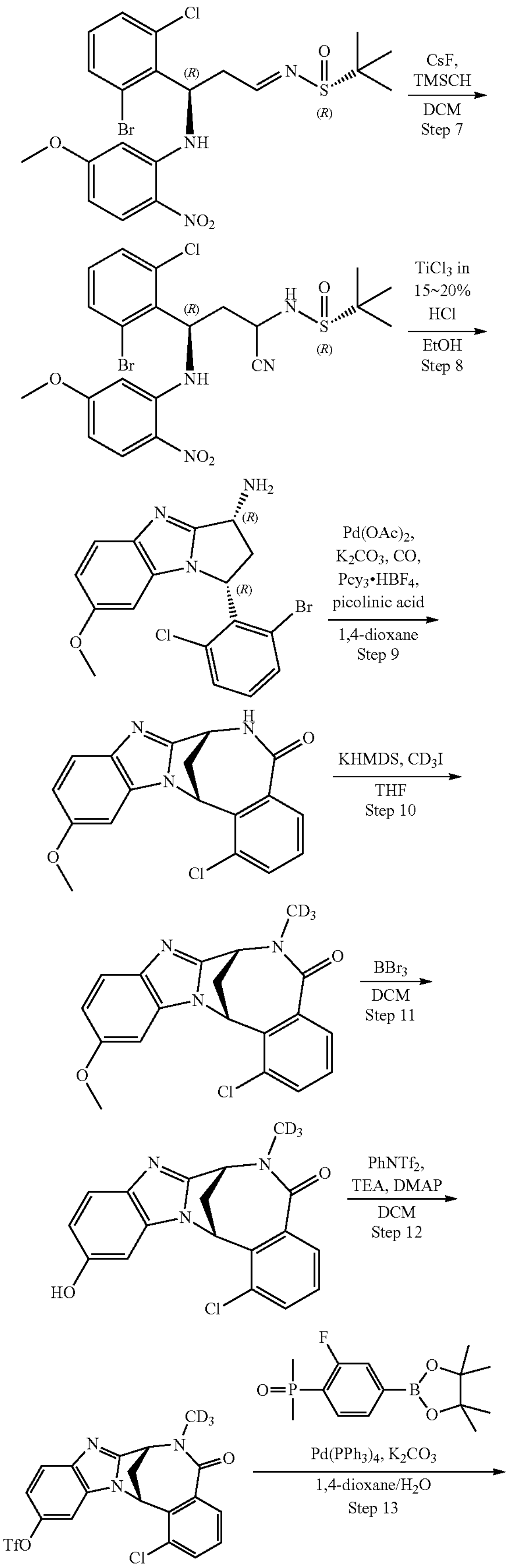

-continued

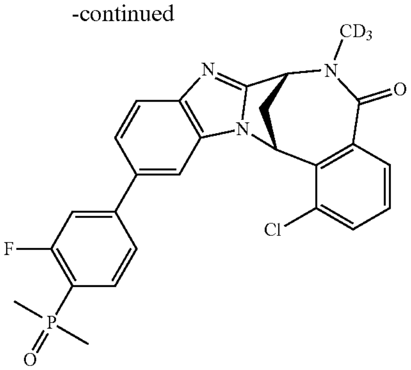

Preparation 1A: (S,E)-N-(2-bromo-6-chlorobenzylidene)-2-methylpropane-2-sulfinamide To a stirred solution of 2-bromo-6-chlorobenzaldehyde (100.00 g, 455.664 mmol) and $Cs_2CO_3$ (163 g, 501.230 mmol) in DCM (1 L) was added(S)-2-methylpropane-2-sulfinamide (66.27 g, 546.797 mmol) in portions at room temperature. The resulting mixture was stirred for 3 h at room temperature. The resulting mixture was diluted with water (1 L) and extracted with $CH_2Cl_2$ (3×500 mL). The combined organic layers were washed with brine (3×500 mL), dried over anhydrous $Na_2SO_4$. After filtration, the filtrate was concentrated under reduced pressure. The residue was purified by silica gel column chromatography, eluted with PE/EA (10:1) to afford (S, E)-N-(2-bromo-6-chlorobenzylidene)-2-methylpropane-2-sulfinamide (121.00 g, 82%) as a yellow oil. MS ESI calculated for $C_{11}H_{13}BrClNOS$ $[M+H]^+$, 321.96 323.96 found 322.00 323.95. $^1H$ NMR (400 MHz, Chloroform-d) δ 8.85 (s, 1H), 7.60 (d, J=8.1 Hz, 1H), 7.45 (d, J=8.1 Hz, 1H), 7.22 (t, J=8.1 Hz, 1H), 1.33 (s, 9H).

Preparation 1B: tert-butyl (R)-3-(2-bromo-6-chlorophenyl)-3-(((S)-tert-butylsulfinyl)amino) propanoate A mixture of Zn (164.54 g, 2516.661 mmol) and CuCl (53.39 g, 539.284 mmol) in THF (1 L) was stirred for 2 h at 60° C. under nitrogen atmosphere. The mixture was allowed to cool down to room temperature. To the above mixture was added tert-butyl 2-bromoacetate (175.32 g, 898.808 mmol) dropwise over 5 min at 25° C. The resulting mixture was stirred for additional 2 h at 60° C. The mixture was allowed to cool down to room temperature. To the above mixture was added (S, E)-N-(2-bromo-6-chlorobenzylidene)-2-methylpropane-2-sulfinamide (116.00 g, 359.523 mmol) in portions over 5 min at 10° C. The resulting mixture was stirred for additional 3 h at room temperature. The resulting mixture was filtered, the filter cake was washed with MTBE (3×100 mL). To the above filtrate were added MTBE (1500 mL) and saturated citric acid solution (500 mL). The aqueous layer was extracted with MTBE (3×500 mL) and the combined organic layers were washed with saturated $NaHCO_3$ solution (500 mL), dried over anhydrous $Na_2SO_4$. After filtration, the filtrate was concentrated under reduced pressure. This resulted in tert-butyl (R)-3-(2-bromo-6-chlorophenyl)-3-(((S)-tert-butylsulfinyl)amino) propanoate (127.00 g, 81%) as a yellow oil. MS ESI calculated for $C_{17}H_{25}BrClNO_3S$ $[M+H]^+$, 438.04 440.04, found 438.05 440.05. $^1H$ NMR (300 MHz, Chloroform-d) δ 7.51 (d, J=8.1 Hz, 1H), 7.32 (d, J=9.0 Hz, 1H), 7.06 (t, J=8.0 Hz, 1H), 5.85-5.65 (m, 1H), 4.57-4.33 (m, 1H), 3.31-3.12 (m, 1H), 3.11-2.87 (m, 1H), 1.38 (s, 9H), 1.11 (s, 9H).

Preparation 1C: tert-butyl (R)-3-amino-3-(2-bromo-6-chlorophenyl)propanoate

To a stirred solution of tert-butyl (R)-3-(2-bromo-6-chlorophenyl)-3-(((S)-tert-butylsulfinyl)amino)propanoate (127.00 g, 289.419 mmol) in THF (500 mL) and $H_2O$ (100 mL) was added $I_2$ (18.36 g, 72.533 mmol) at room temperature under nitrogen atmosphere. The resulting mixture was stirred for overnight at 50° C. The reaction was quenched by the addition of sat. $NaHCO_3$ (aq.) (1 L) at 0° C. The resulting mixture was extracted with EtOAc (3×500 mL). The combined organic layers were washed with brine (3×2 L), dried over anhydrous $Na_2SO_4$. After filtration, the filtrate was concentrated under reduced pressure. The residue was dissolved in ACN (200 mL) followed by the addition of solution (2S)-2-hydroxy-2-phenylacetic acid (44.03 g, 289.419 mmol) in ACN (200 mL) dropwise at room temperature. The resulting mixture was stirred for additional 15 min at room temperature. The precipitated solids were collected by filtration and washed with ACN (200 mL). The above solids in $CH_2Cl_2$ (500 mL) and sat. $NaHCO_3$ (aq.) (1.5 L). The mixture was stirred for additional 15 min at room temperature. The resulting mixture was extracted with $CH_2Cl_2$ (3×500 mL). The combined organic layers were washed with brine (3×500 mL), dried over anhydrous $Na_2SO_4$. After filtration, the filtrate was concentrated under reduced pressure to afford tert-butyl (R)-3-amino-3-(2-bromo-6-chlorophenyl)propanoate (84.00 g, 87%) as a colorless oil. MS ESI calculated for $C_{13}H_{17}BrClNO_2$ $[M+H]^+$, 334.01 336.01 found 334.00 336.00. $^1H$ NMR (400 MHz, Chloroform-d) δ 7.55-7.46 (m, 1H), 7.33 (d, J=8.0 Hz, 1H), 7.02 (t, J=8.0 Hz, 1H), 5.25-5.17 (m, 1H), 3.09-2.96 (m, 1H), 2.90-2.73 (m, 1H), 2.25 (s, 2H), 1.41 (s, 9H).

Preparation 1D: tert-butyl (R)-3-(2-bromo-6-chlorophenyl)-3-((5-methoxy-2-nitrophenyl)amino)propanoate To a stirred solution of tert-butyl (R)-3-amino-3-(2-bromo-6-chlorophenyl)propanoate (42.00 g, 125.508 mmol) and 2-fluoro-4-methoxy-1-nitrobenzene (23.63 g, 138.059 mmol) in DMAc (500 mL) was added DIEA (24.33 g, 188.262 mmol) at room temperature under nitrogen atmosphere. The resulting mixture was stirred for overnight at 80° C. The resulting mixture was diluted with water (500 mL), extracted with EA (3×500 mL). The combined organic layers were concentrated under vacuum. The residue was purified by silica gel column chromatography, eluted with PE/EA (10:1) to afford tert-butyl (R)-3-(2-bromo-6-chlorophenyl)-3-((5-methoxy-2-nitrophenyl)amino)propanoate (50.00 g, 82%) as a yellow oil. MS ESI calculated for $C_{20}H_{22}BrClN_2O_5$ $[M+H]^+$, 485.04 487.04 found 485.00 487.00. $^1H$ NMR (300 MHz, Chloroform-d) δ 9.29 (d, J=8.0 Hz, 1H), 8.09 (d, J=9.5 Hz, 1H), 7.52 (s, 1H), 7.34 (s, 1H), 7.09 (t, J=8.0 Hz, 1H), 6.27-6.08 (m, 2H), 6.01-5.79 (m, 1H), 3.78 (s, 3H), 3.27 (t, J=13.0 Hz, 1H), 2.91-2.74 (m, 1H), 1.42 (s, 9H).

Preparation 1E: (R)-3-(2-bromo-6-chlorophenyl)-3-((5-methoxy-2-nitrophenyl)amino)propanal To tert-butyl (R)-3-(2-bromo-6-chlorophenyl)-3-((5-methoxy-2-nitrophenyl)amino)propanoate (50.00 g, 102.931 mmol) in DCM (1 L) was added DIBAL-H (113.2 mL, 113.224 mmol) dropwise at −78° C. under nitrogen atmosphere. The resulting mixture was stirred for 3 h at −78° C. under nitrogen atmosphere. The reaction was quenched with HCl (1N) at −78° C. The resulting mixture was extracted with $CH_2Cl_2$ (3×1 L). The combined organic layers were washed with brine (3×1 L), dried over anhydrous $Na_2SO_4$. After filtration, the filtrate was concentrated under reduced pressure. The residue was purified by silica gel column chromatography, eluted with $CH_2Cl_2$/PE (1:1) to afford (R)-3-(2-bromo-6-chlorophenyl)-3-((5-methoxy-2-nitrophenyl)amino)propanal (38.01 g, 89%). MS ESI calculated for $C_{16}H_{14}BrClN_2O_4$ $[M+H]^+$, 412.98 414.98 found 413.00 415.00. $^1H$ NMR (300 MHz, Chloroform-d) δ 9.86 (s, 1H), 9.25 (d, J=8.3 Hz, 1H), 8.15-8.08 (m, 1H), 7.63-7.50 (m, 1H), 7.51-7.34 (m, 1H), 7.12 (t, J=8.0 Hz, 1H), 6.28-6.21 (m, 2H), 6.13-6.00 (m, 1H), 3.82 (s, 3H), 3.74-3.55 (m, 1H), 3.06 (d, J=17.5 Hz, 1H).

Preparation 1F: (R)—N—((R,E)-3-(2-bromo-6-chlorophenyl)-3-((5-methoxy-2-nitrophenyl)amino) propylidene)-2-methylpropane-2-sulfinamide To a stirred solution of (R)-3-(2-bromo-6-chlorophenyl)-3-((5-methoxy-2-nitrophenyl)amino)propanal (39.00 g, 94.283 mmol) and $Ti(Oi\text{-}Pr)_4$ (53.59 g, 188.566 mmol) in DCM (300 mL) was added (R)-2-methylpropane-2-sulfinamide (13.71 g, 113.140 mmol) in portions at room temperature. The resulting mixture was stirred for 3 h at room temperature. The resulting mixture was diluted with water (500 mL), extracted with $CH_2Cl_2$ (3×500 mL). The combined organic layers were washed with brine (3×500 mL), dried over anhydrous $Na_2SO_4$. After filtration, the filtrate was concentrated under reduced pressure. The residue was purified by silica gel column chromatography, eluted with PE/EA (10:1) to afford (R)—N—((R,E)-3-(2-bromo-6-chlorophenyl)-3-((5-methoxy-2-nitrophenyl)amino)propylidene)-2-methylpropane-2-sulfinamide (44.10 g, 90%) as a yellow oil. MS ESI calculated for $C_{20}H_{23}BrClN_3O_4S$ $[M+H]^+$, 516.03 518.03 found 516.10 518.00. $^1H$ NMR (400 MHz, Chloroform-d) δ 9.35-9.19 (m, 1H), 8.19-8.13 (m, 1H), 8.08 (d, J=9.5 Hz, 1H), 7.61-7.30 (m, 2H), 7.12 (t, J=8.1 Hz, 1H), 6.27-6.17 (m, 1H), 6.12-6.05 (m, 1H), 5.97-5.82 (m, 1H), 3.77 (s, 3H), 3.71-3.58 (m, 1H), 3.19-3.04 (m, 1H), 1.17 (s, 9H).

Preparation 1G: (R)—N—((R,E)-3-(2-bromo-6-chlorophenyl)-3-((5-methoxy-2-nitrophenyl)amino) propylidene)-2-methylpropane-2-sulfinamide To a stirred solution of (R)—N-[(1E,3R)-3-(2-bromo-6-chlorophenyl)-3-[(5-methoxy-2-nitrophenyl)amino]propylidene]-2-methylpropane-2-sulfinamide (44.00 g, 85.133 mmol) and CsF (25.86 g, 170.266 mmol) in DCM (500 mL) was added TMSCN (16.89 g, 170.266 mmol) in portions at room temperature. The resulting mixture was stirred for 3 h at room temperature. The resulting mixture was diluted with water (500 mL), extracted with $CH_2Cl_2$ (3×200 mL). The combined organic layers were washed with brine (3×500 mL), dried over anhydrous $Na_2SO_4$. After filtration, the filtrate was concentrated under reduced pressure. The residue was purified by silica gel column chromatography, eluted with PE/EA (10:1) to afford (R)—N-((3R)-3-(2-bromo-6-chlorophenyl)-1-cyano-3-((5-methoxy-2-nitrophenyl)amino) propyl)-2-methylpropane-2-sulfinamide (39.80 g, 86%) as a yellow oil. MS ESI calculated for $C_{21}H_{24}BrClNO_4S$ $[M+H]^+$, 543.04 545.04 found 543.00 545.00. $^1H$ NMR (400 MHz, Chloroform-d) δ 9.36-9.16 (m, 1H), 8.20-8.08 (m, 1H), 7.63-7.32 (m, 2H), 7.17-7.06 (m, 1H), 6.32-6.12 (m, 2H), 5.87-5.70 (m, 1H), 4.76-4.43 (m, 1H), 3.84-3.73 (m, 3H), 3.14-2.91 (m, 1H), 2.50-2.34 (m, 1H), 1.26-1.17 (m, 9H).

Preparation 1H: (1R,3R)-1-(2-bromo-6-chlorophenyl)-7-methoxy-2,3-dihydro-1H-benzo[d]pyrrolo[1,2-a]imidazol-3-amine To a stirred solution of (R)—N—((R,E)-3-(2-bromo-6-chlorophenyl)-3-((5-methoxy-2-nitrophenyl)amino)propylidene)-2-methylpropane-2-sulfinamide (39.80 g, 73.181 mmol) and $TiCl_3$ (451.44 g, 585.448 mmol, 20%) in EtOH (500 mL) at room temperature. The resulting mixture was stirred for overnight at 80° C. The resulting mixture was diluted with EtOAc (100 mL). The residue was basified to pH 7 with saturated $NaHCO_3$ (aq.). The resulting mixture was filtered and the filter cake was washed with EtOAc (3×100 mL). The filtrate was washed with 2×1 L of water. The organic layer was concentrated under vacuum. The residue was purified by silica gel column chromatography, eluted with $CH_2Cl_2$/MeOH (10:1) to afford (1R,3R)-1-(2-bromo-6-chlorophenyl)-7-methoxy-2,3-dihydro-1H-benzo [d]pyrrolo[1,2-a]imidazol-3-amine (18.70 g, 65%). MS ESI calculated for $C_{17}H_{15}BrClN_3O$ $[M+H]^+$, 392.01 394.01 found 391.85 393.85. $^1H$ NMR (300 MHz, Chloroform-d) δ 7.72-7.62 (m, 2H), 7.59-7.44 (m, 1H), 7.20 (t, J=8.0 Hz, 1H), 6.92-6.80 (m, 1H), 6.33-6.19 (m, 1H), 6.13-6.06 (m, 1H), 4.87-4.65 (m, 1H), 3.73-3.66 (m, 3H), 3.60-3.20 (m, 1H), 3.01-2.59 (m, 1H).

Preparation 1I: (7R,14R)-1-chloro-11-methoxy-6,7-dihydro-7,14-methanobenzo[f]benzo[4,5]imidazo[1,2-a][1,4]diazocin-5(14H)-one To a stirred mixture of (1R,3R)-1-(2-bromo-6-chlorophenyl)-7-methoxy-2,3-dihydro-1H-benzo[d]pyrrolo[1,2-a] imidazol-3-amine (7.80 g, 19.864 mmol) and pyridine-2-carboxylic acid (1.22 g, 9.932 mmol), $K_2CO_3$ (13.73 g, 99.320 mmol) in 1,4-dioxane (150 mL) were added $PCy_3 \cdot HBF_4$ (1.11 g, 3.973 mmol) and $Pd(OAc)_2$ (0.89 g, 3.973 mmol) at room temperature. The resulting mixture was stirred for 16 h at 100° C. under carbon monoxide atmosphere (10 atm.). The resulting mixture was concentrated under vacuum. The residue was purified by silica gel column chromatography, eluted with $CH_2Cl_2$/MeOH (10:1) to afford (7R,14R)-1-chloro-11-methoxy-6,7-dihydro-7,14-methanobenzo[f]benzo[4,5]imidazo[1,2-a][1,4]diazocin-5 (14H)-one (2.10 g, 31%). MS ESI calculated for $C_{18}H_{14}ClN_3O_2$ $[M+H]^+$, 340.08 found 340.05. $^1H$ NMR (400 MHz, Chloroform-d) δ 8.56-8.47 (m, 1H), 7.71-7.53 (m, 2H), 7.45 (d, J=6.4 Hz, 1H), 7.36 (t, J=8.1 Hz, 1H), 7.12 (d, J=2.5 Hz, 1H), 6.93-6.84 (m, 1H), 6.45 (d, J=7.3 Hz, 1H), 4.90 (t, J=6.5 Hz, 1H), 3.83 (s, 3H), 3.49-3.34 (m, 1H), 2.84 (d, J=13.3 Hz, 1H).

Preparation 1J: (7R,14R)-1-chloro-11-methoxy-6-(methyl-$d_3$)-6,7-dihydro-7,14methanobenzo[f]benzo [4,5]imidazo[1,2-a][1,4]diazocin-5(14H)-one To a stirred mixture of (7R,14R)-1-chloro-11-methoxy-6, 7-dihydro-7,14-methanobenzo[f]benzo[4,5]imidazo[1,2-a] [1,4]diazocin-5(14H)-one (2.39 g, 7.034 mmol) in THF (25 mL) was added KHMDS (8.44 mL, 8.441 mmol, 1M in THF) at −78° C. under nitrogen atmosphere. The resulting mixture was stirred for 1 h at −78° C. under nitrogen atmosphere. To the above mixture was added $CD_3I$ (1.33 g, 9.144 mmol) at −78° C. The resulting mixture was stirred for additional 16 h at room temperature. The resulting mixture was concentrated under vacuum and purified by silica gel column chromatography, eluted with $CH_2Cl_2$/MeOH (10:1) to afford (7R,14R)-1-chloro-11-methoxy-6-(methyl-$d_3$)-6,7-dihydro-7,14methanobenzo[f]benzo[4,5]imidazo[1,2-a][1,4]diazocin-5(14H)-one (2.10 g, 84%). MS ESI calculated for $C_{19}H_{13}D3ClN_3O_2$ [M+H]$^+$, 357.11 found 357.15. $^1$H NMR (400 MHz, Chloroform-d) δ 8.60-8.54 (m, 1H), 7.60 (d, J=8.9 Hz, 2H), 7.36 (t, J=8.1 Hz, 1H), 7.15 (d, J=2.5 Hz, 1H), 6.91-6.84 (m, 1H), 6.37 (d, J=7.3 Hz, 1H), 4.92 (d, J=7.1 Hz, 1H), 3.83 (s, 3H), 3.50-3.38 (m, 1H), 2.86 (d, J=13.5 Hz, 1H).

Preparation 1K: (7R,14R)-1-chloro-11-hydroxy-6-(methyl-d3)-6,7-dihydro-7,14methanobenzo[f]benzo[4,5]imidazo[1,2-a][1,4]diazocin-5(14H)-one To a stirred solution of (7R,14R)-1-chloro-11-hydroxy-6-(methyl-d3)-6,7-dihydro-7,14methanobenzo[f]benzo[4,5]imidazo[1,2-a][1,4]diazocin-5(14H)-one (2.10 g, 5.885 mmol) in DCM (50 mL) was added $BBr_3$ (17.7 mL, 17.655 mmol) at 0° C. under nitrogen atmosphere. The resulting mixture was stirred for 3 h at room temperature under nitrogen atmosphere. The resulting mixture was concentrated under vacuum. The residue was purified by reversed-phase flash chromatography with the following conditions: column, C18 silica gel; mobile phase, $CH_3CN$ in Water (10 mmol/L $NH_4HCO_3$), 10% to 50% gradient in 10 min; detector, 254 nm to afford (7R,14R)-1-chloro-11-hydroxy-6-(methyl-d3)-6,7-dihydro-7,14methanobenzo[f]benzo[4,5]imidazo[1,2-a][1,4]diazocin-5(14H)-one (2.01 g, 99%). MS ESI calculated for $C_{18}H_{11}D_3ClN_3O_2$ [M+H]$^+$, 343.10 found 343.15. $^1$H NMR (400 MHz, DMSO-$d_6$) δ 9.36 (s, 1H), 8.43-8.33 (m, 1H), 7.84-7.76 (m, 1H), 7.47 (d, J=8.1 Hz, 1H), 7.38 (d, J=8.7 Hz, 1H), 6.94 (d, J=2.3 Hz, 1H), 6.70-6.59 (m, 1H), 6.30 (d, J=7.2 Hz, 1H), 5.11 (d, J=7.0 Hz, 1H), 3.52-3.40 (m, 1H), 2.79 (d, J=13.8 Hz, 1H).

Preparation 1L: (7R,14R)-1-chloro-6-(methyl-d3)-5-oxo-5,6,7,14-tetrahydro-7,14-methanobenzo[f]benzo[4,5]imidazo[1,2-a][1,4]diazocin-11-yl trifluoromethanesulfonate To a stirred solution of (7R,14R)-1-chloro-11-hydroxy-6-(methyl-d3)-6,7-dihydro-7,14methanobenzo[f]benzo[4,5]imidazo[1,2-a][1,4]diazocin-5(14H)-one (300 mg, 0.875 mmol) and 1,1,1-trifluoro-N-phenyl-N-(trifluoromethane)sulfonylmethanesulfonamide (500 mg, 1.400 mmol) in DCM (2 mL) were added DMAP (11 mg, 0.088 mmol), TEA (177 mg, 1.750 mmol) at room temperature. The resulting mixture was stirred for additional 2 h at 25° C. under nitrogen atmosphere. The resulting mixture was concentrated under reduced pressure and purified by silica gel column chromatography, eluted with $CH_2Cl_2$/MeOH (10:1) to afford (7R,14R)-1-chloro-6-(methyl-d3)-5-oxo-5,6,7,14-tetrahydro-7,14-methanobenzo[f]benzo[4,5]imidazo[1,2-a][1,4]diazocin-11-yl trifluoromethanesulfonate (320 mg, 77%). MS ESI calculated for $C_{19}H_{10}D_3ClF_3N_3O_4S$ [M+H]$^+$, 475.05 found 475.00. $^1$H NMR (400 MHz, Chloroform-d) δ 8.61-8.54 (m, 1H), 7.79-7.72 (m, 1H), 7.67-7.59 (m, 2H), 7.43-7.34 (m, 1H), 7.20-7.12 (m, 1H), 6.47-6.40 (m, 1H), 5.00-4.92 (m, 1H), 3.54-3.42 (m, 1H), 2.91 (d, J=13.8 Hz, 1H).

Example 1: (7R,14R)-1-chloro-11-(4-(dimethylphosphoryl)-3-fluorophenyl)-6-(methyl-d3)-6,7-dihydro-7,14-methanobenzo[f]benzo[4,5]imidazo[1,2-a][1,4]diazocin-5(14H)-one To a stirred mixture of (7R,14R)-1-chloro-6-(methyl-d3)-5-oxo-5,6,7,14-tetrahydro-7,14-methanobenzo[f]benzo[4,5]imidazo[1,2-a][1,4]diazocin-11-yl trifluoromethanesulfonate (1.25 g, 2.632 mmol), $K_2CO_3$ (0.73 g, 5.264 mmol) and $Pd(PPh_3)_4$ (0.30 g, 0.263 mmol) in 1,4-dioxane (10 mL) and $H_2O$ (2 mL) was added 2-[4-(dimethylphosphoryl)-3-fluorophenyl]-4,4,5,5-tetramethyl-1,3,2-dioxaborolane (0.94 g, 3.158 mmol) at room temperature under nitrogen atmosphere. The resulting mixture was stirred at 80° C. for 2 h under nitrogen atmosphere. The resulting mixture was concentrated under vacuum. The residue was purified by silica gel column chromatography, eluted with $CH_2Cl_2$/MeOH (12:1) followed by reversed-phase flash chromatography with the following conditions: column, C18 silica gel; mobile phase, $CH_3CN$ in Water (10 mmol/L $NH_4HCO_3$), 30% to 50% gradient in 30 min; detector, 254 nm to afford (7R,14R)-1-chloro-11-(4-(dimethylphosphoryl)-3-fluorophenyl)-6-(methyl-d3)-6,7-dihydro-7,14-methanobenzo[f]benzo[4,5]imidazo[1,2-a][1,4]diazocin-5(14H)-one (985 mg, 75%). MS ESI calculated for $C_{26}H_{19}D_3ClFN_3O_2P$ [M+H]$^+$, 497.13, found 497.10. $^1$H NMR (400 MHz, DMSO-$d_6$) δ 8.42-8.36 (m, 1H), 7.89-7.81 (m, 2H), 7.80-7.73 (m, 2H), 7.64 (d, J=7.9 Hz, 1H), 7.61-7.54 (m, 2H), 7.46 (t, J=8.1 Hz, 1H), 6.48 (d, J=7.2 Hz, 1H), 5.26 (d, J=7.1 Hz, 1H), 3.57-3.48 (m, 1H), 2.89 (d, J=13.9 Hz, 1H), 1.76 (s, 3H), 1.73 (s, 3H). $^{19}$F NMR (377 MHz, DMSO-$d_6$) δ −105.43. $^{31}$P NMR (162 MHz, Chloroform-d) δ 30.63.

Example 2: (7R,14R)-1-chloro-11-(6-(dimethylphosphoryl)pyridin-3-yl)-6-(methyl-d3)-6,7-dihydro-7,14-methanobenzo[f]benzo[4,5]imidazo[1,2-a][1,4]diazocin-5(14H)-one

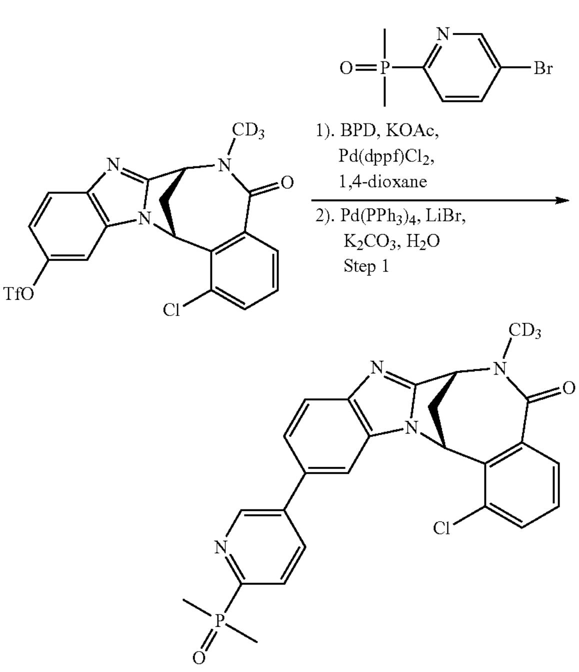

To a stirred solution of 5-bromo-2-(dimethylphosphoryl) pyridine (37 mg, 0.158 mmol) and BPD (40 mg, 0.158 mmol) in 1,4-dioxane (2 mL) were added KOAc (20.67 mg, 0.210 mmol) and $Pd(dppf)Cl_2 \cdot CH_2Cl_2$ (11 mg, 0.014 mmol) at room temperature under nitrogen atmosphere. The resulting mixture was stirred for 16 h at 80° C. under nitrogen atmosphere. The mixture was allowed to cool down to room temperature. To the above mixture was added (7R,14R)-1-chloro-6-(methyl-$d_3$)-5-oxo-5,6,7,14-tetrahydro-7,14-methanobenzo[f]benzo[4,5]imidazo[1,2-a][1,4]diazocin-11-yl trifluoromethanesulfonate (50 mg, 0.105 mmol), LiBr (1 mg, 0.011 mmol), $Pd(PPh_3)_4$ (16 mg, 0.014 mmol), $K_2CO_3$ (29 mg, 0.210 mmol) and $H_2O$ (0.2 mL). The resulting mixture was stirred for additional 4 h at 100° C. under nitrogen atmosphere. The filtrate was concentrated under reduced pressure. The residue was purified by reversed-phase flash chromatography with the following conditions: column, C18 silica gel; mobile phase, $CH_3CN$ in Water (10 mmol/L $NH_4HCO_3$), 10% to 50% gradient in 10 min; detector, 254 nm to afford (7R,14R)-1-chloro-11-(6-(dimethylphosphoryl)pyridin-3-yl)-6-(methyl-d3)-6,7-dihydro-7,14-methanobenzo[f]benzo[4,5]imidazo[1,2-a][1,4]diazocin-5(14H)-one (7 mg, 12%). MS ESI calculated for $C_{25}H_{19}D_3ClN_4O_2P$ $[M+H]^+$, 480.14 found 480.00. $^1H$ NMR (400 MHz, DMSO-$d_6$) δ 9.02 (d, J=2.2 Hz, 1H), 8.43-8.36 (m, 1H), 8.25-8.17 (m, 1H), 8.07-7.99 (m, 1H), 7.91 (d, J=1.8 Hz, 1H), 7.82-7.75 (m, 2H), 7.65-7.58 (m, 1H), 7.46 (t, J=8.1 Hz, 1H), 6.49 (d, J=7.2 Hz, 1H), 5.26 (d, J=7.1 Hz, 1H), 3.61-3.49 (m, 1H), 2.89 (d, J=13.9 Hz, 1H), 1.72 (s, 3H), 1.68 (s, 3H). $^{31}P$ NMR (162 MHz, DMSO-$d_6$) δ 33.95.

Example 3: (7R,14R)-1-chloro-11-(4-(dimethylphosphoryl)-3-fluorophenyl)-4-methyl-6-(methyl-d3)-6,7-dihydro-7,14-methanobenzo[f]benzo[4,5]imidazo[1,2-a][1,4]diazocin-5(14H)-one

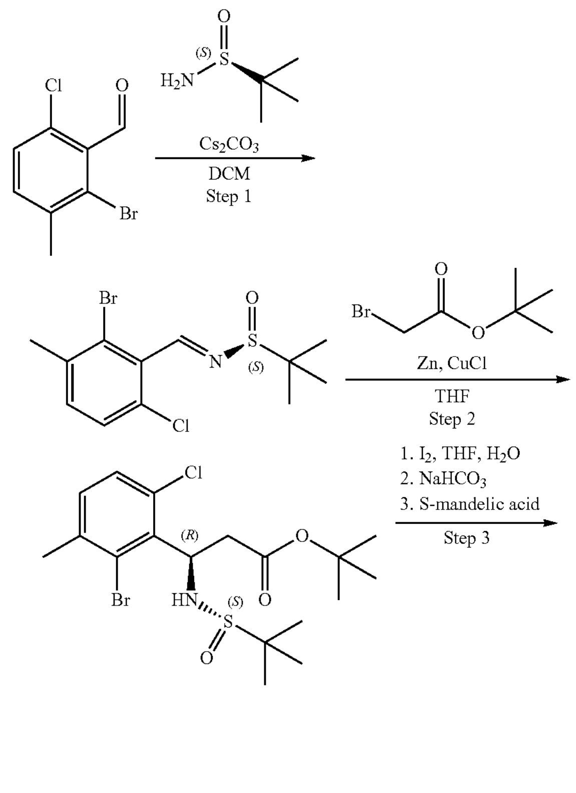

-continued

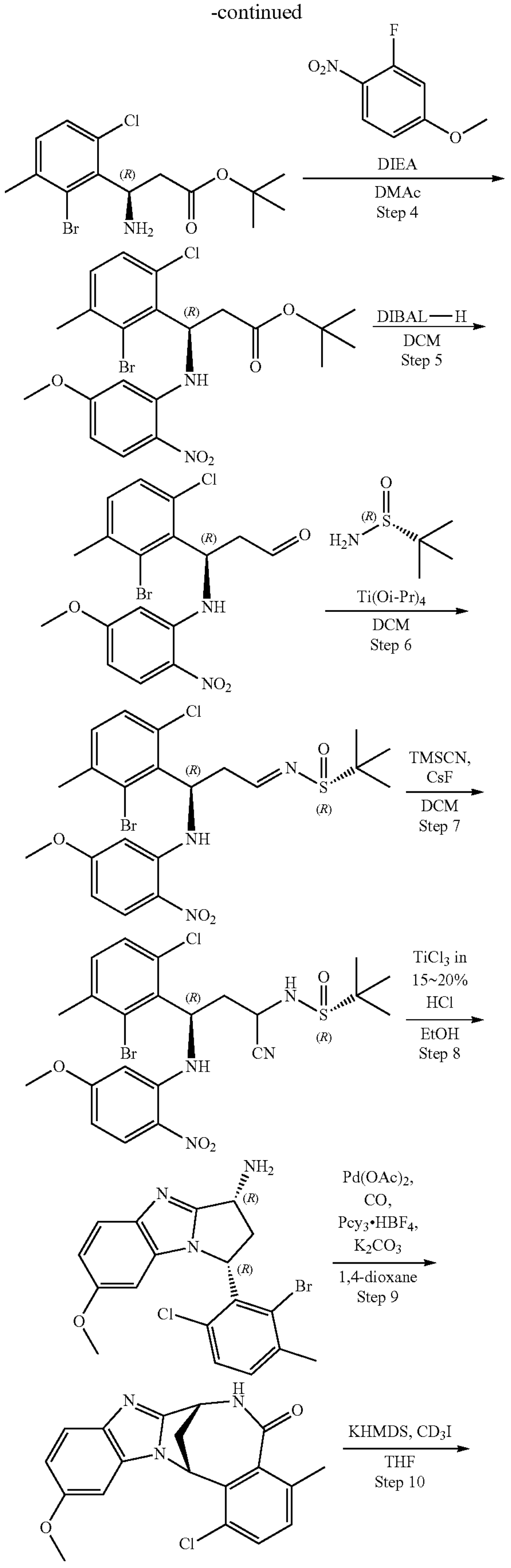

-continued

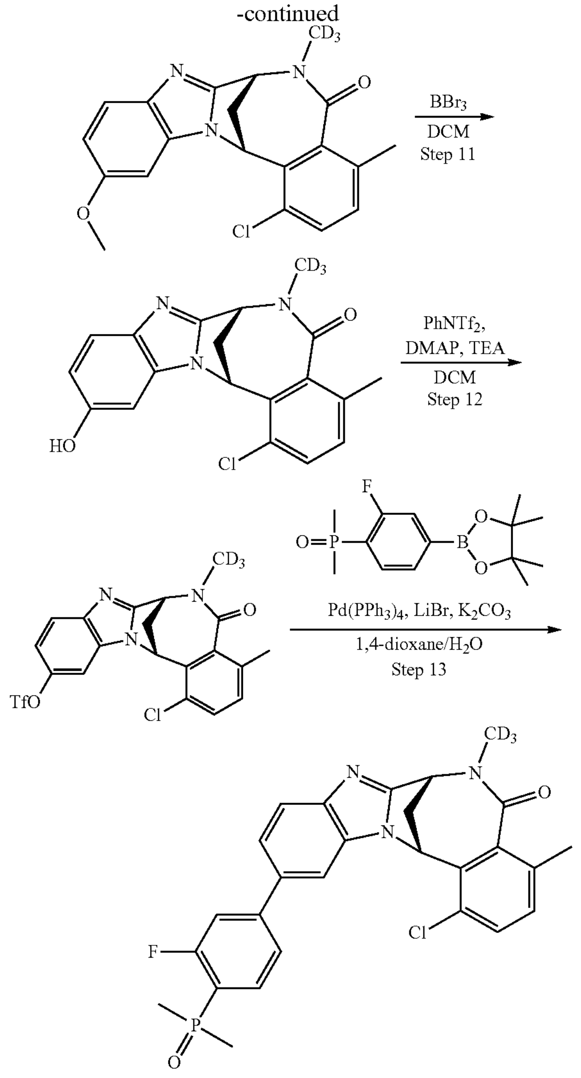

Preparation 3A: (S)—N-[(2-bromo-6-chloro-3-methylphenyl)methylidene]-2-methylpropane-2-sulfinamide To a stirred solution of 2-bromo-6-chloro-3-methylbenzaldehyde (36.00 g, 154.182 mmol) and(S)-2-methylpropane-2-sulfinamide (20.56 g, 169.600 mmol) in DCM (360 mL) was added $Cs_2CO_3$ (60.28 g, 185.018 mmol) at room temperature. The resulting mixture was stirred for 16 h at room temperature. The resulting mixture was filtered, the filter cake was washed with $CH_2Cl_2$ (3×50 mL). The filtrate was concentrated under reduced pressure and purified by silica gel column chromatography, eluted with PE/EA=(1/1) to afford(S)—N-[(2-bromo-6-chloro-3-methylphenyl)methylidene]-2-methylpropane-2-sulfinamide (49.20 g, 95%). MS ESI calculated for $C_{12}H_{15}BrClNOS$ $[M+H]^+$, 335.97 337.97, found 336.10 338.10. $^1H$ NMR (400 MHz, Chloroform-d) δ 8.83 (s, 1H), 7.33 (d, J=8.2 Hz, 1H), 7.24 (d, J=8.2 Hz, 1H), 2.43 (s, 3H), 1.33 (s, 9H).

Preparation 3B: tert-butyl (3R)-3-(2-bromo-6-chloro-3-methylphenyl)-3-{[(S)-2-methylpropane-2-sulfinyl]amino}propanoate A mixture of Zn (46.61 g, 712.865 mmol) and CuCl (14.11 g, 142.573 mmol) in THF (440 mL) was stirred for 2 h at 60° C. under nitrogen atmosphere. The mixture was allowed to cool down to 10° C. To the above mixture was added tert-butyl 2-bromoacetate (69.52 g, 356.433 mmol) dropwise at 10° C. The resulting mixture was stirred for additional 2 h at 60° C. To the above mixture was added(S)—N-[(2-bromo-6-chloro-3-methylphenyl)methylidene]-2-methylpropane-2-sulfinamide (48.00 g, 142.573 mmol) in THF (40 mL) dropwise at room temperature. The resulting mixture was stirred for additional 16 h at room temperature. The resulting mixture was filtered, the filter cake was washed with EtOAc (3×100 mL). The filtrate was concentrated under reduced pressure to afford tert-butyl (3R)-3-(2-bromo-6-chloro-3-methylphenyl)-3-{[(S)-2-methylpropane-2-sulfinyl]amino}propanoate (60.00 g, 93%) as a light yellow oil. MS ESI calculated for $C_{18}H_{27}BrClNO_3S$ $[M+H]^+$, 452.06 454.06, found 452.20 454.20.

Preparation 3C: tert-butyl (3R)-3-amino-3-(2-bromo-6-chloro-3-methylphenyl)propanoate To a stirred solution of tert-butyl (3R)-3-(2-bromo-6-chloro-3-methylphenyl)-3-{[(S)-2-methylpropane-2-sulfinyl]amino}propanoate (58.00 g, 128.083 mmol) in THF (300 mL) and $H_2O$ (60 mL) was added $I_2$ (16.25 g, 64.041 mmol) at room temperature. The resulting mixture was stirred for 16 h at 50° C. The mixture was allowed to cool down to room temperature. The mixture was basified to pH 9 with saturated $NaHCO_3$ (aq.). The resulting mixture was extracted with EtOAc (3×300 mL). The combined organic layers were washed with brine (3×200 mL), dried over anhydrous $Na_2SO_4$. After filtration, the filtrate was concentrated under reduced pressure. The residue was dissolved in MTBE (200 mL). To the above solution was added (2S)-2-hydroxy-2-phenylacetic acid (19.49 g, 128.083 mmol) at room temperature. The resulting mixture was stirred for additional 1 h at room temperature. The precipitated solids were collected by filtration and washed with MTBE (3×50 mL). The resulting solids were dissolved in water (100 mL). The mixture was basified to pH 9 with saturated $NaHCO_3$ (aq.). The resulting mixture was extracted with EtOAc (3×200 mL). The combined organic layers were washed with brine (3×200 mL), dried over anhydrous $Na_2SO_4$. After filtration, the filtrate was concentrated under reduced pressure to afford tert-butyl (3R)-3-amino-3-(2-bromo-6-chloro-3-methylphenyl)propanoate (27.50 g, 62%) as a light yellow oil. MS ESI calculated for $C_{14}H_{19}BrClNO_2$ $[M+H]^+$, 348.03 350.03, found 348.13 350.13. $^1H$ NMR (400 MHz, Chloroform-d) δ 7.22 (d, J=8.1 Hz, 1H), 7.07 (d, J=8.1 Hz, 1H), 5.34 (t, J=7.4 Hz, 1H), 3.12-2.99 (m, 1H), 2.87-2.71 (m, 1H), 2.40 (s, 3H), 1.41 (s, 9H).

Preparation 3D: tert-butyl (3R)-3-(2-bromo-6-chloro-3-methylphenyl)-3-[(5-methoxy-2-nitrophenyl)amino]propanoate A solution of tert-butyl (3R)-3-amino-3-(2-bromo-6-chloro-3-methylphenyl)propanoate (26.50 g, 76.003 mmol), 2-fluoro-4-methoxy-1-nitrobenzene (13.66 g, 79.803 mmol) and DIEA (11.54 g, 114.005 mmol) in DMAc (265 mL) was stirred for 16 h at 80° C. The mixture was allowed to cool down to room temperature. The resulting mixture was diluted with EtOAc (1 L). The resulting mixture was washed with 3×300 mL of water, dried over anhydrous $Na_2SO_4$. After filtration, the filtrate was concentrated under reduced pressure. The residue was purified by silica gel column chromatography, eluted with PE/EA (5/1) to afford tert-butyl (3R)-3-(2-bromo-6-chloro-3-methylphenyl)-3-[(5-methoxy- 2-nitrophenyl)amino]propanoate (31.40 g, 83%). MS ESI calculated for $C_{21}H_{24}BrClN_2O_5$ $[M+H]^+$, 499.06 501.06, found 499.20 501.15. $^1$H NMR (400 MHz, Chloroform-d) δ 9.45-9.24 (m, 1H), 8.08 (d, J=9.3 Hz, 1H), 7.20 (d, J=8.2 Hz, 1H), 7.13 (d, J=8.0 Hz, 1H), 6.22-6.14 (m, 2H), 6.07-5.91 (m, 1H), 3.76 (s, 3H), 3.43-3.18 (m, 1H), 2.89-2.71 (m, 1H), 2.49-2.31 (m, 3H), 1.42 (s, 9H).

Preparation 3E: (3R)-3-(2-bromo-6-chloro-3-methylphenyl)-3-[(5-methoxy-2-nitrophenyl)amino]propanal To a stirred solution of tert-butyl (3R)-3-(2-bromo-6-chloro-3-methylphenyl)-3-[(5-methoxy-2-nitrophenyl) amino]propanoate (32.00 g, 64.027 mmol) in DCM (480 mL) was added DIBAL-H (70 mL, 70.430 mmol, 1 M in THF) dropwise at −78° C. under nitrogen atmosphere. The resulting mixture was stirred for 3 h at −78° C. under nitrogen atmosphere. The reaction was quenched with HCl (1N) at −78° C. The resulting mixture was extracted with $CH_2Cl_2$ (3× 500 mL). The combined organic layers were washed with brine (3×1 L), dried over anhydrous $Na_2SO_4$. After filtration, the filtrate was concentrated under reduced pressure. The residue was purified by silica gel column chromatography, eluted with PE/EA (5/1) to afford (3R)-3-(2-bromo-6-chloro-3-methylphenyl)-3-[(5-methoxy-2-nitrophenyl)amino]propanal (20.50 g, 75%). MS ESI calculated for $C_{17}H_{16}BrClN_2O_4$ $[M+H]^+$, 427.00 429.00, found 426.95 428.95. $^1$H NMR (400 MHz, Chloroform-d) δ 9.85 (s, 1H), 9.41-9.19 (m, 1H), 8.09 (d, J=9.1 Hz, 1H), 7.36-7.10 (m, 2H), 6.24-6.06 (m, 3H), 3.79 (s, 3H), 3.72-3.54 (m, 1H), 3.16-2.94 (m, 1H), 2.51-2.31 (m, 3H).

Preparation 3F: (R)—N—((R,E)-3-(2-bromo-6-chloro-3-methylphenyl)-3-((5-methoxy-2-nitrophenyl)amino)propylidene)-2-methylpropane-2-sulfinamide To a stirred solution of (3R)-3-(2-bromo-6-chloro-3-methylphenyl)-3-[(5-methoxy-2-nitrophenyl)amino]propanal (20.00 g, 46.764 mmol) and (R)-2-methylpropane-2-sulfinamide (11.34 g, 93.528 mmol) in DCM (200 mL) was added $Ti(Oi\text{-}Pr)_4$ (26.58 g, 93.528 mmol) at room temperature. The resulting mixture was stirred for 16 h at room temperature. The reaction was quenched with water at room temperature. The resulting mixture was extracted with $CH_2Cl_2$ (3×500 mL). The combined organic layers were washed with brine (3×500 mL), dried over anhydrous $Na_2SO_4$. After filtration, the filtrate was concentrated under reduced pressure. The residue was purified by silica gel column chromatography, eluted with PE/EA (4/1) to afford (R)—N—((R,E)-3-(2-bromo-6-chloro-3-methylphenyl)-3-((5-methoxy-2-nitrophenyl)amino)propylidene)-2-methylpropane-2-sulfinamide (22.50 g, 91%). MS ESI calculated for $C_{21}H_{25}BrClN_3O_4S$ $[M+H]^+$, 530.04 532.04 found 530.20 532.20. $^1$H NMR (400 MHz, Chloroform-d) δ 9.43-9.20 (m, 1H), 8.19-8.12 (m, 1H), 8.08 (d, J=9.5 Hz, 1H), 7.38-7.21 (m, 1H), 7.15 (t, J=7.1 Hz, 1H), 6.22-6.17 (m, 1H), 6.08 (d, J=2.6 Hz, 1H), 6.04-5.92 (m, 1H), 3.76 (s, 3H), 3.68-3.56 (m, 1H), 3.20-3.02 (m, 1H), 2.49-2.31 (m, 3H), 1.17 (s, 9H).

Preparation 3G: (R)—N-((3R)-3-(2-bromo-6-chloro-3-methylphenyl)-1-cyano-3-((5-methoxy-2-nitrophenyl)amino) propyl)-2-methylpropane-2-sulfinamide A mixture of (R)—N—((R,E)-3-(2-bromo-6-chloro-3-methylphenyl)-3-((5-methoxy-2-nitrophenyl)amino)propylidene)-2-methylpropane-2-sulfinamide (22.50 g, 42.384 mmol), TMSCN (8.41 g, 84.768 mmol) and CsF (12.88 g, 84.768 mmol) in DCM (225 mL) was stirred for 16 h at room temperature. The reaction was quenched with sat. $NaHCO_3$ (aq.) at room temperature. The resulting mixture was extracted with $CH_2Cl_2$ (3×300 mL). The combined organic layers were washed with brine (3×500 mL), dried over anhydrous $Na_2SO_4$. After filtration, the filtrate was concentrated under reduced pressure. The residue was purified by silica gel column chromatography, eluted with $CH_2Cl_2$/MeOH (12/1) to afford (R)—N-[(3R)-3-(2-bromo-6-chloro-3-methylphenyl)-1-cyano-3-[(5-methoxy-2-nitrophenyl)amino]propyl]-2-methylpropane-2-sulfinamide (20.50 g, 87%). MS ESI calculated for $C_{22}H_{26}BrClN_4O_4S$ $[M+H]^+$, 557.05 559.05 found 557.20 559.20.

Preparation 3H: (1R,3R)-1-(2-bromo-6-chloro-3-methylphenyl)-7-methoxy-2,3-dihydro-1H-benzo[d]pyrrolo[1,2-a]imidazol-3-amine To a stirred solution of (R)—N-[(3R)-3-(2-bromo-6-chloro-3-methylphenyl)-1-cyano-3-[(5-methoxy-2-nitrophenyl)amino]propyl]-2-methylpropane-2-sulfinamide (20.50 g, 36.746 mmol) in EtOH (150 mL) was added $TiCl_3$ (259.06 g, 293.968 mmol, 17.5%) in EtOH (300 mL) dropwise at room temperature. The resulting mixture was stirred at 80° C. for 3 h. The mixture was allowed to cool down to room temperature. The resulting mixture was concentrated under vacuum. The residue was basified to pH 9 with saturated $NaHCO_3$ (aq.). The resulting mixture was extracted with EtOAc (3×500 mL). The combined organic layers were washed with brine (3×500 mL), dried over anhydrous $Na_2SO_4$. After filtration, the filtrate was concentrated under reduced pressure. The residue was purified by silica gel column chromatography, eluted with $CH_2Cl_2$/MeOH (12/1) to afford (1R,3R)-1-(2-bromo-6-chloro-3-methylphenyl)-7-methoxy-2,3-dihydro-1H-benzo[d]pyrrolo[1,2-a]imidazol-3-amine (11.10 g, 74%). MS ESI calculated for $C_{18}H_{17}BrClN_3O$ $[M+H]^+$, 406.02 408.02 found 406.15 408.15.

Preparation 31: (7R,14R)-1-chloro-11-methoxy-4-methyl-6,7-dihydro-7,14-methanobenzo[f]benzo[4,5]imidazo[1,2-a][1,4]diazocin-5(14H)-one To a solution of (1R,3R)-1-(2-bromo-6-chloro-3-methylphenyl)-7-methoxy-2,3-dihydro-1H-benzo[d]pyrrolo[1,2-a]imidazol-3-amine (4.00 g, 9.835 mmol), $PCy_3 \cdot HBF_4$ (0.72 g, 1.967 mmol) and $K_2CO_3$ (5.44 g, 39.340 mmol) in 1,4-dioxane (300 mL) was added $Pd(OAc)_2$ (221 mg, 0.984 mmol) in a pressure tank. The mixture was purged with nitrogen for 2 min and then was pressurized to 10 atm. with carbon monoxide at 140° C. for 24 h. The reaction mixture was cooled to room temperature and filtered to remove insoluble solids. The resulting mixture was extracted with $CH_2Cl_2$ (3×300 mL). The combined organic layers were washed with brine (3×500 mL), dried over anhydrous $Na_2SO_4$. After filtration, the filtrate was concentrated under reduced pressure. The residue was purified by silica gel column chromatography, eluted with PE/EA/EtOH (4/3/1) followed by reversed-phase flash chromatography with the following conditions: column, C18 silica gel; mobile phase, $CH_3CN$ in Water (10 mmol/L $NH_4HCO_3$), 30% to 70% gradient in 20 min; detector, 254 nm. The fractions containing the desired product were collected at 56% B and concentrated under reduced pressure to afford (7R,14R)-1-chloro-11-methoxy-4-methyl-6,7-dihydro-7,14-methanobenzo[f]benzo[4,5]imidazo[1,2-a][1,4]diazocin-5(14H)-one (400 mg, 12%). MS ESI calculated for $C_{19}H_{16}ClN_3O_2$ [M+H]$^+$, 354.09 found 354.15. $^1$H NMR (400 MHz, Chloroform-d) δ 7.63-7.55 (m, 1H), 7.47-7.40 (m, 1H), 7.22-7.16 (m, 1H), 7.05 (t, J=2.0 Hz, 1H), 6.89-6.84 (m, 1H), 6.81-6.70 (m, 1H), 6.37-6.29 (m, 1H), 4.77 (t, J=5.4 Hz, 1H), 3.83 (d, J=1.6 Hz, 3H), 3.42-3.30 (m, 1H), 2.87-2.77 (m, 1H), 2.43 (s, 3H).

Preparation 3J: (7R,14R)-1-chloro-11-methoxy-4-methyl-6-(methyl-d3)-6,7-dihydro-7,14-methanobenzo[f]benzo[4,5]imidazo[1,2-a][1,4]diazocin-5(14H)-one To a stirred solution of (7R,14R)-1-chloro-11-methoxy-4-methyl-6,7-dihydro-7,14-methanobenzo[f]benzo[4,5]imidazo[1,2-a][1,4]diazocin-5(14H)-one (580 mg, 1.639 mmol) in THF (12 mL) was added KHMDS (2 mL, 2.131 mmol) dropwise at −78° C. under nitrogen atmosphere. The resulting mixture was stirred at −78° C. for 1 h under nitrogen atmosphere. To the above mixture was added $CD_3I$ (309 mg, 2.131 mmol) dropwise at −78° C. The resulting mixture was stirred at room temperature for additional 2 h. The reaction was quenched with sat. $NH_4Cl$ (aq.) at 0° C. The resulting mixture was extracted with EtOAc (3×20 mL). The combined organic layers were washed with brine (3×50 mL), dried over anhydrous $Na_2SO_4$. After filtration, the filtrate was concentrated under reduced pressure. The residue was purified by silica gel column chromatography, eluted with $CH_2Cl_2$/MeOH (10/1) to afford (7R,14R)-1-chloro-11-methoxy-4-methyl-6-(methyl-d3)-6,7-dihydro-7,14-methanobenzo[f]benzo[4,5]imidazo[1,2-a][1,4]diazocin-5(14H)-one (550 mg, 90%). MS ESI calculated for $C_{20}H_{15}D_3ClN_3O_2$ [M+H]$^+$, 371.13 found 371.15. $^1$H NMR (400 MHz, Chloroform-d) δ 7.59 (d, J=8.9 Hz, 1H), 7.36 (d, J=8.3 Hz, 1H), 7.17 (d, J=8.2 Hz, 1H), 7.03 (d, J=2.5 Hz, 1H), 6.91-6.82 (m, 1H), 6.19 (d, J=7.5 Hz, 1H), 4.74 (d, J=6.6 Hz, 1H), 3.82 (s, 3H), 3.44-3.29 (m, 1H), 2.81 (d, J=13.4 Hz, 1H), 2.38 (s, 3H).

Preparation 3K: (7R,14R)-1-chloro-11-hydroxy-4-methyl-6-(methyl-d3)-6,7-dihydro-7,14-methanobenzo[f]benzo[4,5]imidazo[1,2-a][1,4]diazocin-5(14H)-one To a stirred solution of (7R,14R)-1-chloro-11-methoxy-4-methyl-6-(methyl-d3)-6,7-dihydro-7,14-methanobenzo[f]benzo[4,5]imidazo[1,2-a][1,4]diazocin-5(14H)-one (500 mg, 1.348 mmol) in DCM (10 mL) was added $BBr_3$ (4 mL, 4.044 mmol) dropwise at 0° C. under nitrogen atmosphere. The resulting mixture was stirred at room temperature for 1 h under nitrogen atmosphere. The reaction was quenched with MeOH at 0° C. The resulting mixture was concentrated under vacuum. The residue was purified by reversed-phase flash chromatography with the following conditions: column, C18 silica gel; mobile phase, $CH_3CN$ in Water (10 mmol/L $NH_4HCO_3$), 20% to 50% gradient in 20 min; detector, 254 nm. The fractions containing the desired product were collected at 34% B and concentrated under reduced pressure to afford (7R,14R)-1-chloro-11-hydroxy-4-methyl-6-(methyl-d3)-6,7-dihydro-7,14-methanobenzo[f]benzo[4,5]imidazo[1,2-a][1,4]diazocin-5(14H)-one (425 mg, 88%). MS ESI calculated for $C_{19}H_{13}D_3ClN_3O_2$ [M+H]$^+$, 357.11 found 357.20. $^1$H NMR (400 MHz, DMSO-$d_6$) δ 9.36 (s, 1H), 7.53 (d, J=8.3 Hz, 1H), 7.41 (d, J=8.7 Hz, 1H), 7.29 (d, J=8.3 Hz, 1H), 6.84 (d, J=2.3 Hz, 1H), 6.69-6.56 (m, 1H), 6.12 (d, J=7.4 Hz, 1H), 4.94 (d, J=6.5 Hz, 1H), 3.48-3.37 (m, 1H), 2.66 (d, J=13.7 Hz, 1H), 2.23 (s, 3H).

Preparation 3L: (7R,14R)-1-chloro-4-methyl-6-(methyl-d3)-5-oxo-5,6,7,14-tetrahydro-7,14-methanobenzo[f]benzo[4,5]imidazo[1,2-a][1,4]diazocin-11-yl trifluoromethanesulfonate To a stirred solution of (7R,14R)-1-chloro-11-hydroxy-4-methyl-6-(methyl-d3)-6,7-dihydro-7,14-methanobenzo[f]benzo[4,5]imidazo[1,2-a][1,4]diazocin-5(14H)-one (400 mg, 1.121 mmol) and 1,1,1-trifluoro-N-phenyl-N-(trifluoromethane) sulfonylmethanesulfonamide (641 mg, 1.794 mmol) in DCM (10 mL) were added DMAP (14 mg, 0.112 mmol) and TEA (227 mg, 2.242 mmol) at room temperature. The resulting mixture was stirred at room temperature for 1 h. The resulting mixture was concentrated under vacuum. The residue was purified by silica gel column chromatography, eluted with $CH_2Cl_2$/MeOH (15/1) to afford (7R,14R)-1-chloro-4-methyl-6-(methyl-d3)-5-oxo-5,6,7,14-tetrahydro-7,14-methanobenzo[f]benzo[4,5]imidazo[1,2-a][1,4]diazocin-11-yl trifluoromethanesulfonate (504 mg, 92%). MS ESI calculated for $C_{20}H_{12}D3ClF_3N_3O_4S$ [M+H]$^+$, 489.06 found 489.15. $^1$H NMR (400 MHz, Chloroform-d) δ 7.75 (d, J=8.9 Hz, 1H), 7.50 (d, J=2.2 Hz, 1H), 7.40 (d, J=8.3 Hz, 1H), 7.20 (d, J=8.3 Hz, 1H), 7.18-7.13 (m, 1H), 6.28 (d, J=7.5 Hz, 1H), 4.81 (d, J=6.7 Hz, 1H), 3.45-3.36 (m, 1H), 2.87 (d, J=13.6 Hz, 1H), 2.39 (s, 3H).

Example 3: (7R,14R)-1-chloro-11-(4-(dimethylphosphoryl)-3-fluorophenyl)-4-methyl-6-(methyl-d3)-6,7-dihydro-7,14-methanobenzo[f]benzo[4,5]imidazo[1,2-a][1,4]diazocin-5(14H)-one

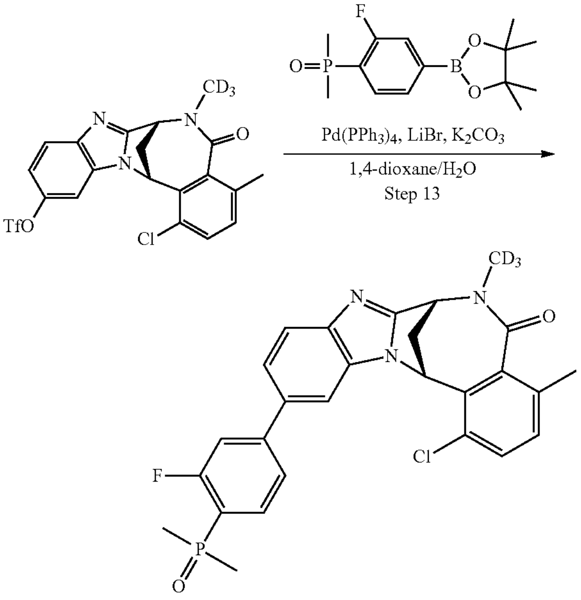

To a stirred solution of (7R,14R)-1-chloro-4-methyl-6-(methyl-d3)-5-oxo-5,6,7,14-tetrahydro-7,14-methanobenzo[f]benzo[4,5]imidazo[1,2-a][1,4]diazocin-11-yl trifluoromethanesulfonate (60 mg, 0.123 mmol) and 2-[4-(dimethylphosphoryl)-3-fluorophenyl]-4,4,5,5-tetramethyl-1,3,2-dioxaborolane (44 mg, 0.148 mmol) in 1,4-dioxane (1 mL) and $H_2O$ (0.2 mL) were added $Pd(PPh_3)_4$ (14 mg, 0.012 mmol), LiBr (1 mg, 0.012 mmol) and $K_2CO_3$ (34 mg, 0.246 mmol) at room temperature under nitrogen atmosphere. The resulting mixture was stirred at 100° C. for 1 h under nitrogen atmosphere. The mixture was allowed to cool down to room temperature. The resulting mixture was concentrated under vacuum. The residue was purified by silica gel column chromatography, eluted with $CH_2Cl_2$/MeOH (10/1) followed by reversed-phase flash chromatography with the following conditions: column, C18 silica gel; mobile phase, $CH_3CN$ in water (10 mmol/L $NH_4HCO_3$), 30% to 70% gradient in 20 min; detector, 254 nm. This resulted in (7R,14R)-1-chloro-11-(4-(dimethylphosphoryl)-3-fluorophenyl)-4-methyl-6-(methyl-d3)-6,7-dihydro-7,14-methanobenzo[f]benzo[4,5]imidazo[1,2-a][1,4]diazocin-5(14H)-one (31 mg, 50%). MS ESI calculated for $C_{27}H_{21}D_3ClFN_3O_2P$ $[M+H]^+$, 511.15 found 511.25. $^1H$ NMR (400 MHz, Chloroform-d) δ 8.07-7.96 (m, 1H), 7.81 (d, J=8.5 Hz, 1H), 7.74 (d, J=1.7 Hz, 1H), 7.58-7.52 (m, 1H), 7.52-7.45 (m, 1H), 7.40 (d, J=8.3 Hz, 1H), 7.36-7.27 (m, 1H), 7.20 (d, J=8.3 Hz, 1H), 6.32 (d, J=7.4 Hz, 1H), 4.84 (d, J=6.6 Hz, 1H), 3.49-3.37 (m, 1H), 2.88 (d, J=13.5 Hz, 1H), 2.39 (s, 3H), 1.85 (d, J=1.1 Hz, 3H), 1.82 (d, J=1.2 Hz, 3H). $^{19}F$ NMR (377 MHz, Chloroform-d) δ −105.76. $^{31}P$ NMR (162 MHz, Chloroform-d) δ 30.37.

Example 4: (7R,14R)-1-chloro-11-(2-(dimethylphosphoryl)pyrimidin-5-yl)-6,7-dihydro-7,14-methanobenzo[f]benzo[4,5]imidazo[1,2-a][1,4]diazocin-5(14H)-one

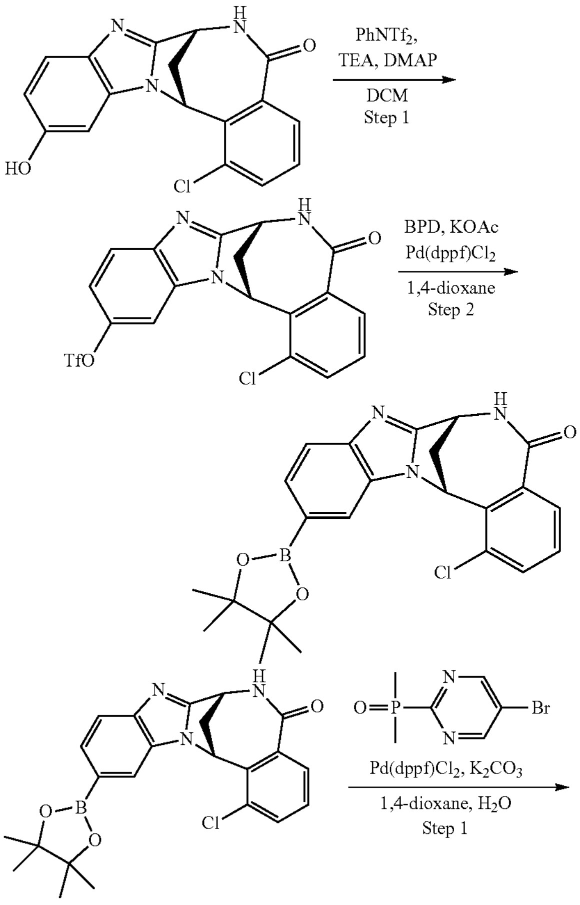

-continued

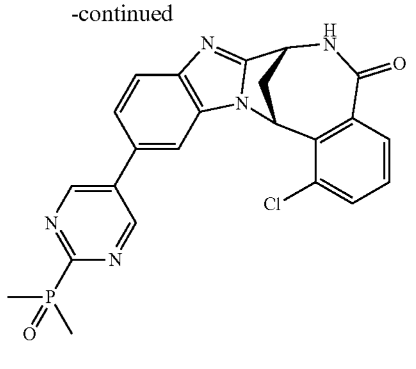

Preparation 4A: (7R,14R)-1-chloro-5-oxo-5,6,7,14-tetrahydro-7,14-methanobenzo[f]benzo[4,5]imidazo[1,2-a][1,4]diazocin-11-yl trifluoromethanesulfonate To a stirred solution of (7R,14R)-1-chloro-11-hydroxy-6,7-dihydro-7,14-methanobenzo[f]benzo[4,5]imidazo[1,2-a][1,4]diazocin-5(14H)-one (500 mg, 1.535 mmol) and 1,1,1-trifluoro-N-phenyl-N-(trifluoromethane)sulfonylmethanesulfonamide (1.37 g, 3.837 mmol), DMAP (19 mg, 0.153 mmol) in DCM (30 mL) was added $Et_3N$ (0.7 mL, 5.372 mmol) dropwise at room temperature. The resulting mixture was stirred at room temperature for additional 1 h. The resulting mixture was concentrated under reduced pressure. The residue was purified by silica gel column chromatography, eluted with $CH_2Cl_2$/MeOH (12:1) to afford (7R,14R)-1-chloro-5-oxo-5,6,7,14-tetrahydro-7,14-methanobenzo[f]benzo[4,5]imidazo[1,2-a][1,4]diazocin-11-yl trifluoromethanesulfonate (230 mg, 30%). MS ESI calculated for $C_{18}H_{11}ClF_3N_3O_4S$ $[M+H]^+$, 458.01 found 458.10. $^1H$ NMR (400 MHz, Chloroform-d) 8.59-8.45 (m, 1H), 7.76 (d, J=8.9 Hz, 1H), 7.72-7.67 (m, 1H), 7.60 (d, J=2.4 Hz, 1H), 7.50 (t, J=6.2 Hz, 1H), 7.45-7.29 (m, 1H), 7.20-7.11 (m, 1H), 6.55 (d, J=7.3 Hz, 1H), 4.98 (t, J=6.6 Hz, 1H), 3.56-3.41 (m, 1H), 2.91 (d, J=13.5 Hz, 1H).

Preparation 4B: (7R,14R)-1-chloro-11-(4,4,5,5-tetramethyl-1,3,2-dioxaborolan-2-yl)-6,7-dihydro-7,14-methanobenzo[f]benzo[4,5]imidazo[1,2-a][1,4]diazocin-5(14H)-one To a stirred solution of (7R,14R)-1-chloro-5-oxo-5,6,7,14-tetrahydro-7,14-methanobenzo[f]benzo[4,5]imidazo[1,2-a][1,4]diazocin-11-yl trifluoromethanesulfonate (150 mg, 0.328 mmol) and 4,4,5,5-tetramethyl-2-(tetramethyl-1,3,2-dioxaborolan-2-yl)-1,3,2-dioxaborolane (100 mg, 0.394 mmol) in 1,4-dioxane (2 mL) were added KOAc (97 mg, 0.984 mmol) and $Pd(dppf)Cl_2{\cdot}CH_2Cl_2$ (27 mg, 0.033 mmol) at room temperature under nitrogen atmosphere. The resulting mixture was stirred at room temperature for 1 h under nitrogen atmosphere. The resulting mixture was concentrated under reduced pressure. The residue was purified by silica gel column chromatography, eluted with $CH_2Cl_2$/MeOH (10:1) to afford (7R,14R)-1-chloro-11-(4,4,5,5-tetramethyl-1,3,2-dioxaborolan-2-yl)-6,7-dihydro-7,14-methanobenzo[f]benzo[4,5]imidazo[1,2-a][1,4]diazocin-5(14H)-one (130 mg, 91%). MS ESI calculated for $C_{23}H_{23}BClN_3O_3$ $[M+H]^+$, 436.15 found 436.05.

Example 4: (7R,14R)-1-chloro-11-(2-(dimethylphosphoryl)pyrimidin-5-yl)-6,7-dihydro-7,14-methanobenzo[f]benzo[4,5]imidazo[1,2-a][1,4]diazocin-5(14H)-one To a stirred mixture of (7R,14R)-1-chloro-11-(4,4,5,5-tetramethyl-1,3,2-dioxaborolan-2-yl)-6,7-dihydro-7,14- methanobenzo[f]benzo[4,5]imidazo[1,2-a][1,4]diazocin-5(14H)-one (40 mg, 0.092 mmol) and 5-bromo-2-(dimethylphosphoryl)pyrimidine (32 mg, 0.138 mmol), $K_2CO_3$ (38 mg, 0.276 mmol) in 1,4-dioxane (1 mL) and $H_2O$ (0.2 mL) was added $Pd(dppf)Cl_2{\cdot}CH_2Cl_2$ (7 mg, 0.009 mmol) at room temperature under nitrogen atmosphere. The resulting mixture was stirred at 80° C. for additional 2 h. The resulting mixture was concentrated under reduced pressure. The residue was purified by silica gel column chromatography, eluted with $CH_2Cl_2$/MeOH (10/1) followed by reversed-phase flash chromatography with the following conditions: column, C18 silica gel; mobile phase, $CH_3CN$ in Water (10 mmol/L $NH_4HCO_3$), 40% to 50% gradient in 10 min; detector, 254 nm. This resulted in (7R,14R)-1-chloro-11-(2-(dimethylphosphoryl)pyrimidin-5-yl)-6,7-dihydro-7,14-methanobenzo[f]benzo[4,5]imidazo[1,2-a][1,4]diazocin-5(14H)-one (30 mg, 70%). MS ESI calculated for $C_{23}H_{19}ClN_5O_2P$ $[M+H]^+$, 464.10 found 463.95. $^1H$ NMR (400 MHz, Chloroform-d) δ 9.09 (s, 2H), 8.58-8.51 (m, 1H), 7.97-7.90 (m, 2H), 7.73-7.66 (m, 1H), 7.60-7.53 (m, 1H), 7.43 (t, J=8.1 Hz, 1H), 7.34 (d, J=6.4 Hz, 1H), 6.66 (d, J=7.3 Hz, 1H), 5.19 (t, J=6.5 Hz, 1H), 3.64-3.52 (m, 1H), 2.97 (d, J=13.5 Hz, 1H), 1.95 (s, 3H), 1.91 (s, 3H). $^{31}P$ NMR (162 MHz, Chloroform-d) δ 34.40.

Example 5: (7R,14R)-1-chloro-11-(6-(dimethylphosphoryl)pyridin-3-yl)-6,7-dihydro-7,14-methanobenzo[f]benzo[4,5]imidazo[1,2-a][1,4]diazocin-5(14H)-one

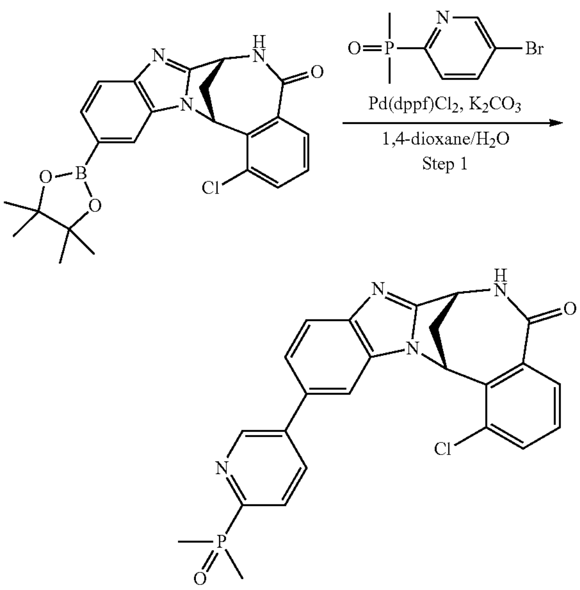

To a stirred mixture of (7R,14R)-1-chloro-11-(4,4,5,5-tetramethyl-1,3,2-dioxaborolan-2-yl)-6,7-dihydro-7,14-methanobenzo[f]benzo[4,5]imidazo[1,2-a][1,4]diazocin-5(14H)-one (40 mg, 0.092 mmol) and 5-bromo-2-(dimethylphosphoryl)pyridine (323 mg, 0.138 mmol), $K_2CO_3$ (38 mg, 0.276 mmol) in 1,4-dioxane (1 mL) and $H_2O$ (0.2 mL) was added $Pd(dppf)Cl_2{\cdot}CH_2Cl_2$ (7 mg, 0.009 mmol) at room temperature under nitrogen atmosphere. The resulting mixture was stirred at 80° C. for additional 2 h. The resulting mixture was concentrated under reduced pressure and purified by silica gel column chromatography, eluted with $CH_2Cl_2$/MeOH (10/1) followed by reversed-phase flash chromatography with the following conditions: column, C18 silica gel; mobile phase, $CH_3CN$ in Water (10 mmol/L $NH_4HCO_3$), 40% to 50% gradient in 10 min; detector, 254 nm. This resulted in (7R,14R)-1-chloro-11-(6-(dimethylphosphoryl)pyridin-3-yl)-6,7-dihydro-7,14-methanobenzo[f]benzo[4,5]imidazo[1,2-a][1,4]diazocin-5(14H)-one (20 mg, 50%). MS ESI calculated for $C_{24}H_{20}ClN_4O_2P$ $[M+H]^+$, 463.10 found 462.95. $^1H$ NMR (400 MHz, Chloroform-d) δ 8.94 (d, J=2.2 Hz, 1H), 8.61-8.52 (m, 1H), 8.34-8.19 (m, 1H), 8.09-7.94 (m, 3H), 7.78-7.67 (m, 2H), 7.60 (d, J=6.3 Hz, 1H), 7.46 (t, J=8.1 Hz, 1H), 6.75 (d, J=7.3 Hz, 1H), 5.57 (t, J=6.6 Hz, 1H), 3.73-3.62 (m, 1H), 3.02 (d, J=13.6 Hz, 1H), 1.86 (s, 3H), 1.82 (s, 3H). $^{31}P$ NMR (162 MHz, Chloroform-d) δ 36.16.

Example 6: (7R,14R)-1-chloro-11-(6-(dimethylphosphoryl)pyridin-3-yl)-4-methyl-6-(methyl-$d_3$)-6,7-dihydro-7,14-methanobenzo[f]benzo[4,5]imidazo[1,2-a][1,4]diazocin-5(14H)-one

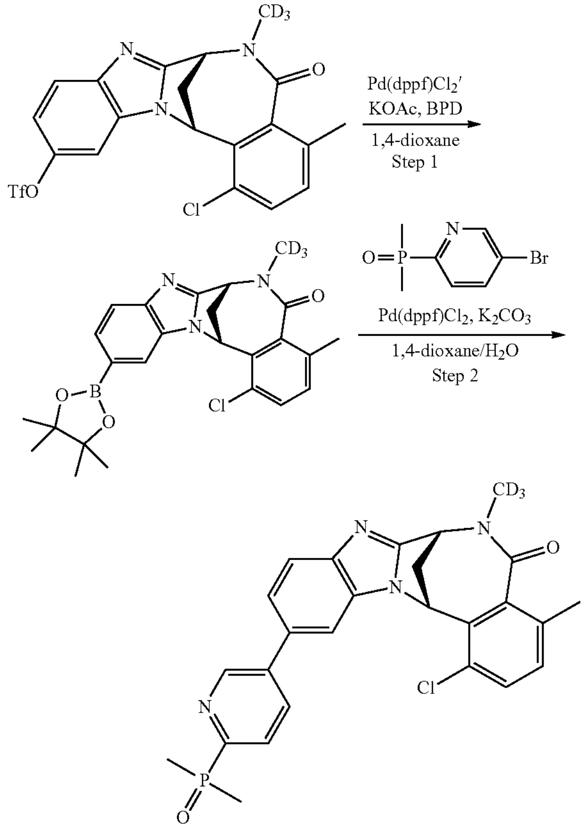

Preparation 6A: (7R,14R)-1-chloro-4-methyl-6-(methyl-$d_3$)-11-(4,4,5,5-tetramethyl-1,3,2-dioxaborolan-2-yl)-6,7-dihydro-7,14-methanobenzo[f]benzo[4,5]imidazo[1,2-a][1,4]diazocin-5(14H)-one To a stirred solution of (7R,14R)-1-chloro-4-methyl-6-(methyl-$d_3$)-5-oxo-5,6,7,14-tetrahydro-7,14-methanobenzo[f]benzo[4,5]imidazo[1,2-a][1,4]diazocin-11-yl trifluoromethanesulfonate (50 mg, 0.102 mmol) and BPD (39 mg, 0.153 mmol) in 1,4-dioxane (1.5 mL) were added Pd(dppf)

$Cl_2 \cdot CH_2Cl_2$ (7 mg, 0.010 mmol) and KOAc (30 mg, 0.306 mmol) at room temperature. The resulting mixture was stirred at 100° C. for 2 h under nitrogen atmosphere. The resulting mixture was concentrated under reduced pressure. The residue was purified by silica gel column chromatography, eluted with $CH_2Cl_2$/MeOH (10:1) to afford (7R,14R)-1-chloro-4-methyl-6-(methyl-$d_3$)-11-(4,4,5,5-tetramethyl-1,3,2-dioxaborolan-2-yl)-6,7-dihydro-7,14-methanobenzo[f]benzo[4,5]imidazo[1,2-a][1,4]diazocin-5(14H)-one (40 mg, 80%). MS ESI calculated for $C_{25}H_{24}D_3BClN_3O_3$ $[M+H]^+$, 467.20 found 467.20. $^1H$ NMR (400 MHz, Chloroform-d) δ 7.99 (s, 1H), 7.73 (d, J=3.0 Hz, 2H), 7.39 (d, J=8.3 Hz, 1H), 7.18 (d, J=8.3 Hz, 1H), 6.32 (d, J=6.9 Hz, 1H), 4.92-4.83 (m, 1H), 3.70 (s, 3H), 3.44-3.32 (m, 1H), 2.84 (d, J=13.2 Hz, 1H), 1.34 (s, 12H).

Example 6: (7R,14R)-1-chloro-11-(6-(dimethylphosphoryl)pyridin-3-yl)-4-methyl-6-(methyl-$d_3$)-6,7-dihydro-7,14-methanobenzo[f]benzo[4,5]imidazo[1,2-a][1,4]diazocin-5(14H)-one To a stirred solution of (7R,14R)-1-chloro-4-methyl-6-(methyl-$d_3$)-11-(4,4,5,5-tetramethyl-1,3,2-dioxaborolan-2-yl)-6,7-dihydro-7,14-methanobenzo[f]benzo[4,5]imidazo[1,2-a][1,4]diazocin-5(14H)-one (35 mg, 0.075 mmol) and 5-bromo-2-(dimethylphosphoryl)pyridine (19 mg, 0.083 mmol) in 1,4-dioxane (1 mL) and $H_2O$ (0.2 mL) were added Pd(dppf)$Cl_2 \cdot CH_2Cl_2$ (6 mg, 0.007 mmol) and $K_2CO_3$ (31 mg, 0.225 mmol) at room temperature. The resulting mixture was stirred at 80° C. for 2 h under nitrogen atmosphere. The resulting mixture was concentrated under reduced pressure and purified by reverse phase flash with the following conditions (Column: YMC-Actus Triart C18 ExRS 30*150 mm, 5 m; Mobile Phase A: 10 mmol $NH_4HCO_3$+0.05% $NH_3H_2O$, Mobile Phase B: MeOH; Flow rate: 60 mL/min; Gradient: isocratic 45% B to 59% B; Wave Length: 254 nm; RT1 (min): 11.08) to afford (7R,14R)-1-chloro-11-(6-(dimethylphosphoryl)pyridin-3-yl)-4-methyl-6-(methyl-$d_3$)-6,7-dihydro-7,14-methanobenzo[f]benzo[4,5]imidazo[1,2-a][1,4]diazocin-5(14H)-one (3 mg, 4%). MS ESI calculated for $C_{26}H_{21}D_3ClN_4O_2P$ $[M+H]^+$, 494.15 found 494.15. $^1H$ NMR (400 MHz, Chloroform-d) 8.95 (d, J=2.2 Hz, 1H), 8.23-8.12 (m, 1H), 8.07-8.00 (m, 1H), 7.84 (d, J=8.5 Hz, 1H), 7.76 (d, J=1.7 Hz, 1H), 7.53-7.45 (m, 1H), 7.39 (d, J=8.3 Hz, 1H), 7.20 (d, J=8.4 Hz, 1H), 6.32 (d, J=7.5 Hz, 1H), 4.83 (d, J=6.6 Hz, 1H), 3.49-3.38 (m, 1H), 2.88 (d, J=13.5 Hz, 1H), 2.39 (s, 3H), 1.84 (s, 3H), 1.80 (s, 3H). $^{31}P$ NMR (162 MHz, Chloroform-d) δ 36.76.

Example 7: (7R,14R)-1-chloro-11-(4-(dimethylphosphoryl)phenyl)-6-(methyl-d3)-6,7-dihydro-7,14-methanobenzo[f]benzo[4,5]imidazo[1,2-a][1,4]diazocin-5(14H)-one To a stirred mixture of (7R,14R)-1-chloro-6-(methyl-d3)-5-oxo-5,6,7,14-tetrahydro-7,14-methanobenzo[f]benzo[4,5]imidazo[1,2-a][1,4]diazocin-11-yl trifluoromethanesulfonate (40 mg, 0.084 mmol) and 2-[4-(dimethylphosphoryl)phenyl]-4,4,5,5-tetramethyl-1,3,2-dioxaborolane (28 mg, 0.101 mmol) in 1,4-dioxane (1 mL) and $H_2O$ (0.1 mL) were added Pd(dppf)$Cl_2$ (6 mg, 0.008 mmol) and $K_2CO_3$ (34 mg, 0.252 mmol) at room temperature under nitrogen atmosphere. The resulting mixture was stirred at 80° C. for 2 h under nitrogen atmosphere. The resulting mixture was concentrated under reduced pressure and purified by reversed-phase flash chromatography with the following conditions: column, C18 silica gel; mobile phase, $CH_3CN$ in Water (10 mmol/L $NH_4HCO_3$), 30% to 50% gradient in 15 min; detector, 254 nm. This resulted in (7R,14R)-1-chloro-11-(4-(dimethylphosphoryl)phenyl)-6-(methyl-d3)-6,7-dihydro-7,14-methanobenzo[f]benzo[4,5]imidazo[1,2-a][1,4]diazocin-5(14H)-one (20 mg, 50%). MS ESI calculated for $C_{26}H_{20}D_3ClN_3O_2P$ $[M+H]^+$, 479.14 found 479.15. $^1H$ NMR (400 MHz, DMSO-$d_6$) δ 8.43-8.33 (m, 1H), 7.90-7.82 (m, 3H), 7.80-7.71 (m, 4H), 7.57-7.53 (m, 1H), 7.46 (t, J=8.1 Hz, 1H), 6.49 (d, J=7.2 Hz, 1H), 5.25 (d, J=7.1 Hz, 1H), 3.63-3.47 (m, 1H), 2.89 (d, J=13.8 Hz, 1H), 1.70 (s, 3H), 1.66 (s, 3H). $^{31}P$ NMR (162 MHz, DMSO-$d_6$) δ 32.37.

Example 8: (7R,14R)-1-chloro-11-(4-(dimethylphosphoryl)-2-fluorophenyl)-6-(methyl-d3)-6,7-dihydro-7,14-methanobenzo[f]benzo[4,5]imidazo[1,2-a][1,4]diazocin-5(14H)-one To a solution of (7R,14R)-1-chloro-6-(methyl-d3)-5-oxo-5,6,7,14-tetrahydro-7,14-methanobenzo[f]benzo[4,5]imidazo[1,2-a][1,4]diazocin-11-yl trifluoromethanesulfonate (50 mg, 0.105 mmol) in 1,4-dioxane/$H_2O$ (5/1, 1.2 mL) were added 2-[4-(dimethylphosphoryl)-2-fluorophenyl]-4,4,5,5-tetramethyl-1,3,2-dioxaborolane (38 mg, 0.126 mmol), $Pd(PPh_3)_4$ (12 mg, 0.011 mmol) and $K_2CO_3$ (44 mg, 0.315 mmol). The resulting mixture was stirred at 80° C. for 2 h under nitrogen atmosphere. The resulting mixture was concentrated under reduced pressure. The residue was purified by silica gel column chromatography, eluted with $CH_2Cl_2$/MeOH (12/1) followed by reversed-phase flash chromatography with the following conditions: column, C18 silica gel; mobile phase, $CH_3CN$ in Water (10 mmol/L $NH_4HCO_3$), 40% to 50% gradient in 10 min; detector, 254 nm. This resulted in (7R,14R)-1-chloro-11-(4-(dimethylphosphoryl)-2-fluorophenyl)-6-(methyl-d3)-6,7-dihydro-7,14-methanobenzo[f]benzo[4,5]imidazo[1,2-a][1,4]diazocin-5(14H)-one (21 mg, 40%). MS ESI calculated for $C_{26}H_{19}D_3ClFN_3O_2P$ $[M+H]^+$, 497.13 found 497.00. $^1H$ NMR (400 MHz, DMSO-$d_6$) δ 8.46-8.35 (m, 1H), 7.81 (d, J=1.9 Hz, 1H), 7.80-7.73 (m, 2H), 7.73-7.64 (m, 3H), 7.50-7.40 (m, 2H), 6.47 (d, J=7.2 Hz, 1H), 5.26 (d, J=7.0 Hz, 1H), 3.62-3.48 (m, 1H), 2.88 (d, J=13.9 Hz, 1H), 1.73 (s, 3H), 1.69 (s, 3H). $^{19}F$ NMR (377 MHz, DMSO-$d_6$) δ −117.81. $^{31}P$ NMR (162 MHz, DMSO-$d_6$) δ 32.00.

Example 9: (7R,14R)-11-(4-(dimethylphosphoryl)-3-fluorophenyl)-1-fluoro-6-(methyl-d3)-6,7-dihydro-7,14-methanobenzo[f]benzo[4,5]imidazo[1,2-a][1,4]diazocin-5(14H)-one

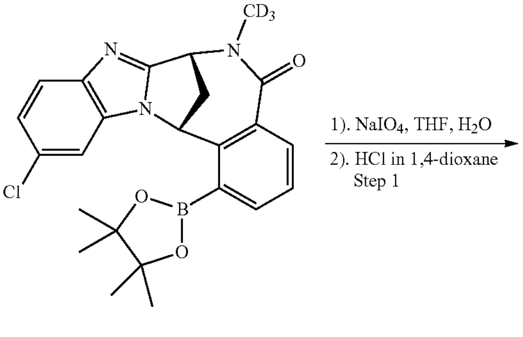

-continued

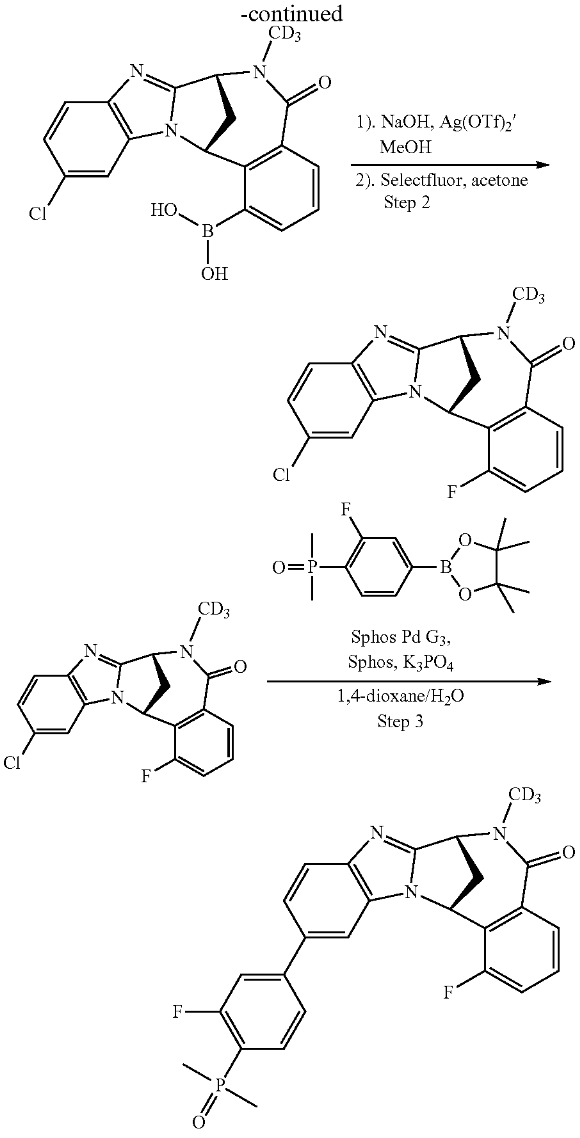

Preparation 9A: ((7R,14R)-11-chloro-6-(methyl-d3)-5-oxo-5,6,7,14-tetrahydro-7,14-methanobenzo[f]benzo[4,5]imidazo[1,2-a][1,4]diazocin-1-yl) boronic acid To a stirred solution of (7R,14R)-11-chloro-6-(methyl-d3)-1-(4,4,5,5-tetramethyl-1,3,2-dioxaborolan-2-yl)-6,7-dihydro-7,14-methanobenzo[f]benzo[4,5]imidazo[1,2-a][1,4]diazocin-5(14H)-one (170 mg, 0.375 mmol) in THF (4 mL) and $H_2O$ (0.8 mL) was added $NaIO_4$ (241 mg, 1.125 mmol) at room temperature. The resulting mixture was stirred at room temperature for 2 h. To the above mixture was added HCl (gas) in 1,4-dioxane (0.3 mL, 0.262 mmol, 4M in THF) dropwise at room temperature. The resulting mixture was stirred at room temperature for additional 4 h. The resulting mixture was filtered, the filter cake was washed with MeOH (3×5 mL). The filtrate was concentrated under reduced pressure. The residue was purified by reversed-phase flash chromatography with the following conditions: column, C18 silica gel; mobile phase, $CH_3CN$ in Water (0.1% FA), 30% to 50% gradient in 10 min; detector, 254 nm. This resulted in ((7R,14R)-11-chloro-6-(methyl-d3)-5-oxo-5,6,7,14-tetrahydro-7,14-methanobenzo[f]benzo[4,5]imidazo[1,2-a][1,4]diazocin-1-yl) boronic acid (108 mg, 72%). MS ESI calculated for $C_{18}H_{12}D_3BClN_3O_3$ $[M+H]^+$, 371.11 found 371.15.

Preparation 9B: (7R,14R)-11-chloro-1-fluoro-6-(methyl-d3)-6,7-dihydro-7,14-methanobenzo[f]benzo[4,5]imidazo[1,2-a][1,4]diazocin-5(14H)-one To a stirred solution of ((7R,14R)-11-chloro-6-(methyl-d3)-5-oxo-5,6,7,14-tetrahydro-7,14-methanobenzo[f]benzo[4,5]imidazo[1,2-a][1,4]diazocin-1-yl) boronic acid (108 mg, 0.291 mmol) in dry methanol (2 mL) was added NaOH (12 mg, 0.291 mmol) at room temperature. The resulting mixture was stirred at room temperature for 15 min. To the above mixture was added $Ag(OTf)_2$ (225 mg, 0.873 mmol) at 0° C. The resulting mixture was stirred at 0° C. for additional 30 min. The resulting mixture was concentrated under reduced pressure. The residue was dissolved in acetone (3 mL) at 0° C. The residue was dissolved in acetone (3 mL). To the above solution was added Selectfluor (103 mg, 0.291 mmol) at room temperature. The resulting mixture was stirred at room temperature for additional 2 h. The residue was purified by reversed-phase flash chromatography with the following conditions: column, C18 silica gel; mobile phase, $CH_3CN$ in water (10 mmol/L $NH_4HCO_3$), 50% to 60% gradient in 10 min; detector, 254 nm to afford (7R,14R)-11-chloro-1-fluoro-6-(methyl-d3)-6,7-dihydro-7,14-methanobenzo[f]benzo[4,5]imidazo[1,2-a][1,4]diazocin-5(14H)-one (32 mg, 32%). MS ESI calculated for $C_{18}H_{10}D_3ClFN_3O$ $[M+H]^+$, 345.09 found 345.10. $^1H$ NMR (400 MHz, DMSO-$d_6$) δ 8.28-8.17 (m, 1H), 7.65 (d, J=8.7 Hz, 1H), 7.60-7.53 (m, 1H), 7.51-7.43 (m, 1H), 7.38 (d, J=2.1 Hz, 1H), 7.25-7.19 (m, 1H), 6.23 (d, J=6.9 Hz, 1H), 5.25 (d, J=7.2 Hz, 1H), 3.54-3.42 (m, 1H), 2.86 (d, J=13.9 Hz, 1H). $^{19}F$ NMR (377 MHz, DMSO-$d_6$) δ −117.47.

Example 9: (7R,14R)-11-(4-(dimethylphosphoryl)-3-fluorophenyl)-1-fluoro-6-(methyl-d3)-6,7-dihydro-7,14-methanobenzo[f]benzo[4,5]imidazo[1,2-a][1,4]diazocin-5(14H)-one To a stirred solution of (7R,14R)-11-chloro-1-fluoro-6-(methyl-d3)-6,7-dihydro-7,14-methanobenzo[f]benzo[4,5]imidazo[1,2-a][1,4]diazocin-5(14H)-one (33 mg, 0.096 mmol) and 2-[4-(dimethylphosphoryl)-3-fluorophenyl]-4,4,5,5-tetramethyl-1,3,2-dioxaborolane (43 mg, 0.144 mmol) in 1,4-dioxane (1 mL) and $H_2O$ (0.2 mL) were added Sphos (4 mg, 0.010 mmol), Sphos Pd G3 (4 mg, 0.005 mmol) and $K_3PO_4$ (41 mg, 0.192 mmol) at room temperature under nitrogen atmosphere. The resulting mixture was stirred at 80° C. for 2 h. The resulting mixture was concentrated under reduce pressure. The residue was purified by silica gel column chromatography, eluted with $CH_2Cl_2$/MeOH (10/1) followed by reversed-phase flash chromatography with the following conditions: column, C18 silica gel; mobile phase, $CH_3CN$ in Water (10 mmol/L $NH_4HCO_3$), 35% to 45% gradient in 10 min; detector, 254 nm. This resulted in (7R,14R)-11-(4-(dimethylphosphoryl)-3-fluorophenyl)-1-fluoro-6-(methyl-d3)-6,7-dihydro-7,14-methanobenzo[f]benzo[4,5]imidazo[1,2-a][1,4]diazocin-5(14H)-one (27 mg, 59%). MS ESI calculated for $C_{26}H_{19}D_3F_2N_3O_2P$ $[M+H]^+$, 481.16 found 481.10. $^1H$ NMR (400 MHz, DMSO-$d_6$) δ 8.28-8.16 (m, 1H), 7.91-7.80 (m, 1H), 7.74 (d, J=8.5 Hz, 1H), 7.69-7.66 (m, 1H), 7.66-7.51 (m, 4H), 7.49-7.41 (m, 1H), 6.28 (d, J=6.8 Hz, 1H), 5.28 (d, J=7.1 Hz, 1H), 3.58-3.42 (m, 1H), 2.89 (d, J=13.8 Hz, 1H), 1.76 (s, 3H), 1.73 (s, 3H). $^{31}P$ NMR (162 MHz, DMSO-$d_6$) δ 28.29. $^{19}F$ NMR (377 MHz, DMSO-$d_6$) δ −105.49, −105.50, −117.28.

Example 10: (7R,14R)-1-chloro-11-(4-(dimethylphosphoryl)-3-fluorophenyl)-6-(ethyl-d5)-6,7-dihydro-7,14-methanobenzo[f]benzo[4,5]imidazo[1,2-a][1,4]diazocin-5(14H)-one Synthetic Scheme

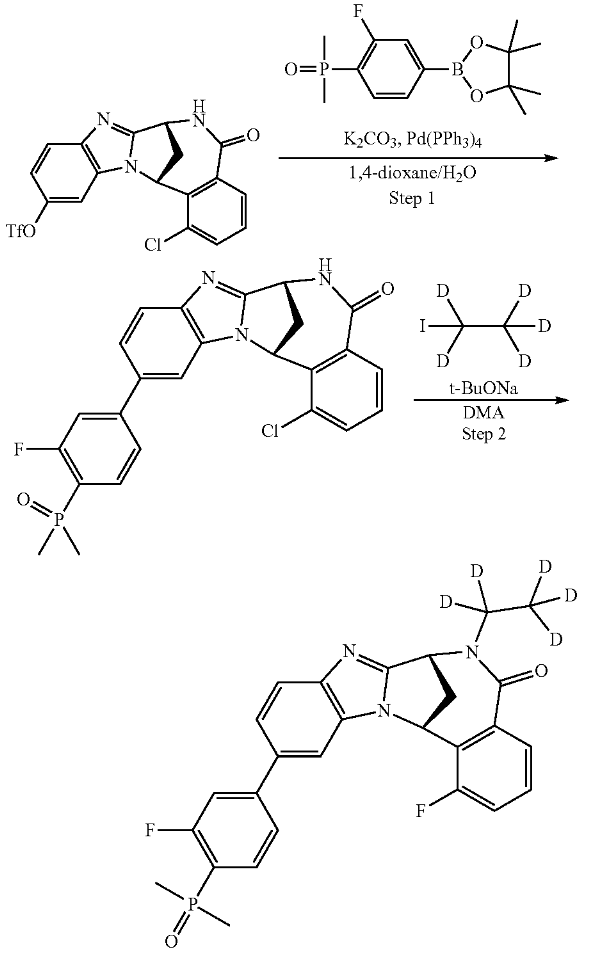

Preparation 10A: (7R,14R)-1-chloro-11-(4-(dimethylphosphoryl)-3-fluorophenyl)-6,7-dihydro-7,14-methanobenzo[f]benzo[4,5]imidazo[1,2-a][1,4]diazocin-5(14H)-one A mixture of (7R,14R)-1-chloro-5-oxo-5,6,7,14-tetrahydro-7,14-methanobenzo[f]benzo[4,5]imidazo[1,2-a][1,4]diazocin-11-yl trifluoromethanesulfonate (300 mg, 0.655 mmol), 2-[4-(dimethylphosphoryl)-3-fluorophenyl]-4,4,5,5-tetramethyl-1,3,2-dioxaborolane (293 mg, 0.983 mmol), $Pd(PPh_3)_4$ (75 mg, 0.066 mmol) and $K_2CO_3$ (181 mg, 1.310 mmol) in 1,4-dioxane (3 mL) and $H_2O$ (0.3 mL) was stirred at 80° C. for 2 h under nitrogen atmosphere. The resulting mixture was concentrated under vacuum and purified by silica gel column chromatography, eluted with $CH_2Cl_2$/MeOH (10:1) to afford (7R,14R)-1-chloro-11-(4-(dimethylphosphoryl)-3-fluorophenyl)-6,7-dihydro-7,14-methanobenzo[f]benzo[4,5]imidazo[1,2-a][1,4]diazocin-5(14H)-one (210 mg, 67%). MS ESI calculated for $C_{25}H_{20}ClFN_3O_2P$ $[M+H]^+$, 480.10 found 480.15. $^1H$ NMR (400 MHz, Chloroform-d) δ 8.53 (d, J=8.1 Hz, 1H), 8.11-7.98 (m, 1H), 7.86 (s, 1H), 7.82 (d, J=8.4 Hz, 1H), 7.68 (d, J=8.0 Hz, 1H), 7.59-7.47 (m, 3H), 7.39 (t, J=8.1 Hz, 1H), 7.36-7.30 (m, 1H), 6.58 (d, J=7.0 Hz, 1H), 5.08-4.93 (m, 1H), 3.60-3.42 (m, 1H), 2.91 (d, J=13.2 Hz, 1H), 1.86 (s, 3H), 1.83 (s, 3H). $^{19}F$ NMR (377 MHz, Chloroform-d) δ −105.68. $^{31}P$ NMR (162 MHz, Chloroform-d) δ 30.45.

Example 10: (7R,14R)-1-chloro-11-(4-(dimethylphosphoryl)-3-fluorophenyl)-6-(ethyl-d5)-6,7-dihydro-7,14-methanobenzo[f]benzo[4,5]imidazo[1,2-a][1,4]diazocin-5(14H)-one To a stirred mixture of (7R,14R)-1-chloro-11-(4-(dimethylphosphoryl)-3-fluorophenyl)-6,7-dihydro-7,14-methanobenzo[f]benzo[4,5]imidazo[1,2-a][1,4]diazocin-5(14H)-one (120 mg, 0.250 mmol) in DMA (2 mL) was added t-BuONa (28 mg, 0.300 mmol) in portions at −10° C. under nitrogen atmosphere. The resulting mixture was stirred at −10° C. for 1 h. The resulting solution was purified by reversed-phase flash chromatography with the following conditions: column, C18 silica gel; mobile phase, $CH_3CN$ in Water (10 mmol/L $NH_4HCO_3$), 20% to 50% gradient in 30 min; detector, 254 nm. This resulted in (7R,14R)-1-chloro-11-(4-(dimethylphosphoryl)-3-fluorophenyl)-6-(ethyl-d5)-6,7-dihydro-7,14-methanobenzo[f]benzo[4,5]imidazo[1,2-a][1,4]diazocin-5(14H)-one (20 mg, 16%). MS ESI calculated for $C_{27}H_{19}D5ClFN_3O_2P$ $[M+H]^+$, 513.16 found 513.20. $^1H$ NMR (400 MHz, Chloroform-d) δ 8.66-8.59 (m, 1H), 8.09-7.97 (m, 1H), 7.91 (d, J=1.7 Hz, 1H), 7.84-7.77 (m, 1H), 7.66-7.59 (m, 1H), 7.59-7.53 (m, 1H), 7.53-7.46 (m, 1H), 7.37 (t, J=8.1 Hz, 1H), 7.35-7.30 (m, 1H), 6.48 (d, J=7.3 Hz, 1H), 5.01 (d, J=7.0 Hz, 1H), 3.57-3.45 (m, 1H), 2.87 (d, J=13.5 Hz, 1H), 1.86 (s, 3H), 1.82 (s, 3H). $^{19}F$ NMR (377 MHz, Chloroform-d) δ −105.71, −105.71. $^{31}P$ NMR (162 MHz, Chloroform-d) δ 30.35.

Example 11: (7R,14R)-1-chloro-11-(4-(dimethylphosphoryl)-3-fluorophenyl)-6-ethyl-6,7-dihydro-7,14-methanobenzo[f]benzo[4,5]imidazo[1,2-a][1,4]diazocin-5(14H)-one

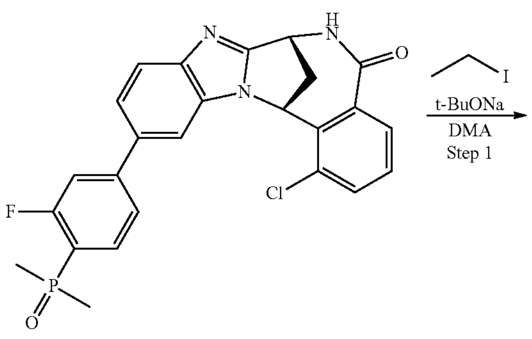

-continued

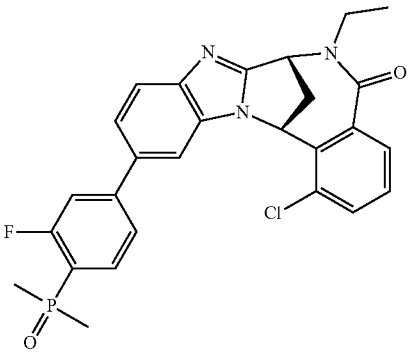

To a stirred mixture of (7R,14R)-1-chloro-11-(4-(dimethylphosphoryl)-3-fluorophenyl)-6,7-dihydro-7,14-methanobenzo[f]benzo[4,5]imidazo[1,2-a][1,4]diazocin-5(14H)-one (50 mg, 0.104 mmol) and t-BuONa (12 mg, 0.125 mmol) in DMA (1 mL) was added ethyl iodide (21 mg, 0.135 mmol) in portions at −10° C. under nitrogen atmosphere. The resulting mixture was stirred at −10° C. for 1 h. The resulting solution was purified by reversed-phase flash chromatography with the following conditions: column, C18 silica gel; mobile phase, $CH_3CN$ in Water (10 mmol/L $NH_4HCO_3$), 20% to 50% gradient in 10 min; detector, 254 nm. This resulted in (7R,14R)-1-chloro-11-(4-(dimethylphosphoryl)-3-fluorophenyl)-6-ethyl-6,7-dihydro-7,14-methanobenzo[f]benzo[4,5]imidazo[1,2-a][1,4]diazocin-5(14H)-one (27 mg, 52%). MS ESI calculated for $C_{27}H_{24}ClFN_3O_2P$ $[M+H]^+$, 508.13 found 508.20. $^1H$ NMR (400 MHz, Chloroform-d) δ 8.68-8.59 (m, 1H), 8.09-7.98 (m, 1H), 7.91 (d, J=1.7 Hz, 1H), 7.81 (d, J=8.5 Hz, 1H), 7.66-7.60 (m, 1H), 7.59-7.52 (m, 1H), 7.52-7.47 (m, 1H), 7.38 (t, J=8.1 Hz, 1H), 7.35-7.30 (m, 1H), 6.50 (d, J=7.0 Hz, 1H), 5.05 (d, J=6.8 Hz, 1H), 4.19-4.05 (m, 1H), 3.93-3.79 (m, 1H), 3.58-3.46 (m, 1H), 2.87 (d, J=13.4 Hz, 1H), 1.86 (s, 3H), 1.82 (s, 3H), 1.46 (t, J=7.1 Hz, 3H). $^{19}F$ NMR (377 MHz, Chloroform-d) δ −105.66, −105.67. $^{31}P$ NMR (162 MHz, Chloroform-d) δ 30.35.

Example 12: (7R,14R)-11-(4-(dimethylphosphoryl)-2,5-difluorophenyl)-1-fluoro-6-(methyl-d3)-6,7-dihydro-7,14-methanobenzo[f]benzo[4,5]imidazo[1,2-a][1,4]diazocin-5(14H)-one

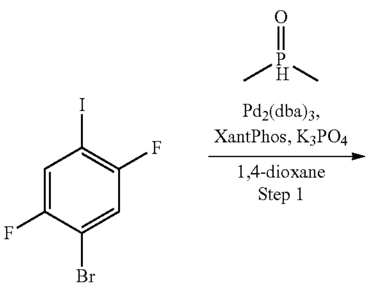

-continued

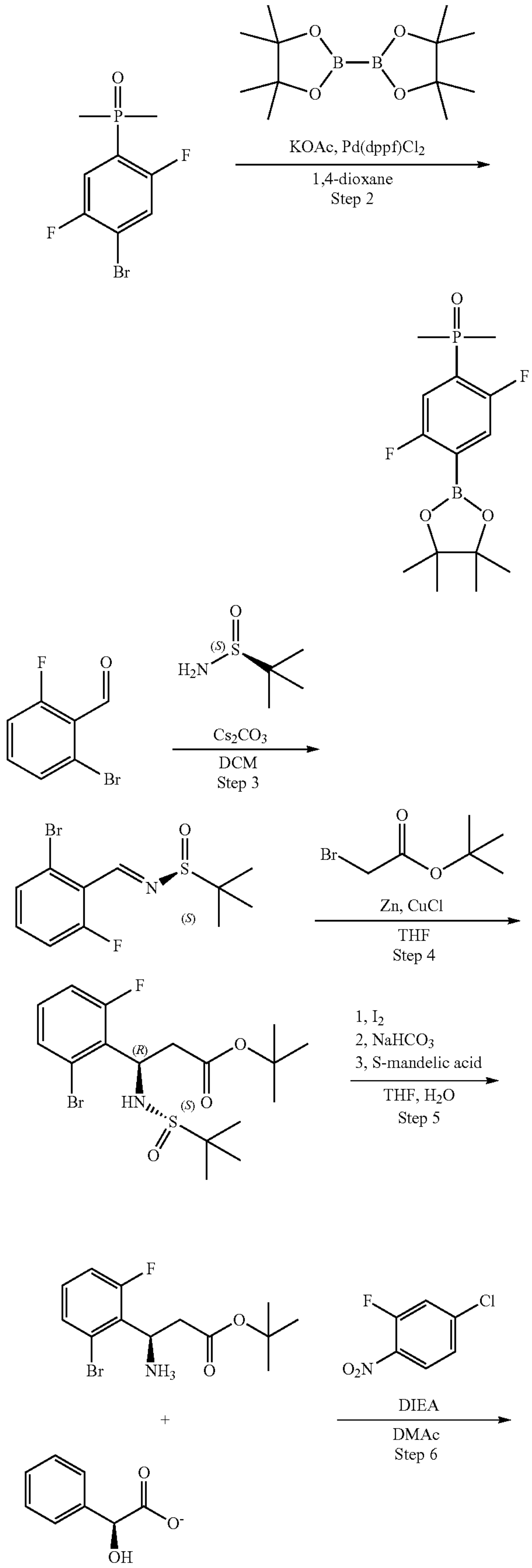

-continued

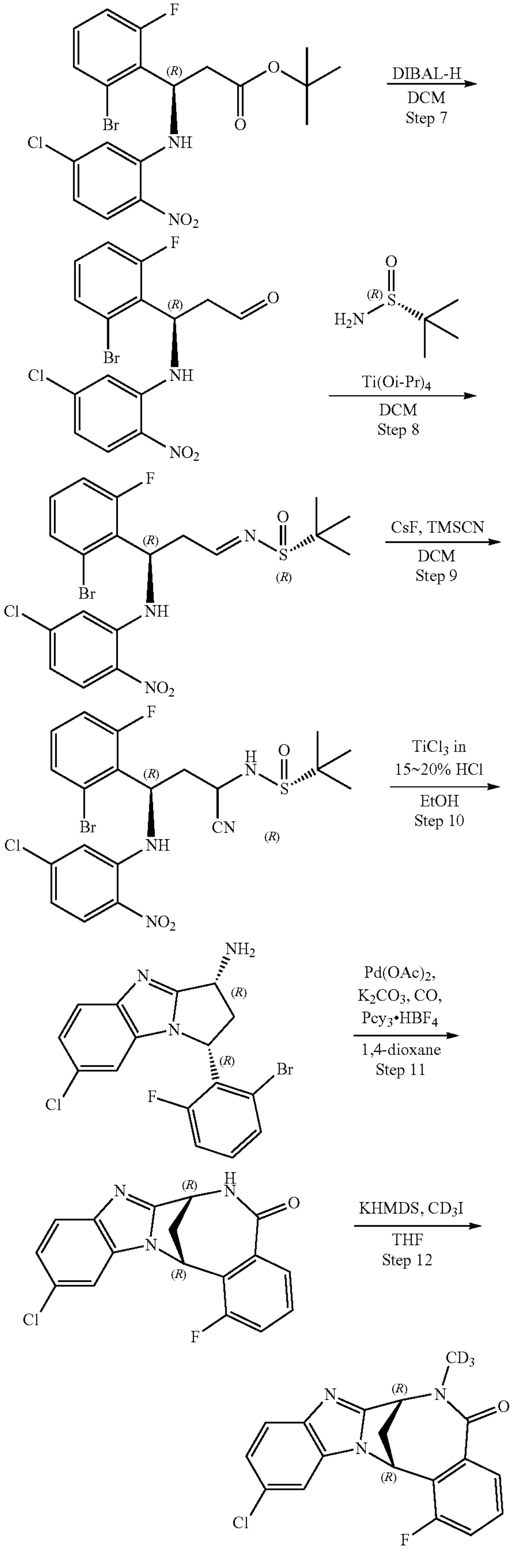

-continued

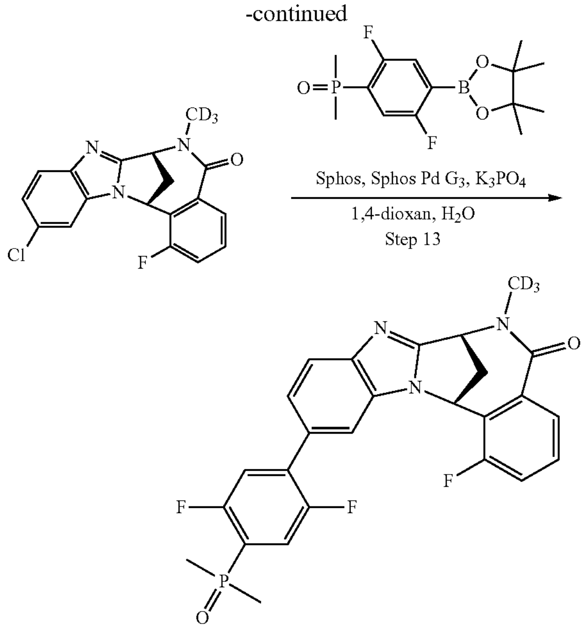

Preparation 12A: (4-bromo-2,5-difluorophenyl)dimethylphosphine oxide

To a stirred solution of 1-bromo-2,5-difluoro-4-iodobenzene (2.00 g, 6.272 mmol) and dimethylphosphine oxide (538 mg, 6.899 mmol) in 1,4-dioxane (5 mL) were added $Pd_2(dba)_3$ (144 mg, 0.157 mmol), XantPhos (181 mg, 0.314 mmol) and $K_3PO_4$ (1.60 g, 7.526 mmol) at room temperature. The resulting mixture was stirred at 80° C. for additional 3 h under nitrogen atmosphere. The mixture was concentrated under reduced pressure. The residue was purified by silica gel column chromatography, eluted with PE/EA (5/1) to (4-bromo-2,5-difluorophenyl)dimethylphosphine oxide (870 mg, 52%) as a yellow solid. MS ESI calculated for $C_8H_8BrF_2OP$ $[M+H]^+$, 268.95 270.95 found 268.95 270.95. $^1H$ NMR (300 MHz, Chloroform-d) δ 7.84-7.67 (m, 1H), 7.44-7.33 (m, 1H), 1.84 (d, J=1.2 Hz, 3H), 1.80 (d, J=1.2 Hz, 3H). $^{31}P$ NMR (121 MHz, Chloroform-d) δ 29.75.

Preparation 12B: (2,5-difluoro-4-(4,4,5,5-tetramethyl-1,3,2-dioxaborolan-2-yl)phenyl)dimethylphosphine oxide To a solution of (4-bromo-2,5-difluorophenyl)dimethylphosphine oxide (200 mg, 0.743 mmol) and 4,4,5,5-tetramethyl-2-(tetramethyl-1,3,2-dioxaborolan-2-yl)-1,3,2-dioxaborolane (283 mg, 1.115 mmol) in 1,4-dioxane (2 mL) were added KOAc (292 mg, 2.972 mmol), Pd(dppf)$Cl_2 \cdot CH_2Cl_2$ (121 mg, 0.149 mmol) at room temperature. After stirring for 5 h at 80° C. under a nitrogen atmosphere, the mixture was filtered and filter cake washed with DCM (10 mL) and diluted with $H_2O$ (20 mL). and extracted with DCM (3×10 mL). The filtrate was concentrated under reduced pressure. This resulted in (2,5-difluoro-4-(4,4,5,5-tetramethyl-1,3,2-dioxaborolan-2-yl)phenyl)dimethylphosphine oxide (100 mg) as a light yellow solid. The crude product was used in next step directly without further purification. MS ESI calculated for $C_{14}H_{20}BF_2O_3P$ $[M+H]^+$, 317.12 found 317.15. $^1H$ NMR (400 MHz, DMSO-$d_6$) δ 7.50-7.38 (m, 2H), 1.75 (d, J=1.2 Hz, 3H), 1.73 (d, J=1.2 Hz, 3H), 1.31 (s, 12H).

Preparation 12C: (S,E)-N-(2-bromo-6-fluorobenzylidene)-2-methylpropane-2-sulfinamide To a stirred solution of 2-bromo-6-fluorobenzaldehyde (100.00 g, 492.587 mmol) and $Cs_2CO_3$ (176.00 g, 541.846 mmol) in DCM (1 L) was added(S)-2-methylpropane-2-sulfinamide (71.64 g, 591.104 mmol) in portions at room temperature. The resulting mixture was stirred for 3 h at room temperature. The resulting mixture was diluted with water (1 L) and extracted with $CH_2Cl_2$ (3×500 mL). The combined organic layers were washed with brine (3×500 mL), dried over anhydrous $Na_2SO_4$. After filtration, the filtrate was concentrated under reduced pressure. The residue was purified by silica gel column chromatography, eluted with PE/EA (10:1) to afford (S,E)-N-(2-bromo-6-fluorobenzylidene)-2-methylpropane-2-sulfinamide (145.00 g, 96%) as yellow oil. MS ESI calculated for $C_{11}H_{13}BrFNOS$ $[M+H]^+$, 305.99 307.99 found 306.00 308.05. $^1H$ NMR (300 MHz, Chloroform-d) δ 8.85 (s, 1H), 7.54-7.45 (m, 1H), 7.39-7.26 (m, 1H), 7.22-7.09 (m, 1H), 1.31 (s, 9H). $^{19}F$ NMR (282 MHz, Chloroform-d) δ −109.16.

Preparation 12D: tert-butyl (R)-3-(2-bromo-6-fluorobenzylidene)-3-(((S)-tert-butylsulfinyl)amino)propanoate A mixture of Zn powder (224.20 g, 3429.245 mmol) and CuCl (101.85 g, 1028.774 mmol) in THF (1 L) was stirred for 2 h at 60° C. under nitrogen atmosphere. The mixture was allowed to cool down to room temperature. To the above mixture was added tert-butyl 2-bromoacetate (334.45 g, 1714.623 mmol) dropwise over 5 min at 25° C. The resulting mixture was stirred for additional 2 h at 60° C. The mixture was allowed to cool down to room temperature again. To the above mixture was added (S, E)-N-(2-bromo-6-fluorobenzylidene)-2-methylpropane-2-sulfinamide (210.00 g, 685.849 mmol) in portions over 5 min at 10° C. The resulting mixture was stirred for additional 3 h at room temperature. The resulting mixture was filtered, the filter cake was washed with EtOAc (3×1000 mL). To the above filtrate were added EtOAc (1.5 L) and saturated citric acid solution (500 mL). The aqueous layer was extracted with EtOAc (3×500 mL) and the combined organic layers were washed with saturated $NaHCO_3$ solution (1.5 L) and dried over anhydrous $Na_2SO_4$. After filtration, the filtrate was concentrated under reduced pressure. The residue was purified by trituration with PE (1 L). This resulted in tert-butyl (R)-3-(2-bromo-6-fluorobenzylidene)-3-(((S)-tert-butylsulfinyl)amino)propanoate (210.00 g, 73%) as colorless oil. MS ESI calculated for $C_{17}H_{25}BrFNO_3S$ $[M+H]^+$, 422.07 424.07, found 421.95 423.90. $^1H$ NMR (400 MHz, Chloroform-d) δ 7.38 (d, J=8.1 Hz, 1H), 7.19-7.09 (m, 1H), 7.08-6.98 (m, 1H), 5.49-5.39 (m, 1H), 4.20 (d, J=7.5 Hz, 1H), 3.15-3.05 (m, 1H), 2.97-2.87 (m, 1H), 1.39 (s, 9H), 1.14 (s, 9H). $^{19}F$ NMR (377 MHz, Chloroform-d) δ −110.59.

Preparation 12E: (R)-1-(2-bromo-6-fluorophenyl)-3-(tert-butoxy)-3-oxopropan-1-aminium (S)-2-hydroxy-2-phenylacetate To a stirred solution of tert-butyl (R)-3-(2-bromo-6-fluorobenzylidene)-3-(((S)-tert-butylsulfinyl)amino)propanoate (201.00 g, 475.909 mmol) in THF (1000 mL) and $H_2O$ (200 mL) was added $I_2$ (30.20 g, 118.977 mmol) at room temperature under nitrogen atmosphere. The resulting mixture was stirred for overnight at 50° C. The reaction was quenched by the addition of sat. $NaHCO_3$ (aq.) (1 L) at 0° C. The resulting mixture was extracted with EtOAc (3×500 mL). The combined organic layers were washed with brine (3×2 L) and dried over anhydrous $Na_2SO_4$. After filtration, the filtrate was concentrated under reduced pressure. The residue was dissolved in MTBE (500 mL) followed by the addition of solution (2S)-2-hydroxy-2-phenylacetic acid (72.41 g, 475.909 mmol) in MTBE (200 mL) dropwise at room temperature. The resulting mixture was stirred for additional 16 h at room temperature. The precipitated solids were collected by filtration. This resulted in (R)-1-(2-bromo-6-fluorophenyl)-3-(tert-butoxy)-3-oxopropan-1-aminium (S)-2-hydroxy-2-phenylacetate (170.00 g, 76%) as a white solid. MS ESI calculated for $C_{13}H_{17}BrFNO_2$ $[M+H]^+$, 318.04 320.04 found 318.10 320.10. $^1H$ NMR (400 MHz, Chloroform-d, free base) δ 7.35 (d, J=7.9 Hz, 1H), 7.12-6.98 (m, 2H), 4.92-4.85 (m, 1H), 2.89-2.80 (m, 1H), 2.76-2.68 (m, 1H), 1.41 (s, 9H). $^{19}F$ NMR (377 MHz, Chloroform-d) δ −112.37.

Preparation 12F: tert-butyl (R)-3-(2-bromo-6-fluorophenyl)-3-((5-chloro-2-nitrophenyl)amino)propanoate To a stirred solution of (R)-1-(2-bromo-6-fluorophenyl)-3-(tert-butoxy)-3-oxopropan-1-aminium (S)-2-hydroxy-2-phenylacetate (174.00 g, 369.949 mmol) and 4-chloro-2-fluoro-1-nitrobenzene (68.19 g, 388.446 mmol) in DMAc (1 L) was added DIEA (143.44 g, 1109.847 mmol) at room temperature under nitrogen atmosphere. The resulting mixture was stirred overnight at 80° C. The resulting mixture was diluted with water (1 L) followed by extraction with MTBE (2×1 L) and washed with 5% critic acid (2×1 L). The combined organic layers were washed with 5% $NaHCO_3$ (2×1 L). The combined organic layers were washed with 5% NaCl (2×1 L). The combined organic layers were concentrated under vacuum to afford tert-butyl (3R)-3-(2-bromo-6-fluorophenyl)-3-[(5-chloro-2-nitrophenyl)amino]propanoate (170.00 g, 97%) as yellow oil. MS ESI calculated for $C_{19}H_{19}BrClFN_2O_4$ $[M+H]^+$, 473.02 475.02 found 473.00 474.95. $^1H$ NMR (400 MHz, Chloroform-d) δ 8.79 (d, J=8.7 Hz, 1H), 8.09 (d, J=9.1 Hz, 1H), 7.41 (d, J=8.0 Hz, 1H), 7.21-7.13 (m, 1H), 7.09-7.04 (m, 1H), 7.03 (d, J=2.0 Hz, 1H), 6.66-6.54 (m, 1H), 5.73-5.59 (m, 1H), 3.14-3.04 (m, 1H), 2.90-2.82 (m, 1H), 1.40 (s, 9H). $^{19}F$ NMR (377 MHz, Chloroform-d) δ −111.95.

Preparation 12G: (R)-3-(2-bromo-6-fluorophenyl)-3-((5-chloro-2-nitrophenyl)amino)propanal To tert-butyl (R)-3-(2-bromo-6-fluorophenyl)-3-((5-chloro-2-nitrophenyl)amino)propanoate (86.50 g, 182.597 mmol) in DCM (1 L) was added Diisobutylaluminum hydride (1.0 M in DCM) (237.4 mL, 237.376 mmol) dropwise at −78° C. under nitrogen atmosphere. The resulting mixture was stirred for 1 h at −78° C. under nitrogen atmosphere. The reaction was quenched with HCl (1N) at −78° C. followed by extraction with $CH_2Cl_2$ (3×1 L). The combined organic layers were washed with brine (3×1 L) and dried over anhydrous $Na_2SO_4$. After filtration, the filtrate was concentrated under reduced pressure. The residue was purified by silica gel column chromatography, eluted with PE/EA (3:1) to afford (R)-3-(2-bromo-6-fluorophenyl)-3-((5-chloro-2-nitrophenyl)amino)propanal (59.00 g, 80%) as a yellow solid. MS ESI calculated for $C_{15}H_{11}BrClFN_2O_3$ $[M+H]^+$, 400.96 402.96, found 400.80 402.75. $^1H$ NMR (400 MHz, Chloroform-d) δ 9.82 (s, 1H), 8.73 (d, J=8.9 Hz, 1H), 8.09 (d, J=9.1 Hz, 1H), 7.45-7.37 (m, 1H), 7.25-7.12 (m, 1H), 7.12-7.00 (m, 2H), 6.67-6.55 (m, 1H), 5.85-5.74 (m, 1H), 3.48-3.38 (m, 1H), 3.13-3.03 (m, 1H). $^{19}F$ NMR (377 MHz, Chloroform-d) δ −112.20.

Preparation 12H: (R)—N—((R,E)-3-(2-bromo-6-fluorophenyl)-3-((5-chloro-2-nitrophenyl)amino)propylidene)-2-methylpropane-2-sulfinamide To a stirred solution of (R)-3-(2-bromo-6-fluorophenyl)-3-((5-chloro-2-nitrophenyl)amino)propanal (116.00 g, 288.830 mmol) and $Ti(Oi\text{-}Pr)_4$ (164.18 g, 577.660 mmol) in DCM (1.2 L) was added (R)-2-methylpropane-2-sulfinamide (42.01 g, 346.596 mmol) in portions at room temperature. The resulting mixture was stirred for 3 h at room temperature. The resulting mixture was diluted with water (1 L) followed by extraction with $CH_2Cl_2$ (3×1 L). The combined organic layers were washed with brine (3×1 L) and dried over anhydrous $Na_2SO_4$. After filtration, the filtrate was concentrated under reduced pressure. The residue was purified by silica gel column chromatography, eluted with PE/EA (3:1) to afford (R)—N—((R,E)-3-(2-bromo-6-fluorophenyl)-3-((5-chloro-2-nitrophenyl)amino)propylidene)-2-methylpropane-2-sulfinamide (117.00 g, 80%) as yellow oil. MS ESI calculated for $C_{19}H_{20}BrClFN_3O_3S$ $[M+H]^+$, 504.01 506.01 found 503.85 505.75. $^1H$ NMR (400 MHz, Chloroform-d) δ 8.75 (d, J=8.8 Hz, 1H), 8.14-7.98 (m, 2H), 7.46-7.37 (m, 1H), 7.24-7.13 (m, 1H), 7.12-7.03 (m, 1H), 6.98 (d, J=2.1 Hz, 1H), 6.68-6.59 (m, 1H), 5.73-5.63 (m, 1H), 3.51-3.39 (m, 1H), 3.21-3.10 (m, 1H), 1.14 (s, 9H). $^{19}F$ NMR (377 MHz, Chloroform-d) δ −112.19.

Preparation 12I: (R)—N-((3R)-3-(2-bromo-6-fluorophenyl)-3-((5-chloro-2-nitrophenyl)amino)-1-cyanopropyl)-2-methylpropane-2-sulfinamide To a stirred solution of (R)—N—((R,E)-3-(2-bromo-6-fluorophenyl)-3-((5-chloro-2-nitrophenyl)amino)propylidene)-2-methylpropane-2-sulfinamide (116.00 g, 229.794 mmol) in DCM (1.2 L) were added CsF (69.81 g, 459.588 mmol) and TMSCN (45.59 g, 459.588 mmol) in portions at room temperature. The resulting mixture was stirred for 2 h at room temperature. The resulting mixture was diluted with water (500 mL) followed by extraction with $CH_2Cl_2$ (3×500 mL). The combined organic layers were washed with brine (3×500 mL) and dried over anhydrous $Na_2SO_4$. After filtration, the filtrate was concentrated under reduced pressure. The residue was purified by trituration with PE/DCM (10:1, 500 mL) to afford (R)—N-((3R)-3-(2-bromo-6-fluorophenyl)-3-((5-chloro-2-nitrophenyl)amino)-1-cyanopropyl)-2-methylpropane-2-sulfinamide (116.00 g, 94%, ee>98%) as a yellow solid. MS ESI calculated for $C_{20}H_{21}BrClFN_4O_3S$ $[M+H]^+$, 531.02 533.02 found 530.85 532.80. $^1H$ NMR (400 MHz, Chloroform-d) δ 8.67 (d, J=9.6 Hz, 1H), 8.12 (d, J=9.1 Hz, 1H), 7.46-7.39 (m, 1H), 7.25-7.15 (m, 1H), 7.13-7.04 (m, 1H), 6.97 (d, J=2.1 Hz, 1H), 6.71-6.64 (m, 1H), 5.56-5.45 (m, 1H), 4.42-4.32 (m, 1H), 4.05 (d, J=9.9 Hz, 1H), 2.82 (t, J=10.5 Hz, 1H), 2.47-2.36 (m, 1H), 1.26 (s, 9H). $^{19}F$ NMR (377 MHz, Chloroform-d) δ −112.39.

Preparation 12J: (1R,3R)-1-(2-bromo-6-fluorophenyl)-7-chloro-2,3-dihydro-1H-benzo[d]pyrrolo[1,2-a]imidazol-3-amine To a stirred solution of (R)—N-((3R)-3-(2-bromo-6-fluorophenyl)-3-((5-chloro-2-nitrophenyl)amino)-1-cyanopropyl)-2-methylpropane-2-sulfinamide (55.00 g, 103.417 mmol) and $TiCl_3$ (637.96 g, 827.336 mmol, 20%) in EtOH (500 mL) at room temperature. The resulting mixture was stirred overnight at 80° C. The resulting mixture was diluted with EtOAc (500 mL). The residue was basified to pH 7 with saturated $NaHCO_3$ (aq.). The resulting mixture was filtered and the filter cake was washed with EtOAc (3×500 mL). The filtrate was washed with 2×1 L of water. The organic layer was concentrated under vacuum. The residue was purified by trituration with PE/DCM (10:1, 500 mL) to afford (1R,3R)-1-(2-bromo-6-chlorophenyl)-7-methoxy-2,3-dihydro-1H-benzo[d]pyrrolo[1,2-a]imidazol-3-amine (33.00 g, 83%) as a white solid. MS ESI calculated for $C_{16}H_{12}BrClFN_3$ $[M+H]^+$, 379.99 381.99 found 379.85 381.80. $^1H$ NMR (400 MHz, Chloroform-d) & 7.68-7.60 (m, 1H), 7.55 (d, J=8.1 Hz, 1H), 7.43-7.21 (m, 1H), 7.19-7.13 (m, 1H), 7.03-6.94 (m, 1H), 6.78-6.58 (m, 1H), 6.08-5.93 (m, 1H), 4.74-4.60 (m, 1H), 3.68-3.53 (m, 1H), 2.61-2.46 (m, 1H). $^{19}F$ NMR (377 MHz, Chloroform-d) δ −111.99.

Preparation 12K: (7R,14R)-11-chloro-1-fluoro-6,7-dihydro-7,14-methanobenzo[f]benzo[4,5]imidazo[1,2-a][1,4]diazocin-5(14H)-one To a stirred mixture of (1R,3R)-1-(2-bromo-6-fluorophenyl)-7-chloro-2,3-dihydro-1H-benzo[d]pyrrolo[1,2-a]imidazol-3-amine (70.00 g, 183.896 mmol) and $K_2CO_3$ (101.66 g, 735.584 mmol) in 1,4-dioxane (3.5 L) were added $PCy_3·HBF$ (13.54 g, 36.779 mmol) and $Pd(OAc)_2$ (4.13 g, 18.390 mmol) at room temperature. The mixture was purged with nitrogen for 30 min and then was pressurized to 10 atm. with carbon monoxide at 140° C. for 16 h. The resulting mixture was concentrated under vacuum. The residue was purified by silica gel column chromatography, eluted with $CH_2Cl_2$/MeOH (10:1) to afford (7R,14R)-11-chloro-1-fluoro-6,7-dihydro-7,14-methanobenzo[f]benzo[4,5]imidazo[1,2-a][1,4]diazocin-5(14H)-one (46.00 g, 76%) as a yellow solid. MS ESI calculated for $C_{17}H_{11}ClFN_3O$ $[M+H]^+$, 328.06 found 327.95. $^1H$ NMR (400 MHz, Chloroform-d) δ 8.38-8.31 (m, 1H), 7.66 (d, J=8.7 Hz, 1H), 7.60 (d, J=6.7 Hz, 1H), 7.46-7.33 (m, 3H), 7.26-7.18 (m, 1H), 6.19 (d, J=7.0 Hz, 1H), 5.01 (t, J=6.7 Hz, 1H), 3.53-3.42 (m, 1H), 2.88 (d, J=13.2 Hz, 1H). $^{19}F$ NMR (377 MHz, Chloroform-d) δ −117.82.

Preparation 12L: (7R,14R)-11-chloro-1-fluoro-6-(methyl-$d_3$)-6,7-dihydro-7,14-methanobenzo[f]benzo[4,5]imidazo[1,2-a][1,4]diazocin-5(14H)-one To a stirred mixture of (7R,14R)-11-chloro-1-fluoro-6,7-dihydro-7,14-methanobenzo[f]benzo[4,5]imidazo[1,2-a][1,4]diazocin-5(14H)-one (16.00 g, 48.819 mmol) in THF (200 mL) was added KHMDS (63.46 mL, 63.465 mmol, 1M in THF) at −78° C. The resulting mixture was stirred for 1 h at −78° C. under nitrogen atmosphere. To the above mixture was added $CD_3I$ (12.74 g, 87.874 mmol) at −78° C. The resulting mixture was stirred for additional 2 h at room temperature. The resulting mixture was concentrated under vacuum and purified by silica gel column chromatography, eluted with $CH_2Cl_2$/MeOH (10:1) to afford (7R,14R)-11-chloro-1-fluoro-6-(methyl-$d_3$)-6,7-dihydro-7,14-methanobenzo[f]benzo[4,5]imidazo[1,2-a][1,4]diazocin-5(14H)-one (12.80 g, 76%) as a white solid. MS ESI calculated for $C_{18}H_{10}D_3ClFN_3O$ $[M+H]^+$, 345.09 found 345.15. $^1H$ NMR (400 MHz, Chloroform-d) δ 8.44-8.37 (m, 1H), 7.63 (d, J=8.7 Hz, 1H), 7.45 (d, J=2.0 Hz, 1H), 7.43-7.37 (m, 1H), 7.37-7.28 (m, 1H), 7.26-7.19 (m, 1H), 6.10 (d, J=7.1 Hz, 1H), 4.98 (d, J=7.2 Hz, 1H), 3.51-3.40 (m, 1H), 2.89 (d, J=13.5 Hz, 1H). $^{19}F$ NMR (377 MHz, Chloroform-d) δ −118.21.

Example 12: (7R,14R)-11-(4-(dimethylphosphoryl)-2,5-difluorophenyl)-1-fluoro-6-(methyl-d3)-6,7-dihydro-7,14-methanobenzo[f]benzo[4,5]imidazo[1,2-a][1,4]diazocin-5(14H)-one To a stirred solution of (7R,14R)-11-chloro-1-fluoro-6-(methyl-d3)-6,7-dihydro-7,14-methanobenzo[f]benzo[4,5]imidazo[1,2-a][1,4]diazocin-5(14H)-one (40 mg, 0.116 mmol) and (2,5-difluoro-4-(4,4,5,5-tetramethyl-1,3,2-dioxaborolan-2-yl)phenyl)dimethylphosphine oxide (55 mg, 0.174 mmol) in 1,4-dioxane (2 mL) and $H_2O$ (0.4 mL) were added Sphos Pd G3 (5 mg, 0.006 mmol), Sphos (5 mg, 0.012 mmol), $K_3PO_4$ (49 mg, 0.232 mmol) at room temperature under nitrogen atmosphere. The resulting mixture was stirred overnight at 80° C. The mixture was concentrated under reduced pressure. The residue was purified by silica gel column chromatography, eluted with $CH_2Cl_2$/MeOH (10/1) followed by reversed-phase flash chromatography with the following conditions: column, C18 silica gel; mobile phase, $CH_3CN$ in Water (10 mmol/L $NH_4HCO_3$), 40% to 50% gradient in 10 min; detector, 254 nm. This resulted in (7R,14R)-11-(4-(dimethylphosphoryl)-2,5-difluorophenyl)-1-fluoro-6-(methyl-d3)-6,7-dihydro-7,14-methanobenzo[f]benzo[4,5]imidazo[1,2-a][1,4]diazocin-5(14H)-one (10 mg, 18%) as a white solid. MS ESI calculated for $C_{26}H_{18}D_3F_3N_3O_2P$ $[M+H]^+$, 499.15 found 499.00. $^1H$ NMR (400 MHz, DMSO-$d_6$) δ 8.23 (d, J=8.0 Hz, 1H), 7.76 (d, J=8.5 Hz, 1H), 7.63 (s, 1H), 7.61-7.51 (m, 3H), 7.50-7.41 (m, 2H), 6.27 (d, J=6.8 Hz, 1H), 5.29 (d, J=7.2 Hz, 1H), 3.57-3.46 (m, 1H), 2.88 (d, J=13.8 Hz, 1H), 1.79 (s, 3H), 1.75 (s, 3H). 19F NMR (377 MHz, DMSO-$d_6$) δ −111.00, −111.06, −117.54, −122.94, −122.99. $^{31}P$ NMR (162 MHz, DMSO-$d_6$) δ 28.57.

Example 13: (7R,14R)-11-(4-(dimethylphosphoryl)-3-fluorophenyl)-1,3-difluoro-6-(methyl-d3)-6,7-dihydro-7,14-methanobenzo[f]benzo[4,5]imidazo[1,2-a][1,4]diazocin-5(14H)-one

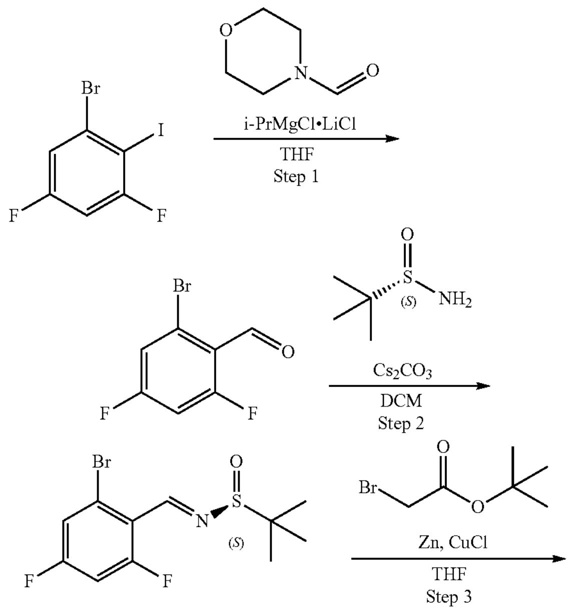

-continued

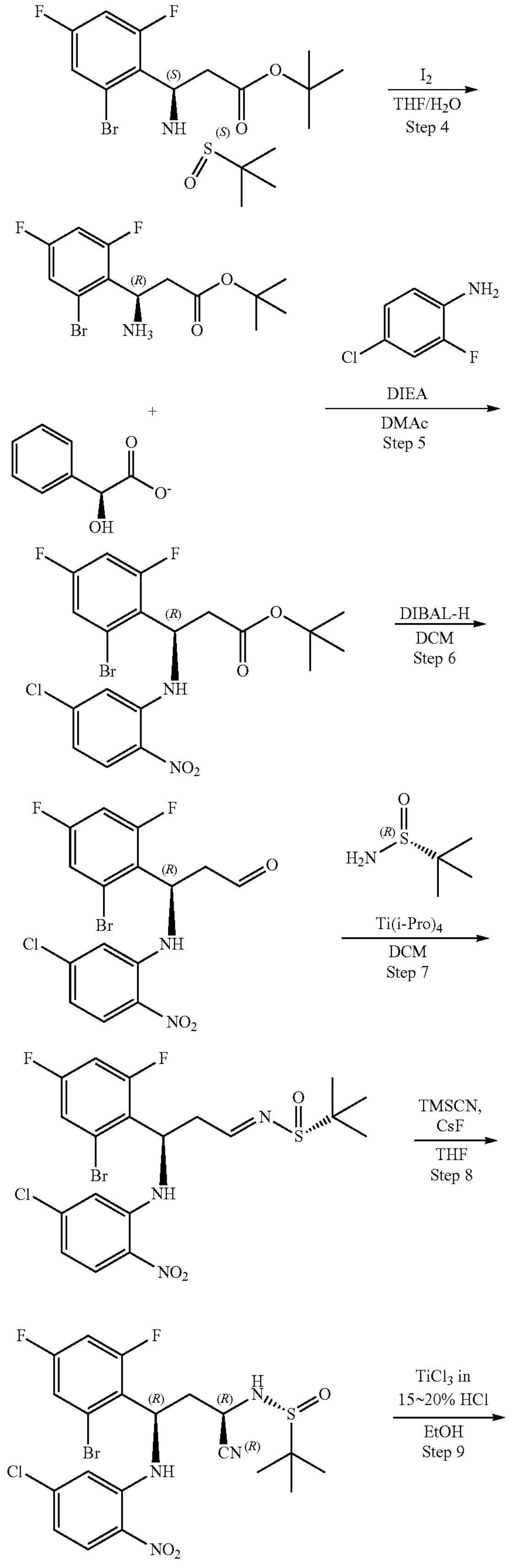

-continued

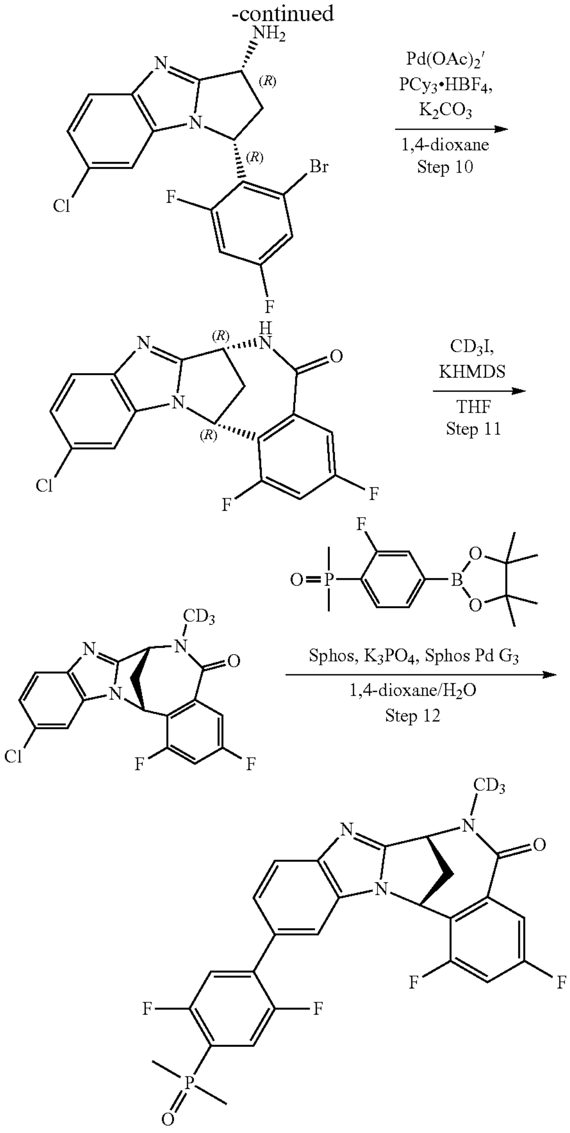

Preparation 13A: 2-bromo-4,6-difluorobenzaldehyde

To a stirred solution of 1-bromo-3,5-difluoro-2-iodobenzene (160.00 g, 501.745 mmol) in THF (1.5 L) was added chloro(propan-2-yl) magnesium; chlorolithium (405.26 mL, 526.832 mmol, 1.3 M in THF) dropwise at −78° C. under nitrogen atmosphere. The resulting mixture was stirred at −78° C. for 1 h under nitrogen atmosphere. To the above mixture was added formyl morpholine (63.54 g, 551.920 mmol) at −78° C. and stirred at −78° C. for additional 1 h. The reaction was quenched with sat. $NH_4Cl$ (aq.) at 0° C. followed by extraction with $CH_2Cl_2$ (3×800 mL). The combined organic layers were washed with brine (800 mL) and dried over anhydrous $Na_2SO_4$. After filtration, the filtrate was concentrated under reduced pressure. The residue was purified by silica gel column chromatography, eluted with PE/EA (15/1) to afford 2-bromo-4,6-difluorobenzaldehyde (65.01 g, 59%) as a white solid. MS ESI calculated for $C_7H_3BrF_2O$ $[M+H]^+$, 220.93 222.93 found N/A. 1H NMR (400 MHz, Chloroform-d) δ 10.29 (s, 1H), 7.30-7.26 (m, 1H), 6.97-6.88 (m, 1H). $^{19}F$ NMR (377 MHz, Chloroform-d) δ −98.89, −98.92, −109.93, −109.96.

Preparation 13B: (S,E)-N-(2-bromo-4,6-difluorobenzylidene)-2-methylpropane-2-sulfinamide To a stirred solution of 2-bromo-4,6-difluorobenzaldehyde (9.60 g, 43.439 mmol) and(S)-2-methylpropane-2-sulfinamide (6.32 g, 52.127 mmol) in $CH_2Cl_2$ (100 mL) was added $Cs_2CO_3$ (15.57 g, 47.783 mmol) at room temperature. The resulting mixture was stirred at room temperature for 3 h. The resulting mixture was diluted with water (200 mL) and extracted with $CH_2Cl_2$ (3×100 mL). The combined organic layers were washed with brine (100 mL) and dried over anhydrous $Na_2SO_4$. After filtration, the filtrate was concentrated under reduced pressure. The residue was purified by silica gel column chromatography, eluted with PE/EA (12/1) to afford (S,E)-N-(2-bromo-4,6-difluorobenzylidene)-2-methylpropane-2-sulfinamide (1.70 g, 12%) as an off-white solid. MS ESI calculated for $C_{11}H_{12}BrF_2NOS$ $[M+H]^+$, 323.98 325.98 found 323.80 325.80. $^1H$ NMR (400 MHz, Chloroform-d) δ 8.78 (s, 1H), 7.31-7.25 (m, 1H), 6.96-6.89 (m, 1H), 1.29 (s, 9H). $^{19}F$ NMR (377 MHz, Chloroform-d) δ −102.94, −102.97, −105.06, −105.09.

Preparation 13C: tert-butyl (R)-3-(2-bromo-4,6-difluorophenyl)-3-(((S)-tert-butylsulfinyl)amino)propanoate Into a 250 mL 3-necked round-bottom flask were added Zinc (12.95 g, 198.009 mmol), CuCl (4.20 g, 42.430 mmol) and THF (100 mL) at room temperature under nitrogen atmosphere. The resulting mixture was stirred at 60° C. for 2 h under nitrogen atmosphere. The mixture was allowed to cool down to room temperature followed by addition of tert-butyl 2-bromoacetate (13.79 g, 70.718 mmol) dropwise at room temperature. The resulting mixture was stirred at 60° C. for additional 2 h. The mixture was allowed to cool down to 0° C. To the above mixture was added (S,E)-N-(2-bromo-4,6-difluorobenzylidene)-2-methylpropane-2-sulfinamide (9.17 g, 28.287 mmol) in THF (10 mL) dropwise at 0° C. The resulting mixture was stirred overnight at room temperature. The resulting mixture was filtered and the filter cake was washed with EtOAc (3×100 mL). The filtrate was acidified with citric acid (0.3 g/mL in water, 200 mL) at room temperature followed by extraction with EtOAc (3×200 mL). The combined organic layers were washed with saturated $NaHCO_3$ (aq.) (2×100 mL) and brine for once and dried over anhydrous $Na_2SO_4$. After filtration, the filtrate was concentrated under reduced pressure to afford tert-butyl (R)-3-(2-bromo-4,6-difluorophenyl)-3-(((S)-tert-butylsulfinyl)amino)propanoate (crude) as light green oil. The crude product was used in the next step directly without further purification. MS ESI calculated for $C_{17}H_{24}BrF_2NO_3S$ $[M+H]^+$, 440.06 442.06 found 440.00 442.00. $^1H$ NMR (400 MHz, Chloroform-d) δ 7.20-7.14 (m, 1H), 6.86-6.77 (m, 1H), 5.45-5.33 (m, 1H), 4.18 (d, J=6.9 Hz, 1H), 3.14-3.02 (m, 1H), 2.95-2.84 (m, 1H), 1.40 (s, 9H), 1.15 (s, 9H). $^{19}F$ NMR (377 MHz, Chloroform-d) δ −107.12, −107.14, −109.25, −109.27.

Preparation 13D: (R)-1-(2-bromo-4,6-difluorophenyl)-3-(tert-butoxy)-3-oxopropan-1-aminium (S)-2-hydroxy-2-phenylacetate To a stirred solution of tert-butyl (R)-3-(2-bromo-4,6-difluorophenyl)-3-(((S)-tert-butylsulfinyl)amino)propanoate (12.55 g, 28.501 mmol) in THF (60 mL) and $H_2O$ (12 mL) was added Iodine (1.81 g, 7.125 mmol) at room temperature. The resulting mixture was stirred at 50° C. for overnight under nitrogen atmosphere. The reaction was quenched with saturated $NaHCO_3$ (aq.) followed by extraction with EtOAc (3×100 mL). The combined organic layers were washed with brine (100 mL) and dried over anhydrous $Na_2SO_4$. After filtration, the filtrate was concentrated under reduced pressure to afford crude product as yellow oil. The crude product was dissolved in MTBE (60 mL) followed by addition of S-mandelic acid (4.50 g). The resulting mixture was stirred at room temperature for 1 h. The precipitated solids were collected by filtration and washed with MTBE (3×20 mL). This resulted in (R)-1-(2-bromo-4,6-difluorophenyl)-3-(tert-butoxy)-3-oxopropan-1-aminium (S)-2-hydroxy-2-phenylacetate (11.00 g, 79%) as a white solid. MS ESI calculated for $C_{13}H_{16}BrF_2NO_2$ $[M+H]^+$, 336.03 338.03, found 335.95 337.95. $^1H$ NMR (400 MHz, Chloroform-d, free base) δ 7.17-7.11 (m, 1H), 6.85-6.77 (m, 1H), 4.93-4.78 (m, 1H), 2.88-2.78 (m, 1H), 2.75-2.65 (m, 1H), 1.41 (s, 9H). $^{19}F$ NMR (377 MHz, Chloroform-d) δ −109.25, −109.27, −110.94, −110.96.

Preparation 13E: tert-butyl (R)-3-(2-bromo-4,6-difluorophenyl)-3-((5-chloro-2-nitrophenyl)amino) propanoate To a stirred solution of (R)-1-(2-bromo-4,6-difluorophenyl)-3-(tert-butoxy)-3-oxopropan-1-aminium (S)-2-hydroxy-2-phenylacetate (11.00 g, 22.526 mmol) and 4-chloro-2-fluoro-1-nitrobenzene (4.15 g, 23.652 mmol) in N,N-Dimethylacetamide (50 mL) was added DIEA (11.8 mL, 67.578 mmol) at room temperature. The resulting mixture was stirred at 50° C. for 1 h and then 80° C. for 16 h. The mixture was allowed to cool down to room temperature, charged MTBE (200 mL) and $H_2O$ (100 mL). Separated and the organic layer was washed with citric acid (100 mL) and saturated $NaHCO_3$ (aq.) (2×100 mL) and brine for once. The combined organic layer dried over anhydrous $Na_2SO_4$. After filtration, the filtrate was concentrated under reduced pressure. This resulted in tert-butyl (R)-3-(2-bromo-4,6-difluorophenyl)-3-((5-chloro-2-nitrophenyl)amino)propanoate (11.00 g, crude) as yellow oil. MS ESI calculated for $C_{19}H_{18}BrClF_2N_2O_4$ $[M+H]^+$, 491.01 493.01, found 490.90 492.85. $^1H$ NMR (400 MHz, Chloroform-d) δ 8.75 (d, J=8.6 Hz, 1H), 8.10 (d, J=9.2 Hz, 1H), 7.23-7.17 (m, 1H), 7.00-6.96 (m, 1H), 6.89-6.80 (m, 1H), 6.67-6.58 (m, 1H), 5.64-5.53 (m, 1H), 3.11-3.01 (m, 1H), 2.90-2.81 (m, 1H), 1.41 (s, 9H). $^{19}F$ NMR (377 MHz, Chloroform-d) δ −108.24, −108.26, −108.72, −108.74.

Preparation 13F: (R)-3-(2-bromo-4,6-difluorophenyl)-3-((5-chloro-2-nitrophenyl)amino)propanal To a stirred solution of tert-butyl (R)-3-(2-bromo-4,6-difluorophenyl)-3-((5-chloro-2-nitrophenyl)amino)propanoate (11.00 g, 23.388 mmol) in DCM (150 mL) was added Diisobutylaluminum hydride (1.0 M in DCM) (23.4 mL, 23.388 mmol) dropwise at −78° C. under nitrogen atmosphere. The resulting mixture was stirred at −78° C. for 3 h under nitrogen atmosphere. The reaction was quenched with 1N HCl (aq.) at −78° C. followed by extraction with EtOAc (3×100 mL). The combined organic layers were washed with brine (100 mL) and dried over anhydrous $Na_2SO_4$. After filtration, the filtrate was concentrated under reduced pressure. The residue was purified by silica gel column chromatography, eluted with PE/EA (4/1) to afford (R)-3-(2-bromo-4,6-difluorophenyl)-3-((5-chloro-2-nitrophenyl)amino)propanal (5.80 g, 62%) as yellow oil. MS ESI calculated for $C_{15}H_{10}BrClF_2N_2O_3$ $[M+H]^+$, 418.95 420.95, found 418.85 420.85. $^1H$ NMR (400 MHz, Chloroform-d) δ 9.81 (s, 1H), 8.68 (d, J=8.9 Hz, 1H), 8.10 (d, J=9.1 Hz, 1H), 7.23-7.17 (m, 1H), 7.05-7.01 (m, 1H), 6.91-6.82 (m, 1H), 6.69-6.63 (m, 1H), 5.85-5.68 (m, 1H), 3.51-3.36 (m, 1H), 3.12-3.03 (m, 1H). $^{19}F$ NMR (377 MHz, Chloroform-d) δ −107.83, −107.85, −109.01, −109.03.

Preparation 13G: (R)—N—((R,E)-3-(2-bromo-4,6-difluorophenyl)-3-((5-chloro-2-nitrophenyl)amino) propylidene)-2-methylpropane-2-sulfinamide To a stirred solution of (R)-3-(2-bromo-4,6-difluorophenyl)-3-((5-chloro-2-nitrophenyl)amino)propanal (5.70 g, 13.584 mmol) and (R)-2-methylpropane-2-sulfinamide (1.98 g, 16.301 mmol) in DCM (60 mL) was added tetrakis (propan-2-yloxy) titanium (7.72 g, 27.168 mmol) at room temperature. The resulting mixture was stirred at room temperature overnight. The reaction was quenched with water at room temperature. The resulting mixture was filtered, the filter cake was washed with $CH_2Cl_2$ (3×50 mL) followed by extraction with $CH_2Cl_2$ (3×100 mL). The combined organic layers were washed with brine (100 mL) and dried over anhydrous $Na_2SO_4$. After filtration, the filtrate was concentrated under reduced pressure. The residue was purified by silica gel column chromatography, eluted with PE/EA (4/1) to afford (R)—N—((R,E)-3-(2-bromo-4,6-difluorophenyl)-3-((5-chloro-2-nitrophenyl)amino)propylidene)-2-methylpropane-2-sulfinamide (5.20 g, 73%) as yellow oil. MS ESI calculated for $C_{19}H_{19}BrClF_2N_3O_3S$ $[M-H]^-$, 520.00 522.00 found 519.85 521.85. $^1H$ NMR (400 MHz, Chloroform-d) δ 8.70 (d, J=8.8 Hz, 1H), 8.14-8.04 (m, 2H), 7.24-7.18 (m, 1H), 6.93 (d, J=2.1 Hz, 1H), 6.90-6.82 (m, 1H), 6.68-6.62 (m, 1H), 5.66-5.57 (m, 1H), 3.49-3.38 (m, 1H), 3.18-3.08 (m, 1H), 1.14 (s, 9H). $^{19}F$ NMR (377 MHz, Chloroform-d) δ −107.84, −107.86, −109.01, −109.03.

Preparation 13H: (R)—N-((3R)-3-(2-bromo-6-(difluoromethoxy)-3-fluorophenyl)-3-((5-chloro-2-nitrophenyl)amino)-1-cyanopropyl)-2-methylpropane-2-sulfinamide To a stirred mixture of (R)—N—((R,E)-3-(2-bromo-4,6-difluorophenyl)-3-((5-chloro-2-nitrophenyl)amino)propylidene)-2-methylpropane-2-sulfinamide (5.20 g, 9.947 mmol) and CsF (3.02 g, 19.894 mmol) in THF (50 mL) was added trimethylsilyl cyanide (1.97 g, 19.894 mmol) dropwise at room temperature. The resulting mixture was stirred at room temperature for 1 h under nitrogen atmosphere. The resulting mixture was diluted with water (200 mL) and extracted with EtOAc (3×100 mL). The combined organic layers were washed with brine (100 mL) and dried over anhydrous $Na_2SO_4$. After filtration, the filtrate was concentrated under reduced pressure. The residue was purified by silica gel column chromatography, eluted with PE/EA (4/1) to afford (R)—N-((1R,3R)-3-(2-bromo-4,6-difluorophenyl)-3-((5-chloro-2-nitrophenyl)amino)-1-cyanopropyl)-2-methylpropane-2-sulfinamide (4.50 g, 82%) as a yellow solid. MS ESI calculated for $C_{20}H_{20}BrClF_2N_4O_3S$ $[M+H]^+$, 549.01 551.01 found 549.00 551.00. $^1H$ NMR (400 MHz, Chloroform-d) δ 8.74-8.54 (m, 1H), 8.15-8.10 (m, 1H), 7.24-7.18 (m, 1H), 7.00-6.82 (m, 2H), 6.74-6.66 (m, 1H), 5.53-5.40 (m, 1H), 4.41-4.28 (m, 1H), 2.93-2.69 (m, 1H), 2.54-2.34 (m, 1H), 1.61 (s, 1H), 1.25 (d, J=5.0 Hz, 9H). $^{19}F$ NMR (377 MHz, Chloroform-d) δ −107.10, −107.12, −107.19, −107.21, −109.30.

Preparation 131: (1R,3R)-1-(2-bromo-4,6-difluorophenyl)-7-chloro-2,3-dihydro-1H-benzo[d]pyrrolo[1,2-a]imidazol-3-amine To a stirred solution of (R)—N-((1R,3R)-3-(2-bromo-4,6-difluorophenyl)-3-((5-chloro-2-nitrophenyl)amino)-1-cyanopropyl)-2-methylpropane-2-sulfinamide (4.50 g, 8.184 mmol) in EtOH (50 mL) was added Titanium (III) chloride, 15-20% in HCl) (50.49 g, 65.472 mmol) dropwise at room temperature under nitrogen atmosphere. The resulting mixture was stirred at 80° C. for 3 h. The resulting mixture was concentrated under vacuum. The residue was dissolved in EtOAc (100 mL). The mixture was basified to pH 8 with saturated $NaHCO_3$ (aq.). The resulting mixture was filtered, the filter cake was washed with EtOAc (3×100 mL). The filtrate was extracted with EtOAc (2×100 mL). The combined organic layers were washed with brine (1×100 mL), dried over anhydrous $Na_2SO_4$. After filtration, the filtrate was concentrated under reduced pressure. The residue was purified by silica gel column chromatography, eluted with $CH_2Cl_2$/MeOH (9/1) to afford (1R,3R)-1-(2-bromo-4,6-difluorophenyl)-7-chloro-2,3-dihydro-1H-benzo[d]pyrrolo[1,2-a]imidazol-3-amine (2.40 g, 74%, dr=70/30) as a white solid. MS ESI calculated for $C_{16}H_{11}BrClF_2N_3$ $[M+H]^+$, 397.98 399.98 found 397.70 399.70. $^1$H NMR (400 MHz, Chloroform-d) & 7.63 (d, J=8.7 Hz, 1H), 7.37-7.31 (m, 1H), 7.21-7.13 (m, 1H), 7.08-6.54 (m, 2H), 6.19-5.84 (m, 1H), 4.91-4.51 (m, 1H), 3.71-3.35 (m, 1H), 2.80-2.39 (m, 1H).

Preparation 13J: (7R,14R)-11-chloro-1,3-difluoro-6,7-dihydro-7,14-methanobenzo[f]benzo[4,5]imidazo[1,2-a][1,4]diazocin-5(14H)-one To a stirred solution of (1R,3R)-1-(2-bromo-4,6-difluorophenyl)-7-chloro-2,3-dihydro-1H-benzo[d]pyrrolo[1,2-a]imidazol-3-amine (1.40 g, 3.512 mmol) and $PCy_3 \cdot HBF_4$ (258 mg, 0.702 mmol) in 1,4-dioxane (80 mL) were added $K_2CO_3$ (2.60 g, 18.815 mmol) and $Pd(OAc)_2$ (158 mg, 0.702 mmol) in a pressure tank. The mixture was purged with nitrogen for 2 min and then was pressurized to 10 atm with carbon monoxide atmosphere at 140° C. for 16 h. The resulting mixture was diluted with water (50 mL) followed by extraction with $CH_2Cl_2$ (3×50 mL). The combined organic layers were washed with brine (50 mL) and dried over anhydrous $Na_2SO_4$. After filtration, the filtrate was concentrated under reduced pressure. The residue was purified by silica gel column chromatography, eluted with $CH_2Cl_2$/MeOH (10/1) to afford (7R,14R)-11-chloro-1,3-difluoro-6,7-dihydro-7,14-methanobenzo[f]benzo[4,5]imidazo[1,2-a][1,4]diazocin-5(14H)-one (700 mg, 58%) as a yellow solid. MS ESI calculated for $C_{17}H_{10}ClF_2N_3O$ $[M+H]^+$, 346.05 found 346.05. $^1$H NMR (400 MHz, Chloroform-d) δ 8.26 (d, J=6.6 Hz, 1H), 8.13-8.07 (m, 1H), 7.68 (d, J=8.6 Hz, 1H), 7.42-7.37 (m, 1H), 7.25-7.20 (m, 1H), 7.16-7.09 (m, 1H), 6.11 (d, J=7.1 Hz, 1H), 5.01 (t, J=6.7 Hz, 1H), 3.53-3.43 (m, 1H), 2.85 (d, J=13.3 Hz, 1H). $^{19}$F NMR (377 MHz, Chloroform-d) δ −106.57, −106.59, −113.08, −113.11.

Preparation 13K: (7R,14R)-11-chloro-1-(difluoromethoxy)-4-fluoro-6-(methyl-d3)-6,7-dihydro-7,14-methanobenzo[f]benzo[4,5]imidazo[1,2-a][1,4]diazocin-5(14H)-one To a stirred solution of (7R,14R)-11-chloro-1,3-difluoro-6,7-dihydro-7,14-methanobenzo[f]benzo[4,5]imidazo[1,2-a][1,4]diazocin-5(14H)-one (100 mg, 0.289 mmol) in THF (3 mL) was added KHMDS (0.35 mL, 0.347 mmol) dropwise at −78° C. under nitrogen atmosphere. The resulting mixture was stirred at −78° C. for 1 h under nitrogen atmosphere. To the above mixture was added iodomethane-d3 (75 mg, 0.520 mmol) dropwise at −78° C. The resulting mixture was stirred at room temperature for additional overnight. The reaction was quenched with sat. $NH_4Cl$ (aq.) at room temperature. The residue was purified by silica gel column chromatography, eluted with $CH_2Cl_2$/MeOH (10/1) to afford (7R,14R)-11-chloro-1,3-difluoro-6-(methyl-d3)-6,7-dihydro-7,14-methanobenzo[f]benzo[4,5]imidazo[1,2-a][1,4]diazocin-5(14H)-one (90 mg, 86%) as a light yellow solid. MS ESI calculated for $C_{18}H_9D_3ClF_2N_3O$ $[M+H]^+$, 363.08 found 363.15. $^1$H NMR (400 MHz, Chloroform-d) δ 8.23-8.12 (m, 1H), 7.64 (d, J=8.7 Hz, 1H), 7.44-7.39 (m, 1H), 7.25-7.21 (m, 1H), 7.12-7.04 (m, 1H), 6.04 (d, J=7.1 Hz, 1H), 4.98 (d, J=7.2 Hz, 1H), 3.54-3.39 (m, 1H), 2.86 (d, J=13.6 Hz, 1H). $^{19}$F NMR (377 MHz, Chloroform-d) δ −106.73, −106.75, −113.50, −113.52.

Example 13: (7R,14R)-11-(4-(dimethylphosphoryl)-3-fluorophenyl)-1,3-difluoro-6-(methyl-d3)-6,7-dihydro-7,14-methanobenzo[f]benzo[4,5]imidazo[1,2-a][1,4]diazocin-5(14H)-one To a stirred solution of (7R,14R)-11-chloro-1,3-difluoro-6-(methyl-d3)-6,7-dihydro-7,14-methanobenzo[f]benzo[4,5]imidazo[1,2-a][1,4]diazocin-5(14H)-one (40 mg, 0.110 mmol) and (2-fluoro-4-(4,4,5,5-tetramethyl-1,3,2-dioxaborolan-2-yl)phenyl)dimethylphosphine oxide (39 mg, 0.132 mmol) in 1,4-dioxane (0.8 mL) and $H_2O$ (0.2 mL) were added $K_3PO_4$ (70 mg, 0.330 mmol), Sphos (9 mg, 0.022 mmol), and Sphos Pd G3 (9 mg, 0.011 mmol) at room temperature. The resulting mixture was stirred at 80° C. for 2 h under nitrogen atmosphere. The resulting mixture was concentrated under vacuum. The residue was purified by silica gel column chromatography, eluted with $CH_2Cl_2$/MeOH (10/1) followed by Prep-HPLC with the following conditions (Column: XBridge Prep OBD C18 Column 30*150 mm, 5 um; Mobile Phase A: Water (10 mmol/L $NH_4HCO_3$), Mobile Phase B: ACN; Flow rate: 60 mL/min; Gradient: 16% B to 40% B in 16 min; Wave Length: 254/220 nm; RT1 (min): 12.32) to afford (7R,14R)-11-(4-(dimethylphosphoryl)-3-fluorophenyl)-1,3-difluoro-6-(methyl-d3)-6,7-dihydro-7,14-methanobenzo[f]benzo[4,5]imidazo[1,2-a][1,4]diazocin-5(14H)-one (31 mg, 55%) as a white solid. MS ESI calculated for $C_{26}H_{18}D_3F_3N_3O_2P$ $[M+H]^+$, 499.15 found 499.20. $^1$H NMR (400 MHz, Chloroform-d) δ 8.21-8.13 (m, 1H), 8.08-7.99 (m, 1H), 7.81 (d, J=8.5 Hz, 1H), 7.61 (s, 1H), 7.57-7.47 (m, 2H), 7.36-7.30 (m, 1H), 7.11-7.04 (m, 1H), 6.12 (d, J=7.0 Hz, 1H), 5.02 (d, J=7.2 Hz, 1H), 3.55-3.45 (m, 1H), 2.90 (d, J=13.5 Hz, 1H), 1.86 (s, 3H), 1.82 (s, 3H). $^{19}$F NMR (377 MHz, Chloroform-d) δ −105.71, −105.72, −106.80, −106.82, −113.71, −113.73. $^{31}$P NMR (162 MHz, Chloroform-d) δ 30.38.

Example 14: (7R,14R)-11-(4-(dimethylphosphoryl)-2,3-difluorophenyl)-1-fluoro-6-(methyl-d3)-6,7-dihydro-7,14-methanobenzo[f]benzo[4,5]imidazo[1,2-a][1,4]diazocin-5(14H)-one

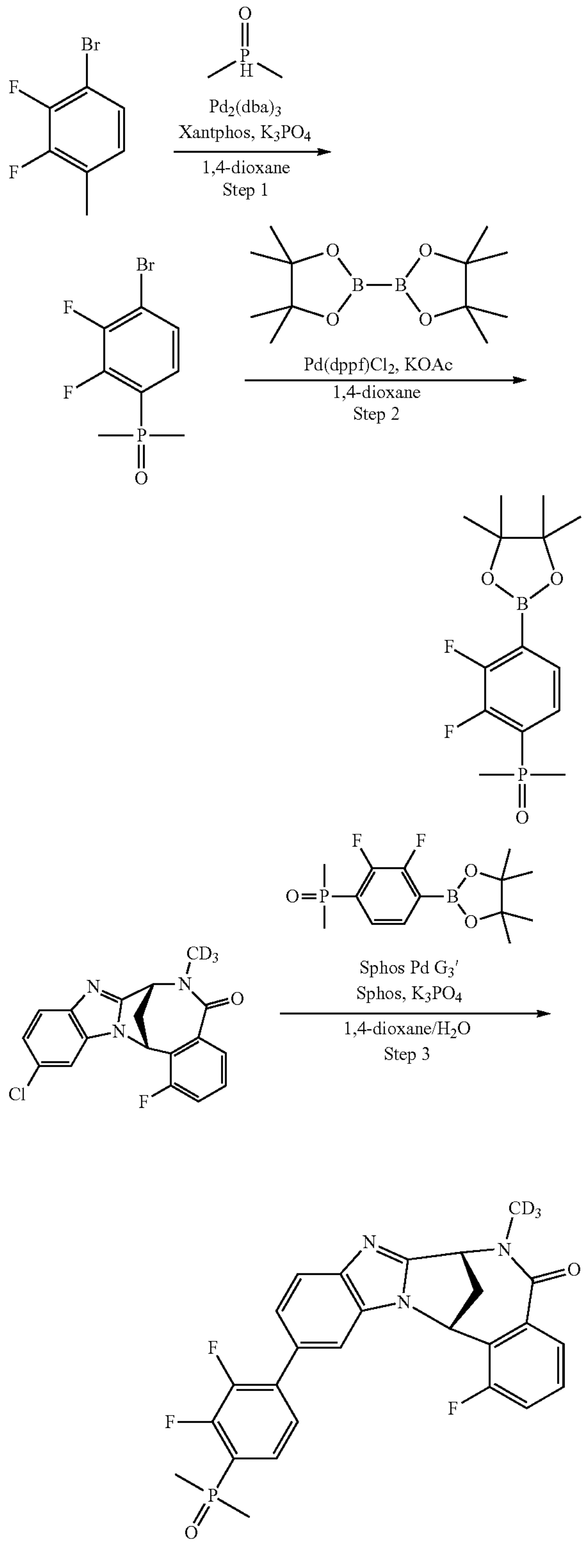

Preparation 14A: 1-bromo-4-(dimethylphosphoryl)-2,3-difluorobenzene

To a stirred solution of 1-bromo-2,3-difluoro-4-iodobenzene (100.00 g, 313.591 mmol) and (methylphosphonoyl) methane (29.37 g, 376.309 mmol) in 1,4-dioxane (1 L) were added $Pd_2(dba)_3$ (14.36 g, 15.680 mmol), Xantphos (18.15 g, 31.359 mmol) and $K_3PO_4$ (79.88 g, 376.309 mmol) at room temperature under nitrogen atmosphere. The resulting mixture was stirred at 65° C. for additional 2 h. The resulting mixture was filtered, the filter cake was washed with water (3×10 mL). The resulting mixture was diluted with water (300 mL) followed by extraction with EtOAc (3×500 mL). The combined organic layers were washed with water (3×50 mL) and dried over anhydrous $Na_2SO_4$. After filtration, the filtrate was concentrated under reduced pressure. This resulted in 1-bromo-4-(dimethylphosphoryl)-2,3-difluorobenzene (63.01 g, 75%) as a yellow solid. MS ESI calculated for $C_8H_8BrF_2OP$ $[M+H]^+$, 268.95 270.95 found 268.95 270.95. $^1H$ NMR (300 MHz, Chloroform-d) δ 7.71-7.59 (m, 1H), 7.59-7.46 (m, 1H), 1.85 (d, J=1.3 Hz, 3H), 1.80 (d, J=1.2 Hz, 3H). $^{19}F$ NMR (282 MHz, Chloroform-d) δ −128.07, −128.08, −128.15, −128.17, −129.37, −129.39, −129.45, −129.47.

Preparation 14B: 2-[4-(dimethylphosphoryl)-2,3-difluorophenyl]-4,4,5,5-tetramethyl-1,3,2-dioxaborolane A mixture of 1-bromo-4-(dimethylphosphoryl)-2,3-difluorobenzene (31.40 g, 116.717 mmol) and 4,4,5,5-tetramethyl-2-(tetramethyl-1,3,2-dioxaborolan-2-yl)-1,3,2-dioxaborolane (35.57 g, 140.060 mmol) in 1,4-dioxane (320 mL) were added $Pd(dppf)Cl_2{\cdot}CH_2Cl_2$ (4.77 g, 5.836 mmol) and KOAc (28.64 g, 291.793 mmol) at room temperature. The resulting mixture was stirred at 100° C. for 2 h under nitrogen atmosphere. The resulting mixture was diluted with water (100 mL) followed by extraction with $CH_2Cl_2$/IPA (3/1) (3×200 mL). The combined organic layers were washed with brine (3×50 mL) and dried over anhydrous $Na_2SO_4$. After filtration, the filtrate was concentrated under reduced pressure. The residue was purified by silica gel column chromatography, eluted with $CH_2Cl_2$/MeOH (12:1) to afford 2-[4-(dimethylphosphoryl)-2,3-difluorophenyl]-4,4,5,5-tetramethyl-1,3,2-dioxaborolane (33.01 g, 89%) as brown oil. MS ESI calculated for $C_{14}H_{20}BF_2O_3P$ $[M+H]^+$, 317.12 found 317.15.

Example 14: (7R,14R)-11-(4-(dimethylphosphoryl)-2,3-difluorophenyl)-1-fluoro-6-(methyl-d3)-6,7-dihydro-7,14-methanobenzo[f]benzo[4,5]imidazo[1,2-a][1,4]diazocin-5(14H)-one To a stirred solution of (7R,14R)-11-chloro-1-fluoro-6-(methyl-d3)-6,7-dihydro-7,14-methanobenzo[f]benzo[4,5]imidazo[1,2-a][1,4]diazocin-5(14H)-one (12.50 g, 36.254 mmol) and 2-[4-(dimethylphosphoryl)-2,3-difluorophenyl]-4,4,5,5-tetramethyl-1,3,2-dioxaborolane (16.04 g, 50.756 mmol) in 1,4-dioxane (15 mL) and $H_2O$ (1.5 mL) were added Sphos (1.49 g, 3.625 mmol), Sphos Pd G3 (1.41 g, 1.813 mmol) and $K_3PO_4$ (15.39 g, 72.508 mmol) at room temperature under nitrogen atmosphere. The resulting mixture was stirred at 80° C. for additional 2 h. The resulting mixture was concentrated under reduced pressure. The residue was purified by silica gel column chromatography, eluted with $CH_2Cl_2$/MeOH (15:1) to afford the crude product. The crude product was dissolved in $CH_2Cl_2$ (10 mL) and purified by trituration with hexane (50 mL). The precipitated solids were collected by filtration and washed with hexane (3×10 mL). The residue was again purified by trituration with water (200 mL) at 80° C. The precipitated solids were collected by filtration and washed with water (3×10 mL). This resulted in (7R,14R)-11-(4-(dimethylphosphoryl)-2,3-difluorophenyl)-1-fluoro-6-(methyl-d3)-6,7-dihydro-7,14-methanobenzo[f]benzo[4,5]imidazo[1,2-a][1,4]diazocin-5(14H)-one (11.88 g, 66%) as a white solid. MS ESI calculated for $C_{26}H_{18}D_3F_3N_3O_2P$ [M+H]$^+$, 499.15 found 499.15. $^1H$ NMR (400 MHz, Chloroform-d) δ 8.43-8.40 (m, 1H), 7.84-7.74 (m, 2H), 7.68-7.64 (m, 1H), 7.46-7.42 (m, 1H), 7.42-7.35 (m, 2H), 7.33-7.27 (m, 1H), 6.19 (d, J=7.0 Hz, 1H), 5.04 (d, J=7.1 Hz, 1H), 3.54-3.46 (m, 1H), 2.92 (d, J=13.5 Hz, 1H), 1.88 (s, 3H), 1.85 (s, 3H). 1° F. NMR (377 MHz, Chloroform-d) δ −118.30, −131.15, −131.21, −142.98, −143.04. $^{31}P$ NMR (162 MHz, Chloroform-d) δ 29.70.

Example 15: (7R,14R)-11-(4-(dimethylphosphoryl)-3-fluorophenyl)-1,2-difluoro-6-(methyl-d3)-6,7-dihydro-7,14-methanobenzo[f]benzo[4,5]imidazo[1,2-a][1,4]diazocin-5(14H)-one

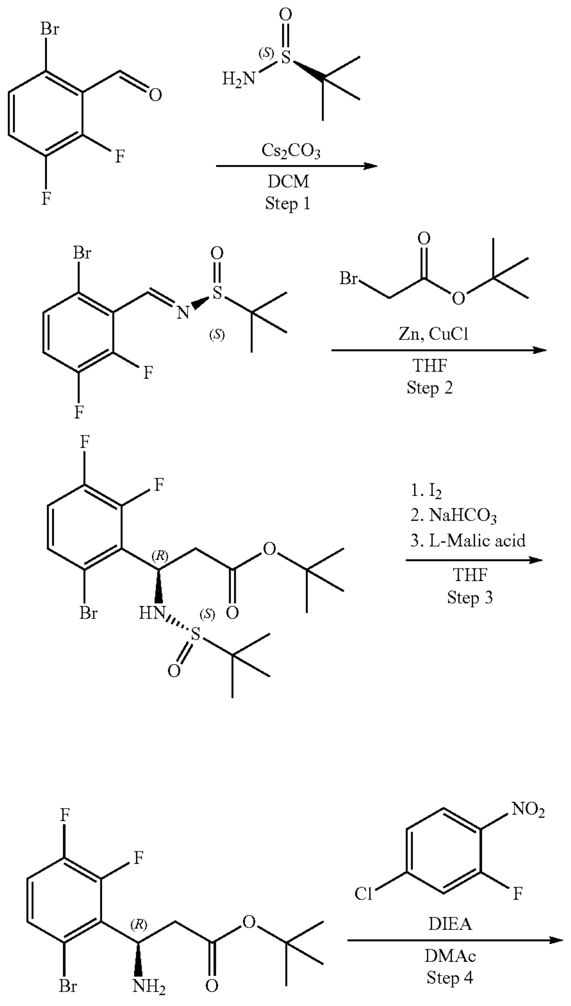

-continued

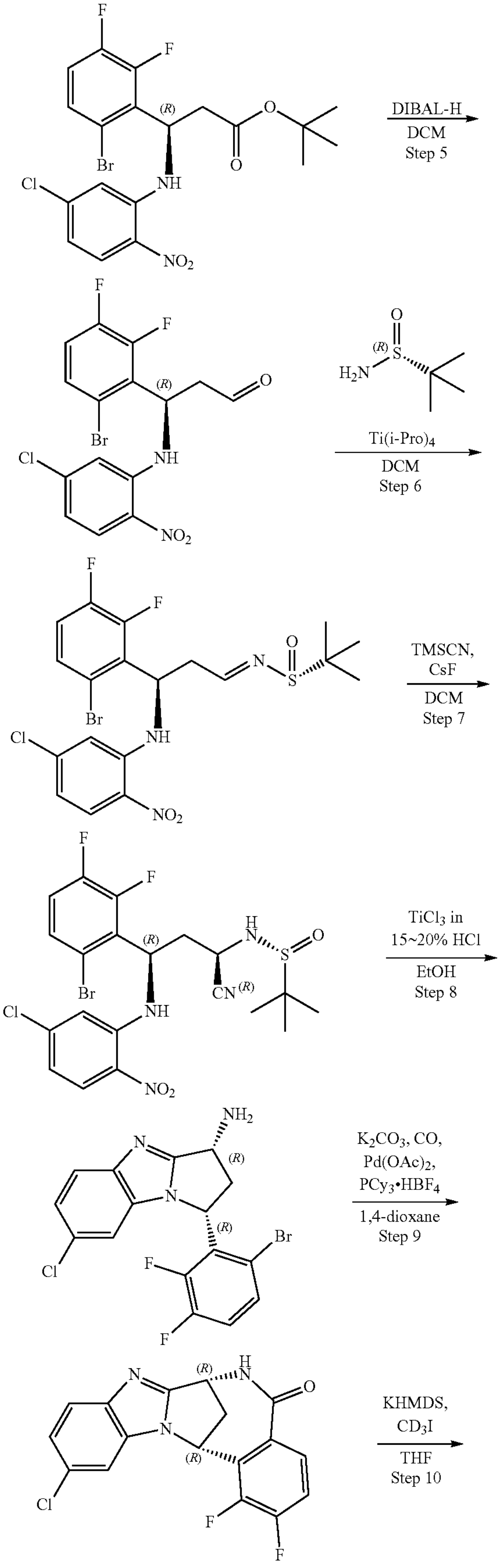

-continued

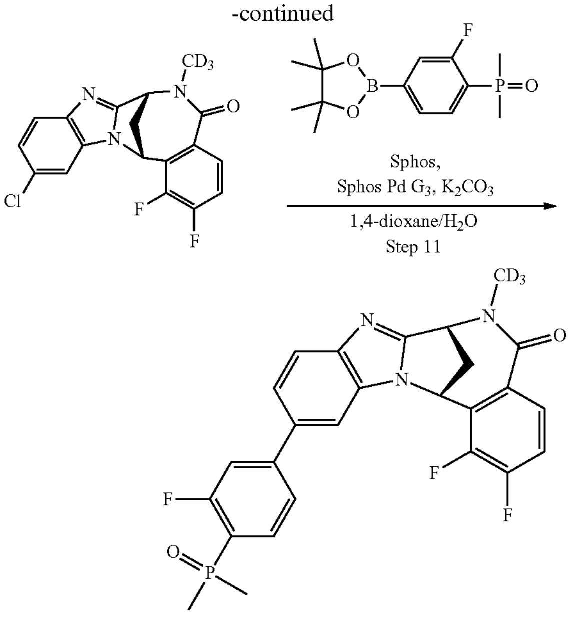

Preparation 15A: (S)—N-[(6-bromo-2,3-difluoro-phenyl)methylidene]-2-methylpropane-2-sulfinamide A mixture of 6-bromo-2,3-difluorobenzaldehyde (50.00 g, 226.243 mmol), $Cs_2CO_3$ (81.09 g, 248.867 mmol) and(S)-2-methylpropane-2-sulfinamide (32.90 g, 271.492 mmol) in $CH_2Cl_2$ (500 mL) was stirred at room temperature for 2 h under nitrogen atmosphere. The resulting mixture was filtered, the filter cake was washed with DCM (3×30 mL). The filtrate was concentrated under reduced pressure. The residue was purified by silica gel column chromatography, eluted with EA in PE (0~25%) to afford(S)—N-[(6-bromo-2,3-difluorophenyl)methylidene]-2-methylpropane-2-sulfinamide (73.00 g, 99%) as yellow oil. MS ESI calculated for $C_{11}H_{12}BrF_2NOS$ $[M+H]^+$, 323.98 325.98 found 324.00 326.05. $^1H$ NMR (400 MHz, Chloroform-d) δ 8.79 (s, 1H), 7.46-7.38 (m, 1H), 7.23-7.12 (m, 1H), 1.28 (s, 9H). $^{19}F$ NMR (377 MHz, Chloroform-d) δ −134.01, −134.06, −136.50, −136.55.

Preparation 15B: tert-butyl (3R)-3-(6-bromo-2,3-difluorophenyl)-3-{[(S)-2-methylpropane-2-sulfinyl]amino}propanoate A mixture of CuCl (20.43 g, 206.367 mmol) and Zinc (62.96 g, 963.046 mmol) in THF (1.45 L) was stirred at 60° C. for 2 h under nitrogen atmosphere. The mixture was allowed to cool down to room temperature followed by addition of tert-butyl 2-bromoacetate (67.09 g, 343.945 mmol) at room temperature (<40° C.) and then stirred for additional 2 h at 60° C. (S)—N-[(6-bromo-2,3-difluorophenyl)methylidene]-2-methylpropane-2-sulfinamide (44.6 g, 137.578 mmol) in THF (160 mL) was added to above mixture at 0~10° C. and stirred overnight at room temperature. The resulting mixture was filtered, the filter cake was washed with EA (3×50 mL). The filtrate was concentrated under reduced pressure. The resulting mixture was diluted with 25%~30% citric acid (aq.) (1.5 L) followed by extraction with EtOAc (2×1 L). The combined organic layers were washed with sat. $NaHCO_3$ (aq.) (2×800 mL) and brine (1×1 L) and dried over anhydrous $Na_2SO_4$. After filtration, the filtrate was concentrated under reduced pressure. This resulted in tert-butyl (3R)-3-(6-bromo-2,3-difluorophenyl)-3-{[(S)-2-methylpropane-2-sulfinyl]amino}propanoate (54.01 g, 89%) as a light yellow solid. MS ESI calculated for $C_{17}H_{24}BrF_2NO_3S$ $[M+H]^+$, 440.06 442.06 found 440.10 442.10. $^1H$ NMR (400 MHz, Chloroform-d) δ 7.36-7.27 (m, 1H), 7.06-6.95 (m, 1H), 5.42-5.32 (m, 1H), 4.25 (d, J=7.1 Hz, 1H), 3.11-3.01 (m, 1H), 2.95-2.85 (m, 1H), 1.38 (s, 9H), 1.13 (s, 9H). $^{19}F$ NMR (377 MHz, Chloroform-d) δ −135.32, −135.37, −137.05, −137.10.

Preparation 15C: tert-butyl (3R)-3-amino-3-(6-bromo-2,3-difluorophenyl)propanoate To a stirred mixture of tert-butyl (3R)-3-(6-bromo-2,3-difluorophenyl)-3-{[(S)-2-methylpropane-2-sulfinyl]amino}propanoate (54.01 g, 122.633 mmol) in THF (270 mL) and $H_2O$ (54 mL) was added Iodine (7.78 g, 30.658 mmol) at room temperature. The mixture was stirred for 16 h at 50° C. The mixture was allowed to cool down to room temperature. The reaction was quenched by the addition of sat. $NaHCO_3$ (aq.) (1.5 L) at 0° C. followed by extraction with EtOAc (3×1 L). The combined organic layers were washed with brine (3×1 L) and dried over anhydrous $Na_2SO_4$. After filtration, the filtrate was concentrated under reduced pressure. The crude product was dissolved in MTBE (420 mL) followed by the addition of tert-butyl (3R)-3-amino-3-(6-bromo-2,3-difluorophenyl)propanoate (17.30 g) and stirred for 16 h at room temperature. The precipitated solids were collected by filtration and washed with MTBE (3×20 mL). The solids was purified by trituration with MTBE (100 mL). Then the solid was dissolved in sat. $NaHCO_3$ (aq.) (pH ~8) followed by extraction with MTBE (3×800 mL). The combined organic layers were washed with brine (2×800 mL) and dried over anhydrous $Na_2SO_4$. After filtration, the filtrate was concentrated under reduced pressure. This resulted in tert-butyl (3R)-3-amino-3-(6-bromo-2,3-difluorophenyl)propanoate (25.80 g, 63%) as light yellow oil. MS ESI calculated for $C_{13}H_{16}BrF_2NO_2$ $[M+H]^+$, 336.03 338.08 found 335.90 337.85. $^1H$ NMR (400 MHz, Chloroform-d) δ 7.34-7.27 (m, 1H), 6.97 (q, J=8.8 Hz, 1H), 4.90-4.82 (m, 1H), 2.91-2.80 (m, 1H), 2.78-2.69 (m, 1H), 1.42 (s, 9H). $^{19}F$ NMR (377 MHz, Chloroform-d) δ −137.51.

Preparation 15D: tert-butyl (3R)-3-(6-bromo-2,3-difluorophenyl)-3-[(5-chloro-2-nitrophenyl)amino]propanoate To a stirred mixture of tert-butyl (3R)-3-amino-3-(6-bromo-2,3-difluorophenyl)propanoate (87.10 g, 259.090 mmol) and DIEA (68 mL, 388.635 mmol) in N,N-Dimethylacetamide (900 mL) was added 4-chloro-2-fluoro-1-nitrobenzene (47.75 g, 272.044 mmol) at room temperature under nitrogen atmosphere. The mixture was stirred for 16 h at 80° C. The resulting mixture was diluted with water (500 mL) followed by extraction with EtOAc (3×1 L). The combined organic layers were washed with brine (3×1 L) and dried over anhydrous $Na_2SO_4$. After filtration, the filtrate was concentrated under reduced pressure. The residue was purified by silica gel column chromatography, eluted with EA in PE (0~20%) to afford tert-butyl (3R)-3-(6-bromo-2,3-difluorophenyl)-3-[(5-chloro-2-nitrophenyl)amino]propanoate (117.20 g, 92%) as a yellow solid. MS ESI calculated for $C_{19}H_{18}BrClF_2N_2O_4$ $[M+H]^+$, 491.01 493.01 found 491.05 493.05. $^1H$ NMR (400 MHz, Chloroform-d) δ 8.77 (d, J=8.5 Hz, 1H), 8.09 (d, J=9.1 Hz, 1H), 7.41-7.32 (m, 1H), 7.10-6.99 (m, 1H), 6.95 (d, J=2.0 Hz, 1H), 6.66-6.59 (m, 1H), 5.63-5.53 (m, 1H), 3.13-3.02 (m, 1H), 2.92-2.82 (m, 1H), 1.40 (s, 9H). $^{19}$F NMR (377 MHz, Chloroform-d) δ −135.92, −135.97, −136.75, −136.80.

Preparation 15E: (3R)-3-(6-bromo-2,3-difluorophenyl)-3-[(5-chloro-2-nitrophenyl)amino]propanal To a stirred solution of tert-butyl (3R)-3-(6-bromo-2,3-difluorophenyl)-3-[(5-chloro-2-nitrophenyl)amino]propanoate (6.84 g, 13.911 mmol) in DCM (100 mL) was added Diisobutylaluminum hydride (1.0M in DCM) (15.3 mL, 15.302 mmol) dropwise at −78° C. under nitrogen atmosphere. The mixture was stirred for 0.5 h at −78° C. The reaction was poured into sat. $NH_4Cl$ (aq.) 20 mL at −78° C. The resulting mixture was filtered, the filter cake was washed with EtOAc (3×30 mL). The filtrate was extracted with EtOAc (3×300 mL) and dried over anhydrous $Na_2SO_4$. After filtration, the filtrate was concentrated under reduced pressure. The residue was purified by silica gel column chromatography, eluted with EA in PE (0~30%) to afford (3R)-3-(6-bromo-2,3-difluorophenyl)-3-[(5-chloro-2-nitrophenyl)amino]propanal (3.55 g, 61%) as yellow oil. MS ESI calculated for $C_{15}H_{10}BrClF_2N_2O_3$ [M+H]$^+$, 418.95 420.95 found 419.00 420.95. $^1$H NMR (400 MHz, Chloroform-d) δ 9.82 (s, 1H), 8.69 (d, J=8.8 Hz, 1H), 8.09 (d, J=9.1 Hz, 1H), 7.41-7.31 (m, 1H), 7.10-7.00 (m, 2H), 6.69-6.60 (m, 1H), 5.80-5.70 (m, 1H), 3.51-3.40 (m, 1H), 3.16-3.05 (m, 1H). $^{19}$F NMR (377 MHz, Chloroform-d) δ −135.56, −135.61, −136.95, −137.00.

Preparation 15F: (R)—N-[(3R)-3-(6-bromo-2,3-difluorophenyl)-3-[(5-chloro-2-nitrophenyl)amino]propylidene]-2-methylpropane-2-sulfinamide To a stirred solution of (3R)-3-(6-bromo-2,3-difluorophenyl)-3-[(5-chloro-2-nitrophenyl)amino]propanal (3.55 g, 8.460 mmol) and (R)-2-methylpropane-2-sulfinamide (1.23 g, 10.152 mmol) in DCM (40 mL) was added tetrakis (propan-2-yloxy) titanium (4.81 g, 16.920 mmol) dropwise at room temperature. The mixture was stirred for 16 h. The reaction was quenched with water at 0° C. followed by extraction with DCM (3×300 mL). The combined organic layers were washed with brine (3×300 mL) and dried over anhydrous $Na_2SO_4$. After filtration, the filtrate was concentrated under reduced pressure. The residue was purified by silica gel column chromatography, eluted with EA in PE (0~20%) to afford (R)—N-[(3R)-3-(6-bromo-2,3-difluorophenyl)-3-[(5-chloro-2-nitrophenyl)amino]propylidene]-2-methylpropane-2-sulfinamide (3.70 g, 84%) as yellow oil. MS ESI calculated for $C_{19}H_{19}BrClF_2N_3O_3S$ [M+H]$^+$, 522.00 524.00 found 522.05 524.05. $^1$H NMR (400 MHz, Chloroform-d) δ 8.73 (d, J=8.8 Hz, 1H), 8.15-8.07 (m, 2H), 7.43-7.35 (m, 1H), 7.15-7.01 (m, 1H), 6.92 (d, J=2.1 Hz, 1H), 6.70-6.62 (m, 1H), 5.69-5.59 (m, 1H), 3.52-3.39 (m, 1H), 3.23-3.12 (m, 1H), 1.14 (s, 9H). 1° F. NMR (377 MHz, Chloroform-d) δ −135.46, −135.51, −136.92, −136.97.

Preparation 15G: (R)—N-[(3R)-3-(6-bromo-2,3-difluorophenyl)-3-[(5-chloro-2-nitrophenyl)amino]-1-cyanopropyl]-2-methylpropane-2-sulfinamide To a stirred mixture of (R)—N-[(1E,3R)-3-(6-bromo-2,3-difluorophenyl)-3-[(5-chloro-2-nitrophenyl)amino]propylidene]-2-methylpropane-2-sulfinamide (3.70 g, 7.077 mmol) and CsF (2.15 g, 14.154 mmol) in THF (40 mL) was added trimethylsilanecarbonitrile (1.40 g, 14.154 mmol) dropwise at room temperature. The mixture was stirred for 1 h at room temperature. The reaction was quenched with Water (100 mL) at room temperature followed by extraction with EtOAc (3×200 mL). The combined organic layers were washed with brine (3×200 mL) and dried over anhydrous $Na_2SO_4$. After filtration, the filtrate was concentrated under reduced pressure. The residue was purified by silica gel column chromatography, eluted with EA in PE (0~50%) to afford (R)—N-[(3R)-3-(6-bromo-2,3-difluorophenyl)-3-[(5-chloro-2-nitrophenyl)amino]-1-cyanopropyl]-2-methylpropane-2-sulfinamide (3.60 g, 93%) as a yellow solid. MS ESI calculated for $C_{20}H_{20}BrClF_2N_4O_3S$ [M+H]$^+$, 549.01 551.01 found 549.10 551.10. $^1$H NMR (400 MHz, Chloroform-d) δ 8.16-8.07 (m, 1H), 7.43-7.34 (m, 1H), 7.13-7.02 (m, 1H), 6.98-6.88 (m, 1H), 6.74-6.66 (m, 1H), 5.52-5.41 (m, 1H), 4.71-4.33 (m, 1H), 4.23-3.90 (m, 1H), 2.90-2.76 (m, 1H), 2.54-2.37 (m, 1H), 1.24 (d, J=4.3 Hz, 9H). $^{19}$F NMR (377 MHz, Chloroform-d) δ −135.05, −135.10, −135.21, −135.26, −137.26, −137.31, −137.36.

Preparation 15H: (1R,3R)-1-(6-bromo-2,3-difluorophenyl)-7-chloro-2,3-dihydro-1H-benzo[d]pyrrolo[1,2-a]imidazol-3-amine To a stirred solution of (R)—N-[(3R)-3-(6-bromo-2,3-difluorophenyl)-3-[(5-chloro-2-nitrophenyl)amino]-1-cyanopropyl]-2-methylpropane-2-sulfinamide (3.60 g, 6.548 mmol) in EtOH (40 mL) was added Titanium (III) chloride, 15-20% in HCl) (46.16 g, 52.384 mmol) dropwise at room temperature under. The mixture was stirred for 16 h at 80° C. The mixture was allowed to cool down to room temperature and quenched with sat. $Na_2CO_3$ at 0° C. The resulting mixture was filtered, the filter cake was washed with EA (3×50 mL). The filtrate was concentrated under reduced pressure. The residue was diluted with water (500 mL) followed by extraction with EtOAc (3×200 mL). The combined organic layers were washed with brine (3×200 mL) and dried over anhydrous $Na_2SO_4$. After filtration, the filtrate was concentrated under reduced pressure. The residue was purified by silica gel column chromatography, eluted with MeOH in DCM (0~8%) to afford (1R,3R)-1-(6-bromo-2,3-difluorophenyl)-7-chloro-2,3-dihydro-1H-benzo[d]pyrrolo[1,2-a]imidazol-3-amine (2.10 g, 80%) as a grey solid. MS ESI calculated for $C_{16}H_{11}BrClF_2N_3$ [M+H]$^+$, 397.98 399.98 found 398.00 400.05.

Preparation 151: (7R,14R)-11-chloro-1,2-difluoro-6,7-dihydro-7,14-methanobenzo[f]benzo[4,5]imidazo[1,2-a][1,4]diazocin-5(14H)-one To a solution of (1R,3R)-1-(6-bromo-2,3-difluorophenyl)-7-chloro-2,3-dihydro-1H-benzo[d]pyrrolo[1,2-a]imidazol-3-amine (20 g, 50.171 mmol), $Pd(OAc)_2$ (2.25 g, 10.034 mmol), $PCy_3 \cdot HBF_4$ (3.70, 10.034 mmol) and $K_2CO_3$ (34.67 g, 250.855 mmol) in 1,4-dioxane (10 mL) in a pressure tank. The mixture was purged with nitrogen for 3 times and then was pressurized to 10 atm with carbon monoxide at 140° C. for overnight. The reaction mixture was cooled to room temperature and filtered to remove insoluble solids. The filtrate was concentrated under vacuum. The residue was purified by silica gel column chromatography, eluted with MeOH in DCM (0~10%) to afford (7R,14R)-11-chloro-1,2-difluoro-6,7-dihydro-7,14-methanobenzo[f]benzo[4,5]imidazo[1,2-a][1,4]diazocin-5(14H)-one (10.01 g, 58%) as a grey solid. MS ESI calculated for $C_{17}H_{10}ClF_2N_3O$ [M+H]$^+$, 346.05 found 346.15. $^1$H NMR (400 MHz, DMSO-$d_6$) δ 9.17 (d, J=7.0 Hz, 1H), 8.24-8.16 (m, 1H), 7.67-7.61 (m, 1H), 7.58-7.47 (m, 1H), 7.40-7.35 (m, 1H), 7.26-7.17 (m, 1H), 6.31 (d, J=6.8 Hz, 1H), 4.90 (t, J=6.8 Hz, 1H), 3.50-3.39 (m, 1H), 2.78 (d, J=13.5 Hz, 1H). $^{19}F$ NMR (377 MHz, DMSO-$d_6$) δ −131.02, −131.08, −140.87, −140.93.

Preparation 15J: (7R,14R)-11-chloro-1,2-difluoro-6-(methyl-d3)-6,7-dihydro-7,14-methanobenzo[f]benzo[4,5]imidazo[1,2-a][1,4]diazocin-5(14H)-one To a stirred solution of (7R,14R)-11-chloro-1,2-difluoro-6,7-dihydro-7,14-methanobenzo[f]benzo[4,5]imidazo[1,2-a][1,4]diazocin-5(14H)-one (64 mg, 0.185 mmol) in THF (1 mL) was added KHMDS (1.0M in THF) (0.22 mL, 0.222 mmol) dropwise at −78° C. under nitrogen atmosphere. The mixture was stirred for 1 h at −78° C. followed by addition of iodomethane-$d_3$ (40.25 mg, 0.277 mmol) at −78° C. and stirred for 16 h at room temperature. The reaction was quenched by the addition of sat. $NH_4Cl$ (aq.) (2 mL) at 0° C. The resulting mixture was concentrated under vacuum. The residue was purified by silica gel column chromatography, eluted with MeOH in DCM (0~10%) to afford (7R,14R)-11-chloro-1,2-difluoro-6-(methyl-d3)-6,7-dihydro-7,14-methanobenzo[f]benzo[4,5]imidazo[1,2-a][1,4]diazocin-5(14H)-one (57 mg, 85%) as a white solid. MS ESI calculated for $C_{18}H_9D_3ClF_2N_3O$ $[M+H]^+$, 363.08 found 363.10. $^1H$ NMR (400 MHz, Chloroform-d) δ 8.48-8.39 (m, 1H), 7.66 (d, J=8.7 Hz, 1H), 7.47-7.42 (m, 1H), 7.30-7.18 (m, 2H), 6.11 (d, J=7.0 Hz, 1H), 5.04 (d, J=7.2 Hz, 1H), 3.56-3.45 (m, 1H), 2.90 (d, J=13.6 Hz, 1H). $^{19}F$ NMR (377 MHz, Chloroform-d) δ −129.35, −129.41, −141.31, −141.36.

Example 15: (7R,14R)-11-(4-(dimethylphosphoryl)-3-fluorophenyl)-1,2-difluoro-6-(methyl-d3)-6,7-dihydro-7,14-methanobenzo[f]benzo[4,5]imidazo[1,2-a][1,4]diazocin-5(14H)-one A mixture of (7R,14R)-11-chloro-1,2-difluoro-6-(methyl-d3)-6,7-dihydro-7,14-methanobenzo[f]benzo[4,5]imidazo[1,2-a][1,4]diazocin-5(14H)-one (50 mg, 0.138 mmol), Sphos (11 mg, 0.028 mmol), SPhos Pd G3 (11 mg, 0.014 mmol) and $K_2CO_3$ (48 mg, 0.345 mmol) in 1,4-dioxane (1 mL) and $H_2O$ (0.1 mL) was stirred at 80° C. for 2 h under nitrogen atmosphere. The resulting mixture was concentrated under vacuum. The residue was purified by silica gel column chromatography, eluted with MeOH in DCM (0~10%) followed by reversed-phase flash chromatography with the following conditions: column, C18 silica gel; mobile phase, $CH_3CN$ in water (10 mmol/L $NH_4HCO_3$), 25% to 40% gradient in 30 min; detector, 254 nm. This resulted in (7R,14R)-11-(4-(dimethylphosphoryl)-3-fluorophenyl)-1,2-difluoro-6-(methyl-d3)-6,7-dihydro-7,14-methanobenzo[f]benzo[4,5]imidazo[1,2-a][1,4]diazocin-5(14H)-one (44 mg, 63%) as a white solid. MS ESI calculated for $C_{26}H_{18}D_3F_3N_3O_2P$ $[M+H]^+$, 499.15 found 499.05. $^1H$ NMR (400 MHz, Chloroform-d) δ 8.49-8.40 (m, 1H), 8.11-7.99 (m, 1H), 7.83 (d, J=8.5 Hz, 1H), 7.65-7.60 (m, 1H), 7.59-7.49 (m, 2H), 7.38-7.29 (m, 1H), 7.28-7.17 (m, 1H), 6.19 (d, J=6.9 Hz, 1H), 5.08 (d, J=7.1 Hz, 1H), 3.60-3.49 (m, 1H), 2.94 (d, J=13.6 Hz, 1H), 1.86 (s, 3H), 1.83 (s, 3H). $^{19}F$ NMR (377 MHz, Chloroform-d) δ −105.56, −105.57, −129.56, −129.61, −141.46, −141.51. $^{31}P$ NMR (162 MHz, Chloroform-d) δ 30.29, 30.26.

Example 16: (7R,14R)-11-(4-(dimethylphosphoryl)phenyl)-1-fluoro-6-(methyl-d3)-6,7-dihydro-7,14-methanobenzo[f]benzo[4,5]imidazo[1,2-a][1,4]diazocin-5(14H)-one

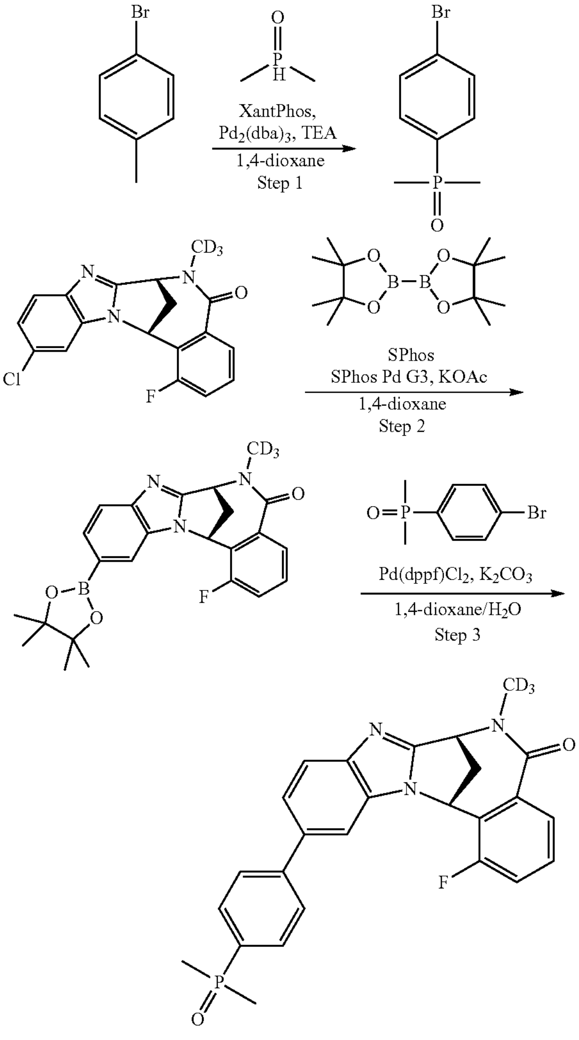

Preparation 16A: (4-bromophenyl)dimethylphosphine oxide

To a stirred solution of 1-bromo-4-iodobenzene (9.60 g, 33.934 mmol) and dimethylphosphine oxide (2.65 g, 33.934 mmol) in 1,4-dioxane (50 mL) were added $Pd_2(dba)_3$ (1.55 g, 1.697 mmol), Xantphos (1.96 g, 3.393 mmol) and $Et_3N$ (4.12 g, 40.721 mmol) at room temperature under nitrogen atmosphere. The resulting mixture was stirred at 80° C. for 2 h. The resulting mixture was concentrated under reduced pressure. The residue was purified by silica gel column chromatography, eluted with $CH_2Cl_2$/MeOH (10/1) followed by reversed-phase flash chromatography with the following conditions: column, C18 silica gel; mobile phase, $CH_3CN$ in Water (10 mmol/L $NH_4HCO_3$), 35% to 45% gradient in 10 min; detector, 254 nm. This resulted in (4-bromophenyl)dimethylphosphine oxide (3.01 g, 38%) as a white solid. MS ESI calculated for $C_8H_{10}BrOP$ $[M+H]^+$, 232.97 234.97 found 232.90 234.90. $^1H$ NMR (400 MHz, DMSO-$d_6$) δ 7.77-7.66 (m, 4H), 1.67 (s, 3H), 1.63 (s, 3H). $^{31}$P NMR (162 MHz, DMSO-$d_6$) δ 32.36.

Preparation 16B: (7R,14R)-1-fluoro-6-(methyl-d3)-11-(4,4,5,5-tetramethyl-1,3,2-dioxaborolan-2-yl)-6,7-dihydro-7,14-methanobenzo[f]benzo[4,5]imidazo[1,2-a][1,4]diazocin-5(14H)-one To a stirred solution of (7R,14R)-11-chloro-1-fluoro-6-(methyl-d3)-6,7-dihydro-7,14-methanobenzo[f]benzo[4,5]imidazo[1,2-a][1,4]diazocin-5(14H)-one (200 mg, 0.580 mmol) and 4,4,5,5-tetramethyl-2-(tetramethyl-1,3,2-dioxaborolan-2-yl)-1,3,2-dioxaborolane (295 mg, 1.160 mmol) in 1,4-dioxane (2 mL) were added Sphos (23.81 mg, 0.058 mmol), Sphos Pd G3 (23 mg, 0.029 mmol) and KOAc (171 mg, 1.740 mmol) at room temperature under nitrogen atmosphere. The resulting mixture was stirred at 80° C. for additional 3 h. The resulting mixture was concentrated under reduced pressure. The residue was purified by silica gel column chromatography, eluted with PE/EA (1:1) to afford (7R,14R)-1-fluoro-6-(methyl-d3)-11-(4,4,5,5-tetramethyl-1,3,2-dioxaborolan-2-yl)-6,7-dihydro-7,14-methanobenzo[f]benzo[4,5]imidazo[1,2-a][1,4]diazocin-5(14H)-one (185 mg, 73%) as a light yellow solid. MS ESI calculated for $C_{24}H_{22}D_3BFN_3O_3$ [M+H]$^+$, 437.22 found 437.25. $^1$H NMR (400 MHz, Chloroform-d) δ 8.43-8.36 (m, 1H), 7.91 (d, J=1.1 Hz, 1H), 7.75-7.66 (m, 2H), 7.44-7.28 (m, 2H), 6.15 (d, J=7.0 Hz, 1H), 4.98 (d, J=7.2 Hz, 1H), 3.49-3.39 (m, 1H), 2.88 (d, J=13.4 Hz, 1H), 1.36 (s, 12H). $^{19}$F NMR (377 MHz, Chloroform-d) δ −117.60.

Example 16: (7R,14R)-11-(4-(dimethylphosphoryl)phenyl)-1-fluoro-6-(methyl-d3)-6,7-dihydro-7,14-methanobenzo[f]benzo[4,5]imidazo[1,2-a][1,4]diazocin-5(14H)-one To a stirred solution of (7R,14R)-1-fluoro-6-(methyl-d3)-11-(4,4,5,5-tetramethyl-1,3,2-dioxaborolan-2-yl)-6,7-dihydro-7,14-methanobenzo[f]benzo[4,5]imidazo[1,2-a][1,4]diazocin-5(14H)-one (50 mg, 0.115 mmol) and (4-bromophenyl)dimethylphosphine oxide (40 mg, 0.173 mmol) in 1,4-dioxane (1 mL) and $H_2O$ (0.2 mL) were added Pd(dppf)$Cl_2$·$CH_2Cl_2$ (9 mg, 0.012 mmol) and $K_2CO_3$ (48 mg, 0.345 mmol) at room temperature under nitrogen atmosphere. The resulting mixture was stirred at 80° C. for 2 h under nitrogen atmosphere. The resulting mixture was concentrated under reduced pressure. The residue was purified by silica gel column chromatography, eluted with $CH_2Cl_2$/MeOH (10/1) followed by reversed-phase flash chromatography with the following conditions: column, C18 silica gel; mobile phase, $CH_3CN$ in Water (10 mmol/L $NH_4HCO_3$), 30% to 40% gradient in 10 min; detector, 254 nm. This resulted in (7R,14R)-11-(4-(dimethylphosphoryl)phenyl)-1-fluoro-6-(methyl-d3)-6,7-dihydro-7,14-methanobenzo[f]benzo[4,5]imidazo[1,2-a][1,4]diazocin-5(14H)-one (10 mg, 20%) as a white solid. MS ESI calculated for $C_{26}H_{20}D_3FN_3O_2P$ [M+H]$^+$, 463.17 found 463.05. $^1$H NMR (400 MHz, DMSO-$d_6$) δ 8.26-8.20 (m, 1H), 7.90-7.81 (m, 2H), 7.78-7.70 (m, 3H), 7.64 (d, J=1.6 Hz, 1H), 7.57-7.50 (m, 2H), 7.49-7.40 (m, 1H), 6.28 (d, J=6.8 Hz, 1H), 5.28 (d, J=7.2 Hz, 1H), 3.56-3.45 (m, 1H), 2.88 (d, J=13.8 Hz, 1H), 1.70 (s, 3H), 1.67 (s, 3H). $^{19}$F NMR (377 MHz, DMSO-$d_6$) δ −117.48. $^{31}$P NMR (162 MHz, DMSO-$d_6$) δ 32.18.

Example 17: (7R,14R)-11-(4-(dimethylphosphoryl)-2-fluorophenyl)-1-fluoro-6-(methyl-d3)-6,7-dihydro-7,14-methanobenzo[f]benzo[4,5]imidazo[1,2-a][1,4]diazocin-5(14H)-one

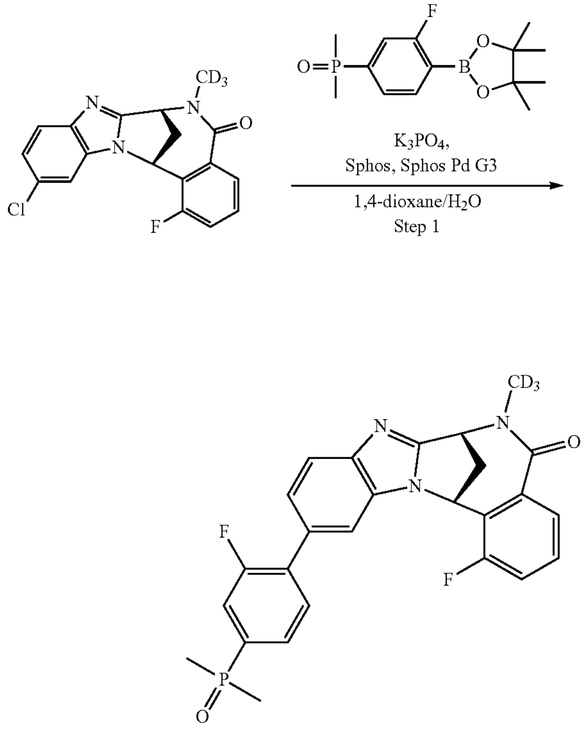

To a stirred solution of (7R,14R)-11-chloro-1-fluoro-6-(methyl-d3)-6,7-dihydro-7,14-methanobenzo[f]benzo[4,5]imidazo[1,2-a][1,4]diazocin-5(14H)-one (1.50 g, 4.350 mmol) and 2-[4-(dimethylphosphoryl)-2-fluorophenyl]-4,4,5,5-tetramethyl-1,3,2-dioxaborolane (1.69 g, 5.669 mmol) in 1,4-dioxane (40 mL) and $H_2O$ (6 mL) were added $K_3PO_4$ (2.31 g, 10.883 mmol), Sphos Pd G3 (0.34 g, 0.436 mmol) and Sphos (0.36 g, 0.870 mmol) at room temperature. The resulting mixture was stirred at 80° C. for 3 h under nitrogen atmosphere. The reaction was quenched with water at room temperature followed by extraction with EtOAc (3×100 mL). The combined organic layers were dried over anhydrous $Na_2SO_4$. After filtration, the filtrate was concentrated under reduced pressure. The residue was purified by reversed-phase flash chromatography with the following conditions: column, C18 silica gel; mobile phase, $CH_3CN$ in Water (10 mmol/L $NH_4HCO_3$), 15% to 30% gradient in 30 min; detector, 254 nm to afford (7R,14R)-11-(4-(dimethylphosphoryl)-2-fluorophenyl)-1-fluoro-6-(methyl-d3)-6,7-dihydro-7,14-methanobenzo[f]benzo[4,5]imidazo[1,2-a][1,4]diazocin-5(14H)-one (1.64 g, 78%) as a white solid. MS ESI calculated for $C_{26}H_{19}D_3F_2N_3O_2P$ [M+H]$^+$, 481.16 found 481.20. $^1$H NMR (400 MHz, Chloroform-d) δ 8.46-8.37 (m, 1H), 7.85-7.78 (m, 1H), 7.67 (s, 1H), 7.63-7.51 (m, 3H), 7.47-7.42 (m, 1H), 7.41-7.34 (m, 1H), 7.33-7.28 (m, 1H), 6.18 (d, J=7.2 Hz, 1H), 5.03 (d, J=7.2 Hz, 1H), 3.60-3.42 (m, 1H), 2.92 (d, J=13.6 Hz, 1H), 1.81 (s, 3H), 1.78 (s, 3H). $^{19}$F NMR (377 MHz, Chloroform-d) δ −116.12, −118.26. $^{31}$P NMR (162 MHz, Chloroform-d) δ 33.07.

Example 18: (7R,14R)-1-bromo-11-(4-(dimethylphosphoryl)-3-fluorophenyl)-6-(methyl-d3)-6,7-dihydro-7,14-methanobenzo[f]benzo[4,5]imidazo[1,2-a][1,4]diazocin-5(14H)-one
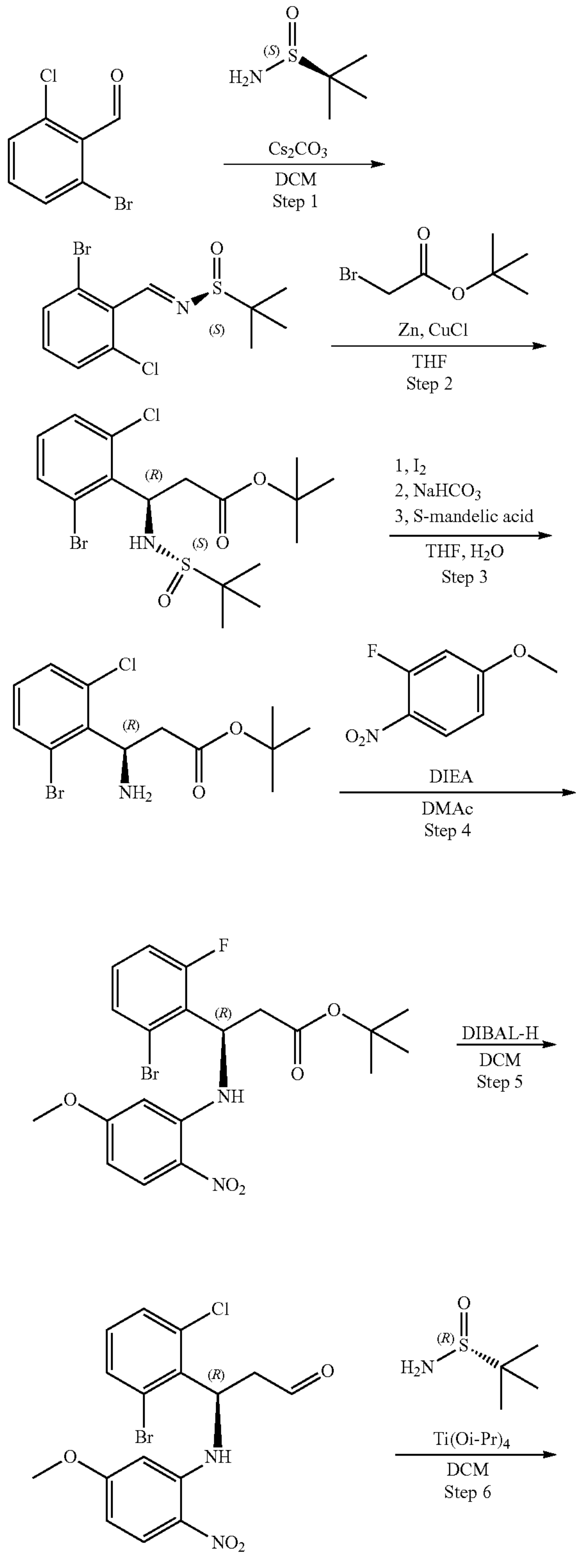
-continued
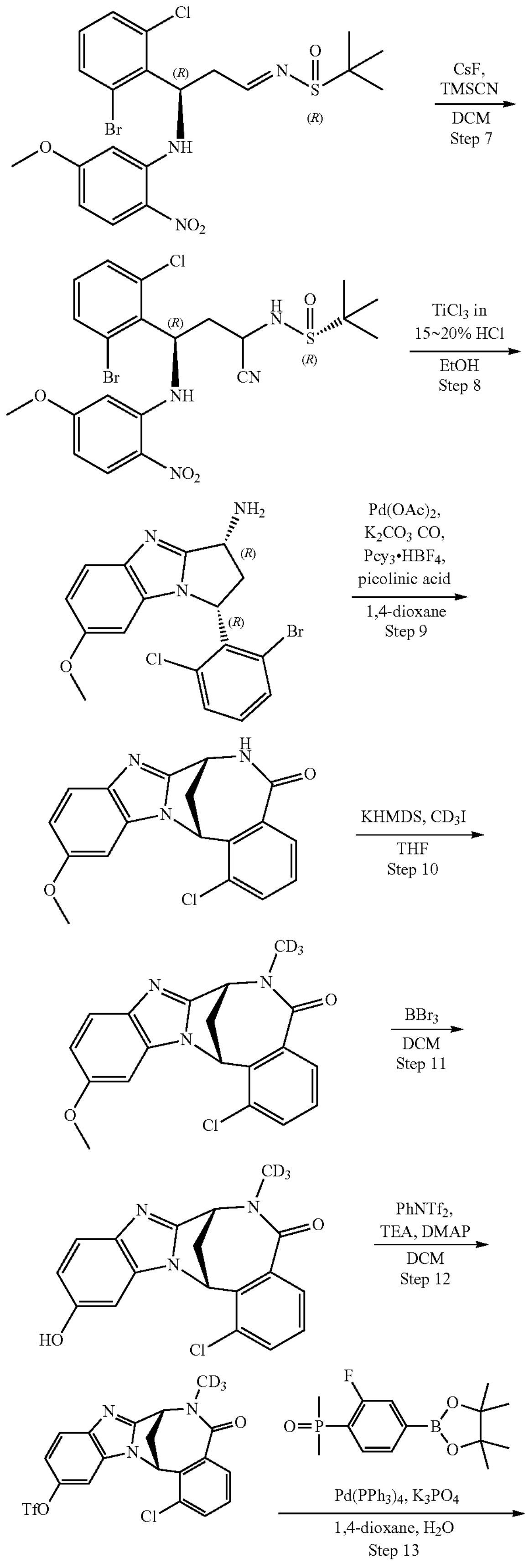

-continued

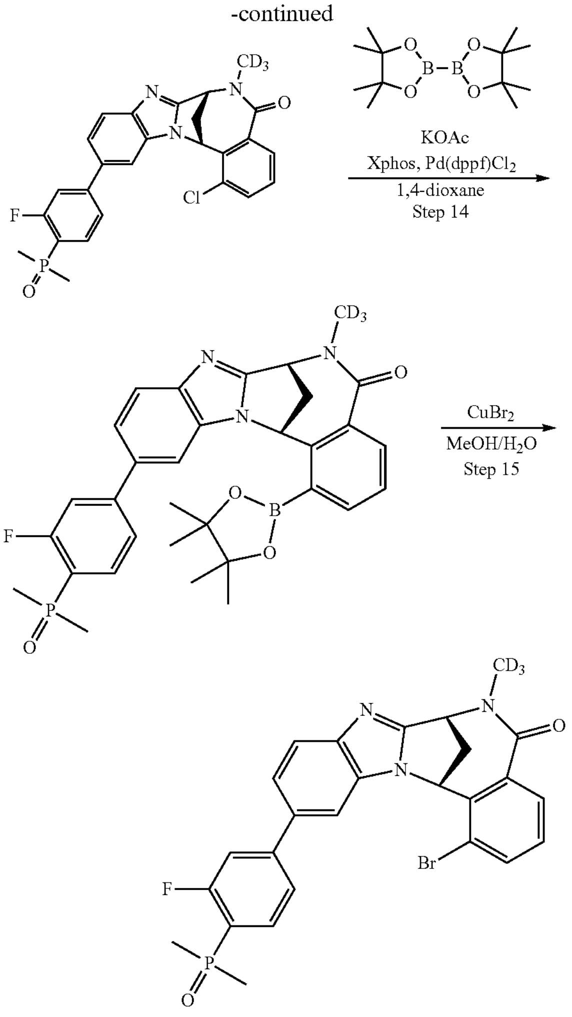

Preparation 18A: (S,E)-N-(2-bromo-6-chlorobenzylidene)-2-methylpropane-2-sulfinamide To a stirred solution of 2-bromo-6-chlorobenzaldehyde (100.00 g, 455.664 mmol) and $Cs_2CO_3$ (163 g, 501.230 mmol) in DCM (1 L) was added(S)-2-methylpropane-2-sulfinamide (66.27 g, 546.797 mmol) in portions at room temperature. The resulting mixture was stirred for 3 h at room temperature. The resulting mixture was diluted with water (1 L) and extracted with $CH_2Cl_2$ (3×500 mL). The combined organic layers were washed with brine (3×500 mL), dried over anhydrous $Na_2SO_4$. After filtration, the filtrate was concentrated under reduced pressure. The residue was purified by silica gel column chromatography, eluted with PE/EA (10:1) to afford (S, E)-N-(2-bromo-6-chlorobenzylidene)-2-methylpropane-2-sulfinamide (121.00 g, 82%) as yellow oil. MS ESI calculated for $C_{11}H_{13}BrClNOS$ $[M+H]^+$, 321.96 323.96 found 322.00 323.95. $^1H$ NMR (400 MHz, Chloroform-d) δ 8.85 (s, 1H), 7.60 (d, J=8.1 Hz, 1H), 7.45 (d, J=8.1 Hz, 1H), 7.22 (t, J=8.1 Hz, 1H), 1.33 (s, 9H).

Preparation 18B: tert-butyl (R)-3-(2-bromo-6-chlorophenyl)-3-(((S)-tert-butylsulfinyl)amino) propanoate A mixture of Zn (164.54 g, 2516.661 mmol) and CuCl (53.39 g, 539.284 mmol) in THF (1 L) was stirred for 2 h at 60° C. under nitrogen atmosphere. The mixture was allowed to cool down to room temperature. To the above mixture was added tert-butyl 2-bromoacetate (175.32 g, 898.808 mmol) dropwise over 5 min at 25° C. The resulting mixture was stirred for additional 2 h at 60° C. The mixture was allowed to cool down to room temperature again. To the above mixture was added (S, E)-N-(2-bromo-6-chlorobenzylidene)-2-methylpropane-2-sulfinamide (116.00 g, 359.523 mmol) in portions over 5 min at 10° C. The resulting mixture was stirred for additional 3 h at room temperature. The resulting mixture was filtered, the filter cake was washed with MTBE (3×100 mL). The filtrate was diluted with MTBE (1500 mL) and saturated citric acid solution (500 mL). The organic layers were poured out and washed with saturated $NaHCO_3$ solution (500 mL), dried over anhydrous $Na_2SO_4$. After filtration, the filtrate was concentrated under reduced pressure. This resulted in tert-butyl (R)-3-(2-bromo-6-chlorophenyl)-3-(((S)-tert-butylsulfinyl)amino)propanoate (127.00 g, 81%) as yellow oil. MS ESI calculated for $C_{17}H_{25}BrClNO_3S$ $[M+H]^+$, 438.04 440.04, found 438.05 440.05. $^1H$ NMR (300 MHz, Chloroform-d) δ 7.51 (d, J=8.1 Hz, 1H), 7.32 (d, J=9.0 Hz, 1H), 7.06 (t, J=8.0 Hz, 1H), 5.85-5.65 (m, 1H), 4.57-4.33 (m, 1H), 3.31-3.12 (m, 1H), 3.11-2.87 (m, 1H), 1.38 (s, 9H), 1.11 (s, 9H).

Preparation 18C: tert-butyl (R)-3-amino-3-(2-bromo-6-chlorophenyl)propanoate

To a stirred solution of tert-butyl (R)-3-(2-bromo-6-chlorophenyl)-3-(((S)-tert-butylsulfinyl)amino)propanoate (127.00 g, 289.419 mmol) in THF (500 mL) and $H_2O$ (100 mL) was added $I_2$ (18.36 g, 72.533 mmol) at room temperature under nitrogen atmosphere. The resulting mixture was stirred overnight at 50° C. The reaction was quenched by the addition of sat. $NaHCO_3$ (aq.) (1 L) at 0° C. followed by extraction with EtOAc (3×500 mL). The combined organic layers were washed with brine (3×2 L) and dried over anhydrous $Na_2SO_4$. After filtration, the filtrate was concentrated under reduced pressure. The residue was dissolved in ACN (200 mL) followed by the addition of solution (2S)-2-hydroxy-2-phenylacetic acid (44.03 g, 289.419 mmol) in ACN (200 mL) dropwise at room temperature. The resulting mixture was stirred for additional 15 min at room temperature. The precipitated solids were collected by filtration and washed with ACN (200 mL). The above solids were dissolved in $CH_2Cl_2$ (500 mL) and sat. $NaHCO_3$ (aq.) (1.5 L). The mixture was stirred for additional 15 min at room temperature followed by extraction with $CH_2Cl_2$ (3×500 mL). The combined organic layers were washed with brine (3×500 mL), dried over anhydrous $Na_2SO_4$. After filtration, the filtrate was concentrated under reduced pressure to afford tert-butyl (R)-3-amino-3-(2-bromo-6-chlorophenyl) propanoate (84.00 g, 87%) as colorless oil. MS ESI calculated for $C_{13}H_{17}BrClNO_2$ $[M+H]^+$, 334.01 336.01 found 334.00 336.00. $^1H$ NMR (400 MHz, Chloroform-d) δ 7.55-7.46 (m, 1H), 7.33 (d, J=8.0 Hz, 1H), 7.02 (t, J=8.0 Hz, 1H), 5.25-5.17 (m, 1H), 3.09-2.96 (m, 1H), 2.90-2.73 (m, 1H), 2.25 (s, 2H), 1.41 (s, 9H).

Preparation 18D: tert-butyl (R)-3-(2-bromo-6-chlorophenyl)-3-((5-methoxy-2-nitrophenyl)amino)propanoate To a stirred solution of tert-butyl (R)-3-amino-3-(2-bromo-6-chlorophenyl)propanoate (42.00 g, 125.508 mmol) and 2-fluoro-4-methoxy-1-nitrobenzene (23.63 g, 138.059 mmol) in DMAc (500 mL) was added DIEA (24.33 g, 188.262 mmol) at room temperature under nitrogen atmosphere. The resulting mixture was stirred overnight at 80° C. The resulting mixture was diluted with water (500 mL) and extracted with EA (3×500 mL). The combined organic layers were concentrated under vacuum. The residue was purified by silica gel column chromatography, eluted with PE/EA (10:1) to afford tert-butyl (R)-3-(2-bromo-6-chlorophenyl)-3-((5-methoxy-2-nitrophenyl)amino)propanoate (50.00 g, 82%) as yellow oil. MS ESI calculated for $C_{20}H_{22}BrClN_2O_5$ $[M+H]^+$, 485.04 487.04 found 485.00 487.00. $^1H$ NMR (300 MHz, Chloroform-d) δ 9.29 (d, J=8.0 Hz, 1H), 8.09 (d, J=9.5 Hz, 1H), 7.52 (s, 1H), 7.34 (s, 1H), 7.09 (t, J=8.0 Hz, 1H), 6.27-6.08 (m, 2H), 6.01-5.79 (m, 1H), 3.78 (s, 3H), 3.27 (t, J=13.0 Hz, 1H), 2.91-2.74 (m, 1H), 1.42 (s, 9H).

Preparation 18E: (R)-3-(2-bromo-6-chlorophenyl)-3-((5-methoxy-2-nitrophenyl)amino)propanal To a solution of tert-butyl (R)-3-(2-bromo-6-chlorophenyl)-3-((5-methoxy-2-nitrophenyl)amino)propanoate (50.00 g, 102.931 mmol) in DCM (1 L) was added DIBAL-H (113.2 mL, 113.224 mmol) dropwise at −78° C. The resulting mixture was stirred for 3 h at −78° C. under nitrogen atmosphere. The reaction was quenched with HCl (1N) at −78° C. followed by extraction with $CH_2Cl_2$ (3×1 L). The combined organic layers were washed with brine (3×1 L) and dried over anhydrous $Na_2SO_4$. After filtration, the filtrate was concentrated under reduced pressure. The residue was purified by silica gel column chromatography, eluted with $CH_2Cl_2$/PE (1:1) to afford (R)-3-(2-bromo-6-chlorophenyl)-3-((5-methoxy-2-nitrophenyl)amino)propanal (38.01 g, 89%) as a yellow solid. MS ESI calculated for $C_{16}H_{14}BrClN_2O_4$ $[M+H]^+$, 412.98 414.98 found 413.00 415.00. $^1H$ NMR (300 MHz, Chloroform-d) δ 9.86 (s, 1H), 9.25 (d, J=8.3 Hz, 1H), 8.15-8.08 (m, 1H), 7.63-7.50 (m, 1H), 7.51-7.34 (m, 1H), 7.12 (t, J=8.0 Hz, 1H), 6.28-6.21 (m, 2H), 6.13-6.00 (m, 1H), 3.82 (s, 3H), 3.74-3.55 (m, 1H), 3.06 (d, J=17.5 Hz, 1H).

Preparation 18F: (R)—N—((R,E)-3-(2-bromo-6-chlorophenyl)-3-((5-methoxy-2-nitrophenyl)amino)propylidene)-2-methylpropane-2-sulfinamide To a stirred solution of (R)-3-(2-bromo-6-chlorophenyl)-3-((5-methoxy-2-nitrophenyl)amino)propanal (39.00 g, 94.283 mmol) and Ti(Oi-Pr)$_4$ (53.59 g, 188.566 mmol) in DCM (300 mL) was added (R)-2-methylpropane-2-sulfinamide (13.71 g, 113.140 mmol) in portions at room temperature. The resulting mixture was stirred for 3 h at room temperature. The resulting mixture was diluted with water (500 mL) and extracted with $CH_2Cl_2$ (3×500 mL). The combined organic layers were washed with brine (3×500 mL) and dried over anhydrous $Na_2SO_4$. After filtration, the filtrate was concentrated under reduced pressure. The residue was purified by silica gel column chromatography, eluted with PE/EA (10:1) to afford (R)—N—((R,E)-3-(2-bromo-6-chlorophenyl)-3-((5-methoxy-2-nitrophenyl)amino)propylidene)-2-methylpropane-2-sulfinamide (44.10 g, 90%) as yellow oil. MS ESI calculated for $C_{20}H_{23}BrClN_3O_4S$ $[M+H]^+$, 516.03 518.03 found 516.10 518.00. $^1H$ NMR (400 MHz, Chloroform-d) δ 9.35-9.19 (m, 1H), 8.19-8.13 (m, 1H), 8.08 (d, J=9.5 Hz, 1H), 7.61-7.30 (m, 2H), 7.12 (t, J=8.1 Hz, 1H), 6.27-6.17 (m, 1H), 6.12-6.05 (m, 1H), 5.97-5.82 (m, 1H), 3.77 (s, 3H), 3.71-3.58 (m, 1H), 3.19-3.04 (m, 1H), 1.17 (s, 9H).

Preparation 18G: (R)—N—((R,E)-3-(2-bromo-6-chlorophenyl)-3-((5-methoxy-2-nitrophenyl)amino)propylidene)-2-methylpropane-2-sulfinamide To a stirred solution of (R)—N-[(1E,3R)-3-(2-bromo-6-chlorophenyl)-3-[(5-methoxy-2-nitrophenyl)amino]propylidene]-2-methylpropane-2-sulfinamide (44.00 g, 85.133 mmol) and CsF (25.86 g, 170.266 mmol) in DCM (500 mL) was added TMSCN (16.89 g, 170.266 mmol) in portions at room temperature. The resulting mixture was stirred for 3 h at room temperature. The resulting mixture was diluted with water (500 mL) and extracted with $CH_2Cl_2$ (3×200 mL). The combined organic layers were washed with brine (3×500 mL) and dried over anhydrous $Na_2SO_4$. After filtration, the filtrate was concentrated under reduced pressure. The residue was purified by silica gel column chromatography, eluted with PE/EA (10:1) to afford (R)—N-((3R)-3-(2-bromo-6-chlorophenyl)-1-cyano-3-((5-methoxy-2-nitrophenyl)amino) propyl)-2-methylpropane-2-sulfinamide (39.80 g, 86%) as yellow oil. MS ESI calculated for $C_{21}H_{24}BrClN_4O_4S$ $[M+H]^+$, 543.04 545.04 found 543.00 545.00. $^1H$ NMR (400 MHz, Chloroform-d) δ 9.36-9.16 (m, 1H), 8.20-8.08 (m, 1H), 7.63-7.32 (m, 2H), 7.17-7.06 (m, 1H), 6.32-6.12 (m, 2H), 5.87-5.70 (m, 1H), 4.76-4.43 (m, 1H), 3.84-3.73 (m, 3H), 3.14-2.91 (m, 1H), 2.50-2.34 (m, 1H), 1.26-1.17 (m, 9H).

Preparation 18H: (1R,3R)-1-(2-bromo-6-chlorophenyl)-7-methoxy-2,3-dihydro-1H-benzo[d]pyrrolo[1,2-a]imidazol-3-amine To a stirred solution of (R)—N—((R,E)-3-(2-bromo-6-chlorophenyl)-3-((5-methoxy-2-nitrophenyl)amino)propylidene)-2-methylpropane-2-sulfinamide (39.80 g, 73.181 mmol) and $TiCl_3$ (451.44 g, 585.448 mmol, 20% in HCl) in EtOH (500 mL) at room temperature. The resulting mixture was stirred overnight at 80° C. The resulting mixture was diluted with EtOAc (100 mL) and basified to pH 7 with saturated $NaHCO_3$ (aq.). The resulting mixture was filtered and the filter cake was washed with EtOAc (3×100 mL). The filtrate was washed with 2×1 L of water. The organic layer was concentrated under vacuum. The residue was purified by silica gel column chromatography, eluted with $CH_2Cl_2$/MeOH (10:1) to afford (1R,3R)-1-(2-bromo-6-chlorophenyl)-7-methoxy-2,3-dihydro-1H-benzo[d]pyrrolo[1,2-a]imidazol-3-amine (18.70 g, 65%) as a white solid. MS ESI calculated for $C_{17}H_{15}BrClN_3O$ $[M+H]^+$, 392.01 394.01 found 391.85 393.85. $^1H$ NMR (300 MHz, Chloroform-d) δ 7.72-7.62 (m, 2H), 7.59-7.44 (m, 1H), 7.20 (t, J=8.0 Hz, 1H), 6.92-6.80 (m, 1H), 6.33-6.19 (m, 1H), 6.13-6.06 (m, 1H), 4.87-4.65 (m, 1H), 3.73-3.66 (m, 3H), 3.60-3.20 (m, 1H), 3.01-2.59 (m, 1H).

Preparation 181: (7R,14R)-1-chloro-11-methoxy-6,7-dihydro-7,14-methanobenzo[f]benzo[4,5]imidazo[1,2-a][1,4]diazocin-5(14H)-one To a stirred mixture of (1R,3R)-1-(2-bromo-6-chlorophenyl)-7-methoxy-2,3-dihydro-1H-benzo[d]pyrrolo[1,2-a]imidazol-3-amine (7.80 g, 19.864 mmol) and pyridine-2-carboxylic acid (1.22 g, 9.932 mmol), $K_2CO_3$ (13.73 g, 99.320 mmol) in 1,4-dioxane (150 mL) were added $PCy_3 \cdot HBF_4$ (1.11 g, 3.973 mmol) and Pd(OAc)$_2$ (0.89 g, 3.973 mmol) at room temperature. The mixture was purged with nitrogen for 30 min and then was pressurized to 10 atm with carbon monoxide at 100° C. for 24 h. The resulting mixture was concentrated under vacuum. The residue was purified by silica gel column chromatography, eluted with $CH_2Cl_2$/MeOH (10:1) to afford (7R,14R)-1-chloro-11-methoxy-6,7-dihydro-7,14-methanobenzo[f]benzo[4,5]imidazo[1,2-a][1,4]diazocin-5(14H)-one (2.10 g, 31%) as a yellow solid. MS ESI calculated for $C_{18}H_{14}ClN_3O_2$ $[M+H]^+$, 340.08 found 340.05. $^1H$ NMR (400 MHz, Chloroform-d) δ 8.56-8.47 (m, 1H), 7.71-7.53 (m, 2H), 7.45 (d, J=6.4 Hz, 1H), 7.36 (t, J=8.1 Hz, 1H), 7.12 (d, J=2.5 Hz, 1H), 6.93-6.84 (m, 1H), 6.45 (d, J=7.3 Hz, 1H), 4.90 (t, J=6.5 Hz, 1H), 3.83 (s, 3H), 3.49-3.34 (m, 1H), 2.84 (d, J=13.3 Hz, 1H).

Preparation 18J: (7R,14R)-1-chloro-11-methoxy-6-(methyl-$d_3$)-6,7-dihydro-7,14methanobenzo[f]benzo[4,5]imidazo[1,2-a][1,4]diazocin-5(14H)-one To a stirred mixture of (7R,14R)-1-chloro-11-methoxy-6,7-dihydro-7,14-methanobenzo[f]benzo[4,5]imidazo[1,2-a][1,4]diazocin-5(14H)-one (2.39 g, 7.034 mmol) in THF (25 mL) was added KHMDS (8.44 mL, 8.441 mmol, 1M in THF) at −78° C. under nitrogen atmosphere. The resulting mixture was stirred for 1 h at −78° C. under nitrogen atmosphere. To the above mixture was added $CD_3I$ (1.33 g, 9.144 mmol) at −78° C. The resulting mixture was stirred for additional 16 h at room temperature. The resulting mixture was concentrated under vacuum and purified by silica gel column chromatography, eluted with $CH_2Cl_2$/MeOH (10:1) to afford (7R,14R)-1-chloro-11-methoxy-6-(methyl-d3)-6,7-dihydro-7,14methanobenzo[f]benzo[4,5]imidazo[1,2-a][1,4]diazocin-5(14H)-one (2.10 g, 84%) as a yellow solid. MS ESI calculated for $C_{19}H_{13}D3ClN_3O_2$ $[M+H]^+$, 357.11 found 357.15. $^1H$ NMR (400 MHz, Chloroform-d) δ 8.60-8.54 (m, 1H), 7.60 (d, J=8.9 Hz, 2H), 7.36 (t, J=8.1 Hz, 1H), 7.15 (d, J=2.5 Hz, 1H), 6.91-6.84 (m, 1H), 6.37 (d, J=7.3 Hz, 1H), 4.92 (d, J=7.1 Hz, 1H), 3.83 (s, 3H), 3.50-3.38 (m, 1H), 2.86 (d, J=13.5 Hz, 1H).

Preparation 18K: (7R,14R)-1-chloro-11-hydroxy-6-(methyl-d3)-6,7-dihydro-7,14methanobenzo[f]benzo[4,5]imidazo[1,2-a][1,4]diazocin-5(14H)-one To a stirred solution of (7R,14R)-1-chloro-11-hydroxy-6-(methyl-d3)-6,7-dihydro-7,14methanobenzo[f]benzo[4,5]imidazo[1,2-a][1,4]diazocin-5(14H)-one (2.10 g, 5.885 mmol) in DCM (50 mL) was added $BBr_3$ (17.7 mL, 17.655 mmol) at 0° C. under nitrogen atmosphere. The resulting mixture was stirred for 3 h at room temperature under nitrogen atmosphere. The resulting mixture was concentrated under vacuum. The residue was purified by reversed-phase flash chromatography with the following conditions: column, C18 silica gel; mobile phase, $CH_3CN$ in Water (10 mmol/L $NH_4HCO_3$), 10% to 50% gradient in 10 min; detector, 254 nm to afford (7R,14R)-1-chloro-11-hydroxy-6-(methyl-d3)-6,7-dihydro-7,14methanobenzo[f]benzo[4,5]imidazo[1,2-a][1,4]diazocin-5(14H)-one (2.01 g, 99%) as a white solid. MS ESI calculated for $C_{18}H_{11}D3ClN_3O_2$ $[M+H]^+$, 343.10 found 343.15. $^1H$ NMR (400 MHz, DMSO-$d_6$) δ 9.36 (s, 1H), 8.43-8.33 (m, 1H), 7.84-7.76 (m, 1H), 7.47 (d, J=8.1 Hz, 1H), 7.38 (d, J=8.7 Hz, 1H), 6.94 (d, J=2.3 Hz, 1H), 6.70-6.59 (m, 1H), 6.30 (d, J=7.2 Hz, 1H), 5.11 (d, J=7.0 Hz, 1H), 3.52-3.40 (m, 1H), 2.79 (d, J=13.8 Hz, 1H).

Preparation 18L: (7R,14R)-1-chloro-6-(methyl-d3)-5-oxo-5,6,7,14-tetrahydro-7,14-methanobenzo[f]benzo[4,5]imidazo[1,2-a][1,4]diazocin-11-yl trifluoromethanesulfonate To a stirred solution of (7R,14R)-1-chloro-11-hydroxy-6-(methyl-d3)-6,7-dihydro-7,14methanobenzo[f]benzo[4,5]imidazo[1,2-a][1,4]diazocin-5(14H)-one (300 mg, 0.875 mmol) and 1,1,1-trifluoro-N-phenyl-N-(trifluoromethane)sulfonylmethanesulfonamide (500 mg, 1.400 mmol) in DCM (2 mL) were added DMAP (11 mg, 0.088 mmol), TEA (177 mg, 1.750 mmol) at room temperature. The resulting mixture was stirred for additional 2 h at 25° C. under nitrogen atmosphere. The resulting mixture was concentrated under reduced pressure and purified by silica gel column chromatography, eluted with $CH_2Cl_2$/MeOH (10:1) to afford (7R,14R)-1-chloro-6-(methyl-d3)-5-oxo-5,6,7,14-tetrahydro-7,14-methanobenzo[f]benzo[4,5]imidazo[1,2-a][1,4]diazocin-11-yl trifluoromethanesulfonate (320 mg, 77%) as a yellow solid. MS ESI calculated for $C_{19}H_{10}D3ClF_3N_3O_4S$ $[M+H]^+$, 475.05 found 475.00. $^1H$ NMR (400 MHz, Chloroform-d) δ 8.61-8.54 (m, 1H), 7.79-7.72 (m, 1H), 7.67-7.59 (m, 2H), 7.43-7.34 (m, 1H), 7.20-7.12 (m, 1H), 6.47-6.40 (m, 1H), 5.00-4.92 (m, 1H), 3.54-3.42 (m, 1H), 2.91 (d, J=13.8 Hz, 1H).

Preparation 18M: (7R,14R)-1-chloro-11-(4-(dimethylphosphoryl)-3-fluorophenyl)-6-(methyl-d3)-6,7-dihydro-7,14-methanobenzo[f]benzo[4,5]imidazo[1,2-a][1,4]diazocin-5(14H)-one To a stirred mixture of (7R,14R)-1-chloro-6-(methyl-d3)-5-oxo-5,6,7,14-tetrahydro-7,14-methanobenzo[f]benzo[4,5]imidazo[1,2-a][1,4]diazocin-11-yl trifluoromethanesulfonate (1.25 g, 2.632 mmol), $K_2CO_3$ (0.73 g, 5.264 mmol) and $Pd(PPh_3)_4$ (0.30 g, 0.263 mmol) in 1,4-dioxane (10 mL) and $H_2O$ (2 mL) was added 2-[4-(dimethylphosphoryl)-3-fluorophenyl]-4,4,5,5-tetramethyl-1,3,2-dioxaborolane (0.94 g, 3.158 mmol) at room temperature under nitrogen atmosphere. The resulting mixture was stirred at 80° C. for 2 h under nitrogen atmosphere. The resulting mixture was concentrated under vacuum. The residue was purified by silica gel column chromatography, eluted with $CH_2Cl_2$/MeOH (12:1) followed by reversed-phase flash chromatography with the following conditions: column, C18 silica gel; mobile phase, $CH_3CN$ in Water (10 mmol/L $NH_4HCO_3$), 30% to 50% gradient in 30 min; detector, 254 nm to afford (7R,14R)-1-chloro-11-(4-(dimethylphosphoryl)-3-fluorophenyl)-6-(methyl-d3)-6,7-dihydro-7,14-methanobenzo[f]benzo[4,5]imidazo[1,2-a][1,4]diazocin-5(14H)-one (985 mg, 75%) as a white solid. MS ESI calculated for $C_{26}H_{19}D_3ClFN_3O_2P$ $[M+H]^+$, 497.13 found 497.10. $^1H$ NMR (400 MHz, DMSO-$d_6$) δ 8.42-8.36 (m, 1H), 7.89-7.81 (m, 2H), 7.80-7.73 (m, 2H), 7.64 (d, J=7.9 Hz, 1H), 7.61-7.54 (m, 2H), 7.46 (t, J=8.1 Hz, 1H), 6.48 (d, J=7.2 Hz, 1H), 5.26 (d, J=7.1 Hz, 1H), 3.57-3.48 (m, 1H), 2.89 (d, J=13.9 Hz, 1H), 1.76 (s, 3H), 1.73 (s, 3H). $^{19}F$ NMR (377 MHz, DMSO-$d_6$) δ −105.43. $^{31}P$ NMR (162 MHz, Chloroform-d) δ 30.63.

Preparation 18N: (7R,14R)-11-(4-(dimethylphosphoryl)-3-fluorophenyl)-6-(methyl-d3)-1-(4,4,5,5-tetramethyl-1,3,2-dioxaborolan-2-yl)-6,7-dihydro-7,14-methanobenzo[f]benzo[4,5]imidazo[1,2-a][1,4]diazocin-5(14H)-one To a stirred mixture of (7R,14R)-1-chloro-11-(4-(dimethylphosphoryl)-3-fluorophenyl)-6-(methyl-d3)-6,7-dihydro-7,14-methanobenzo[f]benzo[4,5]imidazo[1,2-a][1,4]diazocin-5(14H)-one (230 mg, 0.463 mmol) and 4,4,5,5-tetramethyl-2-(tetramethyl-1,3,2-dioxaborolan-2-yl)-1,3,2-dioxaborolane (176 mg, 0.695 mmol) in 1,4-dioxane (3 mL) were added XPhos (44 mg, 0.093 mmol), $Pd(dppf)Cl_2$ (34 mg, 0.046 mmol) and KOAc (136 mg, 1.389 mmol) in portions at room temperature under nitrogen atmosphere. The resulting mixture was stirred at 80° C. for 3 h under nitrogen atmosphere. The resulting mixture was concentrated under reduced pressure. The residue was purified by silica gel column chromatography, eluted with $CH_2Cl_2$/MeOH (12:1) to afford (7R,14R)-11-(4-(dimethylphosphoryl)-3-fluorophenyl)-6-(methyl-d3)-1-(4,4,5,5-tetramethyl-1,3,2-dioxaborolan-2-yl)-6,7-dihydro-7,14-methanobenzo[f]benzo[4,5]imidazo[1,2-a][1,4]diazocin-5(14H)-one (120 mg, 44%) as a brown solid. MS ESI calculated for $C_{32}H_{31}D3BFN_3O_4P$ $[M+H]^+$, 589.26 found 589.30. $^1H$ NMR (400 MHz, Chloroform-d) δ 8.71-8.64 (m, 1H), 8.06-8.01 (m, 1H), 8.00-7.92 (m, 1H), 7.91 (d, J=1.7 Hz, 1H), 7.79 (d, J=8.5 Hz, 1H), 7.51 (d, J=7.8 Hz, 1H), 7.48-7.38 (m, 2H), 7.36-7.27 (m, 1H), 6.67 (d, J=7.0 Hz, 1H), 4.98 (d, J=6.5 Hz, 1H), 3.48-3.38 (m, 1H), 2.87 (d, J=13.4 Hz, 1H), 1.85 (d, J=4.4 Hz, 3H), 1.81 (d, J=4.5 Hz, 3H), 1.47 (s, 12H). $^{19}F$ NMR (377 MHz, Chloroform-d) δ −106.12. $^{31}P$ NMR (162 MHz, Chloroform-d) δ 31.12.

Example 18: (7R,14R)-1-bromo-11-(4-(dimethylphosphoryl)-3-fluorophenyl)-6-(methyl-d3)-6,7-dihydro-7,14-methanobenzo[f]benzo[4,5]imidazo[1,2-a][1,4]diazocin-5(14H)-one To a stirred mixture of (7R,14R)-11-(4-(dimethylphosphoryl)-3-fluorophenyl)-6-(methyl-d3)-1-(4,4,5,5-tetramethyl-1,3,2-dioxaborolan-2-yl)-6,7-dihydro-7,14-methanobenzo[f]benzo[4,5]imidazo[1,2-a][1,4]diazocin-5(14H)-one (110 mg, 0.187 mmol) in MeOH (1.8 mL) and $H_2O$ (0.6 mL) was added $CuBr_2$ (125 mg, 0.561 mmol) in portions at room temperature. The resulting mixture was stirred at 80° C. for 16 h under nitrogen atmosphere. The resulting mixture was concentrated under reduced pressure. The residue was purified by reversed-phase flash chromatography with the following conditions: column, Column: C18, 120 g; Mobile Phase A: Water/0.05% FA, Mobile Phase B: ACN; Flow rate: 65 mL/min; Gradient: 20% B to 70% B in 25 min; Detector, 254 nm. This resulted in (7R,14R)-1-bromo-11-(4-(dimethylphosphoryl)-3-fluorophenyl)-6-(methyl-d3)-6,7-dihydro-7,14-methanobenzo[f]benzo[4,5]imidazo[1,2-a][1,4]diazocin-5(14H)-one (35 mg, 35%) as a white solid. MS ESI calculated for $C_{26}H_{19}D_3BrFN_3O_2P$ $[M+H]^+$, 541.08 543.08 found 541.10 543.09. $^1H$ NMR (400 MHz, Chloroform-d) δ 8.64-8.57 (m, 1H), 8.07-7.96 (m, 2H), 7.84-7.76 (m, 2H), 7.60-7.53 (m, 1H), 7.52-7.45 (m, 1H), 7.38-7.28 (m, 2H), 6.47 (d, J=7.3 Hz, 1H), 4.97 (d, J=7.0 Hz, 1H), 3.54-3.43 (m, 1H), 2.91 (d, J=13.6 Hz, 1H), 1.85 (s, 3H), 1.82 (s, 3H). $^{19}F$ NMR (377 MHz, Chloroform-d) δ −105.70, −105.71. $^{31}P$ NMR (162 MHz, Chloroform-d) δ 30.77.

Example 19: (7R,14R)-1-bromo-11-(4-(dimethylphosphoryl)-2-fluorophenyl)-6-(methyl-d3)-6,7-dihydro-7,14-methanobenzo[f]benzo[4,5]imidazo[1,2-a][1,4]diazocin-5(14H)-one

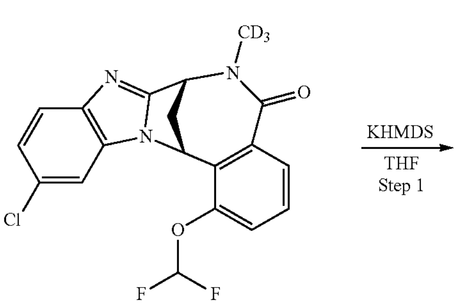

-continued

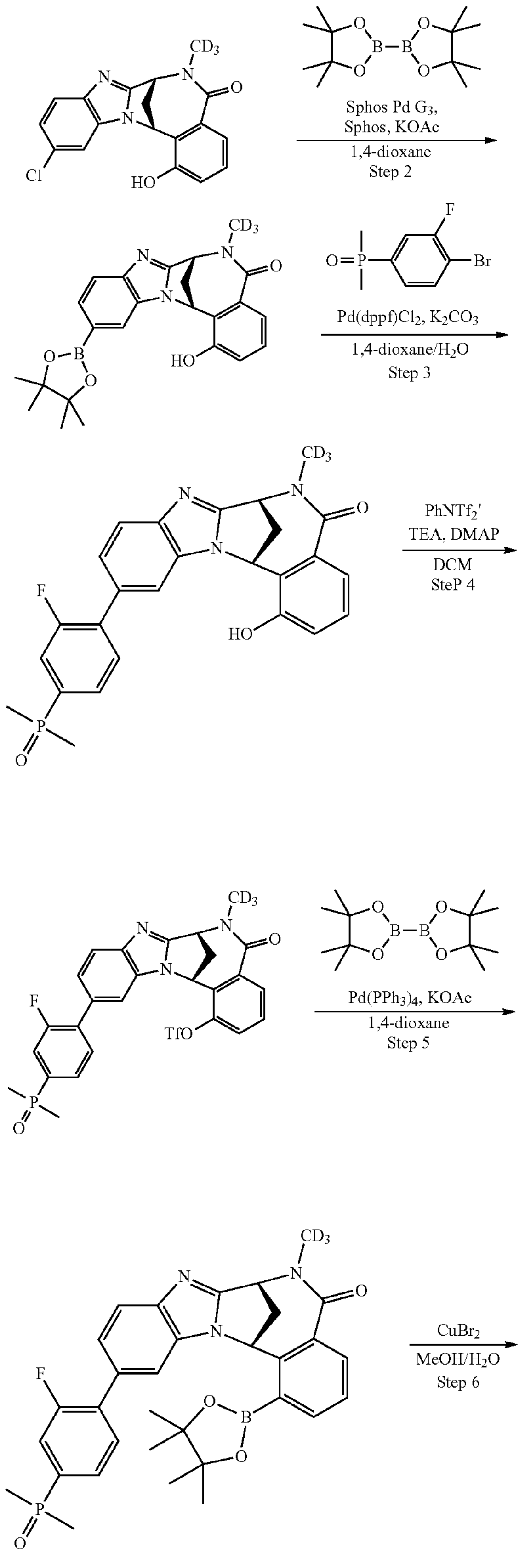

-continued

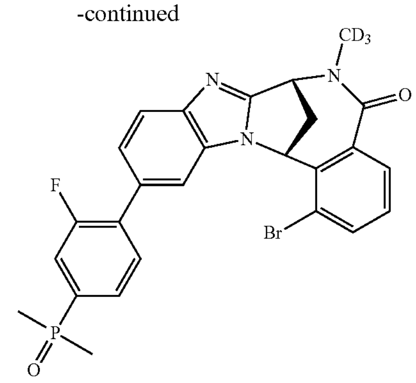

Preparation 19A: (7R,14R)-11-chloro-1-hydroxy-6-(methyl-d3)-6,7-dihydro-7,14-methanobenzo[f]benzo[4,5]imidazo[1,2-a][1,4]diazocin-5(14H)-one To a stirred solution of (7R,14R)-11-chloro-1-(difluoromethoxy)-6-(methyl-d3)-6,7-dihydro-7,14-methanobenzo[f]benzo[4,5]imidazo[1,2-a][1,4]diazocin-5(14H)-one (4.00 g, 10.183 mmol) in THF (20 mL) was added KHMDS (30.55 mL, 30.549 mmol, 1 M in THF) dropwise at −40° C. under $N_2$ atmosphere. The resulting mixture was stirred at −40° C. for 2 h. The reaction was quenched by the addition of water (15 mL) at −40° C. The resulting mixture was concentrated under reduced pressure. The residue was purified by silica gel column chromatography, eluted with $CH_2Cl_2$/MeOH (10:1) to afford (7R,14R)-11-chloro-1-hydroxy-6-(methyl-d3)-6,7-dihydro-7,14-methanobenzo[f]benzo[4,5]imidazo[1,2-a][1,4]diazocin-5(14H)-one (2.90 g, 83%) as a white solid. MS ESI calculated for $C_{18}H_{11}D_3ClN_3O_2$ $[M+H]^+$, 343.10 found 343.05. $^1H$ NMR (400 MHz, DMSO-$d_6$) δ 10.57 (s, 1H), 7.86 (d, J=8.0 Hz, 1H), 7.65-7.58 (m, 1H), 7.58-7.53 (m, 1H), 7.25-7.16 (m, 2H), 7.16-7.09 (m, 1H), 6.28 (d, J=7.1 Hz, 1H), 5.16 (d, J=7.2 Hz, 1H), 3.47-3.35 (m, 1H), 2.73 (d, J=13.9 Hz, 1H).

Preparation 19B: (7R,14R)-1-hydroxy-6-(methyl-d3)-11-(4,4,5,5-tetramethyl-1,3,2-dioxaborolan-2-yl)-6,7-dihydro-7,14-methanobenzo[f]benzo[4,5]imidazo[1,2-a][1,4]diazocin-5(14H)-one To a stirred mixture of (7R,14R)-11-chloro-1-hydroxy-6-(methyl-d3)-6,7-dihydro-7,14-methanobenzo[f]benzo[4,5]imidazo[1,2-a][1,4]diazocin-5(14H)-one (1.00 g, 2.917 mmol) and 4,4,5,5-tetramethyl-2-(tetramethyl-1,3,2-dioxaborolan-2-yl)-1,3,2-dioxaborolane (1.11 g, 4.375 mmol) in 1,4-dioxane (15 mL) were added Sphos Pd G3 (228 mg, 0.292 mmol), KOAc (0.86 g, 8.751 mmol) and Sphos (239 mg, 0.583 mmol) at room temperature. The resulting mixture was stirred at 100° C. for 1 h under nitrogen atmosphere. The resulting mixture was concentrated under reduced pressure. The residue was purified by silica gel column chromatography, eluted with $CH_2Cl_2$/MeOH (10:1) to afford (7R,14R)-1-hydroxy-6-(methyl-d3)-11-(4,4,5,5-tetramethyl-1,3,2-dioxaborolan-2-yl)-6,7-dihydro-7,14-methanobenzo[f]benzo[4,5]imidazo[1,2-a][1,4]diazocin-5(14H)-one (996 mg, 79%) as a white solid. MS ESI calculated for $C_{24}H_{23}D_3BN_3O_4$ $[M+H]^+$, 435.22 found 435.20. $^1H$ NMR (400 MHz, Chloroform-d) δ 8.20-8.07 (m, 2H), 7.83-7.67 (m, 2H), 7.24-7.14 (m, 1H), 7.08 (d, J=8.1 Hz, 1H), 6.49 (d, J=7.0 Hz, 1H), 5.14 (d, J=6.9 Hz, 1H), 3.54-3.36 (m, 1H), 2.90 (d, J=13.4 Hz, 1H), 1.25 (s, 12H).

Preparation 19C: (7R,14R)-11-(4-(dimethylphosphoryl)-2-fluorophenyl)-1-hydroxy-6-(methyl-d3)-6,7-dihydro-7,14-methanobenzo[f]benzo[4,5]imidazo[1,2-a][1,4]diazocin-5(14H)-one To a stirred mixture of (7R,14R)-1-hydroxy-6-(methyl-d3)-11-(4,4,5,5-tetramethyl-1,3,2-dioxaborolan-2-yl)-6,7-dihydro-7,14-methanobenzo[f]benzo[4,5]imidazo[1,2-a][1,4]diazocin-5(14H)-one (200 mg, 0.460 mmol) and 1-bromo-4-(dimethylphosphoryl)-2-fluorobenzene (150 mg, 0.598 mmol) in 1,4-dioxane (2 mL) and $H_2O$ (0.5 mL) were added $K_2CO_3$ (191 mg, 1.380 mmol) and Pd(dppf)$Cl_2$ (38 mg, 0.046 mmol) at room temperature under nitrogen atmosphere. The resulting mixture was stirred at 80° C. for 3 h under nitrogen atmosphere. The resulting mixture was diluted with water (5 mL) followed by extraction with EtOAc (3×10 mL). The combined organic layers were washed with brine (3×10 mL) and dried over $Na_2SO_4$. Filtrated and concentrated under reduced pressure. The residue was purified by silica gel column chromatography, eluted with $CH_2Cl_2$/MeOH (0% to 10%) to afford (7R,14R)-11-(4-(dimethylphosphoryl)-2-fluorophenyl)-1-hydroxy-6-(methyl-d3)-6,7-dihydro-7,14-methanobenzo[f]benzo[4,5]imidazo[1,2-a][1,4]diazocin-5(14H)-one (180 mg, 99%) as a yellow solid. MS ESI calculated for $C_{26}H_{20}D_3FN_3O_3P$ $[M+H]^+$, 479.16 found 479.10. $^1H$ NMR (400 MHz, Chloroform-d) δ 10.70 (s, 1H), 8.12-8.05 (m, 1H), 8.00 (s, 1H), 7.73 (d, J=8.5 Hz, 1H), 7.63-7.41 (m, 3H), 7.34 (d, J=8.5 Hz, 1H), 7.24-7.13 (m, 2H), 6.49 (d, J=7.0 Hz, 1H), 4.96 (d, J=6.8 Hz, 1H), 3.45-3.34 (m, 1H), 2.87 (d, J=13.3 Hz, 1H), 1.85-1.75 (m, 6H).

Preparation 19D: (7R,14R)-11-(4-(dimethylphosphoryl)-2-fluorophenyl)-6-(methyl-d3)-5-oxo-5,6,7,14-tetrahydro-7,14-methanobenzo[f]benzo[4,5]imidazo[1,2-a][1,4]diazocin-1-yl trifluoromethanesulfonate To a stirred solution of (7R,14R)-11-(4-(dimethylphosphoryl)-2-fluorophenyl)-1-hydroxy-6-(methyl-d3)-6,7-dihydro-7,14-methanobenzo[f]benzo[4,5]imidazo[1,2-a][1,4]diazocin-5(14H)-one (200 mg, 0.418 mmol) DMAP (3.0 mg, 0.021 mmol) and $Et_3N$ (0.10 mL, 0.752 mmol) in DCM (5 mL) was added 1,1,1-trifluoro-N-phenyl-N-(trifluoromethane) sulfonylmethanesulfonamide (448 mg, 1.254 mmol) dropwise at 0° C. The resulting mixture was stirred at room temperature for 2 h. The resulting mixture was diluted with water (5 mL) followed by extraction with $CH_2Cl_2$ (3×10 mL). The combined organic layers were washed with brine (3×5 mL) and dried over $Na_2SO_4$. After filtration, the filtrate was concentrated under reduced pressure. The residue was purified by silica gel column chromatography, eluted with $CH_2Cl_2$/MeOH (5% to 15%) to afford (7R,14R)-11-(4-(dimethylphosphoryl)-2-fluorophenyl)-6-(methyl-d3)-5-oxo-5,6,7,14-tetrahydro-7,14-methanobenzo[f]benzo[4,5]imidazo[1,2-a][1,4]diazocin-1-yl trifluoromethanesulfonate (200 mg, 78%) as a yellow solid. MS ESI calculated for $C_{27}H_{19}D_3F_4N_3O_5PS$ $[M+H]^+$, 611.11 found 611.15. $^1H$ NMR (400 MHz, Chloroform-d) δ 8.73-8.64 (m, 1H), 7.83 (d, J=8.0 Hz, 1H), 7.66 (s, 1H), 7.63-7.43 (m, 6H), 6.13 (d, J=6.2 Hz, 1H), 5.21-5.03 (m, 1H), 3.67-3.53 (m, 1H), 2.98 (d, J=13.5 Hz, 1H), 1.81-1.68 (m, 6H).

Preparation 19E: (7R,14R)-11-(4-(dimethylphosphoryl)-2-fluorophenyl)-6-(methyl-d3)-1-(4,4,5,5-tetramethyl-1,3,2-dioxaborolan-2-yl)-6,7-dihydro-7,14-methanobenzo[f]benzo[4,5]imidazo[1,2-a][1,4]diazocin-5(14H)-one To a solution of (7R,14R)-11-(4-(dimethylphosphoryl)-2-fluorophenyl)-6-(methyl-d3)-5-oxo-5,6,7,14-tetrahydro-7,14-methanobenzo[f]benzo[4,5]imidazo[1,2-a][1,4]diazocin-1-yl trifluoromethanesulfonate (200 mg, 0.328 mmol) and 4,4,5,5-tetramethyl-2-(tetramethyl-1,3,2-dioxaborolan-2-yl)-1,3,2-dioxaborolane (125 mg, 0.492 mmol) in 1,4-dioxane (2 mL) were added potassium acetate (96 mg, 0.984 mmo) and $Pd(PPh_3)_4$ (38 mg, 0.033 mmol) at room temperature. The resulting mixture was stirred at 80° C. for 3 h under nitrogen atmosphere. The resulting mixture was diluted with water (5 mL) followed by extraction with EtOAc (3×10 mL). The combined organic layers were washed with brine (3×10 mL) and dried over $Na_2SO_4$. After filtration, the filtrate was concentrated under reduced pressure. The residue was purified by silica gel column chromatography, eluted with $CH_2Cl_2$/MeOH (5% to 15%) to afford (7R,14R)-11-(4-(dimethylphosphoryl)-2-fluorophenyl)-6-(methyl-d3)-1-(4,4,5,5-tetramethyl-1,3,2-dioxaborolan-2-yl)-6,7-dihydro-7,14-methanobenzo[f]benzo[4,5]imidazo[1,2-a][1,4]diazocin-5(14H)-one (190 mg, 98%) as a yellow solid. MS ESI calculated for $C_{32}H_{31}D_3BFN_3O_4P$ $[M+H]^+$, 589.26 found 589.25. $^1H$ NMR (400 MHz, Chloroform-d) δ 8.71-8.64 (m, 1H), 8.06-7.99 (m, 1H), 7.88 (s, 1H), 7.80 (d, J=8.5 Hz, 1H), 7.57-7.45 (m, 3H), 7.45-7.35 (m, 2H), 6.72 (d, J=7.4 Hz, 1H), 5.00 (d, J=7.0 Hz, 1H), 3.47-3.39 (m, 1H), 2.87 (d, J=13.5 Hz, 1H), 1.80 (d, J=3.6 Hz, 3H), 1.76 (d, J=3.6 Hz, 3H), 1.41 (d, J=3.1 Hz, 12H).

Example 19: (7R,14R)-1-bromo-11-(4-(dimethylphosphoryl)-2-fluorophenyl)-6-(methyl-d3)-6,7-dihydro-7,14-methanobenzo[f]benzo[4,5]imidazo[1,2-a][1,4]diazocin-5(14H)-one A solution of (7R,14R)-11-(4-(dimethylphosphoryl)-2-fluorophenyl)-6-(methyl-d3)-1-(4,4,5,5-tetramethyl-1,3,2-dioxaborolan-2-yl)-6,7-dihydro-7,14-methanobenzo[f]benzo[4,5]imidazo[1,2-a][1,4]diazocin-5(14H)-one (80 mg, 0.136 mmol) in methanol (1.5 mL) and $H_2O$ (0.5 mL) was added $CuBr_2$ (91 mg, 0.408 mmol) at room temperature. The resulting mixture was stirred at 80° C. for 16 h. The resulting mixture was purified by silica gel column chromatography, eluted with $CH_2Cl_2$/MeOH (10:1) followed by reversed-phase flash chromatography with the following conditions: column, C18 silica gel; mobile phase, $CH_3CN$ in Water (10 mmol/L $NH_4HCO_3$), 40% to 50% gradient in 15 min; detector, 254 nm to afford (7R,14R)-1-chloro-11-(3-(cyclopropylamino) prop-1-yn-1-yl)-2-fluoro-6-(methyl-d3)-6,7-dihydro-7,14-methanobenzo[f]benzo[4,5]imidazo[1,2-a][1,4]diazocin-5(14H)-one (23 mg, 31%) as a white solid. MS ESI calculated for $C_{26}H_{19}D_3BrFN_3O_2P$ $[M+H]^+$, 541.08 found 541.10. $^1H$ NMR (400 MHz, Chloroform-d) δ 8.60 (d, J=8.1 Hz, 1H), 8.13-7.91 (m, 1H), 7.78 (d, J=8.0 Hz, 2H), 7.65-7.50 (m, 3H), 7.46 (s, 1H), 7.33-7.28 (m, 1H), 6.47 (d, J=6.4 Hz, 1H), 5.07-4.65 (m, 1H), 3.59-3.38 (m, 1H), 2.89 (d, J=13.1 Hz, 1H), 1.80 (s, 3H), 1.77 (s, 3H). $^{19}F$ NMR (377 MHz, Chloroform-d) δ −116.18. $^{31}P$ NMR (162 MHz, Chloroform-d) δ 33.04.

Example 20: (7R,14R)-11-(4-(dimethylphosphoryl)phenyl)-1,10-difluoro-6-(methyl-d3)-6,7-dihydro-7,14-methanobenzo[f]benzo[4,5]imidazo[1,2-a][1,4]diazocin-5(14H)-one

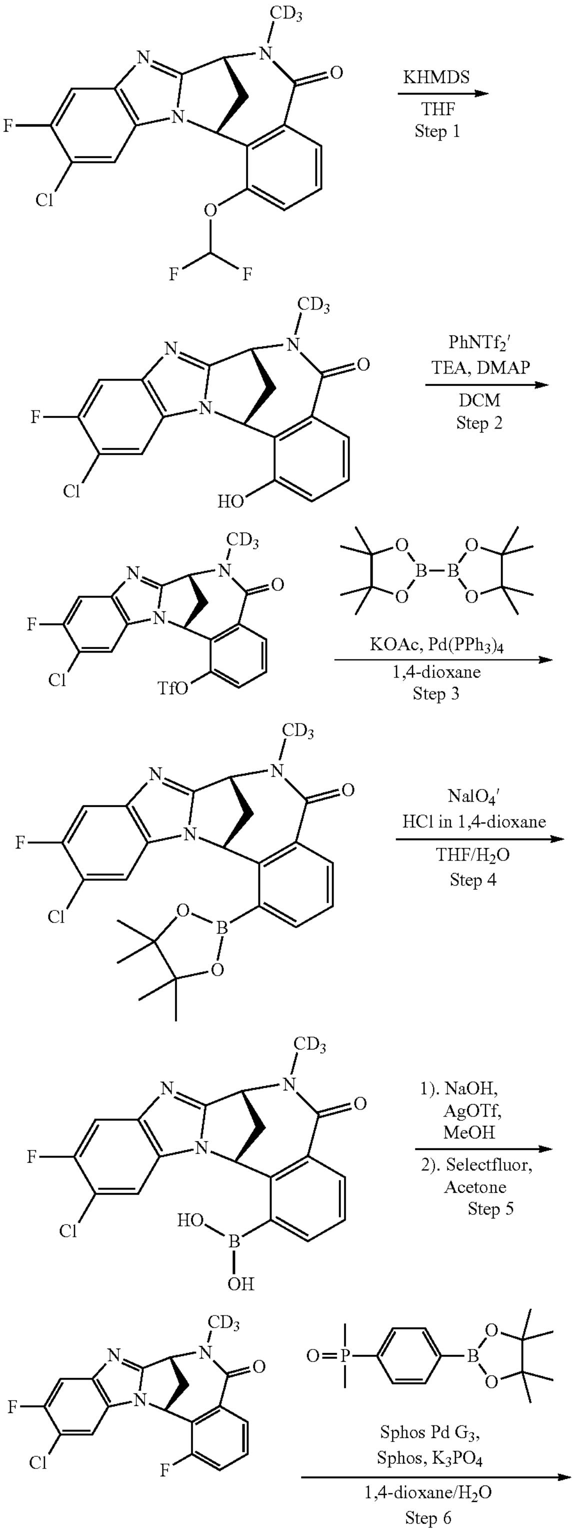

-continued

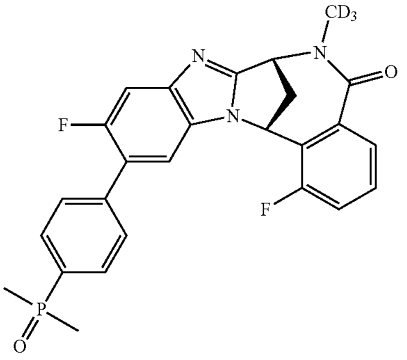 [SMILES: [2H]C([2H])([2H])N1C(=O)c2cccc(F)c2[C@@H]2C[C@@H]1c1nc3cc(F)c(-c4ccc(P(C)(C)=O)cc4)cc3n12]

Preparation 20A: (7R,14R)-11-chloro-10-fluoro-1-hydroxy-6-(methyl-d3)-6,7-dihydro-7,14-methanobenzo[f]benzo[4,5]imidazo[1,2-a][1,4]diazocin-5(14H)-one To a stirred solution of (7R,14R)-11-chloro-1-(difluoromethoxy)-10-fluoro-6-(methyl-d3)-6,7-dihydro-7,14-methanobenzo[f]benzo[4,5]imidazo[1,2-a][1,4]diazocin-5(14H)-one (1.50 g, 3.651 mmol) in THF (15 mL) were added KHMDS (10 mL, 10.953 mmol, 1 M in THF) dropwise at −78° C. under argon atmosphere. The resulting mixture was stirred at −78° C. for 4 h. The reaction was quenched by the addition of water (4 mL) at 0° C. The resulting mixture was concentrated under reduced pressure. The residue was purified by silica gel column chromatography, eluted with $CH_2Cl_2$/MeOH (12:1) to afford (7R,14R)-11-chloro-10-fluoro-1-hydroxy-6-(methyl-d3)-6,7-dihydro-7,14-methanobenzo[f]benzo[4,5]imidazo[1,2-a][1,4]diazocin-5(14H)-one (790 mg, 59%). MS ESI calculated for $C_{18}H_{10}D_3ClFN_3O_2$ $[M+H]^+$, 361.09, found 361.05. $^1H$ NMR (400 MHz, Chloroform-d) δ 10.61 (s, 1H), 7.86 (d, J=8.1 Hz, 1H), 7.69 (d, J=10.1 Hz, 1H), 7.64 (d, J=6.7 Hz, 1H), 7.22 (t, J=8.1 Hz, 1H), 7.12 (d, J=7.9 Hz, 1H), 6.28 (d, J=7.0 Hz, 1H), 5.19 (d, J=7.0 Hz, 1H), 3.47-3.38 (m, 1H), 2.74 (d, J=13.5 Hz, 1H).

Preparation 20B: (7R,14R)-11-chloro-10-fluoro-6-(methyl-d3)-5-oxo-5,6,7,14-tetrahydro-7,14-methanobenzo[f]benzo[4,5]imidazo[1,2-a][1,4]diazocin-1-yl trifluoromethanesulfonate To a stirred mixture of (7R,14R)-11-chloro-10-fluoro-1-hydroxy-6-(methyl-d3)-6,7-dihydro-7,14-methanobenzo[f]benzo[4,5]imidazo[1,2-a][1,4]diazocin-5(14H)-one (770 mg, 2.134 mmol) and N-phenyl-bis(trifluoromethanesulfonimide) (1.22 g, 3.414 mmol) in DCM (15 mL) were added DMAP (26 mg, 0.213 mmol) and TEA (431 mg, 4.268 mmol) at room temperature. The resulting mixture was stirred at room temperature for 1 h. The resulting mixture was concentrated under reduced pressure. The residue was purified by silica gel column chromatography, eluted with PE/EA (1:1) to afford (7R,14R)-11-chloro-10-fluoro-6-(methyl-d3)-5-oxo-5,6,7,14-tetrahydro-7,14-methanobenzo[f]benzo[4,5]imidazo[1,2-a][1,4]diazocin-1-yl trifluoromethanesulfonate (900 mg, 86%). MS ESI calculated for $C_{19}H_9D_3ClF_4N_3O_4S$ $[M+H]^+$, 493.04, found 493.10. $^1H$ NMR (400 MHz, Chloroform-d) δ 8.69-8.65 (m, 1H), 7.58-7.51 (m, 2H), 7.46 (d, J=9.3 Hz, 1H), 7.36 (d, J=6.4 Hz, 1H), 6.01 (d, J=7.2 Hz, 1H), 4.97 (d, J=7.2 Hz, 1H), 3.57-3.49 (m, 1H), 2.93 (d, J=13.8 Hz, 1H).

Preparation 20C: (7R,14R)-11-chloro-10-fluoro-6-(methyl-d3)-1-(4,4,5,5-tetramethyl-1,3,2-dioxaborolan-2-yl)-6,7-dihydro-7,14-methanobenzo[f]benzo[4,5]imidazo[1,2-a][1,4]diazocin-5(14H)-one To a stirred solution of (7R,14R)-11-chloro-10-fluoro-6-(methyl-d3)-5-oxo-5,6,7,14-tetrahydro-7,14-methanobenzo[f]benzo[4,5]imidazo[1,2-a][1,4]diazocin-1-yl trifluoromethanesulfonate (900 mg, 1.826 mmol) and 4,4,5,5-tetramethyl-2-(tetramethyl-1,3,2-dioxaborolan-2-yl)-1,3,2-dioxaborolane (1.85 g, 7.304 mmol) in 1,4-dioxane (15 mL) were added KOAc (537 mg, 5.478 mmol) and $Pd(PPh_3)_4$ (422 mg, 0.365 mmol) at room temperature under nitrogen atmosphere. The resulting mixture was stirred at 90° C. for 16 h under nitrogen atmosphere. The resulting mixture was concentrated under reduced pressure. The residue was purified by silica gel column chromatography, eluted with PE/EA (1:1) to afford (7R,14R)-11-chloro-10-fluoro-6-(methyl-d3)-1-(4,4,5,5-tetramethyl-1,3,2-dioxaborolan-2-yl)-6,7-dihydro-7,14-methanobenzo[f]benzo[4,5]imidazo[1,2-a][1,4]diazocin-5(14H)-one (810 mg, 94%). MS ESI calculated for $C_{24}H_{21}D_3BClFN_3O_3$ $[M+H]^+$, 471.18, found 471.15. $^1H$ NMR (400 MHz, Chloroform-d) δ 8.69 (d, J=8.1 Hz, 1H), 8.07 (d, J=7.5 Hz, 1H), 7.93 (d, J=6.6 Hz, 1H), 7.47-7.41 (m, 2H), 6.57 (d, J=7.4 Hz, 1H), 4.89 (d, J=7.0 Hz, 1H), 3.46-3.34 (m, 1H), 2.82 (d, J=13.5 Hz, 1H), 1.54 (s, 6H), 1.50 (s, 6H).

Preparation 20D: ((7R,14R)-11-chloro-10-fluoro-6-(methyl-d3)-5-oxo-5,6,7,14-tetrahydro-7,14-methanobenzo[f]benzo[4,5]imidazo[1,2-a][1,4]diazocin-1-yl) boronic acid To a stirred solution of (7R,14R)-11-chloro-10-fluoro-6-(methyl-d3)-1-(4,4,5,5-tetramethyl-1,3,2-dioxaborolan-2-yl)-6,7-dihydro-7,14-methanobenzo[f]benzo[4,5]imidazo[1,2-a][1,4]diazocin-5(14H)-one (800 mg, 1.699 mmol) in THF (10 mL) and $H_2O$ (2 mL) was added $NaIO_4$ (1.09 g, 5.097 mmol) at room temperature. The resulting mixture was stirred at room temperature for 2 h. To the above mixture was added HCl (gas) in 1,4-dioxane (1.1 mL, 4.000 mmol) at room temperature. The resulting mixture was stirred at room temperature for additional 16 h. The resulting mixture was filtered, the filter cake was washed with MeOH (3×1 mL). The filtrate was concentrated under reduced pressure. The residue was purified by reversed-phase flash chromatography with the following conditions: column, C18 silica gel; mobile phase, $CH_3CN$ in water (10 mmol/L $NH_4HCO_3$), 10% to 38% gradient in 10 min; detector, 254 nm to afford ((7R,14R)-11-chloro-10-fluoro-6-(methyl-d3)-5-oxo-5,6,7,14-tetrahydro-7,14-methanobenzo[f]benzo[4,5]imidazo[1,2-a][1,4]diazocin-1-yl) boronic acid (457 mg, 69%). MS ESI calculated for $C_{18}H_{11}D_3BClFN_3O_3$ $[M+H]^+$, 389.10, found 389.05. $^1H$ NMR (400 MHz, DMSO-$d_6$) δ 8.99 (s, 2H), 8.35 (d, J=8.1 Hz, 1H), 8.03 (d, J=6.8 Hz, 1H), 7.73-7.63 (m, 2H), 7.41 (t, J=7.7 Hz, 1H), 6.21 (d, J=7.3 Hz, 1H), 5.17 (d, J=7.0 Hz, 1H), 3.53-3.46 (m, 1H), 2.70 (d, J=13.6 Hz, 1H).

Preparation 20E: (7R,14R)-11-chloro-1,10-difluoro-6-(methyl-d3)-6,7-dihydro-7,14-methanobenzo[f]benzo[4,5]imidazo[1,2-a][1,4]diazocin-5(14H)-one To a stirred solution of ((7R,14R)-11-chloro-10-fluoro-6-(methyl-d3)-5-oxo-5,6,7,14-tetrahydro-7,14-methanobenzo

[f]benzo[4,5]imidazo[1,2-a][1,4]diazocin-1-yl) boronic acid (150 mg, 0.386 mmol) in MeOH (2 mL) was added NaOH (19 mg, 0.463 mmol) at room temperature. The resulting mixture was stirred at room temperature for 15 min under nitrogen atmosphere followed by addition of Silver (I) trifluoromethane sulfonate (297 mg, 1.158 mmol) at 0° C. The resulting mixture was stirred at 0° C. for additional 30 min. The resulting mixture was concentrated under reduced pressure. The residue in Acetone (2 mL) was added Selectfluor (136 mg, 0.386 mmol) at 0° C. The resulting mixture was stirred at room temperature for 1 h under nitrogen atmosphere. The resulting mixture was filtered, the filter cake was washed with MeOH (3×2 mL). The filtrate was concentrated under reduced pressure. The residue was purified by reversed-phase flash chromatography with the following conditions: column, C18 silica gel; mobile phase, $CH_3CN$ in water (10 mmol/L $NH_4HCO_3$), 10% to 42% gradient in 10 min; detector, 254 nm to afford (7R,14R)-11-chloro-1,10-difluoro-6-(methyl-d3)-6,7-dihydro-7,14-methanobenzo[f]benzo[4,5]imidazo[1,2-a][1,4]diazocin-5(14H)-one (49 mg, 34%) as a light yellow solid. MS ESI calculated for $C_{18}H_9D_3ClF_2N_3O$ $[M+H]^+$, 363.08, found 363.00. $^1$H NMR (400 MHz, Chloroform-d) δ 8.41 (d, J=8.1 Hz, 1H), 7.51-7.44 (m, 2H), 7.43-7.37 (m, 1H), 7.36-7.29 (m, 1H), 6.09 (d, J=7.0 Hz, 1H), 4.96 (d, J=7.2 Hz, 1H), 3.52-3.38 (m, 1H), 2.70 (d, J=13.6 Hz, 1H).

Example 20: (7R,14R)-11-(4-(dimethylphosphoryl) phenyl)-1,10-difluoro-6-(methyl-d3)-6,7-dihydro-7,14-methanobenzo[f]benzo[4,5]imidazo[1,2-a][1,4] diazocin-5(14H)-one To a stirred mixture of (7R,14R)-11-chloro-1,10-difluoro-6-(methyl-d3)-6,7-dihydro-7,14-methanobenzo[f]benzo[4,5]imidazo[1,2-a][1,4]diazocin-5(14H)-one (45 mg, 0.124 mmol) and 2-[4-(dimethylphosphoryl)phenyl]-4,4,5,5-tetramethyl-1,3,2-dioxaborolane (52 mg, 0.186 mmol) in 1,4-dioxane (2 mL) and $H_2O$ (0.2 mL) were added $K_3PO_4$ (65 mg, 0.310 mmol), S-Phos (10 mg, 0.025 mmol) and Sphos Pd G3 (9 mg, 0.012 mmol) at room temperature under argon atmosphere. The resulting mixture was stirred at 80° C. for 2 h. The resulting mixture was concentrated under reduced pressure. The residue was purified by silica gel column chromatography, eluted with $CH_2Cl_2$/MeOH (10:1) followed by reversed-phase flash chromatography with the following conditions: column, C18 silica gel; mobile phase, $CH_3CN$ in Water (10 mmol/L $NH_4HCO_3$), 10% to 34% gradient in 10 min; detector, 254 nm to afford (7R,14R)-11-(4-(dimethylphosphoryl)phenyl)-1,10-difluoro-6-(methyl-d3)-6,7-dihydro-7,14-methanobenzo[f]benzo[4,5]imidazo[1,2-a][1,4]diazocin-5(14H)-one (35 mg, 59%) as a white solid. MS ESI calculated for $C_{26}H_{19}D_3F_2N_3O_2P$ $[M+H]^+$, 481.16, found 481.20. $^1$H NMR (400 MHz, Chloroform-d) δ 8.42 (d, J=8.1 Hz, 1H), 7.87-7.78 (m, 2H), 7.69-7.63 (m, 2H), 7.54 (d, J=10.8 Hz, 1H), 7.47 (d, J=6.5 Hz, 1H), 7.44-7.37 (m, 1H), 7.34-7.28 (m, 1H), 6.17 (d, J=6.9 Hz, 1H), 5.07 (d, J=7.0 Hz, 1H), 3.58-3.44 (m, 1H), 2.93 (d, J=13.6 Hz, 1H), 1.81 (s, 3H), 1.78 (s, 3H). $^{19}$F NMR (377 MHz, Chloroform-d) δ −118.27, −121.77. $^{31}$P NMR (162 MHz, Chloroform-d) δ 34.01.

Example 21: (7R,14R)-11-(6-(dimethylphosphoryl) pyridin-3-yl)-1,10-difluoro-6-(methyl-d3)-6,7-dihydro-7,14-methanobenzo[f]benzo[4,5]imidazo[1,2-a][1,4]diazocin-5(14H)-one

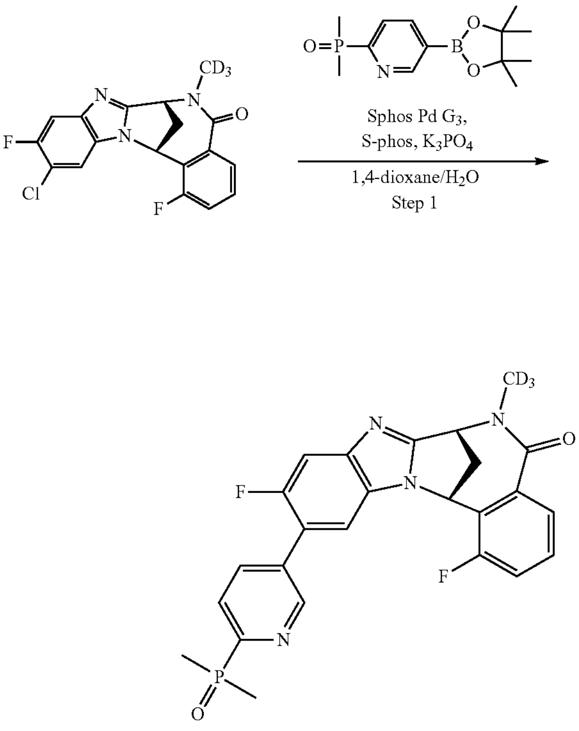

To a stirred mixture of (7R,14R)-11-chloro-1,10-difluoro-6-(methyl-d3)-6,7-dihydro-7,14-methanobenzo[f]benzo[4,5]imidazo[1,2-a][1,4]diazocin-5(14H)-one (30 mg, 0.083 mmol) and 2-(dimethylphosphoryl)-5-(4,4,5,5-tetramethyl-1,3,2-dioxaborolan-2-yl)pyridine (92 mg, 0.332 mmol) in 1,4-dioxane (2 mL) and $H_2O$ (0.2 mL) were added $K_3PO_4$ (43 mg, 0.208 mmol), S-Phos (6 mg, 0.017 mmol) and SPhos Pd G3 (6 mg, 0.008 mmol) at room temperature under argon atmosphere. The resulting mixture was stirred at 80° C. for 4 h under argon atmosphere. The resulting mixture was concentrated under reduced pressure. The residue was purified by silica gel column chromatography, eluted with $CH_2Cl_2$/MeOH (10:1) followed by Prep-HPLC with the following conditions (Column: XBridge Prep OBD C18 Column, 30*150 mm, 5 um; Mobile Phase A: Water (10 mmol/L $NH_4HCO_3$+0.05% $NH_3 \cdot H_2O$), Mobile Phase B: MeOH; Flow rate: 60 mL/min; Gradient: 30% B to 60% B in 10 min; Wave Length: 254 nm; RT1 (min): 9.22) to afford (7R,14R)-11-(6-(dimethylphosphoryl)pyridin-3-yl)-1,10-difluoro-6-(methyl-d3)-6,7-dihydro-7,14-methanobenzo[f]benzo[4,5]imidazo[1,2-a][1,4]diazocin-5(14H)-one (15 mg, 38%). MS ESI calculated for $C_{25}H_{18}D_3F_2N_4O_2P$ $[M+H]^+$, 482.16, found 482.15. $^1$H NMR (400 MHz, Chloroform-d) δ 8.88 (s, 1H), 8.42 (d, J=8.1 Hz, 1H), 8.25-8.15 (m, 1H), 8.01 (d, J=7.6 Hz, 1H), 7.55 (d, J=11.0 Hz, 1H), 7.47 (d, J=6.5 Hz, 1H), 7.43-7.37 (m, 1H), 7.34-7.28 (m, 1H), 6.16 (d, J=6.9 Hz, 1H), 5.01 (d, J=7.1 Hz, 1H), 3.57-3.45 (m, 1H), 2.92 (d, J=13.5 Hz, 1H), 1.85 (s, 3H), 1.82 (s, 3H). $^{19}$F NMR (377 MHz, Chloroform-d) δ −118.38, −122.80. $^{31}$P NMR (162 MHz, Chloroform-d) δ 36.63.

Example 22: (7R,14R)-11-(4-(dimethylphosphoryl)-3-fluorophenyl)-1-fluoro-7-methyl-6-(methyl-d3)-6,7-dihydro-7,14-methanobenzo[f]benzo[4,5]imidazo[1,2-a][1,4]diazocin-5(14H)-one
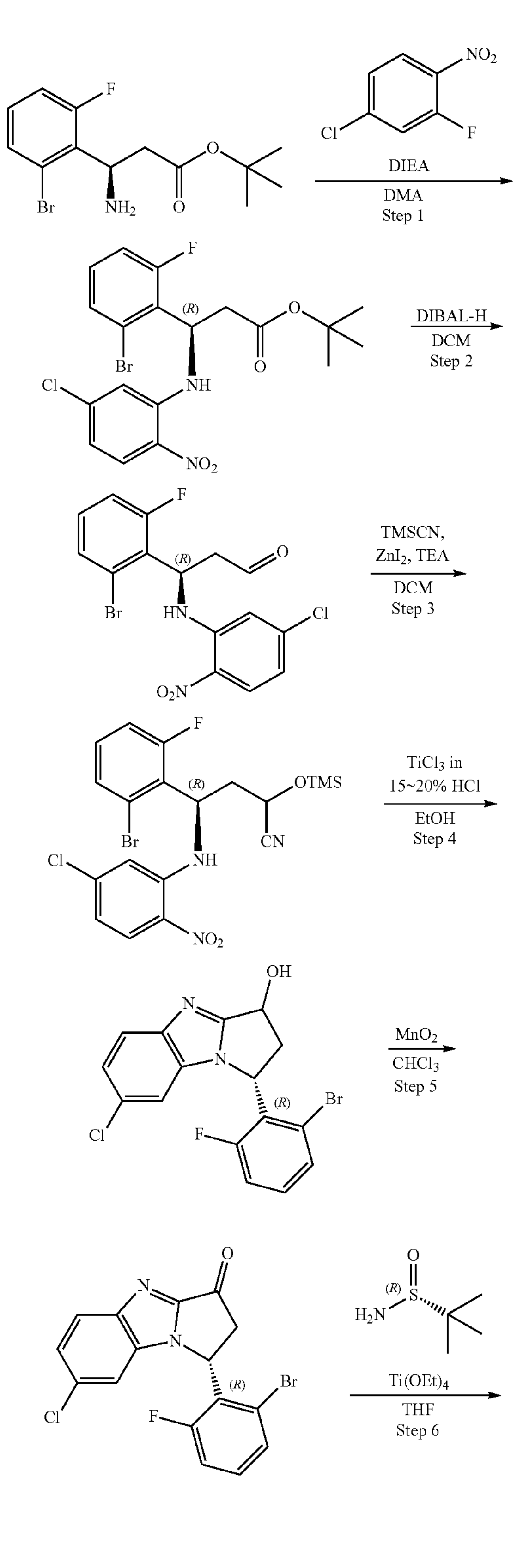
-continued
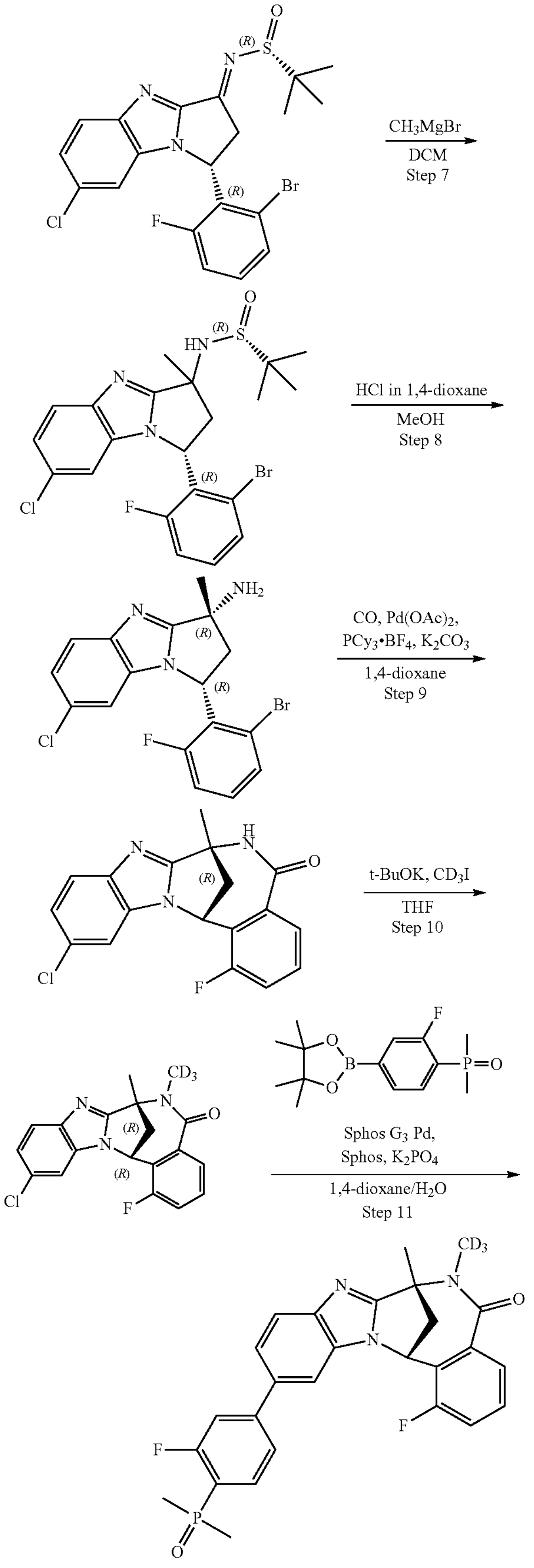

Preparation 22A: (3R)-3-(2-bromo-6-fluorophenyl)-3-[(5-chloro-2-nitrophenyl)amino]propanoate To a stirred solution of tert-butyl (3R)-3-amino-3-(2-bromo-6-fluorophenyl)propanoate (50.00 g, 157.141 mmol) and 4-chloro-2-fluoro-1-nitrobenzene (35.86 g, 204.283 mmol) in DMA (250 mL) were added DIEA (30.46 g, 235.712 mmol) dropwise at room temperature. The resulting mixture was stirred at 80° C. overnight. The reaction was quenched by the addition of water (1 L) followed by extraction with EtOAc (3×1 L). The combined organic layers were washed with brine (2×1 L) and dried over anhydrous $Na_2SO_4$. After filtration, the filtrate was concentrated under reduced pressure. The residue was purified by silica gel column chromatography, eluted with PE/EA (12:1) to afford (3R)-3-(2-bromo-6-fluorophenyl)-3-[(5-chloro-2-nitrophenyl)amino]propanoate (56.40 g, 76%). MS ESI calculated for $C_{19}H_{19}BrClFN_2O_4$ $[M+H]^+$, 473.02 475.02. found 473.00 475.00. $^1H$ NMR (400 MHz, DMSO-$d_6$) δ 8.64 (d, J=8.6 Hz, 1H), 8.13 (d, J=9.1 Hz, 1H), 7.60-7.54 (m, 1H), 7.40-7.30 (m, 2H), 6.97 (d, J=2.2 Hz, 1H), 6.85-6.79 (m, 1H), 5.59-5.50 (m, 1H), 3.09-2.96 (m, 2H), 1.32 (s, 9H). $^{19}F$ NMR (377 MHz, DMSO-$d_6$) δ −112.55, −115.68.

Preparation 22B: (3R)-3-(2-bromo-6-fluorophenyl)-3-[(5-chloro-2-nitrophenyl)amino]propanal To a stirred solution of (3R)-3-(2-bromo-6-fluorophenyl)-3-[(5-chloro-2-nitrophenyl)amino]propanoate (56.40 g, 119.058 mmol) in DCM (1 L) was added Diisobutylaluminum hydride (1.0 M in DCM) (155 mL, 154.775 mmol) dropwise at −78° C. under nitrogen atmosphere. The resulting mixture was stirred at −78° C. for 2 h under nitrogen atmosphere. The reaction was quenched by the addition of sat. $NH_4Cl$ (aq.) (100 mL) at −78° C. followed by extraction with $CH_2Cl_2$ (3×100 mL). The residue was purified by silica gel column chromatography, eluted with PE/EA (12:1) to afford (3R)-3-(2-bromo-6-fluorophenyl)-3-[(5-chloro-2-nitrophenyl)amino]propanal (14.01 g, 29%) as orange oil. MS ESI calculated for $C_{15}H_{11}BrClFN_2O_3$ $[M+H]^+$, 400.96 402.96, found 401.00, 403.00. $^1H$ NMR (400 MHz, Chloroform-d) δ 9.82 (t, J=1.2 Hz, 1H), 8.73 (d, J=8.9 Hz, 1H), 8.09 (d, J=9.2 Hz, 1H), 7.45-7.39 (m, 1H), 7.21-7.15 (m, 1H), 7.12-7.03 (m, 2H), 6.66-6.62 (m, 1H), 5.84-5.76 (m, 1H), 3.52-3.39 (m, 1H), 3.16-3.04 (m, 1H). $^{19}F$ NMR (377 MHz, Chloroform-d) δ −112.21.

Preparation 22C: (4R)-4-(2-bromo-6-fluorophenyl)-4-[(5-chloro-2-nitrophenyl)amino]-2-[(trimethylsilyl)oxy]butanenitrile To a stirred mixture of (3R)-3-(2-bromo-6-fluorophenyl)-3-[(5-chloro-2-nitrophenyl)amino]propanal (14.00 g, 34.859 mmol) and $ZnI_2$ (1.11 g, 3.486 mmol) in DCM (31 mL) were added $Et_3N$ (0.5 mL, 3.486 mmol) and TMSCN (8.7 mL, 69.718 mmol) dropwise at room temperature under nitrogen atmosphere. The resulting mixture was stirred at room temperature overnight. The reaction was quenched by the addition of water (300 mL) at room temperature followed by extraction with $CH_2Cl_2$ (3×500 mL). The combined organic layers were washed with brine (500 mL) and dried over anhydrous $Na_2SO_4$. After filtration, the filtrate was concentrated under reduced pressure. This resulted in (4R)-4-(2-bromo-6-fluorophenyl)-4-[(5-chloro-2-nitrophenyl)amino]-2-[(trimethylsilyl)oxy]butanenitrile (16.10 g, 92%) as yellow oil. MS ESI calculated for $C_{19}H_{20}BrClFN_3O_3Si$ $[M+H]^+$, 500.01 502.01, found 500.00, 502.00.

Preparation 22D: (1R)-1-(2-bromo-6-fluorophenyl)-7-chloro-2,3-dihydro-1H-benzo[d]pyrrolo[1,2-a]imidazol-3-ol To a stirred solution of (4R)-4-(2-bromo-6-fluorophenyl)-4-[(5-chloro-2-nitrophenyl)amino]-2-[(trimethylsilyl)oxy]butanenitrile (16.01 g, 31.948 mmol) in EtOH (540 mL) was added Titanium (III) chloride, 15-20% in 2N Hydrochloric acid) (197.32 g, 255.903 mmol) dropwise at room temperature. The resulting mixture was stirred at 80° C. for 3 h. The mixture was neutralized to pH 8 with saturated $NaHCO_3$ (aq.) followed by extraction with EtOAc (3×10 mL). The combined organic layers were dried over anhydrous $Na_2SO_4$. After filtration, the filtrate was concentrated under reduced pressure. The residue was purified by silica gel column chromatography, eluted with $CH_2Cl_2$/MeOH (12:1) to afford (1R)-1-(2-bromo-6-fluorophenyl)-7-chloro-2,3-dihydro-1H-benzo[d]pyrrolo[1,2-a]imidazol-3-ol (10.00 g, 82%). MS ESI calculated for $C_{16}H_{11}BrClFN_2O$ $[M+H]^+$, 380.97 382.97, found 380.85 382.85. $^1H$ NMR (400 MHz, Chloroform-d) δ 7.71-7.64 (m, 1H), 7.55 (d, J=8.2 Hz, 1H), 7.32-7.27 (m, 1H), 7.24-7.19 (m, 1H), 7.06-6.95 (m, 1H), 6.83 (d, J=38.0 Hz, 1H), 6.70-6.59 (m, 1H), 6.40-5.97 (m, 1H), 5.76-5.57 (m, 1H), 3.70-3.33 (m, 2H). $^{19}F$ NMR (377 MHz, Chloroform-d) δ −112.01.

Preparation 22E: (R)-1-(2-bromo-6-fluorophenyl)-7-chloro-1,2-dihydro-3H-benzo[d]pyrrolo[1,2-a]imidazol-3-one To a stirred solution of (1R)-1-(2-bromo-6-fluorophenyl)-7-chloro-2,3-dihydro-1H-benzo[d]pyrrolo[1,2-a]imidazol-3-ol (16.00 g, 41.925 mmol) in $CHCl_3$ (200 mL) was added $MnO_2$ (36.45 g, 419.250 mmol) in portions at room temperature. The resulting mixture was stirred at room temperature overnight. The resulting mixture was filtered, the filter cake was washed with DCM (3×500 mL). The filtrate was concentrated under reduced pressure. The residue was purified by silica gel column chromatography, eluted with PE/EA (1:1) to afford (R)-1-(2-bromo-6-fluorophenyl)-7-chloro-1,2-dihydro-3H-benzo[d]pyrrolo[1,2-a]imidazol-3-one (4.01 g, 25%) as a brown solid. MS ESI calculated for $C_{16}H_9BrClFN_2O$ $[M+H]^+$, 378.96 380.96, found 378.90 380.90. $^1H$ NMR (400 MHz, DMSO-$d_6$) δ 7.99-7.92 (m, 1H), 7.77-7.70 (m, 1H), 7.49-7.39 (m, 2H), 7.28-7.20 (m, 1H), 7.14-7.01 (m, 1H), 6.58-6.46 (m, 1H), 3.96-3.79 (m, 1H), 3.48-3.38 (m, 1H). $^{19}F$ NMR (377 MHz, DMSO-$d_6$) δ −113.61.

Preparation 22F: (R)—N—((R,E)-1-(2-bromo-6-fluorophenyl)-7-chloro-1,2-dihydro-3H-benzo[d]pyrrolo[1,2-a]imidazol-3-ylidene)-2-methylpropane-2-sulfinamide To a stirred solution of (R)-1-(2-bromo-6-fluorophenyl)-7-chloro-1,2-dihydro-3H-benzo[d]pyrrolo[1,2-a]imidazol-3-one (11.00 g, 28.977 mmol) and Titanium ethoxide (14.54 g, 63.749 mmol) in THF (220 mL) was added (R)-2-methylpropane-2-sulfinamide (6.32 g, 52.159 mmol) at 0° C. The resulting mixture was stirred for 16 h at 65° C. The resulting mixture was concentrated under reduced pressure. The residue was basified to pH 9 with saturated $NaHCO_3$ (aq.) followed by extraction with EtOAc (2×200 mL). The combined organic layers were washed with brine (200 mL) and dried over anhydrous $MgSO_4$. After filtration, the filtrate was concentrated under reduced pressure. The residue was purified by reversed-phase flash chromatography with the following conditions: column, C18 silica gel; mobile phase, $CH_3CN$ in Water (10 mmol/L $NH_4HCO_3$), 10% to 65% gradient in 30 min; detector, 254 nm to afford (R)—N—((R,E)-1-(2-bromo-6-fluorophenyl)-7-chloro-1,2-dihydro-3H-benzo[d]pyrrolo[1,2-a]imidazol-3-ylidene)-2-methylpropane-2-sulfinamide (3.60 g, 26%) as a brown yellow solid. MS ESI calculated for $C_{20}H_{18}BrClFN_3OS$ $[M+H]^+$, 482.00 484.00, found 482.00 484.00. $^1H$ NMR (400 MHz, Chloroform-d) δ 7.85-7.79 (m, 1H), 7.57-7.53 (m, 1H), 7.31-7.27 (m, 2H), 7.10-6.87 (m, 2H), 6.38-6.31 (m, 1H), 4.63-4.51 (m, 1H), 3.89-3.77 (m, 1H), 1.41 (s, 9H).

Preparation 22G: (R)—N-((1R)-1-(2-bromo-6-fluorophenyl)-7-chloro-3-methyl-2,3-dihydro-1H-benzo[d]pyrrolo[1,2-a]imidazol-3-yl)-2-methylpropane-2-sulfinamide To a stirred solution of (R)—N—((R,E)-1-(2-bromo-6-fluorophenyl)-7-chloro-1,2-dihydro-3H-benzo[d]pyrrolo[1,2-a]imidazol-3-ylidene)-2-methylpropane-2-sulfinamide (490 mg, 1.015 mmol) in DCM (10 mL) was added Methyl magnesium bromide, 3 M solution in diethyl ether (1 mL, 3.045 mmol) dropwise at −78° C. under nitrogen atmosphere. The resulting mixture was stirred at room temperature for 16 h under nitrogen atmosphere. The reaction was quenched with water at 0° C. followed by extraction with $CH_2Cl_2$ (3×20 mL). The combined organic layers were washed with brine (10 mL) and dried over anhydrous $MgSO_4$. After filtration, the filtrate was concentrated under reduced pressure. The residue was purified by silica gel column chromatography, eluted with $CH_2Cl_2$/MeOH (10:1) to afford (R)—N-((1R)-1-(2-bromo-6-fluorophenyl)-7-chloro-3-methyl-2,3-dihydro-1H-benzo[d]pyrrolo[1,2-a]imidazol-3-yl)-2-methylpropane-2-sulfinamide (160 mg, 32%) as a brown solid. MS ESI calculated for $C_{21}H_{22}BrClFN_3OS$ $[M+H]^+$, 498.03 500.03, found 498.00 500.00. $^1H$ NMR (400 MHz, Chloroform-d) δ 7.70-7.62 (m, 1H), 7.60-7.52 (m, 1H), 7.35-7.28 (m, 1H), 7.26-7.18 (m, 1H), 7.06-6.94 (m, 1H), 6.74-6.60 (m, 1H), 6.26-5.92 (m, 1H), 4.48-4.23 (m, 1H), 3.43-3.10 (m, 2H), 1.93 (d, J=8.2 Hz, 3H), 1.27 (d, J=12.3 Hz, 9H).

Preparation 22H: (1R,3R)-1-(2-bromo-6-fluorophenyl)-7-chloro-3-methyl-2,3-dihydro-1H-benzo[d]pyrrolo[1,2-a]imidazol-3-amine A solution of (R)—N-((1R)-1-(2-bromo-6-fluorophenyl)-7-chloro-3-methyl-2,3-dihydro-1H-benzo[d]pyrrolo[1,2-a]imidazol-3-yl)-2-methylpropane-2-sulfinamide (1.20 g, 2.406 mmol) and HCl in 1,4-dioxane (4.0 M) (5 mL) in methanol (5 mL) was stirred at 0° C. for 1 h. The resulting mixture was concentrated under reduced pressure. The residue was purified by reversed-phase flash chromatography with the following conditions: column, C18 silica gel; mobile phase, $CH_3CN$ in Water (10 mmol/L $NH_4HCO_3$), 10% to 50% gradient in 20 min; detector, 254 nm to afford (1R,3R)-1-(2-bromo-6-fluorophenyl)-7-chloro-3-methyl-2,3-dihydro-1H-benzo[d]pyrrolo[1,2-a]imidazol-3-amine (850 mg, 90%) as a white solid. MS ESI calculated for $C_{17}H_{14}BrClFN_3$ $[M+H]^+$, 394.00 396.00, found 393.95 395.95. $^1H$ NMR (400 MHz, Chloroform-d) δ 7.62 (d, J=8.6 Hz, 1H), 7.55 (d, J=8.2 Hz, 1H), 7.40-7.29 (m, 1H), 7.22-7.14 (m, 1H), 7.05-6.96 (m, 1H), 6.73-6.58 (m, 1H), 6.06-5.95 (m, 1H), 3.26-3.17 (m, 2H), 1.70 (s, 3H).

Preparation 221: (7R,14R)-11-chloro-1-fluoro-7-methyl-6,7-dihydro-7,14-methanobenzo[f]benzo[4,5]imidazo[1,2-a][1,4]diazocin-5(14H)-one To a stirred solution of (1R,3R)-1-(2-bromo-6-fluorophenyl)-7-chloro-3-methyl-2,3-dihydro-1H-benzo[d]pyrrolo[1,2-a]imidazol-3-amine (400 mg, 1.014 mmol) and $K_2CO_3$ (700 mg, 5.070 mmol) in 1,4-dioxane (15 mL) were added $PCy_3{\cdot}HBF_4$ (75 mg, 0.203 mmol) and $Pd(OAc)_2$ (23 mg, 0.101 mmol) at room temperature. The resulting mixture was stirred at 120° C. for 24 h under carbon monoxide atmosphere. The resulting mixture was concentrated under reduced pressure. The residue was purified by silica gel column chromatography, eluted with $CH_2Cl_2$/MeOH (20:1) to afford (7R,14R)-11-chloro-1-fluoro-7-methyl-6,7-dihydro-7,14-methanobenzo[f]benzo[4,5]imidazo[1,2-a][1,4]diazocin-5(14H)-one (200 mg, 58%). MS ESI calculated for $C_{18}H_{13}ClFN_3O$ $[M+H]^+$, 342.07, found 342.05. $^1H$ NMR (400 MHz, Chloroform-d) δ 8.32 (m, 1H), 7.63 (d, J=8.7 Hz, 1H), 7.48-7.33 (m, 3H), 7.24-7.12 (m, 1H), 6.63 (s, 1H), 6.11 (d, J=7.4 Hz, 1H), 3.37-3.21 (m, 1H), 2.95 (d, J=13.1 Hz, 1H), 2.03 (s, 3H).

Preparation 22J: (7R,14R)-11-chloro-1-fluoro-7-methyl-6-(methyl-d3)-6,7-dihydro-7,14-methanobenzo[f]benzo[4,5]imidazo[1,2-a][1,4]diazocin-5(14H)-one To a stirred mixture of (7R,14R)-11-chloro-1-fluoro-7-methyl-6,7-dihydro-7,14-methanobenzo[f]benzo[4,5]imidazo[1,2-a][1,4]diazocin-5(14H)-on (80 mg, 0.234 mmol) and 1-BuOK (53 mg, 0.468 mmol) in THF (1 mL) was added Iodomethane-d3 (22 uL, 0.351 mmol) dropwise at 0° C. The resulting mixture was stirred at room temperature for 2 h. The resulting mixture was concentrated under reduced pressure. The residue was purified by silica gel column chromatography, eluted with $CH_2Cl_2$/MeOH (20:1) to afford (7R,14R)-11-chloro-1-fluoro-7-methyl-6-(methyl-d3)-6,7-dihydro-7,14-methanobenzo[f]benzo[4,5]imidazo[1,2-a][1,4]diazocin-5(14H)-one (35 mg, 42%) as white solid. MS ESI calculated for $C_{19}H_{12}D_3ClFN_3O$ $[M+H]^+$, 359.11, found 359.10. $^1H$ NMR (400 MHz, Chloroform-d) δ 8.47-8.41 (m, 1H), 7.69 (d, J=8.7 Hz, 1H), 7.50 (d, J=2.0 Hz, 1H), 7.46-7.39 (m, 1H), 7.37-7.28 (m, 2H), 6.01 (d, J=7.5 Hz, 1H), 3.43-3.32 (m, 1H), 3.09 (d, J=13.7 Hz, 1H), 2.18 (s, 3H). $^{19}F$ NMR (377 MHz, Chloroform-d) δ −118.80.

Example 22: (7R,14R)-11-(4-(dimethylphosphoryl)-3-fluorophenyl)-1-fluoro-7-methyl-6-(methyl-d3)-6,7-dihydro-7,14-methanobenzo[f]benzo[4,5]imidazo[1,2-a][1,4]diazocin-5(14H)-one

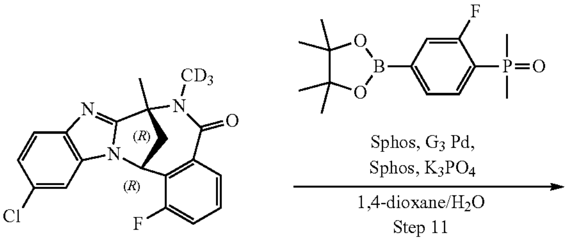

-continued

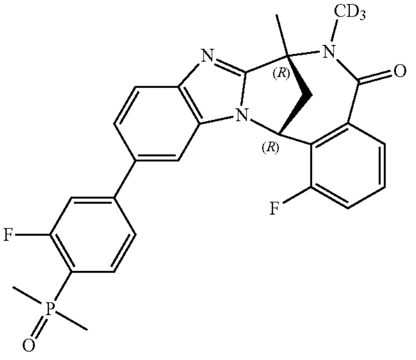

To a stirred mixture of (7R,14R)-11-chloro-1-fluoro-7-methyl-6-(methyl-d3)-6,7-dihydro-7,14-methanobenzo[f]benzo[4,5]imidazo[1,2-a][1,4]diazocin-5(14H)-one (30 mg, 0.084 mmol) and 2-[4-(dimethylphosphoryl)-3-fluorophenyl]-4,4,5,5-tetramethyl-1,3,2-dioxaborolane (50 mg, 0.168 mmol) in $H_2O$ (0.5 mL) and 1,4-dioxane (2.5 mL) were added S-Phos (4 mg, 0.008 mmol), SPhos Pd G3 (3 mg, 0.004 mmol) and $K_3PO_4$ (44 mg, 0.210 mmol) at room temperature. The resulting mixture was stirred at 80° C. for 3 h under nitrogen atmosphere. The resulting mixture was concentrated under reduced pressure. The residue was purified by reversed-phase flash chromatography with the following conditions: column, C18 silica gel; mobile phase, $CH_3CN$ in Water (10 mmol/L $NH_4HCO_3$), 10% to 50% gradient in 10 min; detector, 254 nm. This resulted in (7R,14R)-11-(4-(dimethylphosphoryl)-3-fluorophenyl)-1-fluoro-7-methyl-6-(methyl-d3)-6,7-dihydro-7,14-methanobenzo[f]benzo[4,5]imidazo[1,2-a][1,4]diazocin-5(14H)-one (29 mg, 71%). MS ESI calculated for $C_{27}H_{21}D_3F_2N_3O_2P$ $[M+H]^+$, 495.18, found 495.20. $^1H$ NMR (400 MHz, Chloroform-d) δ 8.44 (d, J=8.1 Hz, 1H), 8.07-7.99 (m, 1H), 7.82 (d, J=8.5 Hz, 1H), 7.68 (s, 1H), 7.59-7.53 (m, 1H), 7.53-7.48 (m, 1H), 7.45-7.37 (m, 1H), 7.37-7.29 (m, 2H), 6.06 (d, J=7.4 Hz, 1H), 3.45-3.35 (m, 1H), 3.11 (d, J=13.6 Hz, 1H), 2.16 (s, 3H), 1.86 (s, 3H), 1.82 (s, 3H). $^{19}F$ NMR (377 MHz, Chloroform-d) δ −105.71, −105.72, −119.13. $^{31}P$ NMR (162 MHz, Chloroform-d) δ 30.56.

Example 23: (7R,14R)-11-(4-(dimethylphosphoryl)-3-fluorophenyl)-1,10-difluoro-6-(methyl-d3)-6,7-dihydro-7,14-methanobenzo[f]benzo[4,5]imidazo[1,2-a][1,4]diazocin-5(14H)-one

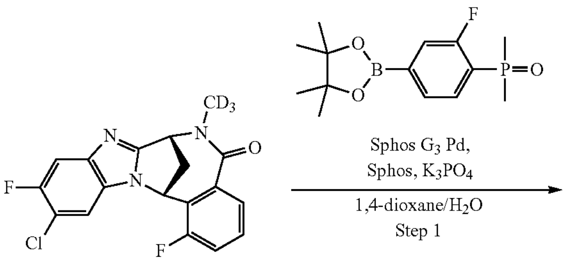

-continued

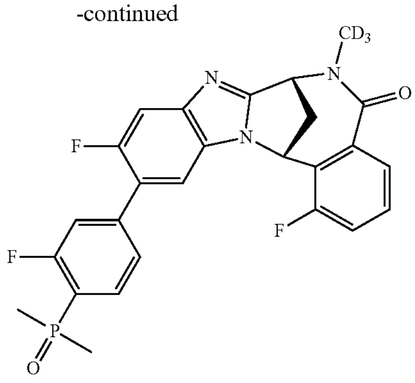

To a stirred mixture of (7R,14R)-11-chloro-1,10-difluoro-6-(methyl-d3)-6,7-dihydro-7,14-methanobenzo[f]benzo[4,5]imidazo[1,2-a][1,4]diazocin-5(14H)-one (50 mg, 0.138 mmol) and 2-[4-(dimethylphosphoryl)-3-fluorophenyl]-4,4,5,5-tetramethyl-1,3,2-dioxaborolane (82 mg, 0.276 mmol) in 1,4-dioxane (2 mL) and $H_2O$ (0.2 mL) were added SPhos Pd G3 (11 mg, 0.014 mmol), S-Phos (2.83 mg, 0.007 mmol) and $K_3PO_4$ (73 mg, 0.345 mmol) at room temperature under nitrogen atmosphere. The resulting mixture was stirred at 80° C. for 2 h. The resulting mixture was filtered and purified by reversed-phase flash chromatography with the following conditions: column, C18 silica gel; mobile phase, $CH_3CN$ in Water (10 mmol/L $NH_4HCO_3$), 10% to 50% gradient in 10 min; detector, 254 nm. This resulted in (7R,14R)-11-(4-(dimethylphosphoryl)-3-fluorophenyl)-1,10-difluoro-6-(methyl-d3)-6,7-dihydro-7,14-methanobenzo[f]benzo[4,5]imidazo[1,2-a][1,4]diazocin-5(14H)-one (43 mg, 63%). MS ESI calculated for $C_{26}H_{18}D_3F_3N_3O_2P$ $[M+H]^+$, 499.15, found 423.00. $^1H$ NMR (400 MHz, Chloroform-d) δ 8.46-8.41 (m, 1H), 8.11-8.02 (m, 1H), 7.60-7.39 (m, 4H), 7.37-7.28 (m, 2H), 6.22 (d, J=7.0 Hz, 1H), 5.21 (d, J=7.1 Hz, 1H), 3.66-3.55 (m, 1H), 2.96 (d, J=13.6 Hz, 1H), 1.87 (s, 3H), 1.83 (s, 3H). $^{19}F$ NMR (377 MHz, Chloroform-d) δ −105.70, −105.71, −118.11, −119.93. $^{31}P$ NMR (162 MHz, Chloroform-d) δ 30.40, 30.38.

Example 24: (7R,14R)-11-(3-amino-4-(dimethylphosphoryl)phenyl)-1-fluoro-6-(methyl-d3)-6,7-dihydro-7,14-methanobenzo[f]benzo[4,5]imidazo[1,2-a][1,4]diazocin-5(14H)-one

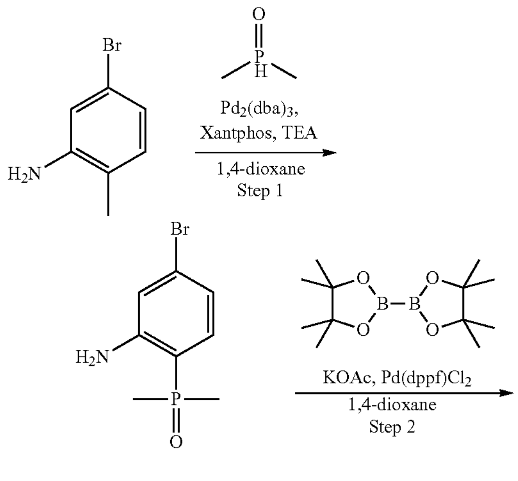

-continued

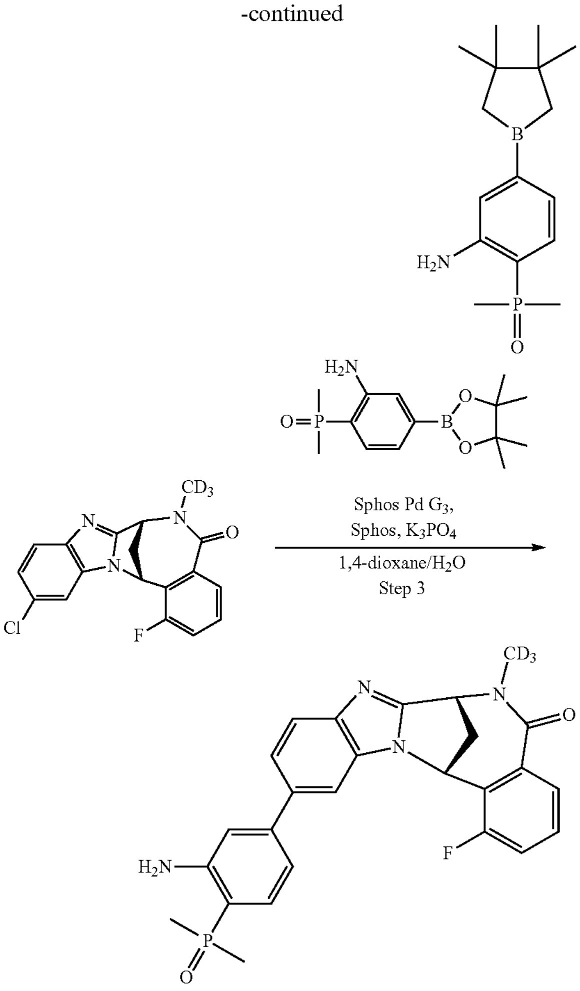

Preparation 24A: 5-bromo-2-(dimethylphosphoryl) aniline

To a stirred solution of 5-bromo-2-iodoaniline (1.00 g, 3.357 mmol) and dimethylphosphine oxide (0.31 g, 4.028 mmol) in 1,4-dioxane (10 mL) were added $Pd_2(dba)_3$ (0.15 g, 0.168 mmol), XantPhos (0.19 g, 0.336 mmol) and $Et_3N$ (0.41 g, 4.028 mmol) at room temperature. The resulting mixture was stirred at 80° C. for 2 h under nitrogen atmosphere. The resulting mixture was concentrated under reduced pressure. The residue was purified by silica gel column chromatography, eluted with $CH_2Cl_2$/MeOH (20:1) to afford 5-bromo-2-(dimethylphosphoryl) aniline (750 mg, 90%). MS ESI calculated for $C_8H_{11}BrNOP$ $[M+H]^+$, 247.98 249.98 found 247.95 249.95. $^1H$ NMR (400 MHz, Chloroform-d) δ 6.94-6.87 (m, 1H), 6.84-6.78 (m, 2H), 1.77 (s, 3H), 1.74 (s, 3H).

Preparation 24B: 2-(dimethylphosphoryl)-5-(4,4,5,5-tetramethyl-1,3,2-dioxaborolan-2-yl) aniline To a stirred solution of 5-bromo-2-(dimethylphosphoryl) aniline (750 mg, 3.023 mmol) and 4,4,4',4',5,5,5',5'-octamethyl-2,2'-bi (1,3,2-dioxaborolane) (1.15 g, 4.535 mmol) in 1,4-dioxane (10 mL) were added $Pd(dppf)Cl_2 \cdot CH_2Cl_2$ (123 mg, 0.151 mmol) and KOAc (742 mg, 7.558 mmol) at room temperature. The resulting mixture was stirred at 80° C. for 2 h under nitrogen atmosphere. The resulting mixture was concentrated under reduced pressure. The residue was purified by silica gel column chromatography, eluted with $CH_2Cl_2$/MeOH (20:1) to afford 2-(dimethylphosphoryl)-5-(4,4,5,5-tetramethyl-1,3,2-dioxaborolan-2-yl) aniline (650 mg, 73%). MS ESI calculated for $C_{14}H_{23}BNO_3P$ $[M+H]^+$, 296.15 found 296.20. $^1H$ NMR (400 MHz, Chloroform-d) δ 7.14-7.07 (m, 3H), 1.34 (s, 12H), 1.25 (s, 3H), 1.23 (s, 3H).

Example 24: (7R,14R)-11-(3-amino-4-(dimethylphosphoryl)phenyl)-1-fluoro-6-(methyl-d3)-6,7-dihydro-7,14-methanobenzo[f]benzo[4,5]imidazo[1,2-a][1,4]diazocin-5(14H)-one To a stirred solution of (7R,14R)-11-chloro-1-fluoro-6-(methyl-d3)-6,7-dihydro-7,14-methanobenzo[f]benzo[4,5]imidazo[1,2-a][1,4]diazocin-5(14H)-one (150 mg, 0.435 mmol) and 2-(dimethylphosphoryl)-5-(4,4,5,5-tetramethyl-1,3,2-dioxaborolan-2-yl) aniline (193 mg, 0.652 mmol) in 1,4-dioxane (5 mL) and $H_2O$ (0.5 mL) were added Sphos Pd G3 (34 mg, 0.044 mmol), Sphos (36 mg, 0.087 mmol) and $K_3PO_4$ (277 mg, 1.305 mmol) at room temperature. The resulting mixture was stirred at 80° C. for 2 h under nitrogen atmosphere. The resulting mixture was concentrated under reduced pressure. The residue was purified by silica gel column chromatography, eluted with $CH_2Cl_2$/MeOH (10:1) followed by reversed-phase flash chromatography with the following conditions: column, C18 silica gel; mobile phase, $CH_3CN$ in Water (10 mmol/L $NH_4HCO_3$), 10% to 50% gradient in 10 min; detector, 254 nm to afford (7R,14R)-11-(3-amino-4-(dimethylphosphoryl)phenyl)-1-fluoro-6-(methyl-d3)-6,7-dihydro-7,14-methanobenzo[f]benzo[4,5]imidazo[1,2-a][1,4]diazocin-5(14H)-one (150 mg, 72%) as a white solid. MS ESI calculated for $C_{26}H_{21}D_3FN_4O_2P$ $[M+H]^+$, 478.18, found 478.10. $^1H$ NMR (400 MHz, DMSO-$d_6$) δ 8.23 (d, J=7.8 Hz, 1H), 7.69 (d, J=8.5 Hz, 1H), 7.57-7.50 (m, 2H), 7.49-7.39 (m, 2H), 7.34-7.26 (m, 1H), 6.91-6.87 (m, 1H), 6.81-6.76 (m, 1H), 6.30 (s, 2H), 6.26 (d, J=6.9 Hz, 1H), 5.27 (d, J=7.2 Hz, 1H), 3.53-3.46 (m, 1H), 2.87 (d, J=13.8 Hz, 1H), 1.70 (s, 3H), 1.67 (s, 3H). $^{19}F$ NMR (377 MHz, DMSO-$d_6$) δ −117.61. $^{31}P$ NMR (162 MHz, DMSO-$d_6$) δ 40.65.

Example 25: (7R,14R)-11-(4-(dimethylphosphoryl)-3-(methylamino)phenyl)-1-fluoro-6-(methyl-d3)-6,7-dihydro-7,14-methanobenzo[f]benzo[4,5]imidazo[1,2-a][1,4]diazocin-5(14H)-one

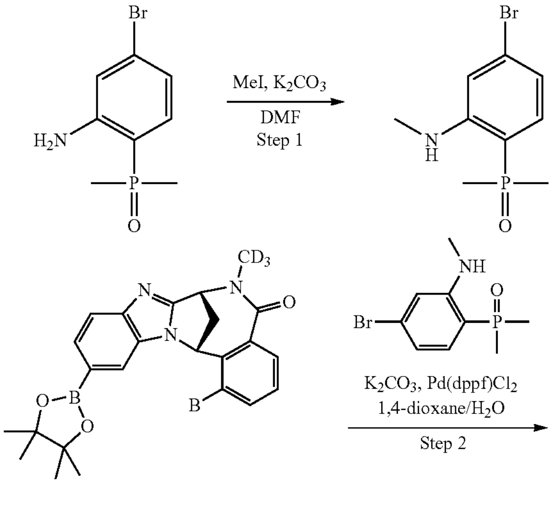

-continued

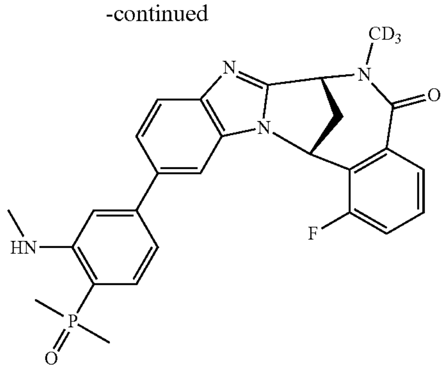

Preparation 25A: 5-bromo-2-(dimethylphosphoryl)-N-methylaniline

To a stirred solution of 5-bromo-2-(dimethylphosphoryl) aniline (500 mg, 2.016 mmol) and $K_2CO_3$ (836 mg, 6.048 mmol) in DMF (5 mL) was added $CH_3I$ (315 mg, 2.218 mmol) at room temperature. The resulting mixture was stirred at 60° C. for 16 h. The resulting mixture was filtered and purified by reversed-phase flash chromatography with the following conditions: column, C18 silica gel; mobile phase, $CH_3CN$ in Water (10 mmol/L, $NH_4HCO_3$), 10% to 70% gradient in 20 min; detector, 254 nm to afford 5-bromo-2-(dimethylphosphoryl)-N-methylaniline (150 mg, 28%). MS ESI calculated for $C_9H_{13}BrNOP$ $[M+H]^+$, 261.99 263.99 found 261.95 263.95. $^1H$ NMR (400 MHz, Chloroform-d) δ 7.31-7.24 (m, 1H), 6.94-6.81 (m, 1H), 6.78-6.67 (m, 2H), 2.80 (d, J=4.7 Hz, 3H), 1.75 (s, 3H), 1.72 (s, 3H).

Example 25: (7R,14R)-11-(4-(dimethylphosphoryl)-3-(methylamino)phenyl)-1-fluoro-6-(methyl-d3)-6,7-dihydro-7,14-methanobenzo[f]benzo[4,5]imidazo[1,2-a][1,4]diazocin-5(14H)-one To a stirred solution of (7R,14R)-1-fluoro-6-(methyl-d3)-11-(4,4,5,5-tetramethyl-1,3,2-dioxaborolan-2-yl)-6,7-dihydro-7,14-methanobenzo[f]benzo[4,5]imidazo[1,2-a][1,4]diazocin-5(14H)-one (60 mg, 0.138 mmol) and 5-bromo-2-(dimethylphosphoryl)-N-methylaniline (43 mg, 0.166 mmol) in 1,4-dioxane (5 mL) and $H_2O$ (0.5 mL) were added $Pd(dppf)Cl_2 \cdot CH_2Cl_2$ (11 mg, 0.014 mmol) and $K_2CO_3$ (57 mg, 0.414 mmol) at room temperature. The resulting mixture was stirred at 80° C. for 2 h under nitrogen atmosphere. The resulting mixture was concentrated under reduced pressure. The residue was purified by silica gel column chromatography, eluted with $CH_2Cl_2$/MeOH (10:1) followed by reversed-phase flash chromatography with the following conditions: column, C18 silica gel; mobile phase, $CH_3CN$ in Water (10 mmol/L $NH_4HCO_3$), 10% to 50% gradient in 30 min; detector, 254 nm to afford (7R,14R)-11-(4-(dimethylphosphoryl)-3-(methylamino)phenyl)-1-fluoro-6-(methyl-d3)-6,7-dihydro-7,14-methanobenzo[f]benzo[4,5]imidazo[1,2-a][1,4]diazocin-5(14H)-one (28 mg, 41%). MS ESI calculated for $C_{27}H_{23}D_3FN_4O_2P$ $[M+H]^+$, 492.20 found 492.15. $^1H$ NMR (400 MHz, DMSO-$d_6$) δ 8.26-8.17 (m, 1H), 7.74-7.66 (m, 1H), 7.61 (s, 1H), 7.58-7.30 (m, 5H), 6.87-6.79 (m, 1H), 6.76-6.69 (m, 1H), 6.29 (d, J=6.8 Hz, 1H), 5.27 (d, J=7.2 Hz, 1H), 3.56-3.44 (m, 1H), 2.88 (d, J=13.8 Hz, 1H), 2.82 (d, J=4.9 Hz, 3H), 1.76-1.67 (m, 6H). $^{19}F$ NMR (377 MHz, DMSO-$d_6$) δ −117.65. $^{31}P$ NMR (162 MHz, DMSO-$d_6$) δ 42.57.

II. Biological Evaluation

TNF-α Induced HEK Blue Cellular Assay

Test articles were diluted in DMSO and serially diluted into 384 well assay plate (Corning 3765), at final concentrations ranging from 30 mM to 0.5 nM. HEK Blue™ TNFα reporter cells were added at a final density of 10,000 cell per well in assay media [DMEM (Gibco, cat #21063-029), 10% fetal bovine serum (ExcelBio, cat #FND500), 1% Penicillin-Streptomycin (Solarbio, cat #P1400-100]. TNF-α (R&D 210-TA-020/CF) was then added to the assay plate at a final concentration of 100 μg/ml. This plate was then incubated for 24 hrs at 37° C. and 5% $CO_2$. Secreted alkaline phosphatase expression was then measured using QUANTI-Blue™ (Invivogen), according to manufacturer instructions and read on an Envision microplate reader at 620 nm.

Inhibition data for test compound over a range of concentration was plotted as percentage inhibition of the test compound (100%=maximum inhibition). $IC_{50}$ values were determined after correcting for background [(sample read-mean of low control)/(mean of high control-mean of low control)] where by the low control is DMSO without stimulation and high control is DMSO with stimulation. The $IC_{50}$ is defined as the concentration of test compound which produces 50% inhibition and was quantified using the 4 parameter logistic equation to fit the data.

Representative data for exemplary compounds is presented in Table 3.

TABLE 3

| Ex. No | $IC_{50}$ value |
|---|---|
| 1 | A |
| 2 | A |
| 3 | A |
| 4 | A |
| 5 | A |
| 6 | A |
| 7 | A |
| 8 | A |
| 9 | A |
| 10 | A |
| 11 | A |
| 12 | A |

Note:
$IC_{50}$ data are designated within the following ranges:
A: ≤0.1 μM
B: >0.1 μM to ≤1.0 μM
C: >1.0 μM to ≤10 μM
D: >10 μM to ≤30 μM TNF-α Induced THP 1 dual Cellular Assay Test articles were diluted in DMSO and serially diluted into 384 well assay plate (Corning 3765), at final concentrations ranging from 30 mM to 0.5 nM. THP1 dual cell reporter cells were added at a final density of 10,000 cell per well in assay media [DMEM (Gibco, cat #21063-029), 10% fetal bovine serum (ExcelBio, cat #FND500), 1% Penicillin-Streptomycin (Solarbio, cat #P1400-100]. TNF-α (R&D 210-TA-020/CF) was then added to the assay plate at a final concentration of 100 μg/ml. This plate was then incubated for 24 hrs at 37° C. and 5% $CO_2$. Secreted alkaline phosphatase expression was then measured using QUANTI-Blue™ (Invivogen), according to manufacturer instructions and read on an Envision microplate reader at 620 nm.

Inhibition data for test compound over a range of concentration was plotted as percentage inhibition of the test compound (100%=maximum inhibition). $IC_{50}$ values were determined after correcting for background [(sample read-mean of low control)/(mean of high control-mean of low control)] whereby the low control is DMSO without stimulation and high control is DMSO with stimulation. The $IC_{50}$ is defined as the concentration of test compound which produces 50% inhibition and was quantified using the 4-parameter logistic equation to fit the data.

Representative data for exemplary compounds is presented in Table 4.

TABLE 4

| Ex. No | $IC_{50}$ value |
|---|---|
| 12 | A |
| 13 | A |
| 14 | A |
| 15 | A |
| 16 | A |
| 17 | A |
| 18 | A |
| 19 | A |
| 20 | A |
| 21 | A |
| 22 | A |
| 23 | A |
| 24 | A |
| 25 | A |

Note:
$IC_{50}$ data are designated within the following ranges:
A: ≤0.1 μM
B: >0.1 μM to ≤1.0 μM
C: >1.0 μM to ≤10 μM
D: >10 μM to ≤30 μM III. Preparation of Pharmaceutical Dosage Forms Example 1: Oral Capsule The active ingredient is a compound of Table 1, or a pharmaceutically acceptable salt or solvate thereof. A capsule for oral administration is prepared by mixing 1-1000 mg of active ingredient with starch or other suitable powder blend. The mixture is incorporated into an oral dosage unit such as a hard gelatin capsule, which is suitable for oral administration.

Example 2: Solution for Injection

The active ingredient is a compound of Table 1, or a pharmaceutically acceptable salt or solvate thereof, and is formulated as a solution in sesame oil at a concentration of 50 mg-eq/mL.

The examples and embodiments described herein are for illustrative purposes only and various modifications or changes suggested to persons skilled in the art are to be included within the spirit and purview of this application and scope of the appended claims.

We claim:

1. A compound selected from the group consisting of:

(7R,14R)-11-(4-(dimethylphosphoryl)-3-fluorophenyl)-1-fluoro-6-(methyl-d3)-6,7-dihydro-7,14-methanobenzo[f]benzo[4,5]imidazo[1,2-a][1,4]diazocin-5(14H)-one;

(7R,14R)-11-(4-(dimethylphosphoryl)-2,5-difluorophenyl)-1-fluoro-6-(methyl-d3)-6,7-dihydro-7,14-methanobenzo[f]benzo[4,5]imidazo[1,2-a][1,4]diazocin-5(14H)-one;

(7R,14R)-11-(4-(dimethylphosphoryl)-3-fluorophenyl)-1,3-difluoro-6-(methyl-d3)-6,7-dihydro-7,14-methanobenzo[f]benzo[4,5]imidazo[1,2-a][1,4]diazocin-5(14H)-one;

(7R,14R)-11-(4-(dimethylphosphoryl)-2,3-difluorophenyl)-1-fluoro-6-(methyl-d3)-6,7-dihydro-7,14-methanobenzo[f]benzo[4,5]imidazo[1,2-a][1,4]diazocin-5(14H)-one;

(7R,14R)-11-(4-(dimethylphosphoryl)-3-fluorophenyl)-1,2-difluoro-6-(methyl-d3)-6,7-dihydro-7,14-methanobenzo[f]benzo[4,5]imidazo[1,2-a][1,4]diazocin-5(14H)-one;

(7R,14R)-11-(4-(dimethylphosphoryl)phenyl)-1-fluoro-6-(methyl-d3)-6,7-dihydro-7,14-methanobenzo[f]benzo[4,5]imidazo[1,2-a][1,4]diazocin-5(14H)-one;

(7R,14R)-11-(4-(dimethylphosphoryl)-2-fluorophenyl)-1-fluoro-6-(methyl-d3)-6,7-dihydro-7,14-methanobenzo[f]benzo[4,5]imidazo[1,2-a][1,4]diazocin-5(14H)-one;

(7R,14R)-11-(4-(dimethylphosphoryl)phenyl)-1,10-difluoro-6-(methyl-d3)-6,7-dihydro-7,14-methanobenzo[f]benzo[4,5]imidazo[1,2-a][1,4]diazocin-5(14H)-one;

(7R,14R)-11-(4-(dimethylphosphoryl)-3-fluorophenyl)-1-fluoro-7-methyl-6-(methyl-d3)-6,7-dihydro-7,14-methanobenzo[f]benzo[4,5]imidazo[1,2-a][1,4]diazocin-5(14H)-one;

(7R,14R)-11-(4-(dimethylphosphoryl)-3-fluorophenyl)-1,10-difluoro-6-(methyl-d3)-6,7-dihydro-7,14-methanobenzo[f]benzo[4,5]imidazo[1,2-a][1,4]diazocin-5(14H)-one;

(7R,14R)-11-(3-amino-4-(dimethylphosphoryl)phenyl)-1-fluoro-6-(methyl-d3)-6,7-dihydro-7,14-methanobenzo[f]benzo[4,5]imidazo[1,2-a][1,4]diazocin-5(14H)-one; and (7R,14R)-11-(4-(dimethylphosphoryl)-3-(methylamino)phenyl)-1-fluoro-6-(methyl-d3)-6,7-dihydro-7,14-methanobenzo[f]benzo[4,5]imidazo[1,2-a][1,4]diazocin-5(14H)-one;

or a pharmaceutically acceptable salt, solvate, deuteroisotope, or N-oxide thereof.

2. The compound of claim 1, wherein the compound is (7R,14R)-11-(4-(dimethylphosphoryl)-3-fluorophenyl)-1-fluoro-6-(methyl-d3)-6,7-dihydro-7,14-methanobenzo[f]benzo[4,5]imidazo[1,2-a][1,4]diazocin-5(14H)-one, or a pharmaceutically acceptable salt, solvate, deuteroisotope, or N-oxide thereof.

3. The compound of claim 1, wherein the compound is (7R,14R)-11-(4-(dimethylphosphoryl)-2,5-difluorophenyl)-1-fluoro-6-(methyl-d3)-6,7-dihydro-7,14-methanobenzo[f]benzo[4,5]imidazo[1,2-a][1,4]diazocin-5(14H)-one, or a pharmaceutically acceptable salt, solvate, deuteroisotope, or N-oxide thereof.

4. The compound of claim 1, wherein the compound is (7R,14R)-11-(4-(dimethylphosphoryl)-3-fluorophenyl)-1,3-difluoro-6-(methyl-d3)-6,7-dihydro-7,14-methanobenzo[f]benzo[4,5]imidazo[1,2-a][1,4]diazocin-5(14H)-one, or a pharmaceutically acceptable salt, solvate, deuteroisotope, or N-oxide thereof.

5. The compound of claim 1, wherein the compound is (7R,14R)-11-(4-(dimethylphosphoryl)-2,3-difluorophenyl)-1-fluoro-6-(methyl-d3)-6,7-dihydro-7,14-methanobenzo[f]benzo[4,5]imidazo[1,2-a][1,4]diazocin-5(14H)-one, or a pharmaceutically acceptable salt, solvate, deuteroisotope, or N-oxide thereof.

6. The compound of claim 1, wherein the compound is (7R,14R)-11-(4-(dimethylphosphoryl)-3-fluorophenyl)-1,2-difluoro-6-(methyl-d3)-6,7-dihydro-7,14-methanobenzo[f]benzo[4,5]imidazo[1,2-a][1,4]diazocin-5(14H)-one, or a pharmaceutically acceptable salt, solvate, deuteroisotope, or N-oxide thereof.

7. The compound of claim 1, wherein the compound is (7R,14R)-11-(4-(dimethylphosphoryl)phenyl)-1-fluoro-6-(methyl-d3)-6,7-dihydro-7,14-methanobenzo[f]benzo[4,5]imidazo[1,2-a][1,4]diazocin-5(14H)-one, or a pharmaceutically acceptable salt, solvate, deuteroisotope, or N-oxide thereof.

8. The compound of claim 1, wherein the compound is (7R,14R)-11-(4-(dimethylphosphoryl)-2-fluorophenyl)-1-fluoro-6-(methyl-d3)-6,7-dihydro-7,14-methanobenzo[f]benzo[4,5]imidazo[1,2-a][1,4]diazocin-5(14H)-one, or a pharmaceutically acceptable salt, solvate, deuteroisotope, or N-oxide thereof.

9. The compound of claim 1, wherein the compound is (7R,14R)-11-(4-(dimethylphosphoryl)phenyl)-1,10-difluoro-6-(methyl-d3)-6,7-dihydro-7,14-methanobenzo[f]benzo[4,5]imidazo[1,2-a][1,4]diazocin-5(14H)-one, or a pharmaceutically acceptable salt, solvate, deuteroisotope, or N-oxide thereof.

10. The compound of claim 1, wherein the compound is (7R,14R)-11-(4-(dimethylphosphoryl)-3-fluorophenyl)-1-fluoro-7-methyl-6-(methyl-d3)-6,7-dihydro-7,14-methanobenzo[f]benzo[4,5]imidazo[1,2-a][1,4]diazocin-5(14H)-one, or a pharmaceutically acceptable salt, solvate, deuteroisotope, or N-oxide thereof.

11. The compound of claim 1, wherein the compound is (7R,14R)-11-(4-(dimethylphosphoryl)-3-fluorophenyl)-1,10-difluoro-6-(methyl-d3)-6,7-dihydro-7,14-methanobenzo[f]benzo[4,5]imidazo[1,2-a][1,4]diazocin-5(14H)-one, or a pharmaceutically acceptable salt, solvate, deuteroisotope, or N-oxide thereof.

12. The compound of claim 1, wherein the compound is (7R,14R)-11-(3-amino-4-(dimethylphosphoryl)phenyl)-1-fluoro-6-(methyl-d3)-6,7-dihydro-7,14-methanobenzo[f]benzo[4,5]imidazo[1,2-a][1,4]diazocin-5(14H)-one, or a pharmaceutically acceptable salt, solvate, deuteroisotope, or N-oxide thereof.

13. The compound of claim 1, wherein the compound is (7R,14R)-11-(4-(dimethylphosphoryl)-3-(methylamino)phenyl)-1-fluoro-6-(methyl-d3)-6,7-dihydro-7,14-methanobenzo[f]benzo[4,5]imidazo[1,2-a][1,4]diazocin-5(14H)-one, or a pharmaceutically acceptable salt, solvate, deuteroisotope, or N-oxide thereof.

14. A pharmaceutical composition comprising a pharmaceutically acceptable excipient, and a compound selected from the group consisting of:

(7R,14R)-11-(4-(dimethylphosphoryl)-3-fluorophenyl)-1-fluoro-6-(methyl-d3)-6,7-dihydro-7,14-methanobenzo[f]benzo[4,5]imidazo[1,2-a][1,4]diazocin-5(14H)-one;

(7R,14R)-11-(4-(dimethylphosphoryl)-2,5-difluorophenyl)-1-fluoro-6-(methyl-d3)-6,7-dihydro-7,14-methanobenzo[f]benzo[4,5]imidazo[1,2-a][1,4]diazocin-5(14H)-one;

(7R,14R)-11-(4-(dimethylphosphoryl)-3-fluorophenyl)-1,3-difluoro-6-(methyl-d3)-6,7-dihydro-7,14-methanobenzo[f]benzo[4,5]imidazo[1,2-a][1,4]diazocin-5(14H)-one;

(7R,14R)-11-(4-(dimethylphosphoryl)-2,3-difluorophenyl)-1-fluoro-6-(methyl-d3)-6,7-dihydro-7,14-methanobenzo[f]benzo[4,5]imidazo[1,2-a][1,4]diazocin-5(14H)-one;

(7R,14R)-11-(4-(dimethylphosphoryl)-3-fluorophenyl)-1,2-difluoro-6-(methyl-d3)-6,7-dihydro-7,14-methanobenzo[f]benzo[4,5]imidazo[1,2-a][1,4]diazocin-5(14H)-one;

(7R,14R)-11-(4-(dimethylphosphoryl)phenyl)-1-fluoro-6-(methyl-d3)-6,7-dihydro-7,14-methanobenzo[f]benzo[4,5]imidazo[1,2-a][1,4]diazocin-5(14H)-one;

(7R,14R)-11-(4-(dimethylphosphoryl)-2-fluorophenyl)-1-fluoro-6-(methyl-d3)-6,7-dihydro-7,14-methanobenzo[f]benzo[4,5]imidazo[1,2-a][1,4]diazocin-5(14H)-one;

(7R,14R)-11-(4-(dimethylphosphoryl)phenyl)-1,10-difluoro-6-(methyl-d3)-6,7-dihydro-7,14-methanobenzo[f]benzo[4,5]imidazo[1,2-a][1,4]diazocin-5(14H)-one;

(7R,14R)-11-(4-(dimethylphosphoryl)-3-fluorophenyl)-1-fluoro-7-methyl-6-(methyl-d3)-6,7-dihydro-7,14-methanobenzo[f]benzo[4,5]imidazo[1,2-a][1,4]diazocin-5(14H)-one;

(7R,14R)-11-(4-(dimethylphosphoryl)-3-fluorophenyl)-1,10-difluoro-6-(methyl-d3)-6,7-dihydro-7,14-methanobenzo[f]benzo[4,5]imidazo[1,2-a][1,4]diazocin-5(14H)-one;

(7R,14R)-11-(3-amino-4-(dimethylphosphoryl)phenyl)-1-fluoro-6-(methyl-d3)-6,7-dihydro-7,14-methanobenzo[f]benzo[4,5]imidazo[1,2-a][1,4]diazocin-5(14H)-one; and (7R,14R)-11-(4-(dimethylphosphoryl)-3-(methylamino)phenyl)-1-fluoro-6-(methyl-d3)-6,7-dihydro-7,14-methanobenzo[f]benzo[4,5]imidazo[1,2-a][1,4]diazocin-5(14H)-one, or a pharmaceutically acceptable salt, solvate, deuteroisotope, or N-oxide thereof.

15. The pharmaceutical composition of claim 14, wherein the compound is (7R,14R)-11-(4-(dimethylphosphoryl)-3-fluorophenyl)-1-fluoro-6-(methyl-d3)-6,7-dihydro-7,14-methanobenzo[f]benzo[4,5]imidazo[1,2-a][1,4]diazocin-5(14H)-one, or a pharmaceutically acceptable salt, solvate, deuteroisotope, or N-oxide thereof.

16. The pharmaceutical composition of claim 14, wherein the compound is (7R,14R)-11-(4-(dimethylphosphoryl)-2,5-difluorophenyl)-1-fluoro-6-(methyl-d3)-6,7-dihydro-7,14-methanobenzo[f]benzo[4,5]imidazo[1,2-a][1,4]diazocin-5(14H)-one, or a pharmaceutically acceptable salt, solvate, deuteroisotope, or N-oxide thereof.

17. The pharmaceutical composition of claim 14, wherein the compound is (7R,14R)-11-(4-(dimethylphosphoryl)-3-fluorophenyl)-1,3-difluoro-6-(methyl-d3)-6,7-dihydro-7,14-methanobenzo[f]benzo[4,5]imidazo[1,2-a][1,4]diazocin-5(14H)-one, or a pharmaceutically acceptable salt, solvate, deuteroisotope, or N-oxide thereof.

18. The pharmaceutical composition of claim 14, wherein the compound is (7R,14R)-11-(4-(dimethylphosphoryl)-2,3-difluorophenyl)-1-fluoro-6-(methyl-d3)-6,7-dihydro-7,14-methanobenzo[f]benzo[4,5]imidazo[1,2-a][1,4]diazocin-5(14H)-one, or a pharmaceutically acceptable salt, solvate, deuteroisotope, or N-oxide thereof.

19. The pharmaceutical composition of claim 14, wherein the compound is (7R,14R)-11-(4-(dimethylphosphoryl)-3-fluorophenyl)-1,2-difluoro-6-(methyl-d3)-6,7-dihydro-7,14-methanobenzo[f]benzo[4,5]imidazo[1,2-a][1,4]diazocin-5(14H)-one, or a pharmaceutically acceptable salt, solvate, deuteroisotope, or N-oxide thereof.

20. The pharmaceutical composition of claim 14, wherein the compound is (7R,14R)-11-(4-(dimethylphosphoryl)phenyl)-1-fluoro-6-(methyl-d3)-6,7-dihydro-7,14-methanobenzo[f]benzo[4,5]imidazo[1,2-a][1,4]diazocin-5(14H)-one, or a pharmaceutically acceptable salt, solvate, deuteroisotope, or N-oxide thereof.

21. The pharmaceutical composition of claim 14, wherein the compound is (7R,14R)-11-(4-(dimethylphosphoryl)-2-fluorophenyl)-1-fluoro-6-(methyl-d3)-6,7-dihydro-7,14- methanobenzo[f]benzo[4,5]imidazo[1,2-a][1,4]diazocin-5(14H)-one, or a pharmaceutically acceptable salt, solvate, deuteroisotope, or N-oxide thereof.

22. The pharmaceutical composition of claim 14, wherein the compound is (7R,14R)-11-(4-(dimethylphosphoryl)phenyl)-1,10-difluoro-6-(methyl-d3)-6,7-dihydro-7,14-methanobenzo[f]benzo[4,5]imidazo[1,2-a][1,4]diazocin-5(14H)-one, or a pharmaceutically acceptable salt, solvate, deuteroisotope, or N-oxide thereof.

23. The pharmaceutical composition of claim 14, wherein the compound is (7R,14R)-11-(4-(dimethylphosphoryl)-3-fluorophenyl)-1-fluoro-7-methyl-6-(methyl-d3)-6,7-dihydro-7,14-methanobenzo[f]benzo[4,5]imidazo[1,2-a][1,4]diazocin-5(14H)-one, or a pharmaceutically acceptable salt, solvate, deuteroisotope, or N-oxide thereof.

24. The pharmaceutical composition of claim 14, wherein the compound is (7R,14R)-11-(4-(dimethylphosphoryl)-3-fluorophenyl)-1,10-difluoro-6-(methyl-d3)-6,7-dihydro-7,14-methanobenzo[f]benzo[4,5]imidazo[1,2-a][1,4]diazocin-5(14H)-one, or a pharmaceutically acceptable salt, solvate, deuteroisotope, or N-oxide thereof.

25. The pharmaceutical composition of claim 14, wherein the compound is (7R,14R)-11-(3-amino-4-(dimethylphosphoryl)phenyl)-1-fluoro-6-(methyl-d3)-6,7-dihydro-7,14-methanobenzo[f]benzo[4,5]imidazo[1,2-a][1,4]diazocin-5(14H)-one, or a pharmaceutically acceptable salt, solvate, deuteroisotope, or N-oxide thereof.

26. The pharmaceutical composition of claim 14, wherein the compound is (7R,14R)-11-(4-(dimethylphosphoryl)-3-(methylamino)phenyl)-1-fluoro-6-(methyl-d3)-6,7-dihydro-7,14-methanobenzo[f]benzo[4,5]imidazo[1,2-a][1,4]diazocin-5(14H)-one, or a pharmaceutically acceptable salt, solvate, deuteroisotope, or N-oxide thereof.

* * * * *